US008076338B2

(12) United States Patent
Anand et al.

(10) Patent No.: US 8,076,338 B2
(45) Date of Patent: Dec. 13, 2011

(54) KINASE MODULATORS AND METHODS OF USE

(75) Inventors: Neel K. Anand, Burlingame, CA (US); Charles M. Blazey, San Francisco, CA (US); Owen Joseph Bowles, Pacifica, CA (US); Joerg Bussenius, Foster City, CA (US); Lynne Canne Bannen, Pacifica, CA (US); Diva Sze-Ming Chan, San Francisco, CA (US); Baili Chen, Palo Alto, CA (US); Erick Wang Co, San Diego, CA (US); Simona Costanzo, Los Altos, CA (US); Steven Charles Defina, Burlingame, CA (US); Larisa Dubenko, San Francisco, CA (US); Maurizio Franzini, San Francisco, CA (US); Ping Huang, Mountain View, CA (US); Vasu Jammalamadaka, Pleasonton, CA (US); Richard George Khoury, Redwood City, CA (US); Moon Hwan Kim, Palo Alto, CA (US); Rhett Ronald Klein, Chicago, IL (US); Donna Tra Le, San Jose, CA (US); Morrison B. Mac, San Francisco, CA (US); John M. Nuss, Danville, CA (US); Jason Jevious Parks, Sacramento, CA (US); Kenneth D. Rice, San Rafael, CA (US); Tsze H. Tsang, El Cerrito, CA (US); Amy Lew Tsuhako, Milpitas, CA (US); Yong Wang, Foster City, CA (US); Wei Xu, Danville, CA (US)

(73) Assignee: Exelixis, Inc., South San Francisco, CA (US)

( * ) Notice: Subject to any disclaimer, the term of this patent is extended or adjusted under 35 U.S.C. 154(b) by 959 days.

(21) Appl. No.: 11/568,173

(22) PCT Filed: Apr. 22, 2005

(86) PCT No.: PCT/US2005/013860
§ 371 (c)(1),
(2), (4) Date: Jul. 26, 2007

(87) PCT Pub. No.: WO2005/117909
PCT Pub. Date: Dec. 15, 2005

(65) Prior Publication Data
US 2008/0076774 A1 Mar. 27, 2008

Related U.S. Application Data

(60) Provisional application No. 60/564,908, filed on Apr. 23, 2004.

(51) Int. Cl.
A61K 31/501 (2006.01)
A61K 31/497 (2006.01)
C07D 473/16 (2006.01)
C07D 401/04 (2006.01)

(52) U.S. Cl. .............. 514/252.02; 514/252.16; 544/277; 544/238; 544/363

(58) Field of Classification Search .................. 544/277, 544/363, 238; 514/252.02, 252.16
See application file for complete search history.

(56) References Cited

U.S. PATENT DOCUMENTS 3,457,263 A 7/1969 Regnier et al.
(Continued)

FOREIGN PATENT DOCUMENTS

JP 2007-531721 A 11/2007
(Continued)

OTHER PUBLICATIONS

Regnier et al., Central Nervous System Depressants. New Purine Derivatives, Chimica Therapeutica 7(3), pp. 192-205, (1972), (abstract).*

(Continued)

*Primary Examiner* — James O Wilson
*Assistant Examiner* — Ebenezer Sackey
(74) *Attorney, Agent, or Firm* — McDonnell Boehnen Hulbert & Berghoff LLP

(57) ABSTRACT

The present invention relates to compounds of the Formula (I) and (II) wherein R, $R_{21}$, $R_{25}$-$R_{33}$, m, n, $X_{21}$-$X_{23}$, and $Q_1$ are defined herein. The compounds modulate protein kinase enzymatic activity to modulate cellular activities such as proliferation, differentiation, programmed cell death, migration and chemoinvasion. Compounds of the invention inhibit, regulate and/or modulate kinases, particularly p70S6 and/or Akt kinases. Methods of using and preparing the compounds, and pharmaceutical compositions thereof, to treat kinase-dependent diseases and conditions are also an aspect of the invention.

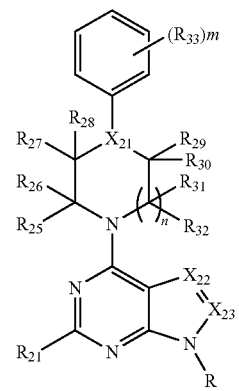

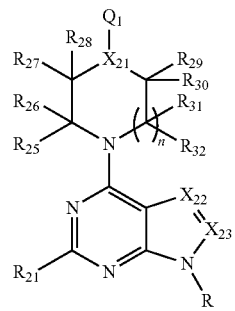

53 Claims, No Drawings

U.S. PATENT DOCUMENTS

| | | | |
|---|---|---|---|
| 6,946,449 B2 * | 9/2005 | Elzein et al. | 514/46 |
| 2005/0197340 A1 | 9/2005 | Arora et al. | |

FOREIGN PATENT DOCUMENTS

| | | |
|---|---|---|
| JP | 2008-525526 A | 7/2008 |
| WO | 99/65909 A1 | 12/1999 |
| WO | 03/031405 A2 | 4/2003 |
| WO | 2004/074287 A1 | 9/2004 |
| WO | 2005/020897 A | 3/2005 |
| WO | 91/04254 A1 | 4/2005 |
| WO | 2006/071819 A | 7/2006 |

OTHER PUBLICATIONS

Riva-Toniolo et al., Substitution Reactions on C2 and C8 of Purines on a Solid Support; International Electronic Conference on Synthetic Organic Chemistry, $5^{th}$, 6th, Sep. 1-30, 2001, 2002 and $7^{th}$, $8^{th}$, Nov. 1-30, 2003 and (2004), 807-815. (abstract).*

Hasan, "Studies in Nucleosides, Part XV. Synthesis of 6-methoxy/methylthio-4-N-substituted-1-(2-tetrahydrofuranyl)-1H-pyrazolo[3,4-d]pyrimidines and their biological activity", Indian Journal of Chemistry, 1987, 284-286, 26B(3).

Prabhakar, Y.S. et al., "QSAR study on the antiviral activity of 2,6,9-substituted purines and related analogs", Indian Journal of Biochemistry & Biophysics, 27(5), 342-7.

Lettre, H. et al., "N-Puryl-(6)-Derivative Von Diaminen", Justus Liebigs Annalen Der Chemie, 1961, vol. 649, 124-130.

Strappaghetti, G. et al., "Adenosine receptors: synthesis, structure-activity relationships and biological activity of new 6-amino purine derivatives", Eur. J. Med. Chem., 1998, vol. 33, 501-208.

\* cited by examiner

KINASE MODULATORS AND METHODS OF USE

REFERENCE TO RELATED APPLICATIONS

This application claims priority to U.S. provisional patent application 60/564,908 filed Apr. 23, 2004. The contents of the prior application are hereby incorporated in their entirety.

BACKGROUND OF THE INVENTION

1. Field of the Invention

This invention relates to compounds for modulating protein kinase enzymatic activity for modulating cellular activities such as proliferation, differentiation, programmed cell death, migration, chemoinvasion and metabolism. Even more specifically, the invention relates to compounds which inhibit, regulate and/or modulate kinase receptor signal transduction pathways related to the changes in cellular activities as mentioned above, compositions which contain these compounds, and methods of using them to treat kinase-dependent diseases and conditions.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins at the hydroxy groups of tyrosine, serine and threonine residues of proteins. The kinase complement of the human genome contains 518 putative protein kinase genes [Manning et al, Science, (2002), 298, 1912]. The consequences of this activity include effects on cell differentiation, proliferation, transcription, translation, metabolism, cell cycle progression, apoptosis, metabolism cytoskeletal rearrangement and movement; i.e., protein kinases mediate the majority of signal transduction in eukaryotic cells. Furthermore, abnormal protein kinase activity has been related to a host of disorders, ranging from relatively non-life threatening diseases such as psoriasis to cancer. Chromosomal mapping has revealed that over 200 kinases map to disease loci, including cancer, inflammatory and metabolic disease.

Tyrosine kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and -beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (Flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Abl, Syk/Zap70, Fes/Fps, Fak, Jak, and Ack. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Serine-theoronine kinases play critical roles in intracellular signal transduction and include the multiple families, including STE, CKI, AGC, CAMK, and CMGC. Important subfamilies include, the MAP kinases, p38, JNK and ERK, which modulate signal transduction resulting from such diverse stimuli as mitogenic, stress, proinflammatory and antiapoptotic pathways. Members of the MAP kinase subfamily have been targeted for therapeutic intervention, including p38a, JNK isozymes and Raf.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec is a selective Abl kinase inhibitor.

Modulation (particularly inhibition) of cell proliferation and angiogenesis, two key cellular processes needed for tumor growth and survival (Matter A. Drug Disc Technol 20016, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

The enzyme, p70S6 kinase (p70S6K) is a serine-theoronine kinase that is a component of the phosphatidylinositol 3 kinase (PI3K)/Akt kinase (AktK) pathway. Both Akt and p70S6K are downstream of phosphatidylinositol-3 kinase (PI3K), and undergo phosphorylation and activation in response to growth factors such as IGF-1, EGF, TGF-α and HGF. The enzyme p70S6K modulates protein synthesis by phosphorylation of the S6 ribosomal protein promoting translation. A role for p70S6K in tumor cell proliferation and protection of cells from apoptosis is supported based on its participation in growth factor receptor signal transduction, overexpression and activation in tumor tissues [Pene et al (2002) Oncogene 21, 6587; Miyakawa et al (2003) Endocrin J. 50, 77, 83; Le et al (2003) Oncogene 22, 484]. Clinical inhibition of p70S6K activation was observed in renal carcinoma patients treated with CCI-779 (rapamycin ester), an inhibitor of the upstream activating kinase, mTOR. A significant linear association between disease progression and inhibition of p70S6K activity was reported [Peralba et al (2003) Clinical Cancer Research 9, 2887].

Recently, the enzyme p70S6K was found to be implicated in metabolic diseases and disorders. It was reported that the absence of p70S6K protects against age- and diet-induced obesity while enhancing insulin sensitivity [Um et al (2004) Nature 431, 200-205 and Pende et al (2000) Nature 408, 994-997]. A role for p70S6K in metabolic diseases and disorders such as obesity, diabetes, metabolic syndrome, insulin resistance, hyperglycemia, hyperaminoacidemia, and hyperlipidemia is supported based upon the findings.

Accordingly, the identification of small-molecule compounds that specifically inhibit, regulate and/or modulate the signal transduction of kinases, particularly p70S6K and/or Akt, is desirable as a means to treat or prevent disease states associated with abnormal cell proliferation and metabolism is an object of this invention.

SUMMARY OF THE INVENTION

The present invention provides compounds for modulating kinase activity and methods of treating diseases mediated by kinase activity, in particular p70S6 and/or Akt kinase activity, utilizing the compounds and pharmaceutical compositions thereof. Diseases mediated by kinase activity are from herein referred to as "kinase-dependent diseases or conditions" (see definition in detailed description of invention below). Inhibitors that are selective for p70S6 and/or Akt kinase are included in this invention.

In another aspect, the invention provides methods of screening for modulators of kinase activity. The methods comprise combining a composition of the invention, a kinase, and at least one candidate agent and determining the effect of the candidate agent on the kinase activity.

In yet another aspect, the invention also provides pharmaceutical kits comprising one or more containers filled with one or more of the ingredients of pharmaceutical compounds and/or compositions of the present invention, including, one or more kinase enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below.

DETAILED DESCRIPTION OF THE INVENTION

The compositions of the invention are used to treat diseases associated with abnormal and/or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as atherosclerosis, myocardioinfarction, ischemia, pulmonary hypertension, stroke and restenosis; other inflammatory and degenerative diseases such as interbowel diseases, osteoarthritis, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally," but proliferation and migration enhancement may be desired. Alternatively, reduction in "normal" cell proliferation and/or migration rate may be desired.

In embodiment A, the present invention comprises a compound for modulating kinase activity, particularly p70S6 and/or Akt kinase activity, of Formula I,

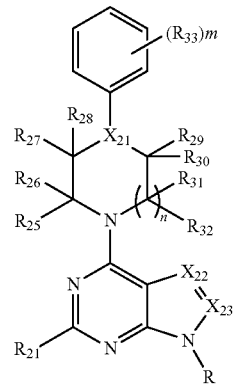

or a pharmaceutically acceptable salt, hydrate, or prodrug thereof, wherein, $X_{21}$ is N or $CR_{22}$;

$X_{22}$ is N or $CR_{23}$;

$X_{23}$ is N or $CR_{24}$, but when $X_{22}$ is N then $X_{23}$ is $CR_{24}$;

each of $R_{21}$, $R_{22}$, $R_{23}$, $R_{24}$, $R_{25}$, $R_{26}$, $R_{27}$, $R_{28}$, $R_{29}$ and $R_{30}$, and each $R_{31}$, $R_{32}$ and $R_{33}$ is independently selected from —H, halogen, trihalomethyl, —CN, —NO$_2$, —NR$_{35}$R$_{35a}$, —S(O)$_{0-2}$R$_{35}$, —SO$_2$NR$_{35}$R$_{35a}$, —CO$_2$R$_{35}$, —C(O)NR$_{35}$R$_{35a}$, —N(R$_{35}$)SO$_2$R$_{35}$, —N(R$_{35}$)C(O)R$_{35}$, —N(R$_{35}$)CO$_2$R$_{35}$, —OR$_{35}$, —C(O)R$_{35}$, optionally substituted lower allyl, optionally substituted aryl, optionally substituted heterocyclyl, optionally substituted heterocyclylallyl, and optionally substituted arylalkyl;

R is selected from —H, halogen, trihalomethyl, —S(O)$_{0-2}$R$_{35}$, —SO$_2$NR$_{35}$R$_{35a}$, —CO$_2$R$_{35}$, —C(O)NR$_{35}$R$_{35a}$, —OR$_{35}$, —C(O)R$_{35}$, optionally substituted lower allyl, optionally substituted aryl, optionally substituted heterocyclyl, optionally substituted heterocyclylallyl, and optionally substituted arylalkyl; or two of $R_{25}$, $R_{26}$, $R_{27}$, $R_{28}$, $R_{29}$, $R_{30}$, $R_{31}$ or $R_{32}$, together with the atom or respective atoms to which they are attached, combine to form an optionally substituted spirocyclic ring system, optionally substituted fused ring system, and optionally substituted saturated bridged ring system;

each of $R_{35}$ and $R_{35a}$ is independently selected from —H, optionally substituted lower allyl, optionally substituted lower alkoxy, optionally substituted aryl, optionally substituted lower arylalkyl, optionally substituted lower aryl alkoxy, optionally substituted heterocyclyl, and optionally substituted lower heterocyclylalkyl; or $R_{35}$ and $R_{35a}$, together with the atom or respective atoms to which they are attached, combine to form an optionally substituted five- to seven-membered heterocyclyl; and m is an integer from 0 to 5;

n is an integer from 1 to 2; and with the provisos that when $X_{22}$ is $CR_{23}$ and $X_{23}$ is N then R is not optionally substituted aryl, aralkyl or heteroaryl, and that when $X_{22}$ is N and $X_{23}$ is $CR_{24}$ then R is not optional substituted aryl or heteroaryl and $R_{21}$ is not —$NR_{35}R_{35a}$, and that when $X_{22}$ is $CR_{23}$ and $X_{23}$ is $CR_{24}$ then $R_{21}$ is not optionally substituted aryl, and that compounds with CAS Registration Nos. 732271-60-2, 565169-26-8, 537667-19-9, 537667-18-8, 537667-17-7, 537667-16-6, 537667-15-5, 537667-14-4, 537667-13-3, 537667-12-2, 537667-11-1, 252722-59-1, 252722-34-2, 47281-43-6, 37425-49-3, 37425-48-2, 24932-89-6 and 24932-78-3 are not included in Formula I.

In one example, the compound is according to Embodiment A, wherein n is 1.

In another example, the compound is according to paragraph [0035], wherein $X_{21}$, is N.

In another example, the compound is according to paragraph [0036], wherein $X_{23}$ is N.

In another example, the compound is according to paragraph [0037], wherein $X_{22}$ is $CR_{23}$.

In another example, the compound is according to paragraph [0038], wherein R is —H.

In another example, the compound is according to paragraph [0038], wherein R is optionally substituted alkyl.

In another example, the compound is according to paragraph [0039], wherein $R_{21}$ is —H.

In another example, the compound is according to paragraph [0039], wherein $R_{21}$ is optionally substituted alkyl.

In another example, the compound is according to paragraph [0041], wherein $R_{25}$ and $R_{26}$ are —H.

In another example, the compound is according to paragraph [0043], wherein $R_{27}$ and $R_{28}$ are —H.

In another example, the compound is according to paragraph [0044], wherein $R_{29}$ is —H.

In another example, the compound is according to paragraph [0045], wherein $R_{30}$ is —H.

In another example, the compound is according to paragraph [0045], wherein $R_{30}$ is optionally substituted alkyl.

In another example, the compound is according to paragraph [0045], wherein $R_{30}$ is —C(O)$R_{35}$.

In another example, the compound is according to paragraph [0045], wherein $R_{30}$ is —C(O)$NR_{35}R_{35a}$.

In another example, the compound is according to paragraph [0046], wherein $R_{31}$ is —H.

In another example, the compound is according to paragraph [0050], wherein $R_{32}$ is —H.

In another example, the compound is according to paragraph [0050], wherein $R_{32}$ is —C(O)$R_{35}$.

In another example, the compound is according to paragraph [0050], wherein $R_{29}$, $R_{30}$, $R_{31}$, and $R_{32}$ are —H.

In another example, the compound is according to paragraph [0051], wherein $R_{23}$ is optionally substituted alkyl.

In another example, the compound is according to paragraph [0051], wherein $R_{23}$ is halogen, preferably F, Cl, or Br, and more preferably Br.

In another example, the compound is according to paragraph [0051], wherein $R_{23}$ is —H.

In another example, the compound is according to paragraph [0051], wherein m is 2.

In another example, the compound is according to paragraph [0051], wherein m is 3.

In another example, the compound is according to paragraph [0051], wherein $R_{33}$ is —H.

In another example, the compound is according to paragraph [0051], wherein $R_{33}$ is halogen.

In another example, the compound is according to paragraph [0051], wherein $R_{33}$ is optionally substituted alkyl.

In another example, the compound is according to paragraph [0051], wherein $R_{33}$ is —$NR_{35}R_{35a}$.

In another example, the compound is according to paragraph [0051], wherein $R_{33}$ is —C(O)$R_{35}$.

In another example, the compound is according to paragraph [0051], wherein $R_{33}$ is trihalomethyl.

In embodiment B, the present invention also comprises a compound for modulating kinase activity, particularly p70S6 and/or Akt kinase activity according to Formula II,

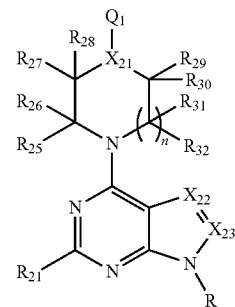

II or a pharmaceutically acceptable salt, hydrate, or prodrug thereof, wherein, $X_{21}$ is N or $CR_{22}$;

$X_{22}$ is N or $CR_{23}$;

$X_{23}$ is N or $CR_{24}$, but when $X_{22}$ is N then $X_{23}$ is $CR_{24}$;

each of $R_{21}$, $R_{22}$, $R_{23}$, $R_{24}$, $R_{25}$, $R_{26}$, $R_{27}$, $R_{28}$, $R_{29}$ and $R_{30}$ and each of $R_{31}$, $R_{32}$ and $R_{33}$ is independently selected from —H, halogen, trihalomethyl, —CN, —NO$_2$, —$NR_{35}R_{35a}$, —S(O)$_{0-2}R_{35}$, —SO$_2NR_{35}R_{35a}$, —CO$_2R_{35}$, —C(O)$NR_{35}R_{35a}$, —N($R_{35}$)SO$_2R_{35}$, —N($R_{35}$)C(O)$R_{35}$, —N($R_{35}$)CO$_2R_{35}$, —OR$_{35}$, —C(O)$R_{35}$, optionally substituted lower alkyl, optionally substituted aryl, optionally substituted heterocyclyl, optionally substituted heterocyclylalkyl, and optionally substituted arylalkyl;

R is selected from —H, halogen, trihalomethyl, —S(O)$_{0-2}R_{35}$, —SO$_2NR_{35}R_{35a}$, —CO$_2R_{35}$, —C(O)$NR_{35}R_{35a}$, —OR$_{35}$, —C(O)$R_{35}$, optionally substituted lower alkyl, optionally substituted aryl, optionally substituted heterocyclyl, optionally substituted heterocyclylalkyl, and optionally substituted arylalkyl; or two of $R_{25}$, $R_{26}$, $R_{27}$, $R_{28}$, $R_{29}$, $R_{30}$, $R_{31}$ or $R_{32}$, together with the atom or respective atoms to which they are attached, combine to form an optionally substituted spirocyclic ring system, optionally substituted fused ring system, and optionally substituted saturated bridged ring system;

each $R_{35}$ and $R_{35a}$ is independently selected from —H, optionally substituted lower alkyl, optionally substituted lower alkoxy, optionally substituted aryl, optionally substituted lower arylalkyl, optionally substituted lower aryl alkoxy, optionally substituted heterocyclyl, and optionally substituted lower heterocyclylalkyl; or $R_{35}$ and $R_{35a}$, together with the atom or respective atoms to which they are attached, combine to form an optionally substituted five- to seven-membered heterocyclyl;

$Q_1$ optionally substituted heterocyclyl;

n is an integer from 1 to 2; and with the provisos that when $X_{22}$ is $CR_{23}$ and $X_{23}$ is N then R is not optionally substituted aryl, aralkyl or heteroaryl, and that when $X_{22}$ is N and $X_{23}$ is $CR_{24}$ then R is not optional substituted aryl or heteroaryl and $R_{21}$ is not —$NR_{35}R_{35a}$, and that when $X_{22}$ is $CR_{23}$ and $X_{23}$ is $CR_{24}$ then $R_{21}$ is not optionally substituted aryl and $X_{21}$ is N, and that compounds with CAS Registration Nos. 749908-53-0, 749908-52-9, 749908-36-9, 749908-35-8, 749908-34-7, 537667-22-4, 252722-35-3, 215524-11-1, 215524-10-0, 215524-09-7, 95950-61-1, 92495-50-6, 24932-90-9, and 24932-77-2 are not included in Formula II.

In one example, the compound is according to Embodiment B, wherein n is 1.

In another example, the compound is according to paragraph [0078], wherein $X_{21}$ is N.

In another example, the compound is according to paragraph [0079], wherein $X_{23}$ is N.

In another example, the compound is according to paragraph [0080], wherein $X_{22}$ is $CR_{23}$.

In another example, the compound is according to paragraph [0081], wherein R is —H.

In another example, the compound is according to paragraph [0081], wherein R is optionally substituted alkyl.

In another example, the compound is according to paragraph [0082], wherein $R_{21}$ is —H.

In another example, the compound is according to paragraph [0082], wherein $R_{21}$ is optionally substituted alkyl.

In another example, the compound is according to paragraph [0084], wherein $R_{25}$ and $R_{26}$ are —H.

In another example, the compound is according to paragraph [0086], wherein $R_{27}$ and $R_{28}$ are —H.

In another example, the compound is according to paragraph [0087], wherein $R_{29}$ is —H.

In another example, the compound is according to paragraph [0088], wherein $R_{30}$ is —H.

In another example, the compound is according to paragraph [0088], wherein $R_{30}$ is optionally substituted alkyl.

In another example, the compound is according to paragraph [0088], wherein $R_{30}$ is —C(O)$R_{35}$.

In another example, the compound is according to paragraph [0088], wherein $R_{30}$ is —C(O)$NR_{35}R_{35a}$.

In another example, the compound is according to paragraph [0089], wherein $R_{31}$ is —H.

In another example, the compound is according to paragraph [0093], wherein $R_{32}$ is —H.

In another example, the compound is according to paragraph [0094], wherein $R_{32}$ is —C(O)$R_{35}$.

In another example, the compound is according to paragraph [0094], wherein $R_{29}$, $R_{30}$, $R_{31}$, and $R_{32}$ are —H.

In another example, the compound is according to paragraph [0094], wherein $R_{23}$ is optionally substituted alkyl.

In another example, the compound is according to paragraph [0094], wherein $R_{23}$ is halogen.

In another example, the compound is according to paragraph [0094], wherein $R_{23}$ is —H.

In another example, the compound is according to paragraph [0099], wherein $Q_1$ is a substituted heterocyclyl wherein the heterocyclyl has at least one nitrogen.

In another example, the compound is according to paragraph [0099], wherein $Q_1$ is a substituted heterocyclyl wherein the heterocyclyl has at least one oxygen.

In embodiment C, the present invention comprises molecules of embodiment A except that each $R_{33}$ is independently selected from:

(a) H, halo, —OH, $NO_2$—, CN;

(b) $C_1$-$C_6$— alkyl, optionally substituted with 1-5 moieties independently selected from halo, —OH, —$C_1$-$C_3$-alkoxy optionally substituted with 1-3 halo, or aryl;

(c) $C_1$-$C_8$-alkoxy optionally substituted with 1-3 moieties independently selected from halo and $C_1$-$C_3$-alkoxy;

(d) $R_{90}$—$C_0$-$C_3$-alkyl, wherein $R_{90}$ is $N(R_{73})(R_{74})$, heterocyclyl, aryl, or heteroaryl, each of which is optionally substituted with 1-3 moieties independently selected from halo, $C_1$-$C_3$-alkyl, $C_1$-$C_3$-alkoxy, aryl, and heteroaryl; or $R_{90}$ is $R_{91}$-aryl optionally substituted with 1-3 halo;

(e) $R_{95}$—$C_1$-$C_3$-alkoxy, wherein $R_{95}$ is $N(R_{73})(R_{74})$, heterocyclyl, aryl, or heteroaryl, each of which is optionally substituted with 1-3 moieties independently selected from halo, $C_1$-$C_3$-alkyl, aryl, and heteroaryl;

(f) $R_{80}$—$C_1$-$C_3$-alkyl-$(Z)_s$—$C_0$-$C_3$-alkyl, wherein $R_{80}$ is $N(R_{75})(R_{76})$— or aryl optionally substituted with $C_1$-$C_3$-alkyl;

(g) $R_{81}$—$C_0$-$C_6$-alkyl-$(Z)_s$—CO—, wherein $R_{81}$ is H, $C_1$-$C_6$-alkyl optionally substituted with 1-3 halo, $C_1$-$C_6$-alkyloxy, $N(R_{70})(R_{71})$—, heteroaryl, or aryl optionally substituted with 1-3 groups independently selected form halo and $C_1$-$C_3$-alkyl;

(h) $N(R_{73})(R_{74})$—C(O)—$C_0$-$C_3$-alkoxy;

(i) trimethylsilyl-$C_1$-$C_3$-alkyl; or (j) $C_1$-$C_3$-alkylS(O)$_2$—;

and wherein $R_{70}$ and $R_{71}$ are independently H, $C_1$-$C_3$-alkyl, or $C_1$-$C_3$-alkoxy, or $R_{70}$ and $R_{71}$ together with the nitrogen to which they are attached form a heterocyclyl optionally substituted with 1-3 $C_1$-$C_6$-alkyl, provided two oxygen atoms are not adjacent;

$R_{72}$ is H or $C_1$-$C_6$-alkyl;

$R_{73}$ and $R_{74}$ are independently H or $C_1$-$C_6$-alkyl;

$R_{75}$ and $R_{76}$ are independently H or $C_1$-$C_6$-alkyl or, together with the nitrogen to which they are attached, form a 5- or 6-membered heterocyclyl optionally substituted with $C_1$-$C_3$-alkyl;

$R_{91}$ is $N(R_{75})(R_{76})$—$C_1$-$C_3$-alkyl-Z—;

Z is —$NR_{72}$— or —O—; and s is 0 or 1.

Table A gives particular examples of $R_{33}$ of groups (b)-(j) (paragraphs [0104]-[0112]), above:

TABLE A

| | |
|---|---|
| (b) | methyl, trifluoromethyl, ethyl, propyl, 2,2-dimethylbutyl, 1,1-difluorobutyl, trifluoromethyl, hydroxymethyl, phenylethyl, styryl, ethynyl, 3,3-dimethylbut-1-ynyl, difluoromethoxymethyl, ethoxymethyl, 3-hydroxypropyl, 1-hydroxybutyl, (2,2,2-trifluoroethoxy)methyl, 4,4,4-trifluoro-1,1-dimethoxybutyl |
| (c) | methoxy, ethoxy, propoxy, isopropoxy, butoxy, isobutoxy, cyclopropylmethoxy, cyclobutylmethoxy, cyclopentylmethoxy, cyclohexylmethoxy, 2-methoxyethoxy, 4-methylbutoxy, 2-ethylbutoxy, 2,2-dimethylpropoxy, 2-fluoro-2-methylpropoxy, difluromethoxy, 2,3-difluoro-2-(fluoromethyl)propoxy, (2,2-difluorocyclopropyl)methoxy, ethoxymethoxy, 3,3,3-trifluroethoxy, 3,3,3-trifluropropoxy |
| (d) | phenyl, 3,4-difluorphenyl, 3-oxo-3,4-dihydro-2H-benzo[b][1,4]oxazin-6-yl, furan-2-yl, thiazol-2-yl, morpholino, pyrrolidinylpropyl, 3-methyl-1,2,4-oxadiazol-5-yl, 3-phenyl-1,2,4-oxadiazol-5-yl, diethylamino, isopentylamino, 2-(2-(pyrrolidin-1-yl)ethoxy)phenyl, 3-(2-(pyrrolidin-1-yl)ethoxy)phenyl, 4-fluoro-2-(2-(pyrrolidin-1-yl)ethoxy)phenyl, 2-(3-(dimethylamino)propoxy)phenyl, 2-(2-morpholinoethoxy)phenyl, 2-(2-(2,5-dioxopyrrolidin-1-yl)ethoxy)phenyl, 3-fluoro-2-(2-(pyrrolidin-1-yl)ethoxy)phenyl |
| (e) | morpholino-propoxy, piperidinyl-propoxy, (tetrahydrofuran-2-yl)methoxy |

TABLE A-continued

| | |
|---|---|
| (f) | (2-(dimethylamino)ethylamino)methyl, 2-(dimethylamino)ethoxy, 2-(diethylamino)ethoxy, 3-(diethylamino)propyl, 3-(diethylamino)propoxy, 3-(dimethylamino)propoxy, 3-(dimethylamino)-prop-1-enyl, 2-(dimethylamino)ethylamino, 2-(diethylamino)ethylamino, 2-(pyrrolidin-1-yl)ethoxy, 3-(pyrrolidin-1-yl)propyl, 3-(pyrrolidin-1-yl)propoxy, 2-(pyrrolidin-1-yl)ethylamino, 2-(piperidin-1-yl)ethoxy, 3-(piperidin-1-yl)propyl, 3-(piperidin-1-yl)propoxy, 2-(1-methylpiperidin-4-yl)ethoxy, (1-methylpiperidin-4-yl)methoxy, (1-methylpiperidin-4-yl)ethoxy, 2-morpholinoethoxy, 3-morpholinopropoxy, 3-morpholinopropyl, 3-(4-methylpiperazin-1-yl)propyl, 3-(4-methylpiperazin-1-yl)propoxy, 3-(4-ethylpiperazin-1-yl)propoxy, 2-(4-methylpiperazin-1-yl)ethoxy, 2-(4-ethylpiperazin-1-yl)ethoxy, phenylmethoxy, 3-methylbenzyloxy, 2-(isopropyl(methyl)amino)ethylamino |
| (g) | 2-(dimethylamino)ethylcarbamoyl, N-methylpiperizinylcarbonyl, (2-(dimethylamino)ethoxy)carbonyl, methylcarbamoyl, ethylcarbamoyl, isopropylcarbamoyl, isopropyl(methyl)carbamoyl, isobutylcarbamoyl, t-butylcarbamoyl, phenylcarbamoyl, benyzlcarbamoyl, 2-chlorophenylcarbamoyl, methoxycarbonyl, pyridin-3-ylcarbamoyl, 4,4,4-trifluorobutanoyl, dimethylcarbamoyl, pyrrolidine-1-carbonyl, 2-(dimethylamino)ethylcarbamoyl, acetyl, propionyl, butyryl, 4,4,4-trifluorobutanoyl, pentoyl, benzoyl, cyclopropylmethoxycarbamoyl, cyclopropanecarbonyl |
| (h) | 2-(ethylamino)-2-oxoethoxy, 2-(cyclopropylamino)-2-oxoethoxy |
| (i) | 2-(trimethylsilyl)ethyl |
| (j) | methylsulfonyl, ethylsulfonyl |

In some examples of Embodiments A-C, each of $R_{25}$-$R_{32}$ is H.

In some examples according to paragraph [0122], $R_{21}$ is H.

In some examples according to paragraph [0122], $X_{21}$ and $X_{23}$ are N.

In some examples according to paragraph [0122] $X_{22}$ is $CR_{23}$ and $R_{23}$ is lower alkyl or halo, preferably Br.

In some examples of embodiments A and C according to paragraph [0122], m is 3. Preferred $R_{33}$ in these examples includes lower alkyl (preferably methyl), $R_{80}$—$C_1$-$C_3$-alkyl-$(Z)_s$—$C_0$-$C_3$-alkyl (preferably wherein $R_{80}$ is heterocyclyl such as pyrrolidinyl; the $C_1$-$C_3$-alkyl is ethyl; s is 1; Z is NH; and $C_0$-$C_3$-alkyl is $C_0$, i.e., a bond), and $R_{81}$—$C_0$-$C_6$-alkyl-$(Z)_S$—CO— (preferably wherein: $R_{81}$ is $C_1$-$C_6$-alkyl optionally substituted with 1-3 halo, more preferably wherein the $C_1$-$C_6$-alkyl optionally substituted with 1-3 halo is trihalopropyl (preferably trifluoropropyl), and even more preferably 3,3,3-trifluoropropyl); the $C_0$-$C_6$-alkyl is $C_0$ (i.e., a bond); and s is 0). Preferably the $R_{80}$—$C_1$-$C_3$-alkyl-$(Z)_s$—$C_0$-$C_3$-alkyl and the $R_{81}$—$C_0$-$C_6$-alkyl-$(Z)_s$—CO— groups are meta to each other and to $X_{21}$.

Another preferred embodiment includes Embodiments A and C with $R_2$, according to paragraph [0123], $R_{25}$-$R_{32}$ according to paragraph [0122], $X_{21}$ and $X_{23}$ are according to paragraph [0124], $X_{22}$ according to paragraph [0125] and m and $R_{33}$ according to paragraph [0126].

In other examples of embodiments A-C, $R_{25}$-$R_{28}$ and $R_{30}$-$R_{32}$ are H and $R_{29}$ is other than H. In such embodiments the annular carbon atom to which $R_{29}$ is bonded is chiral. In some examples of this embodiment, that chiral center is enantiomerically enriched (greater than 60%, 70%, 80%, 90%, or 95%) or pure. Examples of $R_{29}$ when the annular carbon is chiral in this embodiment include methyl and hydroxymethyl.

In a particular embodiment of Embodiment C, when $X_{23}$ is $CR_{24}$, m is 1-5, and at least one $R_{33}$ is selected from:

(i) $C_1$-$C_6$— alkyl 1-5 moieties independently selected from —OH and —$C_1$-$C_3$-alkoxy optionally substituted with 1-3 halo, or aryl;

(ii) $C_1$-$C_8$-alkoxy optionally substituted with 1-3 $C_1$-$C_3$-alkoxy moieties;

(iii) $R_{96}$—$C_0$-$C_3$-alkyl, wherein $R_{90}$ is $N(R_{73})(R_{74})$ if the alkyl moiety is $C_1$-$C_3$-alkyl, heterocyclyl, aryl, or heteroaryl, each of which is optionally substituted with 1-3 moieties independently selected from halo, $C_1$-$C_3$-alkyl, $C_1$-$C_3$-alkoxy, aryl, and heteroaryl; or $R_{90}$ is $R_{91}$-aryl optionally substituted with 1-3 halo;

(iv) $R_{95}$—$C_1$-$C_3$-alkoxy, wherein $R_{95}$ is $N(R_{73})(R_{74})$, heterocyclyl, aryl, or heteroaryl, each of which is optionally substituted with 1-3 moieties independently selected from halo, $C_1$-$C_3$-alkyl, aryl, and heteroaryl;

(v) $R_{80}$—$C_1$-$C_3$-alkyl-$(Z)_s$—$C_0$-$C_3$-alkyl, wherein $R_{80}$ is $N(R_{75})(R_{76})$— or aryl optionally substituted with $C_1$-$C_3$-alkyl;

(vi) $R_{81}$—$C_0$-$C_6$-alkyl-$(Z)_s$—CO—, wherein $R_{81}$ is H, $C_1$-$C_6$-alkyl optionally substituted with 1-3 halo, $C_1$-$C_6$-alkyloxy, $N(R_{70})(R_{71})$—, heteroaryl, or aryl optionally substituted with 1-3 groups independently selected form halo and $C_1$-$C_3$-alkyl;

(vii) $N(R_{73})(R_{74})$—C(O)—$C_0$-$C_3$-alkoxy;

(viii) trimethylsilyl-$C_1$-$C_3$-alkyl; or (ix) $C_1$-$C_3$-alkylS(O)$_2$—;

In each of the aspects, examples, and embodiments of the compounds of the invention, R is preferably H or optionally substituted $C_1$-$C_6$-alkyl, more preferably H or unsubstituted $C_1$-$C_6$-alkyl, and even more preferably H. In one particular embodiment of embodiments A or C, $X_{22}$ is $CR_{23}$, $X_{23}$ is $CR_{24}$, and $R_{21}$ is halogen In another particular embodiment of embodiments A or C, $X_{22}$ is N, $X_{23}$ is $CR_{24}$, and $R_{21}$ is halogen In yet another particular embodiment of embodiments A or C, $X_{22}$ is $CR_{23}$, $X_{23}$ is $CR_{24}$, $X_{21}$ is nitrogen $R_{21}$ is hydrogen, m is 1, 2, 3, 4, or 5 and at least one $R_{33}$ is not hydrogen.

In still another particular embodiment of embodiments A or C, $X_{22}$ is N, $X_{23}$ is $CR_{24}$, $X_{21}$ is nitrogen and $R_{21}$ is hydrogen, then m is 1, 2, 3, 4, or 5 and at least one $R_{33}$ is not hydrogen.

In yet still another particular embodiment of embodiments A or C, $X_{22}$ is N, $X_{23}$ is $CR_{24}$, $X_{21}$ is N, n is 1, $R_{25}$-$R_{32}$ are the same and are H, or only one of $R_{25}$-$R_{32}$ is alkyl, and R is H or alkyl, then $R_{24}$ is H or alkyl.

In another particular embodiment of embodiments A or C, $X_{22}$ is $CR_{23}$, $X_{23}$ is $CR_{24}$, $X_{21}$ is N, n is 1, $R_{25}$-$R_{32}$ are the same and are H, or only one of $R_{25}$-$R_{32}$ is alkyl, R is H or alkyl, and $R_{24}$ is H or alkyl.

In one particular embodiment of embodiment C, $Q_1$ is not pyrid-2-yl, i.e., when $Q_1$ is pyridyl it is not attached to the $X_2$, group at position ortho to the pyridyl nitrogen.

In another particular embodiment of embodiment C, $X_{22}$ is $CR_{23}$, $X_{23}$ is $CR_{24}$, and $R_{21}$ is halogen In still another particular embodiment of embodiment C, $X_{22}$ is N, $X_{23}$ is $CR_{24}$, and $R_{21}$ is halogen In yet another particular embodiment of embodiment C, $X_{22}$ is $CR_{23}$, $X_{23}$ is $CR_{24}$, $X_{21}$ is nitrogen, $R_{21}$ is hydrogen, m is 1, 2, 3, 4, or 5 and at least one $R_{33}$ is not hydrogen In yet still another particular embodiment of embodiment C, $X_{22}$ is N, $X_{23}$ is $CR_{24}$, $X_{21}$ is nitrogen, $R_{21}$ is hydrogen, m is 1, 2, 3, 4, or 5 and at least one $R_{33}$ is not hydrogen In another particular embodiment of embodiment C, $Q_1$ is not pyrimidyl or triazinyl.

In one example, the compound is according to paragraphs [0022]-[0151], wherein the compound is a pharmaceutically acceptable salt.

In one example, the compound is according to paragraphs [0022]-[0151], wherein the compound is a prodrug.

In another example, the compound is according to any one of paragraphs [0022]-[0151], selected from Tables 1 or 2 below.

Another aspect of the invention is a composition comprising the compound according to any one of paragraphs [0022]-[0154] and at least one pharmaceutically acceptable carrier or excipient.

Another aspect of the invention is a metabolite of the compound according to any one of paragraphs [0022]-[0154].

Another aspect of the invention is a method of modulating the in vivo activity of a kinase, the method comprising administering to a subject an effective amount of a composition comprising at least one of the compound according to any of paragraphs [0022]-[0154} and the pharmaceutical composition according to paragraph [0155] and the CAS Registration Nos. 749908-53-0, 749908-52-9, 749908-36-9, 749908-35-8, 749908-34-7, 732271-60-2, 565169-26-8, 537667-22-4, 537667-19-9, 537667-18-8, 537667-17-7, 537667-16-6, 537667-15-5, 537667-14-4, 537667-13-3, 537667-12-2, 537667-11-1, 252722-59-1, 252722-35-3, 252722-34-2, 215524-11-1, 215524-10-0, 215524-09-7, 95950-61-1, 92495-50-6, 47281-43-6, 37425-49-3, 37425-48-2, 24932-90-9, 24932-89-6, 24932-78-3 and 24932-77-2 and also compounds of Formulas I and II when $X_{22}$ is $CR_{23}$ and $X_{23}$ is N then R is optionally substituted aryl, aralkyl or heteroaryl, and when $X_{22}$ is N and $X_{23}$ is $CR_{24}$ then $R_{21}$ is —$NR_{35}R_{35}$, and when $X_{22}$ is $CR_{23}$ and $X_{23}$ is $CR_{24}$ then $R_{21}$ is optionally substituted aryl and $X_{21}$ is N.

Another aspect of the invention is the method according to paragraph [0157], wherein the kinase is p70S6 and/or Akt.

Another aspect of the invention is the method according to paragraph [0158], wherein modulating the in vivo activity of p70S6K and/or AktK comprises inhibition of p70S6K and/or AktK.

Another aspect of the invention is a method of treating and/or inhibiting diseases or disorders associated with uncontrolled, abnormal, and/or unwanted cellular activities, the method comprising administering, to a mammal in need thereof, a therapeutically effective amount of a composition comprising at least one of the compound according to any of paragraphs [0022]-[0154] and the pharmaceutical composition according to paragraph [0155] and the CAS Registration Nos. 749908-53-0, 749908-52-9, 749908-36-9, 749908-35-8, 749908-34-7, 732271-60-2, 565169-26-8, 537667-22-4, 537667-19-9, 537667-18-8, 537667-17-7, 537667-16-6, 537667-15-5, 537667-14-4, 537667-13-3, 537667-12-2, 537667-11-1, 252722-59-1, 252722-35-3, 252722-34-2, 215524-11-1, 215524-10-0, 215524-09-7, 95950-61-1, 92495-50-6, 47281-43-6, 37425-49-3, 37425-48-2, 24932-90-9, 24932-89-6, 24932-78-3 and 24932-77-2 and also compounds of Formulas I and II when $X_{22}$ is $CR_{23}$ and $X_{23}$ is N then R is optionally substituted aryl, aralkyl or heteroaryl, and when $X_{22}$ is N and $X_{23}$ is $CR_{24}$ then $R_{21}$ is —$NR_{35}R_{35}$, and when $X_{22}$ is $CR_{23}$ and $X_{23}$ is $CR_{24}$ then $R_{21}$ is optionally substituted aryl and $X_{21}$ is N.

Another aspect of the invention is a method of screening for modulator of a p70S6K and/or AktK, the method comprising combining either a composition comprising at least one of the compound according to any of paragraphs [0022]-[0154] and the pharmaceutical composition according to paragraph [0155], and the CAS Registration Nos. 749908-53-0, 749908-52-9, 749908-36-9, 749908-35-8, 749908-34-7, 732271-60-2, 565169-26-8, 537667-22-4, 537667-19-9, 537667-18-8, 537667-17-7, 537667-16-6, 537667-15-5, 537667-14-4, 537667-13-3, 537667-12-2, 537667-11-1, 252722-59-1, 252722-35-3, 252722-34-2, 215524-11-1, 215524-10-0, 215524-09-7, 95950-61-1, 92495-50-6, 47281-43-6, 37425-49-3, 37425-48-2, 24932-90-9, 24932-89-6, 24932-78-3 and 24932-77-2 and also compounds of Formulas I and II when $X_{22}$ is $CR_{23}$ and $X_{23}$ is N then R is optionally substituted aryl, aralkyl or heteroaryl, and when $X_{22}$ is N and $X_{23}$ is $CR_{24}$ then $R_{21}$ is —$NR_{35}R_{35}$, and when $X_{22}$ is $CR_{23}$ and $X_{23}$ is $CR_{24}$ then $R_{21}$ is optionally substituted aryl and $X_{21}$ is N, and at least one candidate agent and determining the effect of the candidate agent on the activity of said kinase.

Another aspect of the invention is a method of inhibiting proliferative activity in a cell or a plurality of cells, the method comprising administering an effective amount of at least one of the compound according to any of paragraphs [0022]-[0154] and the pharmaceutical composition according to paragraph [0155], and the CAS Registration Nos. 749908-53-0, 749908-52-9, 749908-36-9, 749908-35-8, 749908-34-7, 732271-60-2, 565169-26-8, 537667-22-4, 537667-19-9, 537667-18-8, 537667-17-7, 537667-16-6, 537667-15-5, 537667-14-4, 537667-13-3, 537667-12-2, 537667-11-1, 252722-59-1, 252722-35-3, 252722-34-2, 215524-11-1, 215524-10-0, 215524-09-7, 95950-61-1, 92495-50-6, 47281-43-6, 37425-49-3, 37425-48-2, 24932-90-9, 24932-89-6, 24932-78-3 and 24932-77-2 and also compounds of Formulas I and II when $X_{22}$ is $CR_{23}$ and $X_{23}$ is N then R is optionally substituted aryl, aralkyl or heteroaryl, and when $X_{22}$ is N and $X_{23}$ is $CR_{24}$ then $R_{21}$ is —$NR_{35}R_{35}$, and when $X_{22}$ is $CR_{23}$ and $X_{23}$ is $CR_{24}$ then $R_{21}$ is optionally substituted aryl and $X_{21}$ is N, to said cell or plurality of cells.

Another aspect of the invention is a method of preparing the compounds according to any of paragraphs [0022]-[0154].

DEFINITIONS

As used in the present specification, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond. The symbol "⌇" refers to a group on a double-bond as occupying either position on the terminus of a double bond to which the symbol is attached; that is, the geometry, E- or Z—, of the double bond is ambiguous. When a group is depicted removed from its parent formula, the "~" symbol will be used at the end of the bond which was theoretically cleaved in order to separate the group from its parent structural formula.

Chemical formulae use descriptors such as "$R^1$" accompanied by a list of formulae or verbage describing the scope of what is meant by the descriptor. A subsequent descriptor such as "$R^{1a}$" is used to describe some subset of the scope of $R^1$, and "$R^{1b}$", is used to describe another subset of the scope of $R^1$, and so on. In such subsequent cases, all other formulae containing simply "$R^1$" are meant to include the entire scope of the descriptor.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

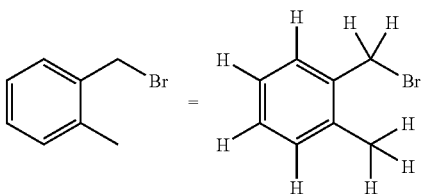

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

If a group "R" is depicted as "floating" on a ring system, as for example in the formula:

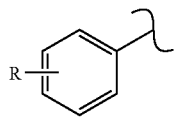

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

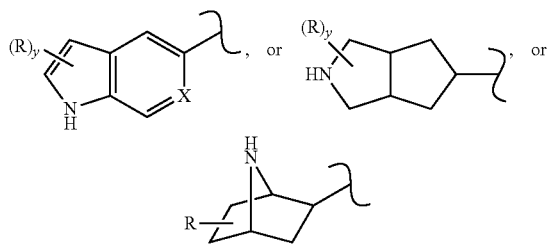

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

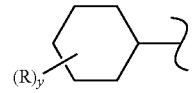

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

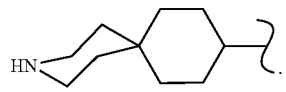

"Alkyl" is intended to include saturated and non-saturated (but not aromatic) linear, branched, and cyclic hydrocarbon structures and combinations thereof, inclusively. For example, "$C_8$ alkyl" may refer to an n-octyl, iso-octyl, cyclohexylethyl, 3-octenyl, -octa-2,4-dienyl, cyclooctane, cyclooctene, and the like. Lower alkyl refers to alkyl groups of from one to six carbon atoms. Examples of lower alkyl groups include methyl, ethyl, propyl, propenyl, isopropyl, butyl, s-butyl, t-butyl, isobutyl, pentyl, hexyl, hex-3-ynyl, and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus, when an alkyl residue having a specific number of carbons is named, all geometric isomers having that number of carbons are intended to be encompassed; thus, for example, either "butyl" or "$C_4$alkyl" is meant to include n-butyl, sec-butyl, isobutyl, t-butyl, isobutenyl and but-2-yne radicals; and for example, "propyl" or "$C_3$alkyl" each include n-propyl, propenyl, and isopropyl. Otherwise, if alkenyl and/or alkynyl descriptors are used in a particular definition of a group, for example "$C_4$alkyl" along with "$C_4$alkenyl," then $C_4$alkenyl geometric isomers are not meant to be included in "$C_4$alkyl," but other 4-carbon isomers are, for example $C_4$alkynyl. For example, a more general description, intending to encompass the invention as a whole may describe a particular group as "$C_{1-8}$alkyl" while a preferred species may describe the same group as including, "$C_{1-8}$alkyl," "$C_{1-6}$alkenyl" and "$C_{1-5}$alkynyl." As used herein, $C_0$ is a bond. So, for example $NH_2$—$C_0$-$C_3$-alkyl includes amino as well as aminomethyl, 2-aminoethyl, 1 aminoethyl, etc.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —$NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, and furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two non-hydrogen groups attached thereto. For a more specific example, "phenylene" refers to a divalent phenyl ring radical. A phenylene, thus may have more than two groups attached, but is defined by a minimum of two non-hydrogen groups attached thereto. The terms "ortho-arylene," "meta-arylene" or "para-arylene" refer to geometrical isomers of a particular arylene wherein, two groups attached to an aryl as depicted in a formula are situated in an ortho, meta or para geometrical relationship about the aryl, respectively.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as aryl $C_{1-6}$alkyl.

"Exo-alkenyl" refers to a double bond that emanates from an annular carbon, and is not within the ring system, for example the double bond depicted in the formula below.

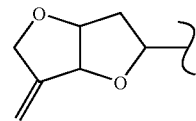

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto. For the purposes of this application, the term "ortho-heteroarylene" refers to a geometrical isomer of a particular heteroarylene wherein two groups attached to a heteroaryl as depicted in a formula are situated on contiguous atoms of the heteroaryl.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2,5-dioxopyrrolidin-1-yl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl C$_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted aryl C$_{1-8}$alkyl," optional substitution may occur on both the "C$_{1-8}$alkyl" portion and the "aryl" portion of the molecule; and for example, optionally substituted alkyl includes optionally substituted cycloalkyl groups, which in turn are defined as including optionally substituted alkyl groups. A list of exemplary optional substitutions is included below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

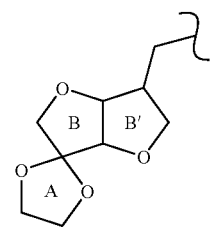

"Substituted" alkyl, aryl, and heterocyclyl, refer respectively to alkyl, aryl, and heterocyclyl, wherein one or more (for example up to about five, in another example, up to about three) hydrogen atoms are replaced by a substituent. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, haloalkoxy, aryloxy, heteroaryloxy, amino, acylamino, alkylcarbamoyl, arylcarbamoyl, aminoalkyl, acyl, carboxy, hydroxyalkyl, alkanesulfonyl, arenesulfonyl, sulfonamido, alkanesulfonamido, arenesulfonamido, aralkylsulfonamido, alkylcarbonyl, acyloxy, cyano, alkylthio, ureido, and ureidoalkyl groups. Preferred substituents, which are themselves not further substituted (unless expressly stated otherwise) are:

(a) halo, cyano, oxo, alkyl, alkoxy, alkylthio, haloalkoxy, aminoalkyl, aminoalkoxy, carboxy, formyl, nitro, amino, amidino, carbamoyl, guanidino, $C_3$-$C_7$ heterocycle, heterocyclylalkyl, heterocyclylcarbonyl, hydroxyalkyl, alkoxyalkyl, (b) $C_1$-$C_5$ alkyl or alkenyl or arylalkyl imino, carbamoyl, carbamate, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, heteroarylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, heteroaryloxy, arylalkyl ether, $C_3$-$C_7$ heterocyclylalkylether, aryl, aryl fused to a cycloalkyl or heterocycle or another aryl ring, $C_3$-$C_7$ heterocycle, heteroaryl, arylcarbamoyl, or any of these rings fused or spiro-fused to a cycloalkyl, heterocyclyl, or aryl, wherein any of the foregoing which are additionally substitutable is further optionally substituted with one more moieties listed in (a), above; and (c) —(CH$_2$)$_s$—NR$_{35}$R$_{35a}$, wherein s is from 0 (in which case the nitrogen is directly bonded to the moiety that is substituted) to 6, and R$_{35}$ and R$_{35a}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or R$_{35}$ and R$_{35a}$ taken together with the N to which they are attached form a heterocyclyl or heteroaryl, each of which is optionally substituted with from 1 to 3 substituents from (a), above.

In addition, substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tri-cyclic fused ring system. For example, an optionally substituted phenyl includes, but not limited to, the following:

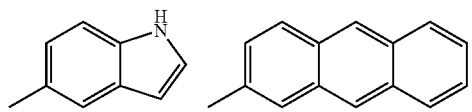

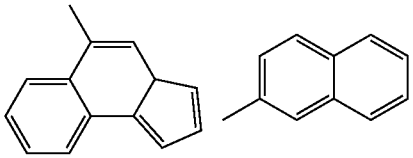

Preferred substituents on cyclic moieties (i.e., cycloalkyl, heterocyclyl, aryl, heteroaryl) also include groups of the formula —K1-N(H)(R36), wherein K$_1$ is a chemical bond or $C_1$-$C_4$ alkylene;
R$_{36}$ is selected from the group consisting of Z' and -Ak$_2$-Z', wherein
Ak$_2$ is $C_1$-$C_4$ alkylene; and
Z' is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings.

Particularly preferred substituents on cyclic moieties (such as aryl, heteroaryl, cycloalkyl, heterocyclyl, or any of these rings fused to one or more aryl or heteroaryl rings, or to one or more saturated or partially unsaturated cycloalkyl or heterocyclic rings), include 1, 2, or 3 groups independently selected from the following:

a) alkoxy, cyano, amino, oxo, haloalkyl, halo, alkyl, R$_{35}$—C(O)—N(R$_{35}$)—, R$_{35}$—O—C(O)—N(R$_{35}$)—, R$_{35}$—NH—C(O)—N(R$_{35}$)—, R$_{35}$—NH—C(O)—O—, (R$_{35a}$)(R$_{35}$)N-alkyl-, (R$_{35a}$)(R$_{35}$)N-alkyl-O—, (R$_{35}$)(R$_{35a}$)N-alkenylene-N(R$_{35}$)—, N(R$_{35}$)-aryl-N(R$_{35}$)—C(O)-aryl-alkyl-N(R$_{35}$)—; wherein R$_{35}$ is cycloakyl, heterocyclyl-$C_1$-$C_6$ alkyl-, or alkyl;

b) aryl-$C_0$-$C_6$ alkyl-, heteroaryl-$C_0$-$C_6$ alkyl-, cycloalkyl-$C_0$-$C_6$ alkyl-, heterocyclyl-$C_0$-$C_6$ alkyl-, aryl-$C_0$-$C_6$ alkyl-N(R$_{35}$)—, aryl—C(O)—, heteroaryl-$C_0$-$C_6$ alkyl-N(R$_{35}$)—, heterocyclyl-$C_0$-$C_6$ alkyl-N(R$_{35}$)—, aryl-O—, heteroaryl-O—, aryl-S—, heteroaryl-S—, aryl-SO$_2$—, heteroaryl-SO$_2$, aryl—C(O)N(R$_{35}$)—, heteroaryl—C(O)N(R$_{35}$)—, heteroaryl-C(H)(SO$_2$-heteroaryl)-N(R$_{35}$)—; wherein R$_{35}$ and R$_{35a}$ are independently H or $C_1$-$C_6$ alkyl, or R$_{35}$ and R$_{35a}$ taken together with the N to which they are attached form a heterocyclyl or heteroaryl;

c) and wherein any of the rings described in paragraphs (a) and (b) immediately above are further optionally substituted with 1, 2, or 3 groups independently selected from alkyl, alkoxy, thioalkoxy, alkyl-SO$_2$—, amino, halo, cyano, haloalkyl, hydroxyalkyl, alkoxyalkoxyalkyl, COOH, alkanoyl, alkanoate, NO$_2$, hydroxy, haloalkoxy, (R$_{35a}$)(R$_{35}$)N—$C_0$-$C_6$ alkyl-, (R$_{35a}$)(R$_{35}$)N—$C_0$-$C_6$ alkyl-O—, (R$_{35a}$)(R$_{35}$)N—C(O)—, heteroaryl, alkyl—C(O)N(R$_{35}$)—, aryl-O—, (R$_{35a}$)(R$_{35}$)N—SO$_2$—, aryl, and (R$_{35a}$)(R$_{35}$)N-alkyl—C(O)N(R$_{35}$)—.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O$_2$)—H, —S(O$_2$)-(optionally substituted alkyl), —S(O$_2$)-optionally substituted aryl), —S(O$_2$)-(optionally substituted heterocyclyl), —S(O$_2$)-(optionally substituted alkoxy), —S(O$_2$)-optionally substituted aryloxy), and —S(O$_2$)-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Compounds were named using the nomenclature engine published by ACD/Labs of Toronto Canada—ACD/Name Batch 7.00 Release, Product v. 7.10, Build 15 Sep. 2003.

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —OCH$_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH$_2$—" is meant to mean not only "—OCH$_2$—" as drawn, but also "—CH$_2$O—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma; chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular p70S6- or Akt-4-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one of ordinary skill in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one of ordinary skill in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

CAS, a division of the American Chemical Society, is one of the world's leader in providing scientists online and web access to chemistry-related research data. CAS produces one of the world's largest and most comprehensive databases of chemical information, indexing abstracts, patents, articles from approximately 9,000 scientific journals, conference proceedings, and other documents pertinent to chemistry, life sciences and many other fields. Certain compounds are set forth in this application using a CAS Registration identifier. The structures of these compounds, as they correspond to the CAS Registration identifier, are set forth below:

749908-53-0

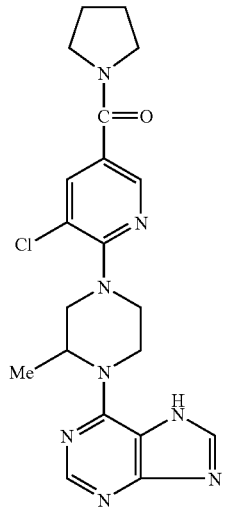

749908-52-9

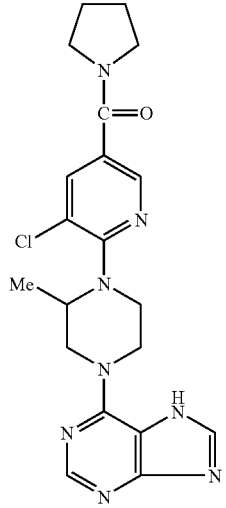

749908-36-9

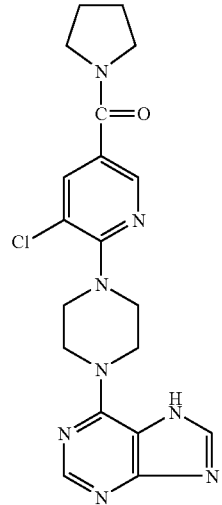

| | |
|---|---|
| 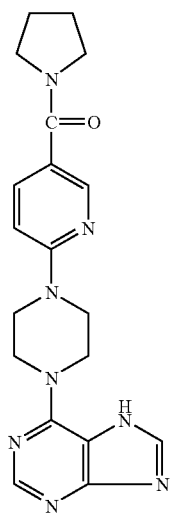 | 749908-35-8 |
| 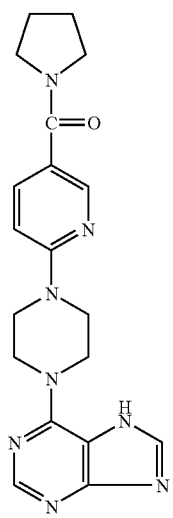 | 749908-34-7 |
| 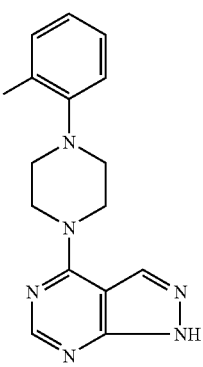 | 732271-60-2 |
| | |
|---|---|
| 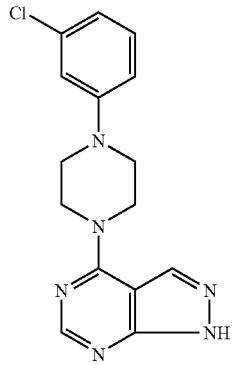 | 565169-26-8 |
| 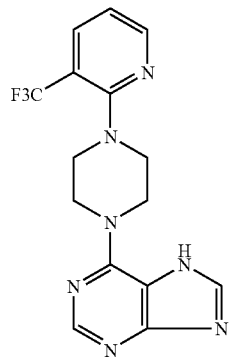 | 537667-22-4 |
| 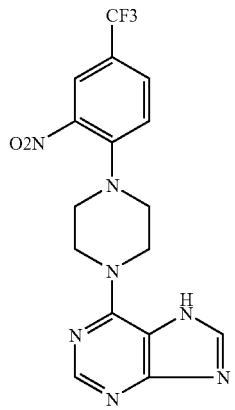 | 537667-19-9 |
| 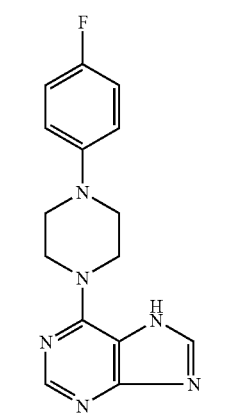 | 537667-18-8 |

-continued
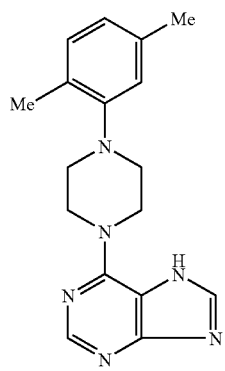
537667-17-7
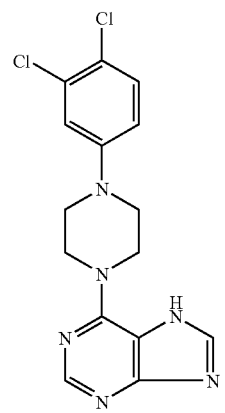
537667-16-6
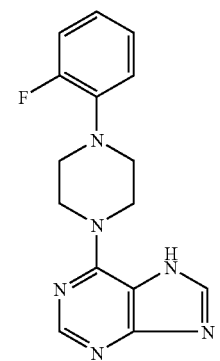
537667-15-5
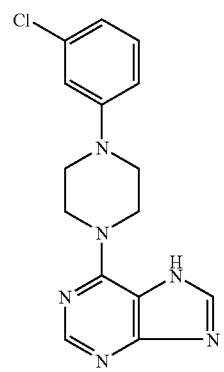
537667-14-4
-continued
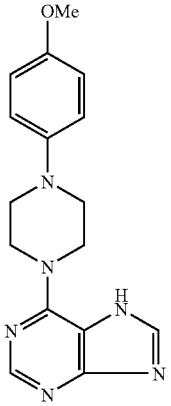
537667-13-3
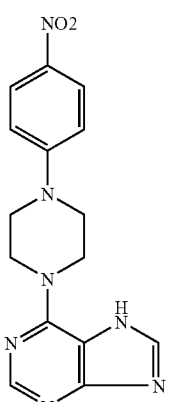
537667-12-2
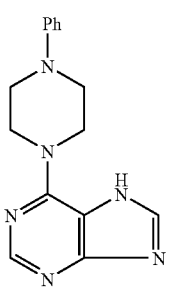
537667-11-1
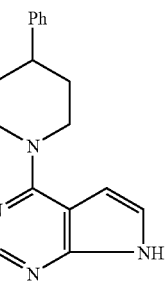
252722-59-1
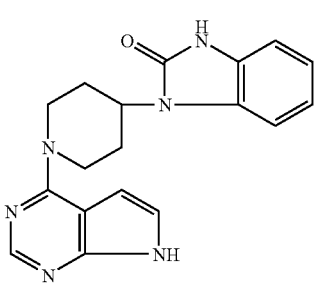
252722-35-3

252722-34-2
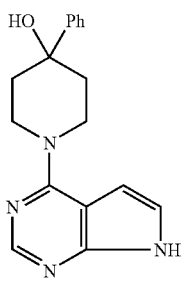
215524-11-1
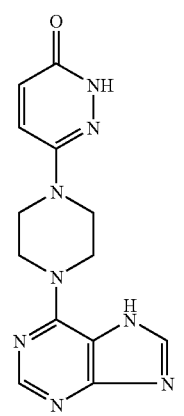
215524-10-0
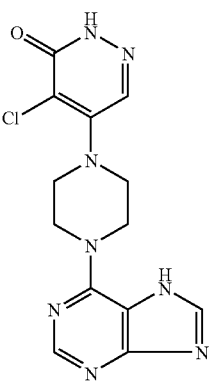
215524-09-7
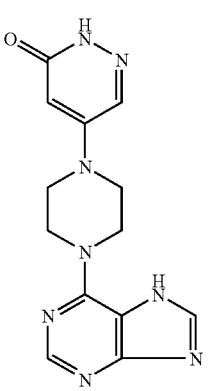
95950-61-1
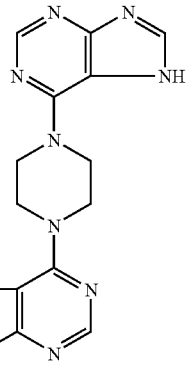
92495-50-6
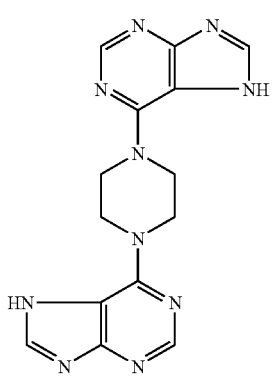
47281-43-6
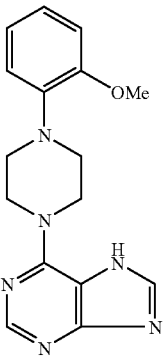
37425-49-3
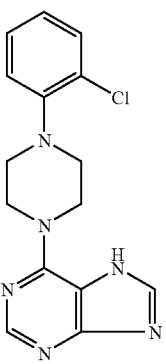

37425-48-2

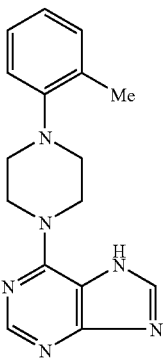

24932-90-9

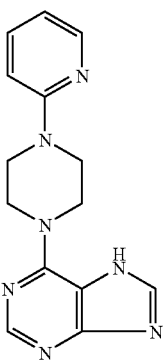

24932-89-6

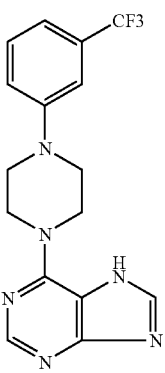

24932-78-3

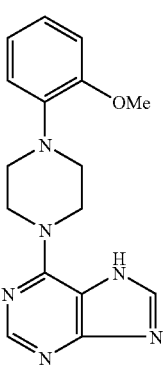

24932-77-2

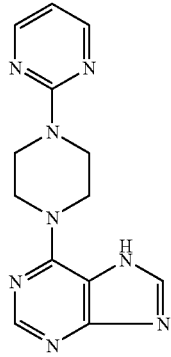

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a compound of the invention as the/an active agent, and, in addition, may include at least one other conventional pharmaceutical carrier or excipient, such as medicinal agents, pharmaceutical agents, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example p70S6 and/or Akt receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, p70S6K and/or AktK protein may be done in a number of ways. In one example, the candidate agent (the compound of the invention) is labeled, for example, with a fluorescent or radioactive moiety and binding determined directly. For example, thus may be done by attaching all or a portion of the p70S6K and/or AktK protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, p70S6K and/or AktK protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to p70S6K and/or AktK.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to p70S6K and/or AktK, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to p70S6K and/or AktK protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to p70S6K and/or AktK and thus is capable of binding to, and potentially modulating, the activity of the p70S6K and/or AktK. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to p70S6K and/or AktK with a higher affinity. Thus, if the candidate agent is labeled, the presence of the label on the support, coupled with a lack of competitor binding, may indicate the candidate agent is capable of binding to p70S6K and/or AktK.

It may be of value to identify the binding site of p70S6K and/or AktK. This can be done in a variety of ways. In one embodiment, once p70S6K and/or AktK has been identified as binding to the candidate agent, the p70S6K and/or AktK is fragmented or modified and the assays repeated to identify the necessary components for binding.

Modulation is tested by screening for candidate agents capable of modulating the activity of p70S6K and/or AktK comprising the steps of combining a candidate agent with p70S6K and/or AktK, as above, and determining an alteration in the biological activity of the p70S6K and/or AktK. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native p70S6K and/or AktK, but cannot bind to modified p70S6K and/or AktK.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, protein-ligand complexes, in particular p70S6K- and/or AktK-ligand complexes, and their corresponding x-ray structure coordinates can be used to reveal new structural information useful for understanding the biological activity of p70S6K and/or AktK's as described herein. As well, the key structural features of the aforementioned proteins, particularly, the shape of the ligand binding site, are useful in methods for designing or identifying selective modulators of p70S6K and/or AktK's and in solving the structures of other proteins with similar features. Ligands of such complexes may include compounds of the invention as described herein.

As well, one of ordinary skill in the art would appreciate that such suitable x-ray quality crystals can be used as part of a method of identifying a candidate agent capable of binding to and modulating the activity of p70S6K and/or AktKs. Such methods may be characterized by the following aspects: a) introducing into a suitable computer program, information defining a ligand binding domain of a p70S6K and/or AktK in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one of ordinary skill in the art would appreciate that such methods may further entail: employing a candidate agent, so-determined to fit spatially into the ligand binding domain, in a biological activity assay for p70S6K and/or AktK modulation, and determining whether said candidate agent modulates p70S6K and/or AktK activity in the assay. Such methods may also include administering the candidate agent, determined to modulate p70S6K and/or AktK activity, to a mammal suffering from a condition treatable by p70S6K and/or AktK modulation, such as those described above.

Also, one of ordinary skill in the art would appreciate that compounds of the invention can be used in a method of evaluating the ability of a test agent to associate with a molecule or molecular complex comprising a ligand binding domain of a p70S6K and/or AktK. Such a method may be characterized by the following aspects: a) creating a computer model of a p70S6K and/or AktK binding pocket using structure coordinates obtained from suitable x-ray quality crystals of the p70S6K and/or AktK, b) employing computational algorithms to perform a fitting operation between the test agent and the computer model of the binding pocket, and c) analyzing the results of the fitting operation to quantify the association between the test agent and the computer model of the binding pocket.

Abbreviations and their Definitions

The following abbreviations and terms have the indicated meanings throughout:

| Abbreviation | Meaning |
|---|---|
| Ac | Acetyl |
| CAN | Acetonitrile |
| ATP | adenosine triphosphate |
| BNB | 4-bromomethyl-3-nitrobenzoic acid |
| Boc | T-butyloxy carbonyl |
| Br | Broad |
| Bu | Butyl |
| ° C. | degrees Celsius |
| c- | Cyclo |
| CBZ | CarboBenZoxy = benzyloxycarbonyl |
| D | Doublet |
| Dd | doublet of doublet |
| Dt | doublet of triplet |
| DBU | Diazabicyclo[5.4.0]undec-7-ere |
| DCM | dichloromethane = methylene chloride = $CH_2Cl_2$ |
| DCE | Dichloroethylene |
| DEAD | diethyl azodicarboxylate |
| DIC | Diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | Ethyl |
| Fmoc | 9-fluorenylmethoxycarbonyl |
| G | gram(s) |
| GC | gas chromatography |
| H or hr | hour(s) |
| HATU | O-(7-Azabenzotriazol-1-yl)-1,1,3,3-tetramethyluronium hexafluorophosphate |
| HMDS | Hexamethyldisilazane |
| HOAc | acetic acid |
| HOBt | Hydroxybenzotriazole |
| HPLC | high pressure liquid chromatography |
| L | liter(s) |
| M | molar or molarity |
| M | Multiplet |
| Me | Methyl |
| Mesyl | Methanesulfonyl |
| Mg | milligram(s) |
| MHz | megahertz (frequency) |
| Min | minute(s) |
| ML | milliliter(s) |
| MM | Millimolar |
| Mmol | millimole(s) |
| Mol | mole(s) |
| MS | Mass spectral analysis |
| MTBE | methyl t-butyl ether |
| N | normal or normality |
| NBS | N-bromosuccinimide |
| NCS | N-chlorosuccinimide |
| NM | Nanomolar |
| NMO | N-methylmorpholine oxide |
| NMR | nuclear magnetic resonance spectroscopy |
| PEG | polyethylene glycol |
| PEY | poly-glutamine, tyrosine |
| Ph | Phenyl |
| PhOH | Phenol |

-continued

| Abbreviation | Meaning |
| --- | --- |
| PfP | Pentafluorophenol |
| PfPy | Pentafluoropyridine |
| PPTS | Pyridinium p-toluenesulfonate |
| Py | Pyridine |
| PyBroP | bromo-tris-pyrrolidino-phosphonium hexafluorophosphate |
| Q | Quartet |
| RT | Room temperature |
| Sat'd | Saturated |
| S | Singlet |
| s- | Secondary |
| t- | Tertiary |
| T or tr | Triplet |
| TBDMS | t-butyldimethylsilyl |
| TES | Triethylsilane |
| TFA | trifluoroacetic acid |
| THF | Tetrahydrofuran |
| TMOF | trimethyl orthoformate |
| TMS | Trimethylsilyl |
| Tosyl | p-toluenesulfonyl |
| Trt | Triphenylmethyl |
| µL | microliter(s) |
| µM | Micromole(s) or micromolar |

Synthesis of Compounds

Scheme 1 depicts a general synthetic route for compounds of the invention and is not intended to be limiting. Specific examples are described subsequently to this general synthetic description. In the generalizations below, specific reaction conditions or details, for example, added reagents, catalysts, solvents, reaction temperature, and the like are not described. The general routes depicted in conjunction with the specific examples provided contain sufficient information to allow one of ordinary skill in the art to synthesize compounds of the invention.

Scheme 1 shows that in general, compounds of Formulas I and II can be made, for example via a linear route. For example, an amino-substituted pyrazolopyrimidine (or purine or pyrrolopyrimidine) of 1 having leaving group "L" is reacted with a substituted piperazine/piperidine of 2, substituted with B which can be an optionally substituted as in Formulas I and II, in an anhydrous solvent such that the leaving group is displaced by the substituted piperazine/piperidine. After heating for a sufficient period of time, the reaction gives compounds of 3, wherein L is an amine and $X_{21}$, $X_{22}$, $X_{23}$, n, R and $R_{21}$-$R_{32}$ are as described above.

Scheme 1

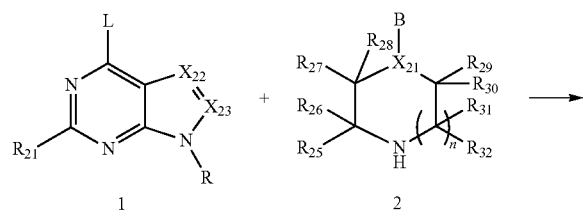

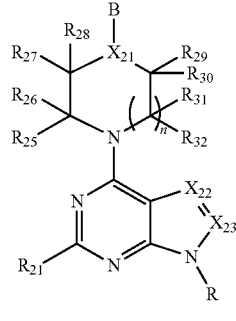

One of ordinary skill in the art would recognize that the descriptions associated with Scheme 1 is a generalization, and that there are other combinations of steps and approaches that can be used to make compounds of the invention. The examples that follow provide much more detailed descriptions of making exemplary compounds of the invention.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, each example is set out below with a corresponding multi-step synthesis scheme. Following specific examples are lists of compounds that were made in a similar way.

Example 1

6-(4-phenylpiperazin-1-yl)-9H-purine

To 6-chloro-9H-purine (60 mg, 0.39 mmol) in ethanol (2 mL) was added diisopropylethylamine (50 mg, 0.39 mmol) and 1-phenylpiperazine (63 mg, 0.39 mmol). The reaction mixture was stirred at 70° C. for 3 h, and then cooled to room temperature. The precipitation was filtered, washed with ethanol, and dried to give 6-(4-phenylpiperazin-1-yl)-9H-purine (77 mg, 71% yield) as a colorless solid. $^1$H NMR (400 MHz, $d_6$-DMSO) δ 13.09 (br s, 1H), 8.25 (s, 1H), 8.16 (s, 1H), 7.24 (m, 2H), 7.01 (m, 2H), 6.82 (m, 1H), 4.37 (br s, 4H), 3.26 (m, 4H); MS (ESI) for $C_{15}H_{16}N_6$: 281 (MH+).

Using the same or analogous synthetic techniques and/or substituting with alternative reagents, the following compounds of the invention were prepared:

6-[4-(3-chlorophenyl)piperazin-1-yl]-9H-purine: $^1$H NMR (400 MHz, $d_6$-DMSO) δ 13.10 (br s, 1H), 8.25 (s, 1H), 8.17 (s, 1H), 7.24 (m, 1H), 7.03 (m, 1H), 6.97 (m, 1H), 6.82 (m, 1H), 4.36 (br s, 4H), 3.32 (m, 4H); MS (ESI) for $C_{15}H_{16}N_6$: 281 (MH+); MS (ESI) for $C_{15}H_{15}ClN_6$: 315 (MH+).

6-[4-(2-chlorophenyl)piperazin-1-yl]-9H-purine: $^1$H NMR (400 MHz, $d_6$-DMSO) δ 13.05 (br s, 1H), 8.22 (s, 1H), 8.13 (s, 1H), 7.43 (d, 1H), 7.31-7.27 (m, 1H), 7.18 (s, 1H), 7.07-7.03 (m, 1H), 4.39 (br s, 4H), 3.09 (m, 4H); MS (ESI) for $C_{15}H_{15}ClN_6$: 315 (MH+).

6-[4-(2-fluorophenyl)piperazin-1-yl]-9H-purine: $^1$H NMR (400 MHz, $d_6$-DMSO) δ 13.05 (br s, 1H), 8.22 (s, 1H), 8.14 (s, 1H), 7.17-6.96 (m, 4H), 4.38 (br s, 4H), 3.12 (m, 4H); MS (ESI) for C$_{15}$H$_{15}$FN$_6$: 299 (MH$^+$).

6-[4-(4-methoxyphenyl)piperazin-1-yl]-9H-purine: $^1$H NMR (400 MHz, d$_6$-DMSO) δ 13.05 (br s, 1H), 8.22 (s, 1H), 8.13 (s, 1H), 6.95 (d, 2H), 6.83 (d, 2H), 4.35 (br s, 4H), 3.68 (s, 3H), 3.12 (m, 4H); MS (ESI) for C$_{16}$H$_{18}$N$_6$O: 311 (MH$^+$).

6-[4-(2-methoxyphenyl)piperazin-1-yl]-9H-purine: $^1$H NMR (400 MHz, d$_6$-DMSO) δ 13.03 (br s, 1H), 8.21 (s, 1H), 8.12 (s, 1H), 6.99-6.84 (m, 4H), 4.35 (br s, 4H), 3.81 (s, 3H), 3.06 (m, 4H); MS (ESI) for C$_{16}$H$_{18}$N$_6$O: 311 (MH$^+$).

6-[4-(4-chlorophenyl)piperazin-1-yl]-9H-purine: $^1$H NMR (400 MHz, d$_6$-DMSO) δ 13.05 (br s, 1H), 8.22 (s, 1H), 8.14 (s, 1H), 7.24 (d, 2H), 7.01 (d, 2H), 4.35 (br s, 4H), 3.26 (m, 4H); MS (ESI) for C$_{15}$H$_{15}$ClN$_6$: 315 (MH$^+$).

6-[4-(4-fluorophenyl)piperazin-1-yl]-9H-purine: $^1$H NMR (400 MHz, d$_6$-DMSO) δ 13.05 (br s, 1H), 8.22 (s, 1H), 8.14 (s, 1H), 7.09-6.99 (m, 4H), 4.35 (br s, 4H), 3.20 (m, 4H); MS (ESI) for C$_{15}$H$_{15}$FN$_6$: 299 (MH$^+$).

6-[4-(3-trifluoromethylphenyl)piperazin-1-yl]-9H-purine: $^1$H NMR (400 MHz, d$_6$-DMSO) δ 13.11 (br s, 1H), 8.26 (s, 1H), 8.18 (s, 1H), 7.45 (m, 1H), 7.30 (d, 1H), 7.26 (s, 1H), 7.11 (d, 1H), 4.38 (br s, 4H), 3.38 (m, 4H); MS (ESI) for C$_{16}$H$_{15}$F$_3$N$_6$: 349 (MH$^+$).

6-(4-o-tolylpiperazin-1-yl)-9H-purine: $^1$H NMR (400 MHz, d$_6$-DMSO) δ 13.09 (br s, 1H), 8.24 (s, 1H), 8.15 (s, 1H), 7.20 (d, 1H), 7.15 (m, 1H), 7.04 (d, 1H), 6.98 (m, 1H), 4.38 (br s, 4H), 2.97-2.94 (m, 4H), 2.33 (s, 3H); MS (ESI) for C$_{16}$H$_{18}$N$_6$: 295 (MH$^+$).

Example 2

4-(4-phenylpiperazin-1-yl)-7H-pyrrolo[2,3-d]pyrimidine

To 4-chloro-7H-pyrrolo[2,3-d]pyrimidine (60 mg, 0.39 mmol) in ethanol (2 mL) was added diisopropylethylamine (50 mg, 0.39 mmol) and 1-phenylpiperazine (63 mg, 0.39 mmol). The reaction mixture was stirred at 70° C. for 16 h, and then cooled to room temperature. The precipitation was filtered, washed with methanol, and dried to give 4-(4-phenylpiperazin-1-yl)-7H-pyrrolo[2,3-d]pyrimidine (74 mg, 68% yield) as a colorless solid. $^1$H NMR (400 MHz, d$_6$-DMSO) δ 11.76 (br s, 1H), 8.18 (s, 1H), 7.24 (m, 3H), 6.98 (m, 2H), 6.81 (m, 1H), 6.68 (d, 1H), 4.03 (m, 4H), 3.29 (m, 4H); MS (ESI) for C$_{16}$H$_{17}$N$_5$: 280 (MH$^+$).

Using the same or analogous synthetic techniques and/or substituting with alternative reagents, the following compounds of the invention were prepared:

4-[4-(3-chlorophenyl)piperazin-1-yl]-7H-pyrrolo[2,3-d]pyrimidine: $^1$H NMR (400 MHz, d$_6$-DMSO) δ 11.76 (br s, 1H), 8.18 (s, 1H), 7.24 (m, 2H), 6.98 (m, 1H), 6.94 (m, 1H), 6.81 (m, 1H), 6.64 (d, 1H), 4.02 (m, 4H), 3.35 (m, 4H); MS (ESI) for C$_{16}$H$_{16}$ClN$_5$: 314 (MH$^+$).

4-[4-(2-methylphenyl)piperazin-1-yl]-7H-pyrrolo[2,3-d]pyrimidine: $^1$H NMR (400 MHz, d$_6$-DMSO) δ 11.71 (br s, 1H), 8.15 (s, 1H), 7.21-7.11 (m, 3H), 7.02 (m, 1H), 6.96 (m, 1H), 6.46 (m, 1H), 4.02 (m, 4H), 2.95 (m, 4H), 2.32 (s, 3H); MS (ESI) for C$_{17}$H$_{19}$N$_5$: 294 (MH$^+$).

4-{4-[2-(methyloxy)phenyl]piperazin-1-yl}-7H-pyrrolo[2,3-d]pyrimidine: $^1$H NMR (400 MHz, d$_6$-DMSO) δ 11.70 (br s, 1H), 8.14 (s, 1H), 7.18 (m, 1H), 7.00-6.84 (m, 4H), 6.64 (m, 1H), 4.00 (m, 4H), 3.81 (s, 3H), 3.07 (m, 4H); MS (ESI) for C$_{17}$H$_{19}$N$_5$O: 310 (MH$^+$).

4-{4-[3-(methyloxy)phenyl]piperazin-1-yl}-7H-pyrrolo[2,3-d]pyrimidine: $^1$H NMR (400 MHz, d$_6$-DMSO) δ 11.71 (br s, 1H), 8.15 (s, 1H), 7.20 (m, 1H), 7.11 (m, 1H), 6.63 (m, 1H), 6.55 (m, 1H), 6.48 (m, 1H), 6.38 (m, 1H), 4.00 (m, 4H), 3.27 (s, 3H), 3.28 (m, 4H); MS (ESI) for C$_{17}$H$_{19}$N$_5$O: 310 (MH$^+$).

4-{4-[4-(methyloxy)phenyl]piperazin-1-yl}-7H-pyrrolo[2,3-d]pyrimidine: $^1$H NMR (400 MHz, d$_6$-DMSO) δ 11.71 (br s, 1H), 8.15 (s, 1H), 7.20 (m, 1H), 6.93 (m, 2H), 6.83 (m, 2H), 6.63 (m, 1H), 3.99 (m, 4H), 3.68 (s, 3H), 3.13 (m, 4H); MS (ESI) for C$_{17}$H$_{19}$N$_5$O: 310 (MH$^+$).

4-{4-[3-(trifluoromethyl)phenyl]piperazin-1-yl}-7H-pyrrolo[2,3-d]pyrimidine: $^1$H NMR (400 MHz, d$_6$-DMSO) δ 11.73 (br s, 1H), 8.16 (s, 1H), 7.44 (m, 1H), 7.26-7.17 (m, 3H), 7.08 (m, 1H), 6.63 (m, 1H), 4.03 (m, 4H), 3.41 (m, 4H); MS (ESI) for C$_{17}$H$_{16}$F$_3$N$_5$: 314 (MH$^+$).

4-[4-(4-fluorophenyl)piperazin-1-yl]-7H-pyrrolo[2,3-d]pyrimidine: $^1$H NMR (400 MHz, d$_6$-DMSO): δ 11.75 (s, 1H), 8.20 (s, 1H), 7.42-7.00 (m, 5H), 6.60 (s, 1H), 4.08-3.98 (t, 4H), 3.26-3.18 (t, 4H); MS (ESI) for C$_{16}$H$_{16}$FN$_5$: 298 (MH$^+$).

4-[4-(4-chlorophenyl)piperazin-1-yl]-7H-pyrrolo[2,3-d]pyrimidine: $^1$H NMR (400 MHz, d$_6$-DMSO): δ 11.70 (s, 1H), 8.40 (s, 1H), 7.30-7.20 (m, 3H), 7.02-6.92 (d, 2H), 6.62 (s, 1H), 4.00 (s, 4H), 3.20 (s, 4H); MS (ESI) for C$_{16}$H$_{16}$ClN$_5$: 314 (MH$^+$).

4-[4-(2-chlorophenyl)piperazin-1-yl]-7H-pyrrolo[2,3-d]pyrimidine: $^1$H NMR (400 MHz, d$_6$-DMSO): δ 11.65 (s, 1H), 8.18 (s, 1H), 7.48-7.42 (s, 1H), 7.34-7.26 (m, 1H), 7.22-7.16 (m, 2H), 7.10-7.04 (m, 1H), 6.68 (s, 1H), 4.04 (t, 4H), 3.12 (t, 4H); MS (ESI) for C$_{16}$H$_{16}$ClN$_5$: 314 (MH$^+$).

4-[4-(2-fluorophenyl)piperazin-1-yl]-7H-pyrrolo[2,3-d]pyrimidine: $^1$H NMR (400 MHz, d$_6$-DMSO): δ 11.70 (s, 1H), 8.20 (s, 1H), 7.22-6.84 (m, 5H), 6.50 (s, 1H), 4.08 (s, 4H), 3.18 (s, 4H); MS (ESI) for C$_{16}$H$_{16}$FN$_5$: 298 (MH$^+$).

Example 3

4-(4-phenylpiperazin-1-yl)-1H-pyrazolo[3,4-d]pyrimidine

To 4-choro-1H-pyrazolo[3,4-d]pyrimidine (60 mg, 0.39 mmol, R. K. Robins, *J. Am. Chem. Soc.* 1956, 78, 784-790) in ethanol (2 mL) was added diisopropylethylamine (50 mg, 0.39 mmol) and 1-phenylpiperazine (63 mg, 0.39 mmol). The reaction mixture was stirred at room temperature for 4 h. The precipitation was filtered, washed with methanol, and dried to give 4-(4-phenylpiperazin-1-yl)-1H-pyrazolo[3,4-d]pyrimidine (68 mg, 62% yield) as a colorless solid. $^1$H NMR (400 MHz, d$_6$-DMSO) δ 13.59 (br s, 1H), 8.33 (s, 1H), 8.28 (s, 1H), 7.26 (m, 2H), 6.98 (m, 2H), 6.82 (m, 1H), 4.09 (m, 4H), 3.33 (m, 4H); MS (ESI) for C$_{15}$H$_{16}$N$_6$: 281 (MH$^+$).

Using the same or analogous synthetic techniques and/or substituting with alternative reagents, the following compounds of the invention were prepared:

4-[4-(3-chlorophenyl)piperazin-1-yl]-1H-pyrazolo[3,4-d]pyrimidine: $^1$H NMR (400 MHz, d$_6$-DMSO) δ 13.59 (br s, 1H), 8.31 (s, 1H), 8.28 (s, 1H), 7.25 (m, 1H), 6.98 (m, 1H), 6.93 (m, 1H), 6.81 (m, 1H), 4.09 (m, 4H), 3.41 (m, 4H); MS (ESI) for C$_{15}$H$_{15}$ClN$_6$: 281 (MH$^+$).

4-{4-[3-(trifluoromethyl)phenyl]piperazin-1-yl}-1H-pyrazolo[3,4-d]pyrimidine: $^1$H NMR (400 MHz, d$_6$-DMSO) δ 13.60 (br s, 1H), 8.31 (s, 1H), 8.29 (s, 1H), 7.47 (m, 1H), 7.26 (m, 1H), 7.20 (m, 1H), 7.10 (m, 1H), 4.11 (m, 4H), 3.47 (m, 4H); MS (ESI) for C$_{16}$H$_{15}$F$_3$N$_6$: 349 (MH$^+$).

4-[4-(2-methylphenyl)piperazin-1-yl]-1H-pyrazolo[3,4-d]pyrimidine: $^1$H NMR (400 MHz, d$_6$-DMSO) δ 13.59 (br s, 1H), 8.33 (s, 1H), 8.28 (s, 1H), 7.21 (m, 1H), 7.16 (m, 1H), 7.05 (m, 1H), 6.99 (m, 1H), 4.09 (m, 4H), 2.98 (m, 4H), 2.33 (s, 3H); MS (ESI) for C$_{16}$H$_{18}$N$_6$: 295 (MH$^+$).

4-[4-(5-chloro-2-methylphenyl)piperazin-1-yl]-1H-pyrazolo[3,4-d]pyrimidine: $^1$H NMR (400 MHz, d$_6$-DMSO) δ 13.60 (br s, 1H), 8.32 (s, 1H), 8.28 (s, 1H), 7.23 (m, 1H), 7.05 (m, 2H), 4.08 (m, 4H), 3.01 (m, 4H), 2.30 (s, 3H); MS (ESI) for C$_{16}$H$_{17}$ClN$_6$: 329 (MH$^+$).

Example 4

4-[4-(5-chloro-2-methylphenyl)piperazin-1-yl]-3-methyl-1H-pyrazolo[3,4-d]pyrimidine To 4-hydroxy-3-methyl-1H-pyrazolo[3,4-d]pyrimidine (270 mg, 1.80 mmol, R. Badger, *Aust. J. Chem.* 1965, 18, 1267-1270) in chloroform (5 mL) was added oxalyl chloride (0.23 mL, 2.68 mmol) and DMF (0.05 mL), and the mixture was refluxed for 8 h. Over the first 4 h reaction time, more oxalyl chloride (1.7 mL) and DMF (1.0 mL) was added in portions. The mixture was added into saturated sodium bicarbonate (50 mL), and extracted with ethyl acetate (3×30 mL). The organic layer was washed with 5% lithium chloride (20 mL), water (20 mL), and brine (20 mL), dried with sodium sulfate, and concentrated to afford 4-chloro-3-methyl-1H-pyrazolo[3,4-d]pyrimidine (130 mg, 43% yield) as a brown solid. $^1$H NMR (400 MHz, d$_6$-DMSO) δ 8.75 (s, 1H), 2.64 (s, 3H); MS (ESI) for C$_6$H$_5$ClN$_4$: 169 (MH$^+$).

To 4-chloro-3-methyl-1H-pyrazolo[3,4-d]pyrimidine (125 mg, 0.74 mmol) in THF (5 mL) was added diisopropylethylamine (96 mg, 0.75 mmol) and 1-(5-chloro-2-methylphenyl)piperazine (156 mg, 0.74 mmol). The reaction mixture was stirred at room temperature for 2 h. The precipitation was filtered, washed with methanol, and dried to give 4-[4-(5-chloro-2-methylphenyl)piperazin-1-yl]-3-methyl-1H-pyrazolo[3,4-d]-pyrimidine (36 mg, 14% yield) as an off-white solid. $^1$H NMR (400 MHz, d$_6$-DMSO) δ 13.27 (br s, 1H), 8.27 (s, 1H), 7.20 (m, 1H), 7.03 (m, 2H), 3.86 (m, 4H), 3.00 (m, 4H), 2.59 (s, 3H), 2.29 (s, 3H); MS (ESI) for C$_{17}$H$_{19}$ClN$_6$: 343 (MH$^+$).

Using the same or analogous synthetic techniques and/or substituting with alternative reagents, the following compounds of the invention were prepared:

4-[4-(3-chlorophenyl)piperazin-1-yl]-3-methyl-1H-pyrazolo[3,4-d]pyrimidine: $^1$H NMR (400 MHz, d$_6$-DMSO): δ 8.40 (br s, 1H), 7.23 (t, 1H), 6.99 (m, 1H), 6.90 (dd, 1H), 6.80 (dd, 1H), 3.98 (s, 4H), 3.40 (s, 4H), 2.68 (s, 3H), MS (ESI) for C$_{16}$H$_{17}$ClN$_6$: 390 (MH$^+$)

3-methyl-4-[4-(2-methylphenyl)piperazin-1-yl]-1H-pyrazolo[3,4-d]pyrimidine: $^1$H NMR (400 MHz, d$_4$-methanol): δ 8.50 (s, 1H), 7.22-6.88 (m, 5H), 4.22 (s, 4H), 3.22 (s, 4H), 2.80 (s, 3H), 2.40 (s, 3H); MS (ESI) for C$_{17}$H$_{20}$N$_6$: 310 (MH$^+$).

Example 5

4-[4-(5-chloro-2-methylphenyl)piperazin-1-yl]-3-ethyl-1H-pyrazolo[3,4-d]pyrimidine To 3-ethyl-1H-pyrazolo[3,4-d]pyrimidin-4-ol (82 mg, 0.50 mmol, DE 1966640, 1973) in thionyl chloride (5 mL) was added DMF (76 mg, 1.02 mmol) and; the reaction mixture was refluxed for 3 h. The mixture was concentrated, the residue added to saturated sodium bicarbonate (50 mL), and extracted with ethyl acetate (3×30 mL). The organic layer was washed with 5% lithium chloride (20 mL), water (20 mL), and brine (20 mL), dried with sodium sulfate, and concentrated to afford 4-chloro-3-ethyl-1H-pyrazolo[3,4-d]pyrimidine (65 mg, 90% yield) as a yellow solid. $^1$H NMR (400 MHz, d$_6$-DMSO) δ 8.73 (s, 1H), 3.05 (q, 2H), 1.32 (t, 3H); MS (ESI) for C$_7$H$_7$ClN$_4$: 183 (MH$^+$).

To 4-chloro-3-ethyl-1H-pyrazolo[3,4-d]pyrimidine (60 mg, 0.33 mmol) in THF (5 mL) was added diisopropylethylamine (45 mg, 0.34 mmol) and 1-(5-chloro-2-methylphenyl)piperazine (83 mg, 0.39 mmol) and the reaction mixture was stirred at 50° C. for 5 h. The mixture was concentrated, and the remaining solid washed with methanol and dried to provide 4-[4-(5-chloro-2-methylphenyl)piperazin-1-yl]-3-ethyl-1H-pyrazolo[3,4-d]pyrimidine (53 mg, 45% yield) as an off-white solid. $^1$H NMR (400 MHz, d$_6$-DMSO) δ 13.35 (br s, 1H), 8.32 (s, 1H), 7.22 (m, 1H), 7.05 (m, 2H), 3.81 (m, 4H), 3.00 (m, 6H), 2.28 (s, 3H), 1.30 (t, 3H); MS (ESI) for C$_{18}$H$_{21}$ClN$_6$: 357 (MH$^+$).

Using the same or analogous synthetic techniques and/or substituting with alternative reagents, the following compounds of the invention were prepared:

4-[4-(3-chlorophenyl)piperazin-1-yl]-3-ethyl-1H-pyrazolo[3,4-d]pyrimidine: $^1$H NMR (400 MHz, d$_6$-DMSO) δ 13.36 (s, 1H), 8.32 (s, 1H), 7.25 (t, 1H), 7.01 (t, 1H), 6.96 (dd, 1H), 6.83 (dd, 1H), 3.80 (m, 4H), 3.34 (m, 4H), 2.98 (q, 2H), 1.29 (t, 3H); MS (ESI) for C$_{17}$H$_{19}$ClN$_6$: 343 (MH$^+$).

4-{4-[5-chloro-2-(methyloxy)phenyl]piperazin-1-yl}-3-ethyl-1H-pyrazolo[3,4-d]pyrimidine: $^1$H NMR (400 MHz, d$_6$-DMSO) δ 13.34 (s, 1H), 8.31 (s, 1H), 7.03 (dd, 1H), 6.98 (d, 1H), 6.93 (d, 1H), 3.82 (s, 3H), 3.79 (m, 4H), 3.14 (m, 4H) 2.97 (q, 2H), 1.29 (t, 3H); MS (ESI) for C$_{18}$H$_{21}$ClN$_6$O: 373 (MH$^+$).

4-[4-(3-chlorophenyl)-1,4-diazepan-1-yl]-3-ethyl-1H-pyrazolo[3,4-d]pyrimidine: $^1$H NMR (400 MHz, CDCl$_3$) δ 12.36 (br s, 1H), 8.36 (s, 1H), 7.09 (t, 1H), 6.67 (t, 1H), 6.62 (dd, 1H), 6.58 (dd, 1H), 4.08 (m, 2H), 3.85 (m, 2H), 3.75 (m, 2H), 3.50 (m, 2H), 3.04 (q, 2H), 2.16 (m, 2H), 1.38 (t, 3H); MS (ESI) for C$_{18}$H$_{21}$ClN$_6$: 357 (MH$^+$).

4-[5-(3-chlorophenyl)-2,5-diazabicyclo[2.2.1]hept-2-yl]-3-ethyl-1H-pyrazolo[3,4-d]pyrimidine: $^1$H NMR (400 MHz, CDCl$_3$) δ 12.52 (br s, 1H), 8.39 (s, 1H), 7.08 (m, 1H), 6.63 (dd, 1H), 6.53 (m, 1H), 6.42 (dd, 1H), 5.30 (s, 1H), 4.55 (s, 1H), 4.06 (dd, 1H), 3.72 (m, 2H), 3.43 (d, 1H), 3.09-2.91 (m, 2H), 2.16 (q, 2H), 1.36 (t, 3H); MS (ESI) for C$_{18}$H$_{19}$ClN$_6$: 356 (MH$^+$).

4-(4-{3-chloro-4-[(2-morpholin-4-yl-ethyl)oxy]phenyl}piperazin-1-yl)-3-ethyl-1H-pyrazolo[3,4-d]pyrimidine: $^1$H NMR (400 MHz, d$_4$-methanol) δ 8.48 (s, 1H), 7.21 (d, 1H), 7.16 (d, 1H), 7.07 (dd, 1H), 4.43 (m, 2H), 4.35 (m, 4H), 4.10 (m, 2H), 3.88-3.81 (m, 2H), 3.73-3.65 (m, 4H), 3.42-3.37 (m, 6H), 3.23 (q, 2H), 1.44 (t, 3H).

2-chloro-4-[4-(3-ethyl-1H-pyrazolo[3,4-d]pyrimidin-4-yl)piperazin-1-yl]-5-methylphenol: $^1$H NMR (400 MHz, CDCl$_3$) δ 8.36 (s, 1H), 6.96 (s, 1H), 6.73 (s, 1H), 4.08 (br s, 4H), 3.02 (q, 2H), 2.99 (m, 4H), 2.30 (s, 3H), 1.39 (t, 3H); MS (ESI) for C$_{18}$H$_{21}$ClN$_6$O: 373 (MH$^+$).

3-({2-chloro-4-[4-(3-ethyl-1H-pyrazolo[3,4-d]pyrimidin-4-yl)piperazin-1-yl]-5-methylphenyl}oxy)-N,N-dimethylpropan-1-amine trifluoroacetate: $^1$H NMR (400 MHz, d$_4$-methanol) δ 8.43 (s, 1H), 7.12 (s, 1H), 6.99 (s, 1H), 4.20 (br s, 4H), 4.15 (t, 2H), 3.39 (t, 2H), 3.16 (q, 2H), 3.02 (t, 4H), 2.96 (s, 6H), 2.38 (s, 3H), 2.25 (m, 2H), 1.40 (t, 3H); MS (ESI) for C$_{23}$H$_{32}$ClN$_7$O: 458 (MH$^+$).

2-({2-chloro-4-[4-(3-ethyl-1H-pyrazolo[3,4-d]pyrimidin-4-yl)piperazin-1-yl]-5-methylphenyl}oxy)-N,N-dimethylethanamine trifluoroacetate: $^1$H NMR (400 MHz, d$_4$-methanol) δ 8.43 (s, 1H), 7.14 (s, 1H), 7.07 (s, 1H), 4.38 (t, 2H), 4.21 (br s, 4H), 3.63 (t, 2H), 3.16 (q, 2H), 3.02 (m, 10H), 2.40 (s, 3H), 1.40 (t, 3H); MS (ESI) for C$_{22}$H$_{30}$ClN$_7$O: 444 (MH$^+$).

4-{4-[5-chloro-2-methyl-4-(methyloxy)phenyl]piperazin-1-yl}-3-ethyl-1H-pyrazolo[3,4-d]pyrimidine: $^1$H NMR (400

MHz, d₄-methanol) δ 8.44 (s, 1H), 7.08 (s, 1H), 6.94 (s, 1H), 4.25 (br s, 4H), 3.83 (s, 3H), 3.18 (q, 2H), 3.02 (t, 4H), 2.39 (s, 3H), 1.41 (t, 3H); MS (ESI) for C₁₉H₂₃ClN₆O: 387 (MH⁺).

4-[4-(3,6-dimethylpyrazin-2-yl)piperazin-1-yl]-3-ethyl-1H-pyrazolo[3,4-d]pyrimidine: ¹H NMR (400 MHz, d₆-DMSO) δ 13.35 (s, 1H), 8.35 (s, 1H), 8.00 (s, 1H), 3.81 (m, 4H), 3.30 (m, 4H), 2.99 (q, 2H), 2.47, (s, 3H), 2.35 (s, 3H) 1.29 (t, 3H); MS (ESI) for C₁₇H₂₂N₈: 339 (MH⁺).

1-[4-(3-ethyl-1H-pyrazolo[3,4-d]pyrimidin-4-yl)piperazin-1-yl]isoquinoline: ¹H NMR (400 MHz, d₆-DMSO) δ 13.31 (s, 1H), 8.31 (s, 1H), 8.18 (d, 1H), 8.12 (d, 1H), 7.89 (d, 1H), 7.71 (m, 1H), 7.62 (m, 1H), 7.41 (d, 1H), 3.94 (m, 4H), 3.48 (m, 4H), 3.00 (q, 2H), 1.30 (t, 3H); MS (ESI) for C₂₀H₂₁N₇: 360 (MH⁺).

4-[4-(4,6-dimethylpyrimidin-2-yl)piperazin-1-yl]-3-ethyl-1H-pyrazolo[3,4-d]pyrimidine: ¹H₁NMR (400 MHz, d₆-DMSO) δ 13.34 (s, 1H), 8.31 (s, 1H), 6.46 (s, 1H), 3.90 (m, 4H), 3.72, (m, 4H), 2.99 (q, 21H), 2.26 (s, 6H), 1.29 (t, 3H); MS (ESI) for C₁₇H₂₂N₈: 339 (MH⁺).

2-[4-(3-ethyl-1H-pyrazolo[3,4-d]pyrimidin-4-yl)piperazin-1-yl]pyridine-3-carboxamide: ¹H NMR (400 MHz, d₆-DMSO) δ 8.46 (s, 1H), 8.26 (m, 1H), 7.96 (s, 1H), 7.81 (m, 1H), 7.62 (s, 1H), 6.95 (dd, 1H), 3.96 (br s, 4H), 3.52 (br s, 4H), 3.05 (br s, 2H), 1.29 (t, 3H); C₁₇H₂₀N₈O: 353 (MH⁺).

N'-{5-chloro-3-[4-(3-ethyl-1H-pyrazolo[3,4-d]pyrimidin-4-yl)piperazin-1-yl]-2-methylphenyl}-N-methyl-N-(1-methylethyl)ethane-1,2-diamine trifluoroacetate: ¹H NMR (400 MHz, d₄-methanol) δ 8.41 (s, 1H), 6.55 (s, 2H), 4.20 (br s, 4H), 3.69 (m, 1H), 3.58 (m, 2H), 3.48 (m, 1H), 3.24 (m, 1H), 3.16 (q, 2H), 3.04 (br s, 4H), 2.88 (s, 3H), 2.24 (s, 3H), 1.42 (t, 3H), 1.36 (m, 6H); MS (ESI) for C₂₄H₃₅CN₈: 471 (MH⁺).

N'-{5-chloro-3-[4-(3-ethyl-1H-pyrazolo[3,4-d]pyrimidin-4-yl)piperazin-1-yl]-2-methylphenyl}-N-ethyl-N-methylethane-1,2-diamine trifluoroacetate: ¹H NMR (400 MHz, d₄-methanol) δ 8.42 (s, 1H), 6.55 (s, 2H), 4.17 (br s, 4H), 3.57 (m, 2H), 3.47 (m, 1H), 3.35 (m, 1H), 3.25 (m, 2H), 3.15 (q, 2H), 3.02 (br s, 4H), 2.93 (s, 3H), 2.21 (s, 3H), 1.40 (t, 3H), 1.34 (t, 3H); MS (ESI) for C₂₃H₃₃ClN₈: 457 (MH⁺).

methyl 4-(3-chlorophenyl)-1-(3-ethyl-1H-pyrazolo[3,4-d]pyrimidin-4-yl)piperazine-2-carboxylate: ¹H NMR (400 MHz, d₄-methanol) δ 8.47 (s, 1H), 7.24 (t, 1H), 6.98 (m, 1H), 6.89 (dd, 1H), 5.97 (br s, 1H), 4.43-4.30 (m, 2H), 4.12 (m, 1H), 3.79 (s, 3H), 3.75 (m, 1H), 3.33-3.14 (m, 4H), 3.03 (dt, 1H), 1.43 (t, 3H); MS (ESI) for C₁₉H₂₁ClN₆O₂: 401 (MH⁺).

4-(3-chlorophenyl)-1-(3-ethyl-1H-pyrazolo[3,4-d]pyrimidin-4-yl)-N-methylpiperazine-2-carboxamide: ¹H NMR (400 MHz, CDCl₃) δ 12.44 (br s, 1H), 8.51 (s, 1H), 7.20 (t, 1H), 6.99 (br m, 1H), 6.94 (dd, 1H), 6.86 (dd, 1H), 6.72-6.65 (br m, 1H), 5.24 (br s, 1H), 4.33 (d, 1H), 4.26 (d, 1H), 3.81-3.70 (m, 1H), 3.58-3.51 (m, 1H), 3.18-2.96 (m, 4H), 2.89 (m, 3H), 1.47 (t, 3H); MS (ESI) for C₁₉H₂₂ClN₇O: 400 (MH⁺).

4-(4-{5-chloro-2-methyl-3-[(2-morpholin-4-ylethyl)oxy]phenyl}piperazin-1-yl)-3-ethyl-1H-pyrazolo[3,4-d]pyrimidine hydrochloride: ¹H NMR (400 MHz, d₄-methanol) δ 8.36 (s, 1H), 6.78 (br s, 1H), 6.73 (br s, 1H), 4.34 (t, 2H), 4.15 (br s, 4H), 4.05-3.69 (br m, 4H), 3.62 (t, 2H), 3.58-3.26 (br m, 4H), 3.09 (q, 2H), 3.03-2.96 (br m, 4H), 2.19 (s, 3H), 1.32 (t, 3H); MS (ESI) for C₂₄H₃₂ClN₇O₂: 486 (MH⁺).

4-(4-{5-chloro-2-methyl-3-[(2-piperidin-1-ylethyl)oxy]phenyl}piperazin-1-yl)-3-ethyl-1H-pyrazolo[3,4-d]pyrimidine hydrochloride: ¹H NMR (400 MHz, d₄-methanol) δ 8.36 (s, 1H), 6.76 (m, 1H), 6.71 (m, 1H), 4.30 (t, 2H), 4.24-4.11 (br m, 4H), 3.62-3.50 (br m, 4H), 3.17-2.95 (br m, 8H), 2.18 (s, 3H), 1.94-1.71 (br m, 5H), 1.54-1.41 (br m, 1H), 1.32 (t, 3H); MS (ESI) for C₂₅H₃₄ClN₇O: 484 (MH⁺).

4-[4-(5-chloro-3-{[2-(4-ethylpiperazin-1-yl)ethyl]oxy}-2-methylphenyl)piperazin-1-yl]-3-ethyl-1H-pyrazolo[3,4-d]pyrimidine hydrochloride: ¹H NMR (400 MHz, d₄-methanol) δ 8.38 (s, 1H), 6.74 (m, 1H), 6.68 (m, 1H), 4.30 (t, 2H), 4.23 (br m, 6H), 3.70-2.88 (m, 18H), 2.18 (s, 3H), 1.37-1.25 (m, 6H); MS (ESI) for C₂₆H₃₇ClN₈O: 513 (MH⁺).

4-(4-{5-chloro-2-methyl-3-[(3-morpholin-4-ylpropyl)oxy]phenyl}piperazin-1-yl)-3-ethyl-1H-pyrazolo[3,4-d]pyrimidine hydrochloride: ¹H NMR (400 MHz, d₄-methanol) δ 8.38 (s, 1H), 6.70 (m, 1H), 6.67 (m, 1H), 4.20 (br m, 4H), 4.08-3.92 (m, 4H), 3.82-3.65 (br m, 2H), 3.56-3.43 (br m, 2H), 3.40-3.27 (br m, 2H), 3.20-3.06 (br m, 4H), 3.03-2.95 (br m, 4H), 2.28-2.18 (br m, 2H), 2.18-2.14 (br m, 3H), 1.39-1.28 (t, 3H); MS (ESI) for C₂₅H₃₄ClN₇O₂: 500 (MH⁺).

4-(4-{5-chloro-2-methyl-3-[(3-pyrrolidin-1-ylpropyl)oxy]phenyl}piperazin-1-yl)-3-ethyl-1H-pyrazolo[3,4-d]pyrimidine hydrochloride: ¹H NMR (400 MHz, d₄-methanol) δ 8.44 (s, 1H), 6.78 (m, 1H), 6.75 (m, 1H), 4.33-4.16 (br m, 4H), 4.15-4.07 (m, 2H), 3.79-3.67 (m, 2H), 3.49-3.38 (m, 2H), 3.24-3.04 (m, 8H), 2.35-1.98 (m, 9H), 1.42 (t, 3H); MS (ESI) for C₂₅H₃₄ClN₇O: 484 (MH⁺).

4-[4-(5-chloro-2-methyl-3-{[3-(4-methylpiperazin-1-yl)propyl]oxy}phenyl)piperazin-1-yl]-3-ethyl-1H-pyrazolo[3,4-d]pyrimidine hydrochloride: ¹H NMR (400 MHz, d₄-methanol) δ 8.36 (s, 1H), 6.67 (m, 1H), 6.63 (m, 1H), 4.26-4.15 (br m, 4H), 4.04-3.96 (m, 2H), 3.60-3.27 (m, 6H), 3.20-3.07 (m, 4H), 3.03-2.92 (m, 4H), 2.88-2.85 (m, 3H), 2.22-2.10 (m, 4H), 1.33 (t, 3H); MS (ESI) for C₂₆H₃₇ClN₈O: 513 (MH⁺).

4-(4-{5-chloro-2-methyl-3-[(3-piperidin-1-ylpropyl)oxy]phenyl}piperazin-1-yl)-3-ethyl-1H-pyrazolo[3,4-d]pyrimidine hydrochloride: ¹H NMR (400 MHz, d₄-methanol) δ 8.33 (s, 1H), 6.69 (m, 1H), 6.67 (m, 1H), 4.18-4.04 (br m, 4H), 4.02 (t, 2H), 3.57-3.49 (m, 2H), 3.27-3.23 (m, 2H), 3.12-3.02 (m, 2H), 3.01-2.86 (m, 6H), 2.24-2.17 (m, 2H), 2.15 (br s, 3H), 1.94-1.84 (m, 2H), 1.82-1.64 (m, 3H), 1.52-1.40 (m, 1H), 1.32 (t, 3H); MS (ESI) for C₂₆H₃₆ClN₇O: 498 (MH⁺).

4-[4-(5-chloro-3-{[3-(4-ethylpiperazin-1-yl)propyl]oxy}-2-methylphenyl)piperazin-1-yl]-3-ethyl-1H-pyrazolo[3,4-d]pyrimidine hydrochloride: ¹H NMR (400 MHz, d₄-methanol) δ 8.37 (s, 1H), 6.68 (m, 1H), 6.64 (m, 1H), 4.27-4.13 (br m, 4H), 4.00 (t, 2H), 3.54-3.23 (m, 6H), 3.20-3.05 (m, 8H), 3.01-2.94 (m, 4H), 2.19-2.07 (m, 5H), 1.35-1.24 (m, 6H); MS (ESI) for C₂₇H₃₉ClN₈O: 527 (MH⁺).

3-({5-chloro-3-[4-(3-ethyl-1H-pyrazolo[3,4-d]pyrimidin-4-yl)piperazin-1-yl]-2-methylphenyl}oxy)-N,N-diethylpropan-1-amine hydrochloride: ¹H NMR (400 MHz, d₄-methanol) δ 8.46 (s, 1H), 6.79 (m, 1H), 6.76 (m, 1H), 4.33-4.21 (m, 4H), 4.11 (t, 2H), 3.42-3.35 (m, 2H), 3.24-3.15 (m, 2H), 3.10-3.03 (m, 4H), 2.32-2.19 (m, 5H), 1.46-1.30 (m, 9H); MS (ESI) for C₂₅H₃₆ClN₇O: 486 (MH⁺).

N-{5-chloro-3-[4-(3-ethyl-1H-pyrazolo[3,4-d]pyrimidin-4-yl)piperazin-1-yl]-2-methylphenyl}-N,N',N'-trimethylethane-1,2-diamine: ¹H NMR (400 MHz, d₄-methanol) δ 8.30 (s, 1H), 6.83 (m, 1H), 6.77 (m, 1H), 4.06-3.81 (br m, 4H), 3.11-3.01 (m, 8H), 2.69 (s, 3H), 2.53 (m, 2H), 2.31 (s, 3H), 2.27 (s, 6H), 1.37 (t, 3H); MS (ESI) for C₂₃H₃₃ClN₈: 457 (MH⁺).

3-[4-(3-ethyl-1H-pyrazolo[3,4-d]pyrimidin-4-yl)piperazin-1-yl]-2-methyl-5-[(2-methylpropyl)oxy]-N-(2-pyrrolidin-1-ylethyl)aniline trifluoroacetate: ¹H NMR (400 MHz, d₄-methanol) δ 8.33 (s, 1H), 6.02 (m, 1H), 5.99 (m, 1H), 4.34-3.92 (m, 4H), 3.69-3.55 (m, 4H), 3.47 (t, 2H), 3.36 (t, 2H), 3.12-2.99 (m, 4H), 2.98-2.88 (m, 4H), 2.12-1.84 (m, 8H), 1.31 (t, 3H), 0.91 (d, 6H); MS (ESI) for C₂₃H₃₃ClN₈: 457 (MH⁺).

3-[4-(3-ethyl-1H-pyrazolo[3,4-d]pyrimidin-4-yl)piperazin-1-yl]-2-methyl-5-[(2-methylpropyl)oxy]-N-(2-pyrrolidin-1-ylethyl)aniline: $^1$H NMR (400 MHz, d$_4$-methanol) δ 8.30 (s, 1H), 7.15 (m, 1H), 7.04 (m, 1H), 4.09-3.80 (br m, 4H), 3.51 (t, 2H), 3.16-2.94 (m, 14H), 2.26 (s, 3H), 2.00-1.93 (m, 4H), 1.71-1.61 (m, 2H), 1.46-1.33 (m, 5H), 0.95 (t, 3H); MS (ESI) for C$_{29}$H$_{42}$ClN$_8$O: 519 (MH$^+$).

N,N-diethyl-2-({3-[4-(3-ethyl-1H-pyrazolo[3,4-d]pyrimidin-4-yl)piperazin-1-yl]phenyl}oxy)ethanamine: $^1$H NMR (400 MHz, CD$_3$OD) δ 8.43 (s, 1H), 7.24-7.20 (t, 1H), 6.70 (dd, 1H), 6.64 (t, 1H), 6.55 (dd, 1H), 4.33 (t, 2H), 4.20 (br s, 4H), 3.59 (t, 2H), 3.41 (t, 4H), 3.35 (t, 4H), 3.18 (m, 2H), 1.42-1.35 (m, 9H); MS (ESI) for C$_{23}$H$_{33}$N$_7$O: 424 (MH$^+$).

N,N-diethyl-2-({3-[4-(3-ethyl-1H-pyrazolo[3,4-d]pyrimidin-4-yl)piperazin-1-yl]-2-methylphenyl}oxy)ethanamine: $^1$H NMR (400 MHz, d$_4$-methanol) δ 8.44 (s, 1H), 7.17 (t, 1H), 6.81 (d, 1H), 6.80 (d, 1H), 4.31 (t, 2H), 4.26 (br s, 4H), 3.68 (t, 2H), 3.40 (m, 4H), 3.18 (m, 2H), 3.08 (t, 4H), 2.31 (s, 3H), 1.40 (m, 9H); MS (ESI) for C$_{24}$H$_{35}$N$_7$O: 438 (MH$^+$).

3-ethyl-4-(4-phenylpiperazin-1-yl)-1H-pyrazolo[3,4-d]pyrimidine: $^1$H NMR (400 MHz, d$_6$-DMSO) δ 13.35 (s, 1H), 8.32 (s, 1H), 7.18 (m, 2H), 7.10 (d, 1H), 7.07 (s, 1H), 6.94 (m, 1H), 3.81 (t, 3H), 3.31 (t, 4H), 2.98 (m, 2H), 1.29 (t, 3H); MS (EI) for C$_{17}$H$_{20}$N$_6$: 309 (MH$^+$).

3-ethyl-4-{4-[3-(methyloxy)phenyl]piperazin-1-yl}-1H-pyrazolo[3,4-d]pyrimidine: $^1$H NMR (400 MHz, d$_4$-methanol) δ 8.43 (s, 1H), 7.17 (t, 1H), 6.61 (dd, 1H), 6.55 (t, 1H), 6.48 (dd, 1H), 4.24 (br s, 4H), 3.78 (s, 3H), 3.41 (t, 4H), 3.20 (m, 2H), 1.42 (t, 3H); MS (ESI) for C$_{18}$H$_{22}$N$_6$O: 339 (MH$^+$).

Ethyl-4-[4-(3-ethyl-1H-pyrazolo]3,4-d]pyrimidin-4-yl)piperazin-1-yl]-2-(trifluoromethyl)pyrimidine-5-carboxylate: $^1$H NMR (400 MHz, d$_4$-methanol) δ 8.81 (s, 1H), 8.48 (s, 1H), 4.43 (m, 2H), 4.30 (t, 4H), 3.96 (t, 4H), 3.21 (q, 2H), 1.42 (m, 6H); MS (ESI) for C$_{19}$H$_{21}$F$_3$N$_8$O$_2$: 451 (MH$^+$).

4-{4-[3-chloro-5-(methyloxy)phenylpiperazin-1-yl}-3-ethyl-1H-pyrazolo[3,4-d]pyrimidine: $^1$H NMR (400 MHz, d$_4$-methanol) δ 8.44 (s, 1H), 6.61 (s, 1H), 6.46 (t, 3H), 4.23 (br s, 4H), 3.78 (s, 3H), 3.44 (t, 4H), 3.19 (q, 2H), 1.42 (t, 3H); MS (ESI) for C$_{18}$H$_{21}$ClN$_6$O: 373 (MH$^+$).

3-ethyl-4-{4-[4-trifluoromethyl)pyridin-2-yl]piperazin-1-yl}-1H-pyrazolo[3,4-d]pyrimidine: $^1$H NMR (400 MHz, d$_4$-methanol) δ 8.46 (s, 1H), 8.34 (d, 1H), 7.08 (s, 1H), 6.93 (dd, 1H), 4.27 (t, 4H), 3.92 (m, 4H), 3.21 (q, 2H), 1.43 (t, 3H); MS (ESI) for C$_{17}$H$_{18}$F$_3$N$_7$: 378 (MH$^+$).

4-{4-[5-chloro-2-methyl-3-(methyloxy)phenyl]piperazin-1-yl}-3-ethyl-1H-pyrazolo[3,4-d]pyrimidine: $^1$H NMR (400 MHz, d$_4$-methanol) δ 8.43 (s, 1H), 6.75 (d, 1H), 4.25 (br s, 4H), 3.83 (s, 3H), 3.19 (q, 2H), 3.07 (t, 4H), 2.21 (s, 3H), 1.42 (t, 3H); MS (ESI) for C$_{19}$H$_{23}$ClN$_6$O: 388 (MH$^+$).

3-ethyl-4-{4-[2-methyl-3-(methyloxy)phenyl]piperazin-1-yl}-1H-pyrazolo[3,4-d]pyrimidine: $^1$H NMR (400 MHz, d$_4$-methanol) δ 8.45 (s, 1H), 7.11 (t, 1H), 6.71 (t, 2H), 4.28 (br s, 4H), 3.81 (s, 3H), 3.19 (q, 2H), 3.07 (t, 4H), 2.24 (s, 3H), 1.41 (t, 3H); MS (ESI) for C$_{19}$H$_{24}$N$_6$O: 353 (MH$^+$).

2-({3-chloro-5-[4-(3-ethyl-1H-pyrazolo[3,4-d]pyrimidin-4-yl)piperazin-1-yl]phenyl}oxy)-N,N-diethylethanamine: $^1$H NMR (400 MHz, d$_4$-methanol) δ 8.42 (s, 1H), 6.70 (s, 1H), 6.55 (m, 2H), 487 (t, 2H), 3.60 (br s, 4H), 3.60-3.43 (t, 2H), 3.31 (m, 4H), 1.42-1.35 (m, 6H); MS (EI) for C$_{23}$H$_{32}$ClN$_7$O: 458 (MH$^+$).

4-(4-{3-chloro-4-[(2-piperidin-1-ylethyl)oxy]phenyl}piperazin-1-yl)-3-ethyl-1H-pyrazolo[3,4-d]pyrimidine trifluoroacetate: $^1$H NMR (400 MHz, d$_4$-methanol) δ 8.42 (s, 1H), 7.13 (d, 1H), 7.10 (d, 1H), 6.98 (dd, 1H), 4.36 (m, 2H), 4.19 (br s, 4H), 3.74 (m, 2H), 3.59 (m, 2H), 3.33 (m, 4H), 3.20-3.11 (m, 4H), 2.00 (m, 2H), 1.88-1.81 (m, 3H), 1.57 (m, 1H), 1.41 (t, 3H); MS (ESI) for C$_{24}$H$_{31}$ClN$_7$O: 470 (MH$^+$).

4-[4-(5-chloro-2-methyl-3-morpholin-4-ylphenyl)piperazin-1-yl]-3-ethyl-1H-pyrazolo[3,4-d]pyrimidine: $^1$H NMR (400 MHz, d$_6$-DMSO) δ 13.31 (s, 1H), 8.29 (s, 1H), 6.78 (d, 1H), 6.74 (d, 1H), 3.79 (m, 4H), 3.73 (m, 4H), 3.01 (m, 4H), 2.96 (q, 2H), 2.85 (m, 4H), 2.25 (s, 3H), 1.29 (t, 3H); MS (ESI) for C$_{22}$H$_{28}$ClN$_7$O: 442 (MH$^+$).

2-{[5-chloro-3-[4-(3-ethyl-1H-pyrazolo[3,4-d]pyrimidin-4-yl)piperazin-1-yl]-2-(methyloxy)phenyl]oxy}-N,N-dimethylethanamine trifluoroacetate: $^1$H NMR (400 MHz, d$_6$-DMSO) δ 9.65 (br s, 1H), 8.36 (br s, 1H), 6.90 (d, 1H), 6.69 (d, 1H), 4.33 (m, 2H), 3.87 (br s, 2H), 3.77 (s, 3H), 3.48 (4H buried under water peak), 3.20 (br s, 4H), 3.00 (q, 2H), 2.90 (m, 6H), 1.30 (t, 3H); MS (ESI) for C$_{22}$H$_{30}$ClN$_7$O$_2$: 260 (MH$^+$).

3-{5-chloro-3-[4-(3-ethyl-1H-pyrazolo[3,4-d]pyrimidin-4-yl)piperazin-1-yl]-2-methylphenyl}-N,N-dimethylprop-2-yn-1-amine trifluoroacetate: $^1$H NMR (400 MHz, d$_6$-DMSO) δ 8.35 (br s, 1H), 7.32 (d, 1H), 7.20 (d, 1H), 4.39 (s, 2H), 3.87 (br s, 2H), 3.46 (2H buried under water peak), 3.07-2.99 (m, 6H), 2.90 (s, 6H), 2.40 (s, 3H), 1.30 (t, 3H); MS (ESI) for C$_{23}$H$_{27}$ClN$_7$: 438 (MH$^+$).

N'-{5-chloro-3-[4-(3-ethyl-1H-pyrazolo[3,4-d]pyrimidin-4-yl)piperazin-1-yl]-2-methylphenyl}-N,N-dimethylethane-1,2-diamine hydrochloride: $^1$H NMR (400 MHz, d$_4$-methanol) δ 8.48 (s, 1H), 6.56 (m, 2H), 4.34 (br s, 4H), 3.58 (t, 2H), 3.41 (t, 2H), 3.21 (q, 2H), 3.07 (br s, 4H), 2.96 (s, 6H), 2.24 (s, 3H), 1.42 (t, 3H); MS (ESI) for C$_{22}$H$_{30}$ClN$_8$: 443 (MH$^+$).

3-{5-chloro-3-[4-(3-ethyl-1H-pyrazolo[3,4-d]pyrimidin-4-yl)piperazin-1-yl]-2-methylphenyl}-N,N-diethylpropan-1-amine hydrochloride: $^1$H NMR (400 MHz, d$_4$-methanol) δ 8.48 (s, 1H), 7.06 (d, 1H), 7.00 (d, 1H), 4.34 (br s, 4H), 3.28-3.20 (m, 8H), 3.09 (m, 4H), 2.76 (m, 2H), 2.40 (s, 3H), 2.00 (m, 2H), 1.44 (t, 3H), 1.33 (t, 6H); MS (ESI) for C$_{25}$H$_{36}$ClN$_7$: 470 (MH$^+$).

4-{4-[5-chloro-2-methyl-3-(3-pyrrolidin-1-ylpropyl)phenyl]piperazin-1-yl}-3-ethyl-1H-pyrazolo[3,4-d]pyrimidine hydrochloride: $^1$H NMR (400 MHz, d$_4$-methanol) δ 8.47 (s, 1H), 7.04 (d, 1H), 6.99 (d, 1H), 4.34 (br s, 4H), 3.67 (m, 2H), 3.29-3.19 (m, 6H), 3.14-3.06 (m, 6H), 2.76 (m, 2H), 2.39 (s, 3H), 2.19-2.14 (m, 2H), 2.06-1.98 (m, 4H), 1.44 (t, 3H); MS (ESI) for C$_{25}$H$_{34}$ClN$_7$: 468 (MH$^+$).

2-({5-chloro-3-[4-(3-ethyl-1H-pyrazolo[3,4-d]pyrimidin-4-yl)piperazin-1-yl]-2-methylphenyl}oxy)-N,N-dimethylethanamine hydrochloride: $^1$H NMR (400 MHz, d$_4$-methanol) δ 8.47 (s, 1H), 6.87 (d, 1H), 6.81 (d, 1H), 4.38 (m, 2H), 4.33 (br s, 4H), 3.67 (m, 2H), 3.22 (q, 2H), 3.10 (m, 4H), 3.04 (s, 6H), 2.30 (s, 3H), 1.43 (t, 3H); MS (ESI) for C$_{22}$H$_{30}$ClN$_7$O: 444 (MH$^+$).

2-({5-chloro-3-[4-(3-ethyl-1H-pyrazolo[3,4-d]pyrimidin-4-yl)piperazin-1-yl]-2-methylphenyl}oxy)-N,N-diethylethanamine hydrochloride: $^1$H NMR (400 MHz, d$_4$-methanol) δ 8.47 (s, 1H), 6.87 (d, 1H), 6.81 (d, 1H), 4.38 (m, 2H), 4.34 (br s, 4H), 3.69 (m, 2H), 3.43-3.37 (m, 4H), 3.22 (q, 2H), 3.10 (m, 4H), 2.29 (s, 3H), 1.45-1.39 (m, 9H); MS (ESI) for C$_{24}$H$_{34}$ClN$_7$O: 472 (MH$^+$).

4-(4-{5-chloro-2-methyl-3-[(2-pyrrolidin-1-ylethyl)oxy]phenyl}piperazin-1-yl)-3-ethyl-1H-pyrazolo[3,4-d]pyrimidine hydrochloride: $^1$H NMR (400 MHz, d$_4$-methanol) 8.47 (s, 1H), 6.86 (d, 1H), 6.81 (d, 1H), 4.36-4.30 (m, 6H), 3.79 (m, 2H), 3.73 (m, 2H), 3.27 (m, 2H), 3.22 (q, 2H), 3.10 (m, 4H), 2.31 (s, 3H), 2.22 (m, 2H), 2.08 (m, 2H), 1.43 (t, 3H); MS (ESI) for C$_{24}$H$_{32}$ClN$_7$O: 470 (MH$^+$).

5-chloro-3-[4-(3-ethyl-1H-pyrazolo[3,4-d]pyrimidin-4-yl)piperazin-1-yl]-2-methyl-N-(2-pyrrolidin-1-ylethyl)aniline hydrochloride: $^1$H NMR (400 MHz, d$_4$-methanol) δ

8.47 (s, 1H), 6.53 (s, 2H), 3.71 (m, 2H), 3.57 (t, 2H), 3.46 (t, 2H), 3.23-3.13 (m, 4H), 3.04 (br s, 4H), 2.23 (s, 3H), 2.18 (m, 2H), 2.05 (m, 2H), 1.42 (t, 3H); MS (ESI) for $C_{24}H_{33}ClN_8$: 469 (MH$^+$).

4-{4-[5-chloro-2-methyl-3-(3-morpholin-4-ylpropyl)phenyl]piperazin-1-yl}-3-ethyl-1H-pyrazolo[3,4-d]pyrimidine hydrochloride: $^1$H NMR (400 MHz, d$_4$-methanol) δ 8.47 (s, 1H), 7.05 (s, 1H), 6.99 (s, 1H), 4.33 (br s, 4H), 4.06 (d, 2H), 3.79 (t, 2H), 3.52 (d, 2H), 3.26-3.04 (m, 10H), 2.76 (m, 2H), 2.40 (s, 3H), 2.06 (m, 2H), 1.44 (t, 3H); MS (ESI) for $C_{25}H_{34}ClN_7O$: 484 (MH$^+$).

N'-{5-chloro-3-[4-(3-ethyl-1H-pyrazolo[3,4-d]pyrimidin-4-yl)piperazin-1-yl]-2-methylphenyl}-N,N-diethylethane-1,2-diamine: $^1$H NMR (400 MHz, d$_4$-methanol) δ 8.47 (s, 1H), 6.55 (m, 2H), 4.31 (br s, 4H), 3.60 (t, 2H), 3.40 (t, 2H), 3.32 (4H buried under solvent), 3.22 (q, 2H), 3.07 (br s, 4H), 2.24 (s, 3H), 1.43 (t, 3H), 1.35 (t, 6H); MS (ESI) for $C_{24}H_{35}ClN_8$: 471 (MH$^+$).

4-{4-[5-chloro-2-methyl-3-(3-piperidin-1-ylpropyl)phenyl]piperazin-1-yl}-3-ethyl-1H-pyrazolo[3,4-d]pyrimidine trifluoroacetate: $^1$H NMR (400 MHz, d$_4$-methanol) δ 8.39 (s, 1H), 7.03 (s, 1H), 7.00 (s, 1H), 4.14 (br s, 4H), 3.55 (d, 2H), 3.16 (m, 4H), 3.06 (br s, 4H), 2.94 (t, 2H), 2.74 (t, 2H), 2.38 (s, 3H), 2.06-1.95 (m, 4H), 1.85 (m, 1H), 1.78 (m, 2H), 1.54 (m, 1H), 1.43 (t, 3H); MS (ESI) for $C_{26}H_{36}ClN_7$: 482 (MH$^+$).

4-[4-(3-bromo-2-chloro-5-fluorophenyl)piperazin-1-yl]-3-ethyl-1H-pyrazolo[3,4-d]pyrimidine: $^1$H NMR (400 MHz, CDCl$_3$) δ 11.21 (s, 1H), 8.44 (s, 1H), 7.12 (dd, 1H), 6.76 (dd, 1H), 3.95 (m, 4H), 3.18 (m, 4H), 3.02 (q, 2H), 1.41 (t, 3H); MS (ESI) for $C_{17}H_{17}BrClFN_6$: 439 (MH$^+$).

2-chloro-3-[4-(3-ethyl-1H-pyrazolo[3,4-d]pyrimidin-4-yl)piperazin-1-yl]-5-fluoro-N-(2-pyrrolidin-1-ylethyl)aniline hydrochloride: $^1$H NMR (400 MHz, d$_4$-methanol) δ 8.47 (s, 1H), 6.44 (dd, 1H), 6.34 (dd, 1H), 4.32 (br s, 4H), 3.73 (m, 2H), 3.62 (t, 2H), 3.45 (t, 2H), 3.26-3.11 (m, 8H), 2.16 (m, 2H), 2.04 (m, 2H), 1.41 (t, 3H); MS (ESI) for $C_{23}H_{30}ClFN_8$: 473 (MH$^+$).

4-[4-(2,5-difluorophenyl)piperazin-1-yl]-3-ethyl-1H-pyrazolo[3,4-d]pyrimidine: $^1$H NMR (400 MHz, d$_6$-DMSO) δ 13.31 (s, 1H), 8.30 (s, 1H), 7.19 (m, 1H), 6.93 (m, 1H), 6.78 (m, 1H), 3.81 (m, 4H), 3.19 (m, 4H), 2.91 (q, 2H), 1.29 (t, 3H); MS (ESI) for $C_{17}H_{18}F_2N_6$: 345 (MH$^+$).

3-[4-(3-ethyl-1H-pyrazolo[3,4-d]pyrimidin-4-yl)piperazin-1-yl]-2-methyl-5-[(phenylmethyl)oxy]-N-(2-pyrrolidin-1-ylethyl)aniline hydrochloride: $^1$H NMR (400 MHz, d$_4$-methanol) δ 8.49 (s, 1H), 7.41 (m, 2H), 7.35 (m, 2H), 7.30 (m, 1H), 5.08 (s, 2H), 4.39 (br s, 4H), 3.71 (br s, 2H), 3.60 (t, 2H), 3.42 (t, 2H), 3.27-3.06 (m, 8H), 2.25 (s, 3H), 2.17 (br s, 2H), 2.05 (br s, 2H), 1.44 (t, 3H); MS (ESI) for $C_{31}H_{40}N_8O$: 542 (M+2).

methyl 1-(3-chlorophenyl)-4-(3-ethyl-1H-pyrazolo[3,4-d]pyrimidin-4-yl)piperazine-2-carboxylate trifluoroacetate: $^1$H NMR (400 MHz, d$_4$-methanol) δ 8.45 (s, 1H), 7.21 (m, 1H), 6.94 (s, 1H), 6.87-6.79 (m, 2H), 5.11-5.04 (d, 2H), 4.64-4.56 (d, 1H), 4.04-3.96 (d, 2H), 3.86-3.59 (m, 3H), 3.52 (s, 3H), 3.22-3.15 (m, 2H), 1.42-1.37 (m, 3H); MS (ESI) for $C_{19}H_{21}ClN_6O_2$: 401 (MH$^+$).

1-(3-chlorophenyl)-4-(3-ethyl-1H-pyrazolo[3,4-d]pyrimidin-4-yl)piperazine-2-carboxylic acid: $^1$H NMR (400 MHz, d$_6$-DMSO) δ 13.34 (s, 1H), 12.75 (s, 1H), 8.30 (s, 1H), 7.22-7.17 (m, 1H), 6.91 (s, 1H), 6.85 (d, 1H), 6.75 (d, 1H), 4.85 (s, 1H), 4.66 (d, 1H), 4.24 (d, 1H), 3.71-3.64 (d, 1H), 3.61-3.51 (m, 2H), 3.03-2.90 (m, 2H), 1.30-1.25 (m, 31H); MS (ESI) for $C_{18}H_{19}ClN_6O_2$: 387 (MH$^+$).

1-(3-chlorophenyl)-4-(3-ethyl-1H-pyrazolo[3,4-d]pyrimidin-4-yl)-N-methylpiperazine-2-carboxamide trifluoroacetate: $^1$H NMR (400 MHz, d$_6$-DMSO) δ 13.34 (s, 1H), 12.75 (s, 1H), 8.30 (s, 1H), 7.20 (m, 1H), 6.91 (s, 1H), 6.85 (d, 1H), 6.75 (d, 1H), 4.85 (s, 1H), 4.66 (d, 1H), 4.24 (d, 1H), 3.71-3.64 (d, 1H), 3.61-3.51 (m, 2H), 3.03-2.90 (m, 2H), 1.30-1.25 (m, 3H); MS (ESI) for $C_{19}H_{22}ClN_7O$: 400 (MH$^+$).

1-(3-chlorophenyl)-N-[2-(dimethylamino)ethyl]-4-(3-ethyl-1H-pyrazolo[3,4-d]pyrimidin-4-yl)piperazine-2-carboxamide trifluoracetate: $^1$H NMR (400 MHz, d$_6$-DMSO) δ 9.37 (s, 1H), 8.50 (s, 1H), 8.28 (s, 1H), 7.25 (m, 1H), 6.80 (m, 2H), 4.70-3.56 (m, 7H), 3.04-2.90 (m, 4H), 2.73 (d, 6H), 1.29-1.22 (m, 3H); MS (ESI) for $C_{22}H_{29}ClN_8O$: 457 (MH$^+$).

[1-(3-chlorophenyl)-4-(3-ethyl-1H-pyrazolo[3,4-d]pyrimidin-4-yl)piperazin-2-yl]methanol trifluoroacetate: $^1$H NMR (400 MHz, d$_4$-methanol) δ 8.48 (s, 1H), 7.25-7.19 (m, 1H), 6.96 (s, 1H), 6.88 (d, 1H), 6.80 (d, 1H), 4.73 (br s, 1H), 4.52 (br s, 1H), 4.13 (br s, 1H), 4.05-3.98 (m, 1H), 3.69-3.57 (m, 2H), 3.53-3.41 (m, 2H), 3.27-3.20 (m, 2H), 1.45-1.40 (m, 3H); MS (ESI) for $C_{18}H_{21}ClN_6O$: 373 (MH$^+$).

1-(3-chlorophenyl)-4-(3-ethyl-1H-pyrazolo[3,4-d]pyrimidin-4-yl)-N-(1-methylpiperidin-4-yl)piperazine-2-carboxamide trifluoroacetate: $^1$H NMR (400 MHz, d$_4$-methanol) δ 8.43 (s, 1H), 7.25 (m, 1H), 6.90-6.78 (m, 3H), 4.80 (d, 1H), 4.42 (s, 1H), 4.38-4.27 (m, 2H), 4.07 (br s, 1H), 3.85 (br s, 2H), 3.77-3.69 (m, 1H), 3.49 (d, 2H), 3.24-3.15 (m, 2H), 3.08-2.97 (m, 2H), 2.80 (s, 3H), 1.91 (br s, 2H), 1.80-1.64 (m, 2H), 1.42-1.36 (m, 3H); MS (ESI) for $C_{24}H_{31}ClN_8O$: 484 (MH$^+$).

1-(3-chlorophenyl)-4-(3-ethyl-1H-pyrazolo[3,4-d]pyrimidin-4-yl)-N-(2-morpholin-4-ylethyl)piperazine-2-carboxamide trifluoroacetate: $^1$H NMR (400 MHz, d$_4$-methanol) δ 8.40 (s, 1H), 7.17 (m, 1H), 6.85 (s, 1H), 6.77 (d, 2H), 4.77 (d, 1H), 4.52 (s, 1H), 4.25 (m, 2H), 4.07 (m, 1H), 3.88 (br s, 2H), 3.77-3.59 (m, 2H), 3.56-3.47 (m, 2H), 3.37 (m, 2H), 3.18-3.07 (m, 4H), 2.99 (br s, 2H), 1.33-1.28 (m, 3H); MS (ESI) for $C_{24}H_{31}ClN_8O_2$: 499 (MH$^+$).

4-[4-(5-chloro-2-methyl-3-{[2-(1-methylpiperidin-4-yl)ethyl]oxy}phenyl)piperazin-1-yl]-3-ethyl-1H-pyrazolo[3,4-d]pyrimidine trifluoroacetate: $^1$H NMR (400 MHz, d$_4$-methanol) δ 8.44 (s, 1H), 6.77 (s, 1H), 6.72 (s, 1H), 4.24 (br s, 4H), 4.06 (m, 2H), 3.52 (d, 2H), 3.17 (m, 2H), 3.06 (m, 4H), 2.99 (d, 2H), 2.86 (s, 3H), 2.21 (s, 3H), 2.08 (d, 2H), 1.85 (m, 3H), 1.52 (m, 2H), 1.43-1.37 (m, 3H); MS (ESI) for $C_{26}H_{36}ClN_7O$: 499 (MH$^+$).

4-[4-(5-chloro-2-methyl-3-{[2-(4-methylpiperazin-1-yl)ethyl]oxy}phenyl)piperazin-1-yl]-3-ethyl-1H-pyrazolo[3,4-d]pyrimidine hydrochloride: $^1$H NMR (400 MHz, d$_4$-methanol) δ 8.44 (s, 1H), 6.79 (s, 1H), 6.75 (s, 1H), 4.26 (br s, 4H), 4.15 (m, 2H), 3.47 (m, 2H), 3.25 (m, 2H), 3.18 (m, 2H), 3.13 (m, 2H), 3.07 (m, 4H), 3.00 (m, 4H), 2.88 (s, 3H), 2.22 (s, 3H), 1.43-1.38 (m, 3H); MS (ESI) for $C_{25}H_{35}ClN_8O$: 500 (MH$^+$).

4-[4-(5-chloro-2-methyl-3-{[(1-methylpiperidin-4-yl)methyl]oxy}phenyl)piperazin-1-yl]-3-ethyl-1H-pyrazolo[3,4-d]pyrimidine trifluoroacetate: MS (ESI) for $C_{27}H_{36}ClN_5O$: 483 (MH$^+$).

4-(4-{5-chloro-2-methyl-3-[3-(4-methylpiperazin-1-yl)propyl]phenyl}piperazin-1-yl)-3-ethyl-1H-pyrazolo[3,4-d]pyrimidine hydrochloride: $^1$H NMR (400 MHz, d$_4$-methanol) δ 8.48 (s, 1H), 7.06 (s, 1H), 6.99 (s, 1H), 4.33 (br s, 2H), 3.87 (br s, 4H), 3.62 (br s, 4H), 3.36 (m, 2H), 3.21 (m, 4H), 3.09 (m, 2H), 3.02 (m, 2H), 2.76 (m, 2H), 2.39 (s, 3H), 2.12 (m, 2H), 1.45-1.38 (m, 3H), 1.35-1.27 (m, 3H); MS (ESI) for $C_{26}H_{37}ClN_8$: 498 (MH$^+$).

5-bromo-3-[4-(3-ethyl-1H-pyrazolo[3,4-d]pyrimidin-4-yl)piperazin-1-yl]-2-methylaniline: $^1$H NMR (400 MHz, d$_6$-DMSO) δ 13.29 (s, 1H), 8.28 (s, 1H), 6.58 (s, 1H), 6.39 (s, 1H), 5.13 (s, 2H), 3.79 (br s, 4H), 3.00-2.93 (m, 2H), 2.92-2.88 (m, 4H), 1.99 (s, 3H), 1.31-1.26 (m, 3H); MS (ESI) for $C_{18}H_{22}BrN_7$: 417 (MH$^+$).

4-{4-[2-chloro-5-(trifluoromethyl)phenyl]piperazin-1-yl}-3-ethyl-1H-pyrazolo[3,4-d]pyrimidine trifluoroacetate: $^1$H NMR (400 MHz, d$_4$-methanol) δ 8.44 (s, 1H), 7.63 (d, 1H), 7.41 (s, 1H), 7.39 (d, 1H), 4.26 (br s, 4H), 3.30 (m, 4H), 3.21-3.15 (m, 2H), 1.46-1.40 (m, 4H); MS (ESI) for C$_{18}$H$_{18}$ClF$_3$N$_6$: 411 (MH$^+$).

3-bromo-5-[4-(3-ethyl-1H-pyrazolo[3,4-d]pyrimidin-4-yl)piperazin-1-yl]-4-methyl-N-phenylbenzamide trifluoroacetate: $^1$H NMR (400 MHz, d$_6$-DMSO) δ 13.31 (s, 1H), 10.22 (s, 1H), 8.31 (s, 1H), 7.94 (s, 1H), 7.73-7.68 (d, 2H), 7.64 (s, 1H), 7.37-7.31 (m, 2H), 7.12-7.07 (m, 1H), 3.86 (br s, 4H), 3.07 (br s, 4H), 3.02-2.95 (m, 2H), 2.46 (s, 3H), 1.33-1.27 (m, 3H); MS (ESI) for C$_{25}$H$_{26}$BrN$_7$O: 521 (MH$^+$).

4-[4-(3-Ethyl-1H-pyrazolo[3,4-d]pyrimidin-4-yl)piperazin-1-yl]-6,7-bis(methyloxy)quinazoline hydrochloride $^1$H NMR (400 MHz, d$_4$-methanol) δ 8.83 (s, 1H), 8.36 (s, 1H), 7.49 (s, 1H), 7.25 (s, 1H), 4.37-4.32 (m, 4H), 4.07-4.02 (m, 4H), 4.00 (s, 3H), 3.96 (s, 3H), 3.04-2.98 (q, 2H), 1.30-1.26 (t, 3H); MS (ESI) for C$_{21}$H$_{24}$N$_8$O$_2$: 421 W).

Example 6

4-[4-(5-chloro-2-methylphenyl)piperazin-1-yl]-3-propyl-1H-pyrazolo[3,4-d]pyrimidine To a suspension of sodium hydride (60% in mineral oil, 2.0 g, 50.0 mmol) in anhydrous THF (35 mL) was added dropwise a solution of malononitrile (3.0 g, 45.4 mmol) in THF (5 mL) at 0° C. The reaction was stirred at room temperature for 20 min, then cooled to 0° C. A solution of butyryl chloride (4.84 g, 45.4 mmol) in THF (10 mL) was added dropwise over 1 h, and the reaction mixture was stirred at room temperature for an additional 16 h. The reaction was concentrated, acidified with 2 N hydrochloric acid (30 mL) and extracted with ethyl acetate (3×50 mL). The combined organic extracts were dried over magnesium sulfate, and concentrated to give crude (1-hydroxybutylidene)propanedinitrile (3.12 g) as a brown oil.

To a solution of (1-hydroxybutylidene)propanedinitrile (288 mg, 2.12 mmol) in diethyl ether (1.5 mL) and methanol (1.5 mL) was added dropwise a solution of TMS-diazomethane in hexanes (2.0M, 483 mg, 4.24 mmol) at 0° C. The reaction was stirred at 0° C. for 3 h, and then quenched with glacial acetic acid (0.5 mL). The solution was basified with saturated sodium bicarbonate (100 mL), and extracted with ethyl acetate (3×25 mL). The combined organic layers were dried over magnesium sulfate, and concentrated. Column chromatography on silica (hexanes:ethyl acetate 1:1) afforded [1-(methyloxy)-butylidene]propanedinitrile (128 mg) as a tan oil.

A mixture of [1-(methyloxy)-butylidene]propanedinitrile (128 mg, 1.87 mmol) and hydrazine hydrate (187 mg, 3.74 mmol) in ethanol (3 mL) was stirred at 80° C. for 3 h, and then concentrated to give 5-amino-3-propyl-1H-pyrazole-4-carbonitrile (115 mg) as a tan oil. $^1$H NMR (400 MHz, d$_6$-DMSO) δ 5.87 (br s, 1H), 3.85 (s, 1H), 2.48-2.44 (m, 2H), 1.62-1.57 (m, 2H), 0.90-0.87 (m, 3H); MS (ESI) for C$_7$H$_{10}$N$_4$: 151 (MH$^+$).

A solution of 5-amino-3-propyl-1H-pyrazole-4-carbonitrile (115 mg, 0.77 mmol) in formic acid (4 mL) was heated at 110° C. for 4 h. The solution was concentrated, ethyl acetate (5 mL) was added, and the precipitate was filtered, and dried to afford 3-propyl-1H-pyrazolo[3,4-d]pyrimidin-4-ol (43.0 mg) as a tan solid.

A suspension of 3-propyl-1H-pyrazolo[3,4-d]pyrimidin-4-ol (43.0 mg, 0.24 mmol) in thionyl chloride (5 mL) and DMF (0.05 ml) was refluxed for 2 h under nitrogen. The solution was concentrated, added into saturated sodium bicarbonate (10 mL), and extracted with ethyl acetate (3×20 mL). The combined organic layers were washed with 5% lithium chloride (50 mL), dried with sodium sulfate, and concentrated to give 4-chloro-3-propyl-1H-pyrazolo[3,4-d]pyrimidine (37 mg). $^1$H NMR (400 MHz, d$_6$-DMSO) δ 8.76 (s, 1H), 7.93 (br s, 1H), 3.03-2.99 (m, 2H), 1.82-1.73 (m, 2H), 0.99-0.95 (m, 3H); MS (ESI) for C$_8$H$_9$ClN$_4$: 197 (MH$^+$).

A solution of 4-chloro-3-propyl-1H-pyrazolo[3,4-d]pyrimidine (35 mg, 0.18 mmol), diisopropylethylamine (24 mg, 0.19 mmol), and 1-(5-chloro-2-methylphenyl)piperazine (40 mg, 0.19 mmol) in THF (5 mL) was stirred at 50° C. for 2 h. The mixture was concentrated, and the remaining solid washed with methanol and dried to provide 4-[4-(5-chloro-2-methylphenyl)piperazin-1-yl]-3-propyl-1H-pyrazolo[3,4-d]pyrimidine (6 mg) as an off-white solid. $^1$H NMR (400 MHz, d$_4$-methanol) δ 8.31 (br s, 1H), 7.19 (d, 1H), 7.04 (s, 1H), 6.99 (d, 1H), 3.95-3.92 (m, 4H), 3.05 (m, 4H), 3.00 (d, 2H), 2.34 (s, 3H), 1.87-1.77 (m, 2H), 1.00-0.96 (m, 3H); MS (ESI) for C$_{19}$H$_{23}$ClN$_6$: 371 (MH$^+$).

Using the same or analogous synthetic techniques and/or substituting with alternative reagents, the following compounds of the invention were prepared:

4-[4-(5-chloro-2-methylphenyl)piperazin-1-yl]-3-(1-methylethyl)-1H-pyrazolo[3,4-d]pyrimidine: $^1$H NMR (400 MHz, d$_6$-DMSO) δ 13.38 (br s, 1H), 8.37 (s, 1H), 7.22 (d, 1H), 7.05 (m, 2H), 3.80 (br s, 4H), 3.38 (m, 1H), 3.02 (m, 4H), 2.29 (s, 3H), 1.34 (d, 6H); MS (ESI) for C$_{19}$H$_{23}$ClN$_6$: 371 (MH$^+$).

4-(4-{5-chloro-2-methyl-3-[(2-pyrrolidin-1-ylethyl)oxy]phenyl}piperazin-1-yl)-3-cyclopropyl-1H-pyrazolo[3,4-d]pyrimidine trifluoroacetate: $^1$H NMR (400 MHz, d$_4$-methanol) δ 8.42 (s, 1H), 6.84 (m, 2H), 4.40 (br s, 4H), 4.34 (t, 2H), 3.78 (m, 2H), 3.71 (t, 2H), 3.25 (m, 2H), 3.10 (m, 4H), 2.31 (m, 1H), 2.28 (s, 3H), 2.21 (m, 2H), 2.06 (m, 2H), 1.24 (m, 2H), 1.12 (m, 2H); MS (ESI) for C$_{25}$H$_{32}$ClN$_7$O: 482 (MH$^+$).

5-chloro-3-[4-(3-cyclopropyl-1H-pyrazolo[3,4-d]pyrimidin-4-yl)piperazin-1-yl]-2-methyl-N-(2-pyrrolidin-1-ylethyl)aniline trifluoroacetate: $^1$H NMR (400 MHz, d$_4$-methanol) δ 8.41 (s, 1H), 6.54 (m, 2H), 4.40 (br s, 4H), 3.72 (m, 2H), 3.56 (t, 2H), 3.46 (t, 2H), 3.15 (m, 2H), 3.06 (br s, 4H), 2.30 (m, 1H), 2.21 (s, 3H), 2.16 (m, 2H), 2.03 (m, 2H), 1.23 (m, 2H), 1.11 (m, 2H); MS (ESI) for C$_{25}$H$_{33}$ClN$_8$: 481 (MH$^+$).

4-[4-(5-chloro-2-methylphenyl)piperazin-1-yl]-3-(phenylmethyl)-1H-pyrazolo[3,4-d]pyrimidine: $^1$H NMR (400 MHz, d$_6$-DMSO) δ 13.5 (s, 1H), 8.33 (s, 1H), 7.34-7.26 (m, 2H), 7.24-7.17 (m, 4H), 7.07-7.00 (m, 1H), 6.99-6.96 (m, 1H), 4.39 (s, 2H), 3.75 (br s, 4H), 2.82 (br s, 4H), 2.24 (s, 3H); MS (ESI) for C$_{23}$H$_{23}$ClN$_6$: 419 (MH$^+$).

4-[4-(5-chloro-2-methylphenyl)piperazin-1-yl]-3-(2-methylpropyl)-1H-pyrazolo[3,4-d]pyrimidine: $^1$H NMR (400 MHz, d$_6$-DMSO) δ 13.38 (s, 1H), 8.32 (s, 1H), 7.24 (s, 1H), 7.04 (m, 2H), 3.83-3.77 (br s, 4H), 3.03-2.98 (br s, 4H), 2.83 (d, 2H), 2.29 (s, 1H), 2.19-2.08 (m, 1H), 0.89-0.84 (d, 6H); MS (ESI) for C$_{22}$H$_{27}$ClN$_4$: 383 (MH$^+$).

5-chloro-2-methyl-3-{4-[3-(2-methylpropyl)-1H-pyrazolo[3,4-d]pyrimidin-4-yl]piperazin-1-yl}-N-(2-pyrrolidin-1-ylethyl)aniline trifluoroacetate: $^1$H NMR (400 MHz, d$_4$-methanol) δ 8.41 (s, 1H), 6.53 (s, 2H), 4.29-4.01 (br s, 4H), 3.75-3.68 (m, 2H), 3.59-3.54 (m, 2H), 3.48-3.42 (m, 2H), 3.21-3.11 (m, 2H), 3.04-2.96 (m, 6H), 2.21 (s, 3H), 2.19-2.14 (d, 2H), 2.10 (m, 1H), 2.06-1.99 (m, 2H), 0.93-0.89 (d, 6H); MS (ESI) for C$_{26}$H$_{37}$ClN$_8$: 498 (MH$^+$).

4-(4-{5-chloro-2-methyl-3-[(2-pyrrolidin-1-ylethyl)oxy]phenyl}piperazin-1-yl)-3-(2-methylpropyl)-1H-pyrazolo[3,4-d]pyrimidine trifluoroacetate: $^1$H NMR (400 MHz, d$_4$-methanol) δ 8.44-8.39 (s, 1H), 6.87-6.84 (s, 1H), 6.81-

6.78 (s, 1H), 4.36-4.30 (m, 2H), 4.21-4.09 (br s, 4H), 3.82-3.74 (m, 2H), 3.73-3.69 (m, 2H), 3.08-3.03 (m, 6H), 3.01-2.96 (d, 2H), 2.30-2.27 (s, 3H), 2.24-2.18 (m, 2H), 2.15-2.00 (m, 3H), 0.94-0.89 (d, 6H); MS (ESI) for $C_{26}H_{36}ClN_7O$: 499 (MH$^+$).

4-(4-{5-chloro-2-methyl-3-[(2-pyrrolidin-1-ylethyl)oxy]phenyl}piperazin-1-yl)-3-(1-methylethyl)-1H-pyrazolo[3,4-d]pyrimidine trifluoroacetate: $^1$H NMR (400 MHz, $d_4$-methanol) δ 8.42 (s, 1H), 6.85 (s, 1H), 6.81 (s, 1H), 4.35 (m, 2H), 4.20-4.11 (br s, 4H), 3.83-3.75 (m, 2H), 3.72 (m, 2H), 3.58-3.49 (m, 1H), 3.30-3.24 (m, 2H), 3.10-3.05 (m, 4H), 2.29 (s, 3H), 2.26-2.17 (m, 2H), 2.13-2.04 (m, 2H), 1.48-1.43 (d, 6H); MS (ESI) for $C_{25}H_{34}ClN_7O$: 485 (MH$^+$).

5-chloro-2-methyl-3-{4-[3-(1-methylethyl)-1H-pyrazolo[3,4-d]pyrimidin-4-yl]piperazin-1-yl}-N-(2-pyrrolidin-1-ylethyl)aniline trifluoroacetate: $^1$H NMR (400 MHz, $d_4$-methanol) δ 8.41 (s, 1H), 6.54 (d, 2H), 4.29-4.00 (br s, 4H), 3.78-3.68 (m, 2H), 3.62-3.44 (m, 5H), 3.58-3.49 (m, 1H), 3.23-3.13 (m, 2H), 3.08-2.99 (br s, 4H), 2.23 (s, 3H), 2.21-2.15 (m, 2H), 2.09-2.01 (m, 2H), 1.48-1.42 (d, 6H); MS (ESI) for $C_{25}H_{35}ClN_8$: 484 (MH$^+$).

Example 7

4-[4-(5-chloro-2-methylphenyl)piperazin-1-yl]-3-({[2-(methyloxy)ethyl]oxy}methyl)-1H-pyrazolo[3,4-d]pyrimidine To a suspension of sodium hydride (60% in mineral oil, 1.21 g, 30.3 mmol) in THF (20 μL) was added dropwise a solution of malononitrile (1.00 g, 15.1 mmol) in THF (5 mL) at 0° C. The resulting mixture was stirred at room temperature for 1 h, and then cooled to 0° C. A solution of 2-(2-methoxyethoxy)acetyl chloride (2.31 g, 15.1 mmol) in THF (5 mL) was added slowly. The reaction mixture was stirred at room temperature for another 3 h, then added into 1N hydrochloric acid (50 mL), and extracted with ethyl acetate (3×50 mL). The combined organic layers were washed with water (25 mL), and brine (25 mL), dried with sodium sulfate, and concentrated to give (1-hydroxy-2-{[2-(methyloxy)ethyl]oxy}ethylidene)propanedinitrile (3.03 g) as a brown oil. $^1$H NMR (400 MHz, $d_6$-DMSO) δ 4.03 (s, 2H), 3.52 (m, 2H), 3.43 (m, 2H), 3.23 (s, 3H).

To a suspension of sodium hydride (60% in mineral oil, 0.27 g, 6.75 mmol) in DMF (5 mL) was added dropwise a solution of (1-hydroxy-2-{[2-(methyloxy)ethyl]oxy}-ethylidene)propanedinitrile (1.23 g, 6.75 mmol) in DMF (5 mL) at 0° C. The resulting mixture was stirred at room temperature for 30 min, and then cooled to 0° C. A solution of dimethylsulfate (0.85 g, 6.75 mmol) in DMF (5 mL) was added slowly, and the reaction mixture was stirred at room temperature for 24 h. More dimethylsulfate (0.85 g, 6.75 mmol) was added, and the reaction mixture was stirred at 50° C. for 12 h, and then at room temperature for 3 d. The resulting suspension was added into 1N hydrochloric acid (100 mL), and extracted with ethyl acetate (3×50 mL). The combined organic layers were washed with 5% lithium chloride (50 mL), water (50 mL), and brine (50 mL), dried with sodium sulfate, and concentrated. Column chromatography on silica (hexanes:ethyl acetate 1:1) afforded impure (1-(methyloxy)-2-{[2-(methyloxy)ethyl]oxy}ethylidene)-propanedinitrile (0.44 g) as a brown oil. $^1$H NMR (400 MHz, $d_6$-DMSO) δ 4.57 (s, 2H), 4.17 (s, 3H), 3.66 (m, 2H), 3.50 (m, 2H), 3.26 (s, 3H).

A solution of (1-(methyloxy)-2-{[2-(methyloxy)ethyl]oxy}ethylidene)propanedinitrile (436 mg, 2.22 mmol) and hydrazine monohydrate (206 mg, 4.12 mmol) in ethanol (5 mL) was stirred at room temperature for 19 h, and then concentrated to give crude 5-amino-3-({[2-(methyloxy)ethyl]oxy}methyl)-1H-pyrazole-4-carbonitrile.

A solution of 5-amino-3-({[2-(methyloxy)ethyl]oxy}methyl)-1H-pyrazole-4-carbonitrile in formic acid (5 mL) was refluxed for 24 h, and then concentrated to afford crude 3-({[2-(methyloxy)ethyl]oxy}methyl)-1H-pyrazolo[3,4-d]pyrimidin-4-ol.

Crude 3-({[2-(methyloxy)ethyl]oxy}methyl)-1H-pyrazolo[3,4-d]pyrimidin-4-ol was suspended in thionyl chloride (5 mL), DMF (188 mg, 2.57 mmol) was added, and the reaction mixture was refluxed for 90 min. The mixture was concentrated, the residue added into saturated sodium bicarbonate (50 mL), and extracted with ethyl acetate (3×30 mL). The organic layer was washed with 5% lithium chloride (20 mL), water (20 mL), and brine (20 mL), dried with sodium sulfate, and concentrated to afford crude 4-chloro-3-({[2-(methyloxy)ethyl]oxy}methyl)-1H-pyrazolo[3,4-d]pyrimidine (36 mg).

A solution of 4-chloro-3-({[2-(methyloxy)ethyl]oxy}methyl)-1H-pyrazolo[3,4-d]pyrimidine (36 mg), diisopropylethylamine (22 mg, 0.17 mmol), and 1-(5-chloro-2-methylphenyl)piperazine (30 mg, 0.14 mmol) in THF (5 mL) was stirred at 50° C. for 3 h. The mixture was concentrated, and the remaining solid washed with methanol and dried to provide 4-[4-(5-chloro-2-methylphenyl)piperazin-1-yl]-3-({[2-(methyloxy)ethyl]oxy}-methyl)-1H-pyrazolo[3,4-d]pyrimidine (6 mg) as an off-white solid. $^1$H NMR (400 MHz, $d_6$-DMSO) δ 8.28 (s, 1H), 7.17 (d, 1H), 7.05 (d, 1H), 6.98 (dd, 1H) 4.81 (s, 2H), 4.11 (m, 4H), 3.67 (m, 2H), 3.55 (m, 2H), 3.31 (s, 3H), 3.05 (m, 4H), 2.35 (s, 3H); MS (ESI) for $C_{20}H_{25}ClN_6O_2$: 417 (MH$^+$).

Example 8

3-bromo-4-[4-(5-chloro-2-methylphenyl)piperazin-1-yl]-1H-pyrazolo[3,4-d]pyrimidine To 3-bromo-4-chloro-1H-pyrazolo[3,4-d]pyrimidine (200 mg, 0.86 mmol, T. Y. H. Wu, P. G. Schultz, S. Ding, Org. Lett. 2003, 5, 3587-3590) in anhydrous dioxane (5 mL) was added triethylamine (0.17 mL, 1.20 mmol) and 1-(5-chloro-2-methylphenyl)-piperazine (254 mg, 1.20 mmol). The reaction mixture was stirred at 85° C. for 30 min, concentrated, and the solid residue was suspended in 2-propanol. The solid was filtered, washed with water and 2-propanol, and dried to provide 3-bromo-4-[4-(5-chloro-2-methylphenyl)piperazin-1-yl]-1H-pyrazolo[3,4-d]pyrimidine (150 mg, 43% yield) as a white solid. $^1$H NMR (400 MHz, $d_6$-DMSO) δ 8.37 (s, 1H), 7.22 (d, 1H), 7.08-7.03 (m, 2H), 3.94 (m, 4H), 3.05 (m, 4H), 2.29 (s, 3H); MS (ESI) for $C_{16}H_{16}BrClN_6$: 407 (MH$^+$).

Using the same or analogous synthetic techniques and/or substituting with alternative reagents, the following compounds of the invention were prepared:

N'-{3-[4-(3-bromo-1H-pyrazolo[3,4-d]pyrimidin-4-yl)piperazin-1-yl]-5-chloro-2-methylphenyl}-N,N-dimethylethane-1,2-diamine trifluoroacetate: 3H NMR (400 MHz, $d_4$-methanol) δ 8.32 (s, 1H), 6.58 (d, 1H), 6.54 (d, 1H), 4.07 (br s, 4H), 3.57 (t, 2H), 3.40 (t, 2H), 3.03 (m, 4H), 2.96 (s, 6H), 2.20 (s, 3H); MS (ESI) for $C_{20}H_{26}BrClN_8$: 495 (MH$^+$).

N'-{3-[4-(3-bromo-1H-pyrazolo[3,4-d]pyrimidin-4-yl)piperazin-1-yl]-5-chloro-2-methylphenyl}-N-methyl-N-(1-methylethyl)ethane-1,2-diamine hydrochloride: $^1$H NMR (400 MHz, $d_4$-methanol) δ 8.44 (s, 1H), 6.58 (m, 2H), 4.28 (br s, 4H), 3.68 (m, 1H), 3.59 (m, 2H), 3.47 (m, 1H), 3.24 (m, 1H), 3.11 (m, 4H), 2.87 (s, 3H), 2.22 (s, 3H), 1.37 (d, 3H), 1.32 (d, 3H); MS (ESI) for $C_{22}H_{30}BrClN_8$: 523 (MH$^+$).

3-[4-(3-bromo-1H-pyrazolo[3,4-d]pyrimidin-4-yl)piperazin-1-yl]-5-[(cyclopropylmethyl)oxy]-2-methyl-N-(2-pyrrolidin-1-ylethyl)aniline hydrochloride: $^1$H NMR (400 MHz, d$_4$-methanol) δ 8.20 (s, 1H), 4.12 (br s, 4H), 3.51 (d, 2H), 3.43 (m, 2H), 3.33 (m, 2H), 3.20 (m, 2H), 3.10 (br s, 4H), 2.86 (m, 2H), 1.97 (s, 3H), 1.85 (m, 2H), 1.74 (m, 2H), 0.90 (m, 1H), 0.28 (m, 2H), 0.01 (m, 2H); MS (ESI) for C$_{26}$H$_{35}$BrN$_8$O: 555, 557 (MH$^+$).

3-[4-(3-bromo-1H-pyrazolo[3,4-d]pyrimidin-4-yl)piperazin-1-yl]-2-methyl-5-[(3-methylbutyl)oxy]-N-(2-pyrrolidin-1-ylethyl)aniline hydrochloride: $^1$H NMR (400 MHz, d$_4$-methanol) δ 8.49 (s, 1H), 4.40 (br s, 4H), 4.00 (t, 2H), 3.74 (m, 2H), 3.63 (t, 2H), 3.50 (t, 2H), 3.38 (br s, 4H), 3.16 (m, 2H), 2.26 (s, 3H), 2.17 (m, 2H), 2.06 (m, 2H), 1.83 (m, 1H), 1.64 (m, 2H), 0.96 (d, 6H); MS (ESI) for C$_{27}$H$_{39}$BrN$_8$O: 551, 553 (MH$^+$).

3-[4-(3-bromo-1H-pyrazolo[3,4-d]pyrimidin-4-yl)piperazin-1-yl]-5-[(cyclohexylmethyl)oxy]-2-methyl-N-(2-pyrrolidin-1-ylethyl)aniline hydrochloride: $^1$H NMR (400 MHz, d$_4$-methanol) δ 8.45 (s, 1H), 4.32 (br s, 4H), 3.76 (m, 4H), 3.60 (t, 2H), 3.48 (t, 2H), 3.17 (m, 2H), 2.23 (s, 3H), 2.18 (m, 2H), 2.07 (m, 2H), 1.87 (m, 2H), 1.76 (m, 4H), 1.30 (m, 4H), 1.10 (m, 2H); MS (ESI) for C$_{29}$H$_{41}$BrN$_8$O: 597, 599 (MH$^+$).

3-[4-(3-bromo-1H-pyrazolo[3,4-d]pyrimidin-4-yl)piperazin-1-yl]-5-[(cyclopentylmethyl)oxy]-2-methyl-N-(2-pyrrolidin-1-ylethyl)aniline: $^1$H NMR (400 MHz, CDCl$_3$) δ 8.44 (s, 1H), 6.11 (d, 1H), 6.05 (d, 1H), 4.09 (br s, 4H), 3.80 (d, 2H), 3.28 (m, 2H), 3.06 (br s, 4H), 2.85 (m, 2H), 2.62 (br s, 4H), 2.14 (m, 1H), 2.10 (s, 3H), 1.82 (m, 6H), 1.61 (m, 4H), 1.35 (m, 2H); MS (ESI) for C$_{28}$H$_{39}$BrN$_8$O: 583, 585 (MH$^+$).

3-[4-(3-bromo-1H-pyrazolo[3,4-d]pyrimidin-4-yl)piperazin-1-yl]-2-methyl-5-(3-phenyl-1,2,4-oxadiazol-5-yl)-N-(2-pyrrolidin-1-ylethyl)aniline: $^1$H NMR (400 MHz, CDCl$_3$) δ 8.46 (s, 1H), 8.18 (m, 2H), 7.51 (m, 3H), 7.39 (s, 1H), 7.24 (s, 1H), 4.65 (s, 1H), 4.12 (br s, 4H), 3.40 (br s, 2H), 3.17 (m, 4H), 2.91 (m, 2H), 2.65 (br s, 4H), 2.25 (s, 3H), 1.84 (br s, 4H); MS (ESI) for C$_{30}$H$_{33}$BrN$_{10}$O: 629, 631 (MH$^+$).

3-[4-(3-bromo-1H-pyrazolo[3,4-d]pyrimidin-4-yl)piperazin-1-yl]-2-methyl-5-(3-methyl-1,2,4-oxadiazol-5-yl)-N-(2-pyrrolidin-1-ylethyl)aniline: $^1$H NMR (400 MHz, CDCl$_3$) δ 8.44 (s, 1H), 7.29 (s, 1H), 7.12 (s, 1H), 4.72 (s, 1H), 4.08 (br s, 4H), 3.39 (br s, 2H), 3.13 (m, 4H), 2.94 (br s, 2H), 2.68 (br s, 4H), 2.47 (s, 3H), 2.25 (s, 3H), 1.86 (br s, 4H); MS (ESI) for C$_{25}$H$_{31}$BrN$_{10}$O: 567, 569 (MH$^+$).

3-[4-(3-bromo-1H-pyrazolo[3,4-d]pyrimidin-4-yl)piperazin-1-yl]-5-(ethylsulfonyl)-2-methyl-N-(2-pyrrolidin-1-ylethyl)aniline: $^1$H NMR (400 MHz, CDCl$_3$) δ 8.46 (s, 1H), 7.01 (s, 1H), 6.88 (s, 1H), 4.75 (s, 1H), 4.08 (br s, 4H), 3.30 (m, 2H), 3.11 (m, 6H), 2.86 (m, 2H), 2.61 (br s, 4H), 2.21 (s, 3H), 1.83 (br s, 4H), 1.30 (t, 3H); MS (ESI) for C$_{24}$H$_{33}$BrN$_8$O$_2$S: 577, 579 (MH$^+$).

3-[4-(3-bromo-1H-pyrazolo[3,4-d]pyrimidin-4-yl)piperazin-1-yl]-2-methyl-5-(methylsulfonyl)-N-(2-pyrrolidin-1-ylethyl)aniline: $^1$H NMR (400 MHz, CDCl$_3$) δ 8.46 (s, 1H), 7.05 (s, 1H), 6.91 (s, 1H), 4.80 (s, 1H), 4.09 (br s, 4H), 3.32 (m, 2H), 3.11 (m, 4H), 3.05 (s, 3H), 2.88 (m, 2H), 2.63 (br s, 4H), 2.21 (s, 3H), 1.83 (br s, 4H); MS (ESI) for C$_{23}$H$_{31}$BrN$_8$O$_2$S: 563, 565 (MH$^+$).

5-bromo-3-[4-(3-bromo-1H-pyrazolo[3,4-d]pyrimidin-4-yl)piperazin-1-yl]-2-methyl-N-(2-pyrrolidin-1-ylethyl)aniline: $^1$H NMR (400 MHz, CDCl$_3$) δ 8.44 (s, 1H), 6.63 (d, 1H), 6.55 (s, 1H), 4.56 (s, 1H), 4.08 (br s, 4H), 3.26 (br s, 2H), 3.05 (m, 4H), 2.86 (br s, 2H), 2.61 (br s, 4H), 2.11 (s, 3H), 1.84 (br s, 4H); MS (ESI) for C$_{22}$H$_{28}$Br$_2$N$_8$: 565 (MH$^+$).

3-bromo-4-[4-(5-chloro-2-methyl-3-{[2-(4-methylpiperazin-1-yl)ethyl]oxy}phenyl)piperazin-1-yl]-1H-pyrazolo[3,4-d]pyrimidine hydrochloride: $^1$H NMR (400 MHz, d$_4$-methanol) δ 8.48 (s, 1H), 6.89 (m, 1H), 6.85 (m, 1H), 4.53-4.46 (m, 2H), 4.41-4.31 (m, 4H), 4.07-3.64 m, 10H), 3.23-3.16 (m, 4H), 3.05 (s, 3H), 2.31 (s, 3H); MS (ESI) for C$_{23}$H$_{30}$BrClN$_8$O: 549 (MH$^+$).

3-bromo-4-[4-(5-chloro-3-{[2-(4-ethylpiperazin-1-yl)ethyl]oxy}-2-methylphenyl)piperazin-1-yl]-1H-pyrazolo[3,4-d]pyrimidine hydrochloride: $^1$H NMR (400 MHz, d$_4$-methanol) δ 8.49 (s, 1H), 6.90 (m, 1H), 6.86 (m, 1H), 4.55-4.44 (m, 2H), 4.42-4.30 (m, 4H), 4.16-3.52 (m, 10H), 3.44-3.35 (m, 2H), 3.24-3.12 (m, 4H), 2.33 (s, 3H), 1.51-1.33 (m, 3H); MS (ESI) for C$_{24}$H$_{32}$BrClN$_8$O: 563 (MH$^+$).

3-[4-(3-bromo-1H-pyrazolo[3,4-d]pyrimidin-4-yl)piperazin-1-yl]-5-[(2-ethylbutyl)oxy]-2-methyl-N-(2-pyrrolidin-1-ylethyl)aniline hydrochloride: $^1$H NMR (400 MHz, d$_4$-methanol) δ 8.37 (s, 1H), 6.20 (br m, 1H), 6.12 (br m, 1H), 4.48-3.93 (m, 4H), 3.85 (d, 2H), 3.81-3.63 (m, 2H), 3.58 (t, 2H), 3.46 (t, 2H), 3.24-3.03 (m, 6H), 2.25-1.96 (m, 8H), 1.66-1.36 (m, 5H), 0.95 (t, 6H); MS (ESI) for C$_{28}$H$_{41}$BrN$_8$O: 585 (MH$^+$).

3-[4-(3-bromo-1H-pyrazolo[3,4-d]pyrimidin-4-yl)piperazin-1-yl]-5-[(2-ethylbutyl)oxy]-2-methyl-N-(2-pyrrolidin-1-ylethyl)aniline hydrochloride: $^1$H NMR (400 MHz, d$_4$-methanol) δ 8.50 (s, 1H), 4.67-4.14, (br m, 4H), 3.98 (t, 2H), 3.81-3.68 (br m, 2H), 3.64 (t, 2H), 3.50 (t, 2H), 3.45-3.33 (m, 4H), 3.23-3.09 (m, 2H), 2.27 (s, 3H), 2.24-1.97 (m, 4H), 1.73 (m, 2H), 1.49 (m, 2H), 0.97 (t, 3H); MS (ESI) for C$_{26}$H$_{37}$BrN$_8$O: 557 (MH$^+$).

3-[4-(3-bromo-1H-pyrazolo[3,4-d]pyrimidin-4-yl)piperazin-1-yl]-5-[(2,2-dimethylpropyl)oxy]-2-methyl-N-(2-pyrrolidin-1-ylethyl)aniline: $^1$H NMR (400 MHz, CDCl$_3$) δ 8.40 (s, 1H), 6.10 (m, 1H), 6.04 (m, 1H), 4.57-3.73 (br m, 4H), 3.56 (br m, 2H), 3.38-3.29 (br m, 2H), 3.12-2.99 (br m, 4H), 2.95-2.85 (br m, 2H), 2.77-2.63 (br m, 4H), 2.10 (s, 3H), 1.91-1.78 (br m, 4H), 1.32-1.16 (br m, 1H), 1.02 (m, 9H); MS (ESI) for C$_{27}$H$_{39}$BrN$_8$O: 571 (MH$^+$).

3-[4-(3-bromo-1H-pyrazolo[3,4-d]pyrimidin-4-yl)piperazin-1-yl]-2-methyl-N-(2-pyrrolidin-1-ylethyl)-5-[(tetrahydrofuran-2-ylmethyl)oxy]aniline acetate: $^1$H NMR (400 MHz, d$_4$-methanol) δ 8.30 (s, 1H), 6.14 (m, 1H), 6.09 (m, 1H), 4.29-3.72 (m, 10H), 3.42 (t, 2H), 3.14-2.93 (m, 10H), 2.16-1.84 (m, 12H), 1.83-1.71 (m, 1H); MS (ESI) for C$_{27}$H$_{37}$BrN$_8$O$_2$: 585 (MH$^+$).

3-[4-(3-bromo-1H-pyrazolo[3,4-d]pyrimidin-4-yl)piperazin-1-yl]-2-methyl-5-{[2-(methyloxy)ethyl]oxy}-N-(2-pyrrolidin-1-ylethyl)aniline hydrochloride: $^1$H NMR (400 MHz, d$_4$-methanol) δ 8.32 (s, 1H), 6.12 (m, 1H), 6.05 (m, 1H), 4.24-3.83 (m, 6H), 3.74-3.54 (m, 6H), 3.48 (t, 2H), 3.37 (t, 2H), 3.32 (s, 3H), 3.17-2.90 (m, 5H), 2.17-1.86 (m, 6H); MS (ESI) for C$_{25}$H$_{35}$BrN$_8$O$_2$: 559 (MH$^+$).

1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}pentan-1-one: $^1$H NMR (400 MHz, d$_4$-methanol) δ 8.31 (s, 1H), 7.16 (m, 1H), 7.05 (m, 1H), 4.41-3.76 (m, 4H), 3.49-3.43 (m, 2H), 3.15-3.04 (m, 4H), 3.03-2.96 (m, 4H), 2.93-2.83 (m, 4H), 2.26 (s, 3H), 2.00-1.85 (m, 4H), 1.72-1.60 (m, 2H), 1.46-1.34 (m, 2H), 0.95 (t, 3H); MS (ESI) for C$_{27}$H$_{37}$BrN$_8$O: 569 (MH$^+$).

{3-[4-(3-bromo-1H-pyrazolo[3,4-d]pyrimidin-4-yl)piperazin-1-yl]-4-methyl-5-[(2-pyrrolidin-1-ylethyl)amino]phenyl}(phenyl)methanone trifluoroacetate: $^1$H NMR (400 MHz, d$_4$-methanol) δ 8.32 (s, 1H), 7.80-7.76 (m, 2H), 7.67-7.60 (m, 1H), 7.56-7.49 (m, 2H), 6.92 (m, 2H), 4.25-3.93 (m, 4H), 3.78-3.67 (m, 2H), 3.61 (t, 2H), 3.47 (t, 2H), 3.22-3.10 (m, 2H), 3.09-3.00 (m, 4H), 2.34 (s, 3H), 2.26-1.94 (m, 4H); MS (ESI) for C$_{29}$H$_{33}$BrN$_8$O: 589 (MH$^+$).

1-{3-[4-(3-bromo-1H-pyrazolo[3,4-d]pyrimidin-4-yl)piperazin-1-yl]-4-methyl-5-[(2-pyrrolidin-1-ylethyl)amino]

phenyl}propan-1-one acetate: ¹H NMR (400 MHz, d₄-methanol) δ 8.26 (s, 1H), 7.19 (br s, 1H), 7.05 (br s, 1H), 4.36-3.81 (br m, 4H), 3.56 (t, 2H), 3.25 (t, 2H), 3.21-3.12 (m, 4H), 3.11-2.96 (m, 6H), 2.27 (s, 3H), 2.04-1.98 (m, 4H), 1.91 (s, 3H), 1.16 (t, 3H); MS (ESI) for $C_{25}H_{33}BrN_8O$: 541 (MH⁺).

1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-one: ¹H NMR (400 MHz, d₄-methanol) δ 8.32 (s, 1H), 7.16 (br s, 1H), 7.05 (br s, 1H), 4.41-3.71 (br m, 4H), 3.46 (t, 2H), 3.16-3.04 (m, 4H), 3.03-2.92 (m, 4H), 2.91-2.80 (m, 4H), 2.25 (s, 3H), 1.99-1.86 (m, 4H), 1.79-1.63 (m, 2H), 0.99 (t, 3H); MS (ESI) for $C_{26}H_{35}BrN_8O$: 555 (MH⁺).

3-[4-(3-bromo-1H-pyrazolo[3,4-d]pyrimidin-4-yl)piperazin-1-yl]-N,4-dimethyl-N-(methyloxy)-5-[(2-pyrrolidin-1-ylethyl)amino]benzamide: ¹H NMR (400 MHz, d₄-methanol) δ 8.31 (s, 1H), 6.80 (br s, 1H), 6.70 (br s, 1H), 4.37-3.77 (br m, 4H), 3.6 (s, 3H), 3.49 (t, 2H), 3.33 (s, 3H), 3.23-2.97 (m, 10H), 2.24 (s, 3H), 2.03-1.94 (m, 4H); MS (ESI) for $C_{25}H_{34}BrN_9O_2$: 572 (MH⁺).

1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}ethanone trifluoroacetate: ¹H NMR (400 MHz, d₄-methanol) δ 8.34 (s, 1H), 7.23 (s, 1H), 7.07 (s, 1H), 4.36-3.88 (br m, 4H), 3.79-3.69 (m, 2H), 3.65 (t, 2H), 3.50 (t, 2H), 3.24-3.03 (m, 6H), 2.59 (s, 3H), 2.30 (s, 3H), 2.24-1.96 (m, 4H); MS (ESI) for $C_{24}H_{31}BrN_8O$: 527 (MH⁺).

3-[4-(3-bromo-1H-pyrazolo[3,4-d]pyrimidin-4-yl)piperazin-1-yl]-5-{[(2,2-difluorocyclopropyl)methyl]oxy}-2-methyl-N-(2-pyrrolidin-1-ylethyl)aniline: ¹H NMR (400 MHz, d₄-methanol) δ 8.21 (s, 1H), 6.04 (s, 1H), 5.99 (s, 1H), 4.05-3.95 (m, 1H), 3.88-3.77 (m, 1H), 3.31 (t, 2H), 3.02-2.77 (m, 10H), 2.06-1.90 (m, 4H), 1.89-1.82 (m, 4H), 1.56-1.41 (m, 1H), 1.27-1.13 (m, 1H); MS (ESI) for $C_{26}H_{33}BrF_2N_8O$: 591 (MH⁺).

1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}-4,4,4-trifluorobutan-1-one hydrochloride: ¹H NMR (400 MHz, d₄-methanol) δ 8.39 (s, 1H), 7.27 (m, 1H), 7.09 (m, 1H), 4.51-3.88 (m, 4H), 3.80-3.71 (m, 2H), 3.67 (t, 2H), 3.52 (t, 2H), 3.36-3.29 (m, 2H), 3.24-3.08 (m, 6H), 2.69-2.51 (m, 2H), 2.33 (s, 3H), 2.27-1.96 (m, 4H); MS (ESI) for $C_{26}H_{32}BrF_3N_8O$: 609 (MH⁺).

{3-[4-(3-bromo-1H-pyrazolo[3,4-d]pyrimidin-4-yl)piperazin-1-yl]-4-methyl-5-[(2-pyrrolidin-1-ylethyl)amino]phenyl}(cyclopropyl)methanone trifluoroacetate: ¹H NMR (400 MHz, d₄-methanol) δ 8.33 (s, 1H), 7.33 (s, 1H), 7.08 (s, 1H), 4.42-3.85 (br m, 4H), 3.78-3.68 (m, 2H), 3.65 (t, 2H), 3.50 (t, 2H), 3.23-3.05 (m, 6H), 2.91-2.78 (m, 1H), 2.31 (s, 3H), 2.24-1.94 (m, 4H), 1.18-1.00 (m, 4H); MS (ESI) for $C_{26}H_{33}BrN_8O$: 553 (MH⁺).

3-bromo-4-[4-(5-chloro-2-methyl-3-{[(1-methylpiperidin-4-yl)methyl]oxy}phenyl)piperazin-1-yl]-1H-pyrazolo[3,4-d]pyrimidine hydrochloride: ¹H NMR (400 MHz, d₄-methanol) δ 8.36 (s, 1H), 6.76 (m, 2H), 4.14 (br s, 4H), 3.93 (d, 2H), 3.60 (d, 2H), 3.10 (m, 6H), 2.90 (s, 3H), 2.23 (s, 3H), 2.17 (m, 3H), 1.72 (q, 2H); MS (ESI) for $C_{23}H_{29}BrClN_7O$: 536 (MH⁺).

3-bromo-4-[4-(5-chloro-2-methyl-3-{[2-(1-methylpiperidin-4-yl)ethyl]oxy}phenyl)piperazin-1-yl]-1H-pyrazolo[3,4-d]pyrimidine hydrochloride: ¹H NMR (400 MHz, d₄-methanol) δ 8.41 (s, 1H), 6.76 (m, 2H), 4.22 (br s, 4H), 4.07 (t, 2H), 3.53 (m, 2H), 3.12 (m, 4H), 3.03 (m, 2H), 2.87 (s, 3H), 2.22 (s, 3H), 2.10 (m, 2H), 2.04-1.83 (m, 3H), 1.53 (m, 2H); MS (ESI) for $C_{24}H_{31}BrClN_7O$: 550 (MH⁺).

3-[4-(3-bromo-1H-pyrazolo[3,4-d]pyrimidin-4-yl)piperazin-1-yl]-2-chloro-5-fluoro-N-(2-pyrrolidin-1-ylethyl)aniline hydrochloride: ¹H NMR (400 MHz, d₄-methanol) δ 8.47 (s, 1H), 6.45 (dd, 1H), 6.38 (dd, 1H), 4.31 (br s, 4H), 3.73 (m, 2H), 3.62 (t, 2H), 3.45 (t, 2H), 3.26 (m, 4H), 3.15 (m, 2H), 2.17 (m, 2H), 2.03 (m, 2H); MS (ESI) for $C_{21}H_{25}BrClFN_8$: 523 (MH⁺).

3-bromo-4-[4-(2,5-difluorophenyl)piperazin-1-yl]-1H-pyrazolo[3,4-d]pyrimidine: ¹H NMR (400 MHz, d₆-DMSO) δ 8.35 (s, 1H), 7.19 (m, 1H), 6.93 (m, 1H), 6.79 (m, 1H), 3.94 (m, 4H), 3.22 (m, 4H); MS (ESI) for $C_{15}H_{13}F_2N_6$: 397 (MH⁺).

3-({3-[4-(3-Bromo-1H-pyrazolo[3,4-d]pyrimidin-4-yl)piperazin-1-yl]-5-chloro-2-methylphenyl}oxy)-N,N-diethylpropan-1-amine hydrochloride: ¹H NMR (400 MHz, d₄-methanol) δ 8.41 (s, 1H), 6.74 (s, 1H), 6.71 (s, 1H), 4.11-4.08 (t, 2H), 3.98-3.93 (m, 4H), 3.55-3.35 (m, 4H), 3.28-3.16 (m, 4H), 3.01-3.00 (t, 2H), 2.24-2.17 (m, 5H), 1.39-1.35 (t, 6H); MS (ESI) for $C_{23}H_{31}BrClN_7O$: 536 (MH⁺).

3-Bromo-4-(4-{5-chloro-2-methyl-3-[(3-pyrrolidin-1-ylpropyl)oxy]phenyl}piperazin-1-yl)-1H-pyrazolo[3,4-d]pyrimidine hydrochloride: ¹H NMR (400 MHz, d₄-methanol) δ 8.47 (s, 1H), 6.80 (s, 2H), 6.71 (s, 1H), 4.37-4.33 (m, 4H), 4.13-4.10 (t, 2H), 3.77-3.72 (m, 2H), 3.46-3.32 (m, 2H), 3.18-3.14 (m, 6H), 2.31-2.20 (m, 7H), 2.11-2.03 (m, 2H); MS (ESI) for $C_{23}H_{29}BrClN_7O$: 534 (MH⁺).

3-Bromo-4-[4-(5-chloro-2-methyl-3-{[3-(4-methylpiperazin-1-yl)propyl]oxy}phenyl)piperazin-1-yl]-1H-pyrazolo[3,4-d]pyrimidine hydrochloride: ¹H NMR (400 MHz, d₄-methanol) δ 8.45 (s, 1H), 6.81-6.79 (m, 2H), 4.33-4.27 (m, 4H), 4.15-4.13 (t, 2H), 4.00-3.45 (m, 12H), 3.17-3.14 (t, 4H), 3.05 (s, 3H), 2.39-2.33 (m, 2H), 2.26 (s, 3H); MS (ESI) for $C_{24}H_{32}BrClN_8O$: 563 (MH⁺).

3-Bromo-4-[4-(5-chloro-3-{[3-(4-ethylpiperazin-1-yl)propyl]oxy}-2-methylphenyl)piperazin-1-yl]-1H-pyrazolo[3,4-d]pyrimidine hydrochloride: ¹H NMR (400 MHz, d₄-methanol) δ 8.45 (s, 1H), 6.81-6.79 (m, 2H), 4.34-4.29 (m, 4H), 4.15-4.13 (t, 2H), 4.00-3.48 (m, 8H), 3.40-3.35 (q, 2H), 3.27-3.25 (m, 2H), 3.17-3.14 (t, 4H), 2.39-2.33 (m, 2H), 2.26 (s, 3H), 1.45-1.42 (t, 3H); MS (ESI) for $C_{25}H_{34}BrClN_8O$: 577 (MH⁺).

3-bromo-5-[4-(3-bromo-1H-pyrazolo[3,4-d]pyrimidin-4-yl)piperazin-1-yl]-4-methyl-N-phenylbenzamide: ¹H NMR (400 MHz, d₆-DMSO) δ 10.26 (s, 1H), 8.39 (s, 1H), 7.97 (s, 1H), 7.74 (d, 2H), 7.67 (s, 1H), 7.39-7.33 (m, 2H), 7.14-7.09 (m, 1H), 4.05-3.95 (br s, 4H), 3.15-3.09 (m, 4H), 2.47 (s, 3H); MS (ESI) for $C_{23}H_{21}Br_2N_7O$: 572 (MH⁺).

3-[4-(3-bromo-1H-pyrazolo[3,4-d]pyrimidin-4-yl)piperazin-1-yl]-5-[(cyclobutylmethyl)oxy]-2-methyl-N-(2-pyrrolidin-1-ylethyl)aniline: ¹H NMR (400 MHz, CDCl₃) δ 8.43 (s, 1H), 6.11 (s, 1H), 6.05 (s, 1H), 4.40-4.32 (br s, 1H), 4.16-4.09 (m, 2H), 3.93-3.89 (d, 2H), 3.30-3.22 (br s, 2H), 3.09-3.03 (m, 2H), 2.87-2.80 (br s, 2H), 2.79-2.71 (m, 1H), 2.64-2.53 (br s, 4H), 2.19-2.12 (m, 2H), 2.11-2.09 (s, 3H), 1.97-1.87 (m, 2H), 1.84-1.78 (m, 4H), 1.29-1.24 (m, 2H); MS (ESI) for $C_{2-17}H_{37}BrN_8O$: 570 (MH⁺).

3-[4-(3-bromo-1H-pyrazolo[3,4-d]pyrimidin-4-yl)piperazin-1-yl]-5-(ethyloxy)-2-methyl-N-(2-pyrrolidin-1-ylethyl)aniline hydrochloride: ¹H NMR (400 MHz, d₄-methanol) δ 8.31 (s, 1H), 6.10 (s, 1H), 6.05 (s, 1H), 4.10-3.94 (m, 6H), 3.04-2.98 (br s, 4H), 2.89-2.85 (m, 2H), 2.77-2.72 (br s, 4H), 2.11 (s, 3H), 1.90-1.86 (m, 4H), 1.37-1.31 (m, 3H); MS (ESI) for $C_{24}H_{33}BrN_8O$: 530 (MH⁺).

3-[4-(3-bromo-1H-pyrazolo[3,4-d]pyrimidin-4-yl)piperazin-1-yl]-2-methyl-5-[(1-methylethyl)oxy]-N-(2-pyrrolidin-1-ylethyl)aniline hydrochloride: MS (ESI) for $C_{25}H_{35}BrN_8O$: 544 (MH⁺).

3-[4-(3-bromo-1H-pyrazolo[3,4-d]pyrimidin-4-yl)piperazin-1-yl]-2-methyl-5-(propyloxy)-N-(2-pyrrolidin-1-ylethyl)aniline acetate: $^1$H NMR (400 MHz, d$_4$-methanol) δ 8.30 (s, 1H), 6.14 (s, 1H), 6.07 (s, 1H), 4.28-3.91 (br s, 4H), 3.90-3.86 (m, 2H), 3.45-3.39 (m, 2H), 3.12-3.06 (m, 2H), 3.06-2.96 (m, 8H), 2.13-2.12 (s, 3H), 1.99-1.93 (m, 4H), 1.80-1.70 (m, 2H), 1.05-1.00 (m, 3H); MS (ESI) for C$_{25}$H$_{35}$BrN$_8$O: 544 (MH$^+$).

3-[4-(3-bromo-1H-pyrazolo[3,4-d]pyrimidin-4-yl)piperazin-1-yl]-2-methyl-5-(phenylethynyl)-N-(2-pyrrolidin-1-ylethyl)aniline: $^1$H NMR (400 MHz, d$_4$-methanol) δ 8.32 (s, 1H), 7.49-7.46 (d, 2H), 7.36-7.32 (m, 3H), 6.76 (s, 1H), 6.69 (s, 1H), 3.78-3.66 (m, 4H), 3.63-3.59 (m, 2H), 3.50-3.45 (m, 2H), 3.26-3.19 (m, 4H), 3.09-3.04 (m, 4H), 2.27 (s, 3H), 2.14-2.07 (m, 4H); MS (ESI) for C$_{30}$H$_{33}$BrN$_8$: 586 (MH$^+$).

3-[4-(3-bromo-1H-pyrazolo[3,4-d]pyrimidin-4-yl)piperazin-1-yl]-5-ethynyl-2-methyl-N-(2-pyrrolidin-1-ylethyl)aniline trifluoroacetate: $^1$H NMR (400 MHz, d$_4$-methanol) δ 8.32 (s, 1H), 6.72 (s, 1H), 6.63 (s, 1H), 4.17-3.95 (br s, 4H), 3.75-3.69 (br s, 2H), 3.59-3.55 (m, 2H), 3.49-3.44 (m, 2H), 2.28 (s, 1H), 3.20-3.12 (m, 2H), 3.07-3.01 (br s, 4H), 2.24 (s, 3H), 2.21-2114 (m, 2H), 2.07-2.00 (m, 2H); MS (ESI) for C$_{24}$H$_{29}$BrN$_8$: 510 (MH$^+$).

3-[4-(3-bromo-1H-pyrazolo[3,4-d]pyrimidin-4-yl)piperazin-1-yl]-5-(3,3-dimethylbut-1-yn-1-yl)-2-methyl-N-(2-pyrrolidin-1-ylethyl)aniline trifluoroacetate: $^1$H NMR (400 MHz, d$_4$-methanol) δ 8.32 (s, 1H), 6.59 (s, 1H), 6.50 (s, 1H), 4.30-3.86 (br s, 4H), 3.76-3.68 (br s, 2H), 3.59-3.54 (m, 2H), 3.49-3.43 (m, 2H), 3.21-3.12 (m, 2H), 3.05-2.98 (br s, 4H), 2.22 (s, 3H), 2.19-2.13 (m, 2H), 2.07-1.98 (m, 2H), 1.31-1.28 (s, 9H); MS (ESI) for C$_{29}$H$_{37}$BrN$_8$: 566 (MH$^+$).

3-[4-(3-bromo-1H-pyrazolo[3,4-d]pyrimidin-4-yl)piperazin-1-yl]-5-(3,3-dimethylbutyl)-2-methyl-N-(2-pyrrolidin-1-ylethyl)aniline: $^1$H NMR (400 MHz, d$_4$-methanol) δ 8.32 (s, 1H), 6.42 (s, 1H), 6.34 (s, 1H), 4.30-3.84 (br s, 4H), 3.75-3.67 (m, 2H), 3.54 (m, 2H), 3.35 (m, 2H), 3.25-3.19 (m, 2H), 3.03 (br s, 4H), 2.53-2.47 (m, 2H), 2.19 (s, 3H), 2.06 (m, 4H), 1.52-1.45 (m, 2H), 0.97 (s, 9H); MS (ESI) for C$_{28}$H$_{41}$BrN$_8$: 570 (MH$^+$).

3-[4-(3-bromo-1H-pyrazolo[3,4-d]pyrimidin-4-yl)piperazin-1-yl]-5-ethyl-2-methyl-N-(2-pyrrolidin-1-ylethyl)aniline trifluoroacetate: $^1$H NMR (400 MHz, d$_4$-methanol) δ 8.34 (s, 1H), 6.49 (s, 1H), 6.40 (s, 1H), 4.22-3.90 (br s, 4H), 3.80-3.67 (br s, 2H), 3.62-3.56 (m, 2H), 3.54-3.48 (m, 2H), 3.22-3.06 (m, 4H), 2.62-2.50 (m, 2H), 2.19 (s, 3H), 2.07-2.00 (m, 4H), 1.22-1.19 (m, 3H); MS (ESI) for C$_{24}$H$_{33}$BrN$_8$: 514 (MH$^+$).

3-[4-(3-bromo-1H-pyrazolo[3,4-d]pyrimidin-4-yl)piperazin-1-yl]-2-methyl-N-(2-pyrrolidin-1-ylethyl)-5-[2-(trimethylsilyl)ethyl]aniline trifluouroacetate: $^1$H NMR (400 MHz, d$_4$-methanol) δ 8.39 (s, 1H), 6.47 (s, 1H), 6.41 (s, 1H), 4.22-3.90 (br s, 4H), 3.80-3.65 (m, 2H), 3.50-3.46 (m, 2H), 3.15 (br s, 6H), 2.60 (m, 2H), 2.21 (s, 3H), 2.20-2.00 (m, 4H), 0.84-0.81 (m, 2H), 0.02 (s, 9H); MS (ESI) for C$_{27}$H$_{41}$BrN$_8$Si: 586 (MH$^+$).

3-[4-(3-bromo-1H-pyrazolo[3,4-d]pyrimidin-4-yl)piperazin-1-yl]-2-methyl-5-(2-phenylethyl)-N-(2-pyrrolidin-1-ylethyl)aniline acetate: $^1$H NMR (400 MHz, d$_4$-methanol) δ 8.29 (s, 1H), 7.23-7.17 (m, 2H), 7.12-7.09 (m, 3H), 6.29 (s, 1H), 6.24 (s, 1H), 4.18-3.77 (br s, 4H), 3.35-3.32 (m, 2H), 2.97-2.78 (m, 14H), 2.13 (s, 3H), 1.93-1.88 (m, 4H); MS (ESI) for C$_{30}$H$_{37}$BrN$_8$: 590 (MH$^+$).

3-bromo-5-[4-(3-bromo-1H-pyrazolo[3,4-d]pyrimidin-4-yl)piperazin-1-yl]-N-(2-pyrrolidin-1-ylethyl)aniline acetate: $^1$H NMR (400 MHz, d$_4$-methanol) δ 8.30 (s, 1H), 6.48 (s, 1H), 6.35 (s, 1H), 6.21 (s, 1H), 4.03-3.98 (m, 4H), 3.42-3.37 (m, 2H), 3.36-3.32 (m, 4H), 3.14-3.06 (m, 6H), 2.02-1.96 (m, 4H); MS (ESI) for C$_{21}$H$_{26}$Br$_2$N$_8$: 551 (MH$^+$).

3-[4-(3-bromo-1H-pyrazolo[3,4-d]pyrimidin-4-yl)piperazin-1-yl]-5-chloro-N-(2-pyrrolidin-1-ylethyl)aniline acetate: $^1$H NMR (400 MHz, d$_4$-methanol) δ 8.31 (s, 1H), 6.32 (s, 1H), 6.17 (s, 2H), 4.03-3.99 (m, 4H), 3.35-3.32 (m, 4H), 2.88 (m, 2H), 2.80-2.77 (m, 4H), 1.91-1.87 (m, 6H); MS (ESI) for C$_{21}$H$_{26}$BrClN$_8$: 506 (MH$^+$).

1-{3-[4-(3-bromo-1H-pyrazolo[3,4-d]pyrimidin-4-yl)piperazin-1-yl]-5-[(2-pyrrolidin-1-ylethyl)amino]phenyl}butan-1-one acetate: $^1$H NMR (400 MHz, d$_4$-methanol) δ 8.24 (s, 1H), 6.91 (s, 1H), 6.72 (s, 1H), 6.48 (s, 1H), 4.54 (br s, 2H), 3.99-3.94 (m, 4H), 3.48-3.42 (m, 2H), 3.34-3.24 (m, 8H), 2.89-2.84 (m, 2H), 2.01-1.93 (br s, 4H), 1.67-1.57 (m, 2H, 0.92-0.86 (m, 3H); MS (ESI) for C$_{25}$H$_{33}$BrN$_8$O: 542 (MH$^+$).

3-[4-(3-bromo-1H-pyrazolo[3,4-d]pyrimidin-4-yl)piperazin-1-yl]-2-methyl-N-(2-pyrrolidin-1-ylethyl)-5-[(3,3,3-trifluoropropyl)oxy]aniline: $^1$H NMR (400 MHz, d$_4$-methanol) δ 8.30 (s, 1H), 6.10 (s, 1H), 4.19-4.15 (m, 2H), 3.41-3.36 (m, 2H), 3.02 (br s, 4H), 2.83-2.79 (m, 2H), 2.71-2.59 (m, 6H), 2.11 (s, 3H), 1.88-1.84 (m, 4H), 1.29 (m, 2H), 0.91-0.82 (m, 2H); MS (ESI) for C$_{25}$H$_{32}$BrF$_3$N$_8$O: 598 (MH$^+$).

Example 9

4-[4-(5-chloro-2-methylphenyl)piperazin-1-yl]-3-phenyl-1H-pyrazolo[3,4-d]pyrimidine A solution of 5-amino-3-phenyl-1H-pyrazole-4-carbonitrile (341 mg, 1.85 mmol, R. J. Bantems, J. D. Anderson, D. F. Smee, A. Jin, H. A. Alaghamandan, B. S. Sharma, W. B. Jolley, R. K. Robins, H. B. Cottam, *J. Med. Chem.* 1990, 33, 2174-2178) in formic acid (5 mL) was refluxed for 12 h. After cooling to room temperature, methanol (5 mL) was added, the precipitate was filtered, washed with methanol (2×3 mL), and dried to give 3-phenyl-1H-pyrazolo[3,4-d]pyrimidin-4-ol (190 mg, 48% yield) as a tan tan solid. $^1$H NMR (400 MHz, d$_6$-DMSO) δ 13.90 (br s, 1H), 12.21 (br s, 1H), 8.36 (d, 2H), 8.05 (s, 1H), 7.50-7.36 (m, 3H); MS (ESI) for C$_{11}$H$_8$N$_4$O: 213 (MH$^+$).

A mixture of 3-phenyl-1H-pyrazolo[3,4-d]pyrimidin-4-ol (95 mg, 0.45 mmol) and DMF (0.5 mL) in 5 ml of thionyl chloride was refluxed for 3 h. The reaction mixture was concentrated, the residue was added into saturated sodium bicarbonate (50 mL), and extracted with ethyl acetate (3×30 mL). The organic layer was washed with 5% lithium chloride (20 mL), water (20 mL), and brine (20 mL), dried with sodium sulfate, and concentrated to afford 4-chloro-3-phenyl-1H-pyrazolo[3,4-d]pyrimidine (104 mg, 100% yield) as a brown solid. $^1$H NMR (400 MHz, d$_6$-DMSO) δ 8.86 (s, 1H), 7.78 (m, 2H), 7.54 (m, 3H); MS (ESI) for C$_{11}$H$_7$ClN$_4$: 231 (MH$^+$).

A mixture of 4-chloro-3-phenyl-1H-pyrazolo[3,4-d]pyrimidine (100 mg, 0.43 mmol), diisopropylethylamine (67 mg, 0.52 mmol), and 1-(5-chloro-2-methylphenyl)-piperazine (91 mg, 0.43 mmol) in dry THF (5 mL) was stirred at 50° C. for 5 h, and then concentrated. The remaining solid was washed with methanol and dried to provide 4-[4-(5-chloro-2-methylphenyl)piperazin-1-yl]-3-phenyl-1H-pyrazolo[3,4-d]pyrimidine (90 mg, 51% yield) as a pale yellow solid. $^1$H NMR (400 MHz, d$_6$-DMSO) δ 13.91 (br s, 1H), 8.44 (s, 1H), 7.70 (m, 2H), 7.55 (m, 2H), 7.46 (m, 1H), 7.15 (d, 1H), 7.00 (dd, 1H), 6.92 (d, 1H), 3.53 (m, 4H), 2.74 (m, 4H), 2.15 (s, 3H); MS (ESI) for C$_{22}$H$_{21}$ClN$_6$: 405 (MH$^+$).

Example 10

4-[4-(5-chloro-2-methylphenyl)piperazin-1-yl]-N-phenyl-1H-pyrazolo[3,4-d]pyrimidin-3-amine A mixture of 4-hydroxy-N-phenyl-1H-pyrazolo[3,4-d]pyrimidin-3-amine (102 mg, 0.45 mmol, Y. Tominaga, Y. Honkawa, M. Hara, A. Hosami, *J. Heterocycl. Chem.* 1990, 27, 775-783) and phosphoryl chloride (5 mL) was refluxed for 2 h. The reaction mixture was concentrated, the residue was added into saturated sodium bicarbonate (50 mL), and extracted with ethyl acetate (3×30 mL). The combined organic layers were washed with brine (30 mL), dried with sodium sulfate, and concentrated to afford 4-chloro-N-phenyl-1H-pyrazolo[3,4-d]pyrimidin-3-amine (67 mg, 61% yield) as a yellow solid. $^1$H NMR (400 MHz, $d_6$-DMSO) δ 13.60 (s, 1H), 8.70 (s, 1H), 8.20 (s, 1H), 7.59 (m, 2H), 7.29 (m, 2H), 6.91 (m, 1H); MS (ESI) for $C_{11}H_8ClN_5$: 246 (MH$^+$).

A mixture of 4-chloro-N-phenyl-1H-pyrazolo[3,4-d]pyrimidine-3-amine (60 mg, 0.24 mmol), diisopropylethylamine (37 mg, 0.29 mmol), and 1-(5-chloro-2-methylphenyl)piperazine (50 mg, 0.24 mmol) in anhydrous THF (5 mL) was stirred at 50° C. for 2 h. The reaction mixture was concentrated, and the remaining solid washed with methanol and purified by reverse phase HPLC to provide 4-[4-(5-chloro-2-methylphenyl)-piperazin-1-yl]-N-phenyl-1H-pyrazolo[3,4-d]pyrimidine-3-amine (18 mg, 17% yield) as a yellow solid. $^1$H NMR (400 MHz, $d_6$-DMSO) δ 13.14 (s, 1H), 8.63 (s, 1H), 8.29 (s, 1H), 7.20 (m, 3H), 7.00 (dd, 1H), 6.93 (d, 2H), 6.82 (t, 1H), 6.76 (d, 1H), 3.87 (br s, 4H), 2.59 (m, 4H), 2.19 (s, 3H); MS (ESI) for $C_{22}H_{22}ClN_7$: 420 (MH$^+$).

Example 11

4-{4-[4-(5-chloro-2-methylphenyl)piperazin-1-yl]-1H-pyrazolo[3,4-d]pyrimidin-3-yl}phenol A mixture of 3-bromo-4-[4-(5-chloro-2-methylphenyl)piperazin-1-yl]-1H-pyrazolo[3,4-d]pyrimidine (50.0 mg, 0.12 mmol), 4-hydroxyphenylboronic acid (51.0 mg, 0.37 mmol), [1,1'-bis(diphenylphosphino)ferrocene]dichloropalladium(II) complex with dichloromethane (1:1) (20 mg, 0.025 mmol), and triethylamine (0.051 mL, 0.37 mmol) in dry DMF (1 mL) was stirred at 140° C. for 16 h. The reaction mixture was cooled, diluted with ethyl acetate (10 mL), and filtered over celite. The filtrate was washed with water and brine, dried over sodium sulfate, and concentrated. The oily residue was purified by reverse phase HPLC. The product containing fraction was concentrated and isolated as the hydrochloride salt by evaporating three times with a solution of 4N hydrochloric acid in dioxane to give 4-{4-[4-(5-chloro-2-methylphenyl)piperazin-1-yl]-1H-pyrazolo[3,4-d]-pyrimidin-3-yl}phenol hydrochloride (25 mg, 44% yield) as a white solid. $^1$H NMR (400 MHz, $d_6$-DMSO) δ 9.73 (br s, 1H), 8.41 (s, 1H), 7.52 (d, 2H), 7.16 (d, 1H), 7.02-6.97 (dd, 1H), 6.94-6.90 (m, 3H), 3.55 (m, 4H), 2.78 (m, 4H), 2.17 (s, 3H); MS (ESI) for $C_{22}H_{21}ClN_6O$: 421 (MH$^+$).

Using the same or analogous synthetic techniques and/or substituting with alternative reagents, the following compounds of the invention were prepared:

3-{4-[4-(5-chloro-2-methylphenyl)piperazin-1-yl]-1H-pyrazolo[3,4-d]pyrimidin-3-yl}phenol hydrochloride: $^1$H NMR (400 MHz, $d_4$-methanol) δ 8.45 (s, 1H), 7.39 (t, 1H), 7.13 (dd, 2H), 7.07 (m, 1H), 6.96 (m, 3H), 3.75 (m, 4H), 2.81 (m, 4H), 2.22 (s, 3H); MS (ESI) for $C_{22}H_{21}ClN_6O$: 421 (MH$^+$).

4-[4-(5-chloro-2-methylphenyl)piperazin-1-yl]-3-{3-[(phenylmethyl)oxy]phenyl}-1H-pyrazolo[3,4-d]pyrimidine hydrochloride: $^1$H NMR (400 MHz, $d_4$-methanol) δ 8.45 (s, 1H), 7.52 (t, 1H), 7.44 (d, 1H), 7.36-7.21 (m, 6H), 7.14 (d, 1H), 6.98 (dd, 1H), 6.92 (d, 1H), 5.20 (s, 2H), 3.77 (br s, 4H), 2.78 (m, 4H), 2.22 (s, 3H); MS (ESI) for $C_{29}H_{27}ClN_6O$: 511 (MH$^+$).

3-(1,3-benzodioxol-5-yl)-4-[4-(5-chloro-2-methylphlenyl)piperazin-1-yl]-1H-pyrazolo[3,4-d]pyrimidine hydrochloride: $^1$H NMR (400 MHz, $d_6$-DMSO) δ 8.45 (s, 1H), 7.26 (d, 1H), 7.17 (d, 2H), 7.12 (d, 1H), $O_2$ (dd, 1H), 6.94 (d, 1H), 6.11 (s, 2H), 3.58 (m, 4H), 2.80 (m, 4H), 2.19 (s, 3H); MS (ESI) for $C_{23}H_{21}ClN_6O_2$: 449 (MH$^+$).

4-[4-(5-chloro-2-methylphenyl)piperazin-1-yl]-3-(2-thienyl)-1H-pyrazolo[3,4-d]pyrimidine hydrochloride: $^1$H NMR (400 MHz, $d_6$-DMSO) δ 8.45 (s, 1H), 7.68 (d, 1H), 7.44 (d, 1H), 7.26 (t, 1H), 7.17 (d, 1H), 7.01 (dd, 1H), 6.97 (d, 1H), 3.61 (m, 4H), 2.84 (m, 4H), 2.12 (s, 3H); MS (ESI) for $C_{20}H_{19}ClN_6S$: 411 (MH$^+$).

3-{4-[4-(5-chloro-2-methylphenyl)piperazin-1-yl]-1H-pyrazolo[3,4-d]pyrimidin-3-yl}aniline hydrochloride: $^1$H NMR (400 MHz, $d_4$-methanol) δ 8.96 (br s, 2H), 8.52 (s, 1H), 7.52 (t, 1H), 7.20 (d, 1H), 7.12 (d, 1H), 7.08 (d, 1H), 7.02 (dd, 1H), 6.97 (m, 2H), 3.88 (m, 4H), 2.83 (m, 4H), 2.22 (s, 3H); MS (ESI) for $C_{22}H_{22}ClN_7$: 420 (MH$^+$).

3-{4-[4-(5-chloro-2-methylphenyl)piperazin-1-yl]-1H-pyrazolo[3,4-d]pyrimidin-3-yl}benzoic acid hydrochloride: $^1$H NMR (400 MHz, $d_4$-methanol) δ 8.51 (s, 1H), 8.37 (s, 1H), 8.20 (d, 1H), 7.99 (d, 1H), 7.72 (t, 1H), 7.11 (d, 1H), 6.97-6.90 (m, 2H), 3.77 (m, 4H), 2.81 (m, 4H), 1.93 (s, 3H); MS (ESI) for $C_{23}H_{21}ClN_6O_2$: 449 (MH$^+$).

4-[4-(5-chloro-2-methylphenyl)piperazin-1-yl]-3-(4-methylphenyl)-1H-pyrazolo[3,4-d]pyrimidine hydrochloride: $^1$H NMR (400 MHz, $d_4$-methanol) δ 8.53 (s, 1H), 7.56 (d, 2H), 7.45 (d, 2H), 7.12 (d, 1H), 6.97 (dd, 1H), 6.92 (d, 1H), 3.89 (m, 4H), 2.81 (m, 4H), 2.22 (s, 6H); MS (ESI) for $C_{22}H_{23}ClN_6$: 421 (MH$^+$).

N-(4-{4-[4-(5-chloro-2-methylphenyl)piperazin-1-yl]-1H-pyrazolo[3,4-d]pyrimidin-3-yl}phenyl)acetamide hydrochloride: $^1$H NMR (400 MHz, $d_4$-methanol) δ 8.52 (s, 1H), 7.83 (d, 2H), 7.63 (d, 2H), 7.12 (d, 1H), 6.96 (dd, 1H), 6.93 (d, 1H), 3.89 (m, 4H), 2.82 (m, 4H), 2.22 (s, 3H), 2.16 (s, 3H); MS (ESI) for $C_{24}H_{24}ClN_7O$: 462 (MH$^+$).

4-[4-(5-chloro-2-methylphenyl)piperazin-1-yl]-3 {4-[2-morphholin-4-ylethyl)oxy]phenyl}-1H-pyrazolo[3,4-d]pyrimidine: $^1$H NMR (400 MHz, $d_4$-methanol) δ 8.47 (s, 1H), 7.70 (s, 1H), 7.68 (s, 1H), 7.26 (s, 1H), 7.24 (s, 1H), 7.13 (d, 1H), 6.97 (dd, 1H), 6.94 (s, 1H), 4.48 (t, 4H), 4.04 (s, 2H), 3.76 (s, 4H), 3.68 (t, 4H), 2.80 (s, 4H), 2.12 (s, 3H); MS (ESI) for $C_{28}H_{32}ClN_7O_2$: 534 (MH$^+$).

3-[(4-{4-[4-(5-chloro-2-methylphenyl)piperazin-1-yl]-1H-pyrazolo[3,4-d]pyrimidin-3-yl}phenyl)oxy]-N,N-dimethylpropan-1-amine: $^1$HNMR (400 MHz, $d_4$-methanol) δ 8.48 (s, 1H), 7.65 (s, 1H), 7.63 (s, 1H), 7.20 (s, 1H), 7.18 (s, 1H), 7.13 (s, 1H), 6.97 (dd, 1H), 6.93 (d, 1H), 4.21 (t, 4H), 3.38 (t, 2H), 2.95 (s, 6H), 2.81 (s, 4H), 2.27 (m, 3H), 2.22 (s, 4H); MS (ESI) for $C_{27}H_{32}ClN_7O$: 506 (MH$^+$).

4-[4-(5-chloro-2-methylphenyl)piperazin-1-yl]-3-(1,2,3,6-tetrahydropyridin-4-yl)-1H-pyrazolo[3,4-d]pyrimidine: $^1$H NMR (400 MHz, $d_4$-methanol) δ 8.42 (s, 1H), 7.17 (d, 1H), 7.00 (m, 2H), 6.23 (s, 1H), 3.98 (s, 6H), 3.53 (t, 4H), 3.00 (t, 4H); MS (ESI) for $C_{21}H_{24}ClN_7$: 411 (MH$^+$).

4-[4-(5-chloro-2-methylphenyl)piperazin-1-yl]-3-(piperidin-4-ylmethyl)-1H-pyrazolo[3,4-d]pyrimidine trifluoroacetate: $^1$H NMR (400 MHz, $d_4$-methanol) δ 8.32 (s, 1H), 7.09 (d, 1H), 6.97-6.89 (m, 2H), 4.03 (br.s, 4H), 3.32-3.24 (m, 2H), 3.07-2.95 (m, 6H), 2.89 (t, 2H), 2.26 (s, 3H), 2.16-2.00 (m, 1H), 1.83-1.68 (m, 2H), 1.46-1.30 (m, 2H), MS (ESI) for $C_{22}H_{28}ClN_7$: 426 (MH$^+$).

4-[4-(5-Chloro-2-methylphenyl)piperazin-1-yl]-3-[4-(methyloxy)phenyl]-1H-pyrazolo[3,4-d]pyrimidine hydrochloride: $^1$H NMR (400 MHz, d$_4$-methanol) δ 8.51 (s, 1H), 7.60 (d, 2H), 7.17 (d, 2H), 7.12 (d, 1H), 6.98-6.95 (d, d 1H), 6.92 (s 1H), 3.93-3.88 (m, 4H), 3.89 (s, 3H), 2.87-2.82 (m, 4H), 2.24 (s, 3H); MS (ESI) for $C_{23}H_{23}ClN_6O$: 435 (MH$^+$).

4-[4-(5-Chloro-2-methylphenyl)piperazin-1-yl]-3-(4-fluorophenyl)-1H-pyrazolo[3,4-d]pyrimidine hydrochloride: $^1$H NMR (400 MHz, d$_4$-methanol) δ 8.54 (s, 1H), 7.73 (m, 2H), 7.41-7.36 (m, 2H), 7.13 (d, 1H), 6.98-6.95 (d, d 1H), 6.92 (s, 1H), 3.93-3.89 (m, 4H), 2.86-2.81 (m, 4H), 2.23 (s, 3H); MS (ESI) for $C_{22}H_{20}ClFN_6$: 423 (MH$^+$).

4-[4-(5-Chloro-2-methylphenyl)piperazin-1-yl]-3-[4-(phenyloxy)phenyl]-1H-pyrazolo[3,4-d]pyrimidine hydrochloride: $^1$H NMR (400 MHz, d$_4$-methanol) δ 8.53 (s, 1H), 7.65 (d, 2H), 7.38-7.35 (m, 2H), 7.20-7.14 (m, 4H), 7.06 (m, 1H), 6.99 (d, d 1H), 6.93 (s 1H), 3.98-3.88 (m, 4H), 2.89-2.83 (m, 4H), 2.27 (s, 3H); MS (ESI) for $C_{28}H_{25}ClN_6O$: 497 (MH$^+$).

4-[4-(5-Chloro-2-methylphenyl)piperazin-1-yl]-3-{4-[(piperidin-4-ylmethyl)oxy]phenyl}-1H-pyrazolo[3,4-d]pyrimidine hydrochloride: $^1$H NMR (400 MHz, d$_4$-methanol) δ 8.50 (s, 1H), 7.63-7.60 (d, 2H), 7.18 (d, 2H), 7.13 (d, 1H), 6.97 (d, d, 1H), 6.92 (d, 1H), 4.02 (d, 2H), 3.94-3.84 (m, 4H), 3.47-3.44 (d, 2H), 3.09-3.03 (t, d, 2H), 2.87-2.80 (m, 4H), 2.24 (s, 3H), 2.23-2.18 (m, 1H), 2.14-2.10 (d, 2H), 1.71-1.06 (q, d, 2H); MS (ESI) for $C_{28}H_{32}ClN_7O$: 518 (MH$^+$).

4-[4-(5-Chloro-2-methylphenyl)piperazin-1-yl]-3-[2-(methyloxy)phenyl]-1H-pyrazolo[3,4-d]pyrimidine hydrochloride: $^1$H NMR (400 MHz, d$_4$-methanol) δ 8.40 (s, 1H), 7.53-7.48 (d, d, d, 1H), 7.45-7.43 (d, d, 1H), 7.14-7.10 (d, 1H), 7.10-7.06 (t, d, 1H), 7.01 (d, d, 1H), 6.87-6.84 (d, d, 1H), 6.80 (d, 1H), 3.82-3.74 (m, 7H), 2.88-2.81 (m, 4H), 2.11 (s, 3H); MS (ESI) for $C_{23}H_{23}ClN_6O$: 435 (MH$^+$).

4-[4-(5-Chloro-2-methylphenyl)piperazin-1-yl]-3-pyridin-4-yl-1H-pyrazolo[3,4-d]pyrimidine hydrochloride: $^1$H NMR (400 MHz, d$_4$-methanol) δ 8.82 (b, 2H), 8.40 (s, 1H), 8.26 (d, 2H), 7.01 (d, 1H), 6.86-6.83 (m, 2H), 3.69-3.63 (m, 4H), 2.79-2.74 (m, 4H), 2.14 (s, 3H); MS (ESI) for $C_{21}H_{20}ClN_7$: 406 (MH$^+$).

4-[4-(5-Chloro-2-methylphenyl)piperazin-1-yl]-3-[3-(methyloxy)phenyl]-1H-pyrazolo[3,4-d]pyrimidine trifluoroacetate: $^1$H NMR (400 MHz, d$_4$-methanol) δ 8.53 (s, 1H), 7.56-7.52 (t, 1H), 7.24-7.17 (m, 3H), 7.13 (d, d 1H), 6.99-6.96 (d, d, 2H), 6.93 (d, 1H), 3.94-3.88 (m, 7H), 2.86-2.78 (m, 4H), 2.23 (s, 3H); MS (ESI) for $C_{23}H_{23}ClN_6O$: 435 (MH$^+$).

4-{4-[4-(5-Chloro-2-methylphenyl)piperazin-1-yl]-1H-pyrazolo[3,4-d]pyrimidin-3-yl}benzonitrile trifluoroacetate: $^1$H NMR (400 MHz, d$_4$-methanol) δ 8.53 (s, 1H), 7.99-7.96 (d, 2H), 7.89 (d, 2H), 7.12 (d, 1H), 6.98-6.93 (m, 2H), 3.88-3.81 (m, 4H), 2.87-2.82 (m, 4H), 2.24 (s, 3H); MS (ESI) for $C_{23}H_{20}ClN_7O$: 430 (MH$^+$).

4-[4-(5-Chloro-2-methylphenyl)piperazin-1-yl]-3-(3-fluoropyridin-4-yl)-1H-pyrazolo[3,4-d]pyrimidine trifluoroacetate: $^1$H NMR (400 MHz, d$_4$-methanol) δ 8.63 (s, 1H), 8.53 (d, 1H), 8.37 (s, 1H), 7.73 (t, 1H), 7.03 (d, 1H), 6.88-6.85 (d, d, 1H), 6.83 (d, 1H), 3.74-3.69 (m, 4H), 2.73-2.69 (m, 4H), 2.13 (s, 3H); MS (ESI) for $C_{21}H_{19}ClFN_7$: 424 (MH$^+$).

4-[4-(5-Chloro-2-methylphenyl)piperazin-1-yl]-3-(3-chloropyridin-4-yl)-1H-pyrazolo[3,4-d]pyrimidine trifluoroacetate: $^1$H NMR (400 MHz, d$_4$-methanol) δ 8.83 (s, 1H), 8.70 (d, 1H), 8.45 (s, 1H), 7.75 (d, 1H), 7.12 (d, 1H), 6.98-6.95 (d, d, 1H), 6.91 (d, 1H), 3.78-3.71 (m, 4H), 2.80-2.74 (m, 4H), 2.22 (s, 3H); MS (ESI) for $C_{21}H_{19}Cl_2N_7$: 440 (MH$^+$).

Example 12

3-{4-[4-(5-chloro-2-methylphenyl)piperazin-1-yl]-1H-pyrazolo[3,4-d]pyrimidin-3-yl}propan-1-ol trifluoroacetate A mixture of 3-bromo-4-[4-(5-chloro-2-methylphenyl)piperazin-1-yl]-1H-pyrazolo[3,4-d]pyrimidine (0.50 g, 1.2 mmol), p-toluenesulfonic acid monohydrate (0.49 g, 2.6 mmol), and dihydropyran (0.18 g, 2.1 mmol) in DMF (3 mL) was stirred at 90° C. for 15 h. The reaction mixture was cooled, diluted with ethyl acetate (30 mL), washed with saturated sodium bicarbonate, water, and brine (30 mL each), dried with sodium sulfate, and concentrated. Column chromatography on silica (hexanes:ethyl acetate 85:15 to 7:3) gave 3-bromo-4-[4-(5-chloro-2-methylphenyl)piperazin-1-yl]-1-(tetrahydro-2H-pyran-2-yl)-1H-pyrazolo[3,4-d]pyrimidine (0.30 g, 50% yield). $^1$H NMR (400 MHz, CDCl$_3$) δ 8.43 (s, 1H), 7.13 (d, 1H), 7.00 (m, 2H), 5.98 (d, d, 1H), 4.14 (m, 1H), 4.03-3.98 (m, 4H), 3.82-3.76 (m, 1H), 3.07 (m, 4H), 2.60-2.51 (m, 1H), 2.32 (s, 3H), 2.12 (m, 1H), 1.95-1.92 (m, 1H), 1.81-1.73 (m, 2H), 1.61 (m, 1H); MS (ESI) for $C_{21}H_{24}BrClN_6O$: 491 (MH$^+$).

A mixture of 3-bromo-4-[4-(5-chloro-2-methylphenyl)piperazin-1-yl]-1-(tetrahydro-2H-pyran-2-yl)-1H-pyrazolo[3,4-d]pyrimidine (0.26 g, 0.52 mmol), potassium phosphate (0.56 g, 2.6 mmol), tert-butyl acrylate (0.30 g, 2.3 mmol), and [1,1'-bis(diphenylphosphino)ferrocene]dichloropalladium (II) complex with dichlormethane (0.86 g, 0.11 mmol) in DMF (3 mL) was degassed with nitrogen for 5 min, and then stirred at 90° C. for 15 h. The reaction mixture was cooled, diluted with ethyl acetate (30 mL), filtered through celite, and the filtrate was washed with water and brine (30 mL each), dried over sodium sulfate, and concentrated. Column chromatography on silica (hexanes:ethyl acetate 85:15 to 7:3) provided 1,1-dimethylethyl (2E)-3-[4-[4-(5-chloro-2-methylphenyl)piperazin-1-yl]-1-(tetrahydro-2H-pyran-2-yl)-1H-pyrazolo[3,4-d]pyrimidin-3-yl]prop-2-enoate (0.13 g, 0.23 mmol, 43% yield). $^1$H NMR (400 MHz, CDCl$_3$) δ 8.48 (s, 1H), 7.75-7.71 (d, 1H), 7.10 (d, 1H), 6.97 (m, 2H), 6.72 (d, 1H), 6.04-6.01 (d, d, 1H), 4.14-4.01 (m, 1H), 3.96-3.92 (m, 1H), 3.86-3.81 (m, 4H), 3.07-3.02 (m, 4H), 2.60-2.51 (m, 1H), 2.29 (s, 3H), 2.12 (m, 1H), 1.95-1.92 (m, 1H), 1.81-1.73 (m, 2H), 1.53 (s, 9H), 1.61 (m, 1H); MS (ESI) for $C_{28}H_{35}ClN_6O_3$: 539 (MH$^+$).

A solution of 1,1-dimethylethyl (2E)-3-[4-[4-(5-chloro-2-methylphenyl)piperazin-1-yl]-1-(tetrahydro-2H-pyran-2-yl)-1H-pyrazolo[3,4-d]pyrimidin-3-yl]prop-2-enoate (20 mg, 0.037 mmol) in 4N hydrogen chloride in dioxane (1.0 mL) was stirred at 60° C. for 15 min. The reaction mixture was concentrated, and the residue partitioned between sodium bicarbonate and ethyl acetate. The organic layer was concentrated and the residue was purified by reverse phase HPLC to give 1,1-dimethylethyl (2E)-3-{4-[4-(5-chloro-2-methylphenyl)piperazin-1-yl]-1H-pyrazolo[3,4-d]pyrimidin-3-yl}prop-2-enoate trifluoroacetate (8.6 mg, 40% yield). $^1$H NMR (400 MHz, d$_6$-DMSO) δ 8.44 (s, 1H), 7.69-7.65 (d, 1H), 7.21 (d, 1H), 7.05-7.02 (m, 2H), 6.57-6.63 (d, 1H), 3.75-3.72 (m, 4H), 3.06-3.03 (m, 4H), 2.27 (s, 3H), 1.48 (s, 9H); MS (ESI) for $C_{23}H_{27}ClN_6O_2$: 455 (MH$^+$).

A solution of 1,1-dimethylethyl (2E)-3-[4-[4-(5-chloro-2-methylphenyl)piperazin-1-yl]-1-(tetrahydro-2H-pyran-2-yl)-1H-pyrazolo[3,4-d]pyrimidin-3-yl]prop-2-enoate (100 mg, 0.19 mmol) in trifluoroacetic acid was stirred at room temperature for 1 h. The reaction mixture was concentrated and the residue was purified by reverse phase HPLC to yield (2E)-3-{4-[4-(5-chloro-2-methylphenyl)piperazin-1-yl]-1H- pyrazolo[3,4-d]pyrimidin-3-yl}prop-2-enoic acid trifluoroacetate (36 mg, 48% yield). $^1$H NMR (400 MHz, $d_6$-DMSO) δ 8.42 (s, 1H), 7.72-7.68 (d, 1H), 7.20 (d, 1H), 7.02 (m, 2H), 6.57-6.63 (d, 1H), 3.78-3.75 (m, 4H), 3.03-2.99 (m, 4H), 2.26 (s, 3H); MS (ESI) for $C_{19}H_{19}ClN_6O_2$: 399 (MH$^+$).

Sodium borohydride (90 mg, 2.4 mmol) was added to a mixture of the 1,1-dimethylethyl (2E)-3-[4-[4-(5-chloro-2-methylphenyl)piperazin-1-yl]-1-(tetrahydro-2H-pyran-2-yl)-1H-pyrazolo[3,4-d]pyrimidin-3-yl]prop-2-enoate (127 mg, 0.24 mmol) and cobalt(II) chloride (310 mg, 2.4 mmol) in methanol (5 mL), and the resulting mixture was stirred at room temperature for 1 h. The reaction was quenched with water (5 mL), concentrated, and ethyl acetate (5 mL) was added. The organic layer was washed with water, and brine (5 mL each), dried over sodium sulfate, and concentrated. The residue was dissolved in trifluoroacetic acid and stirred at room temperature for 15 min. The solution was concentrated and the residue was purified by reverse phase HPLC to provide 3-{4-[4-(5-chloro-2-methylphenyl)piperazin-1-yl]-1H-pyrazolo[3,4-d]pyrimidin-3-yl}propanoic acid trifluoroacetate (30 mg, 31% yield). $^1$H NMR (400 MHz, $d_6$-DMSO) δ 8.41 (s, 1H), 7.18 (d, 1 μl), 7.05 (d, 1H), 7.02-6.99 (d, d, 1H), 4.24-4.21 (m, 4H), 3.43-3.39 (t, 2H), 3.12-3.09 (m, 4H), 2.89-2.85 (t, 1H), 2.37 (s, 3H); MS (ESI) for $C_{19}H_{21}ClN_6O_2$: 401 (MH$^+$).

Sodium borohydride (14 mg, 0.37 mmol) was added to a mixture of the 1,1-dimethylethyl (2E)-3-[4-[4-(5-chloro-2-methylphenyl)piperazin-1-yl]-1-(tetrahydro-2H-pyran-2-yl)-1H-pyrazolo[3,4-d]pyrimidin-3-yl]prop-2-enoate (20 mg, 0.037 mmol) and cobalt(II) chloride (49 mg, 0.37 mmol) in methanol (5 mL), and the resulting mixture was stirred at room temperature for 1 h. The reaction was quenched with water (5 mL), concentrated, diluted with ethyl acetate (5 mL), washed with water and brine solution (5 mL each), dried over sodium sulfate, and concentrated. The residue was dissolved in THF (2 mL), and a solution of lithium aluminum hydride in THF (1.0 M, 37 uL, 0.037 mmol) was added. The resulting mixture was stirred at room temperature for 1 h, and then quenched with 2N aqueous sodium hydroxide (0.2 mL), diluted with ethyl ether (10 mL), and filtered through celite. The filtrate was washed with brine (2 mL), dried over sodium sulfate, and concentrated. The residue was dissolved in trifluoroacetic acid (1 mL), stirred at room temperature of 15 min, and then concentrated. The residue was purified by reverse phase HPLC to give 3-{4-[4-(5-chloro-2-methylphenyl)piperazin-1-yl]-1H-pyrazolo[3,4-d]pyrimidin-3-yl}propan-1-ol trifluoroacetate (5.2 mg, 35% yield). $^1$H NMR (400 MHz, $d_6$-DMSO) δ 8.33 (s, 1H), 7.08-7.06 (d, 1H), 6.94-6.93 (d, 1H), 6.91-6.88 (d, d, 1H), 4.16-416 (m, 4H), 3.54-3.51 (t, 2H), 3.16-3.12 (m, 2H), 3.01-2.98. (m, 4H), 2.89-2.85 (t, 1H), 2.56 (s, 3H), 1.92-1.85 (m, 2H); MS (ESI) for $C_{19}H_{23}ClN_6O$: 387 (MH$^+$).

Using the analogous synthetic techniques and substituting with alternative reagents, the following compounds of the invention were prepared:

methyl (2E)-3-{4-[4-(5-chloro-2-methylphenyl)piperazin-1-yl]-1H-pyrazolo[3,4-d]pyrimidin-3-yl}prop-2-enoate: $^1$H NMR (400 MHz, $d_6$-DMSO) δ 8.42 (s, 1H), 7.82-7.76 (d, 1H), 7.20 (d, 1H), 7.05-7.01 (m, 2H), 6.64 (d, 1H), 3.78-3.74 (m, 7H), 3.03-2.99 (m, 4H), 2.27 (s, 3H); MS (ESI) for $C_{20}H_{21}ClN_6O_2$: 413 (MH$^+$).

3-{4-[4-(5-chloro-2-methylphenyl)piperazin-1-yl]-1H-pyrazolo[3,4-d]pyrimidin-3-yl}-N,N-diethylpropan-1-amine trifluoroacetate: $^1$H NMR (400 MHz, $d_4$-methanol) δ 8.37 (s, 1H), 7.19 (d, 1H), 7.06 (d, 1H), 7.00 (dd, 1H), 4.02 (m, 4H), 3.28-3.18 (m, 8H), 3.07 (m, 4H), 2.35 (m, 3H), 2.27 (m, 2H), 1.32 (t, 6H); MS (ESI) for $C_{23}H_{31}ClN_7$: 442 (MH$^+$).

4-[4-(5-chloro-2-methylphenyl)piperazin-1-yl]-3-(3-pyrrolidin-1-ylpropyl)-1H-pyrazolo[3,4-d]pyrimidine trifluoroacetate: $^1$H NMR (400 MHz, $d_4$-methanol) δ 8.41 (s, 1H), 7.19 (d, 1H), 7.08-6.99 (m, 2H), 4.11 (br s, 4H), 3.68 (br s, 2H), 3.37 (m, 1H), 3.27 (m, 1H), 3.21 (t, 2H), 3.13-3.07 (m, 6H), 2.35 (s, 3H), 2.27 (m, 2H), 2.15 (br s, 2H), 2.02 (br s, 2H).

3-(azetidin-3-ylidenemethyl)-4-[4-(5-chloro-2-methylphenyl)piperazin-1-yl]-1H-pyrazolo[3,4-d]pyrimidine trifluoroacetate: $^1$H NMR (400 MHz, $d_6$-DMSO) δ 8.40 (s, 1H), 7.23 (d, 1H), 7.11-7.08 (m, 1H), 7.05 (dd, 1H), 6.67-6.63 (m, 1H), 5.20-4.48 (m, 5H), 3.83 (br.m, 4H), 3.02 (br.m, 4H), 2.29 (s, 3H), MS (ESI) for $C_{20}H_{22}ClN_7$: 396 (MH$^+$).

Phenylmethyl (3aR,6aS)-5-({4-[4-(5-chloro-2-methylphenyl)piperazin-1-yl]-1H-pyrazolo[3,4-d]pyrimidin-3-yl}methylidene)hexahydrocyclopenta[c]pyrrole-2(1H)-carboxylate trifluoroacetate: $^1$H NMR (400 MHz, $d_4$-methanol) δ 8.44 (s, 1H), 7.27-7.12 (m, 6H), 7.00 (m, 2H), 5.19 (s, 1H), 4.95-4.83 (br s, 2H), 4.22-4.10 (m, 4H), 3.88 (m, 2H), 3.68-3.63 (m, 1H), 3.46-3.36 (m, 3H), 3.02-2.93 (m, 6H), 2.73-2.68 (d, d, 1H), 2.33-2.31 (d, 3H), 2.20-2.16 (d, d, 1H); MS (ESI) for $C_{32}H_{34}ClN_7O_2$: 584 (MH$^+$).

4-[4-(5-Chloro-2-methylphenyl)piperazin-1-yl]-3-[(E)-(3aR,6aS)-hexahydro-cyclopenta[c]pyrrol-5(1H)-ylidenemethyl]-1H-pyrazolo[3,4-d]pyrimidine trifluoroacetate: $^1$H NMR (400 MHz, $d_4$-methanol) δ 8.42 (s, 1H), 7.19 (d, 1H), 7.05-7.00 (m, 2H), 5.27 (s, 1H), 4.13-4.08 (m, 4H), 3.92 (m, 2H), 3.64-3.59 (m, 1H), 3.48-3.42 (d, d, 1H), 3.34 (m, 1H), 3.16 (m, 2H), 3.07-3.03 (m, 5H), 2.78-2.71 (m, 1H), 2.35 (s, 3H), 2.34 (m, 1H); MS (ESI) for $C_{24}H_{28}ClN_7$: 450 (MH$^+$).

Example 13

4-[4-(5-chloro-2-methylphenyl)piperazin-1-yl]-3-(3-pyrrolidin-1-ylprop-1-yn-1-yl)-1H-pyrazolo[3,4-d]pyrimidine trifluoroacetate To a solution of 3-bromo-4-[4-(5-chloro-2-methylphenyl)piperazin-1-yl]-1-(tetrahydro-2H-pyran-2-yl)-1H-pyrazolo[3,4-d]pyrimidine (150 mg, 0.305 mmol) in DMF (3 mL) and triethylamine (0.45 mL) was added (1,1-dimethylethyl)(dimethyl)(prop-2-yn-1-yloxy)silane (156 mg, 0.915 mmol), copper(I) iodide (17.5 mg, 0.092 mmol) and tetrakis(triphenylphosphine)palladium(0) (36 mg, 0.036 mmol). The mixture was stirred in a sealed tube at 105° C. for 3 h, then cooled to room temperature and concentrated. Column chromatography on silica (hexanes:ethyl acetate 3:2) provided 4-[4-(5-chloro-2-methylphenyl)piperazin-1-yl]-3-(3-{[(1,1-dimethylethyl)(dimethyl)silyl]oxy}prop-1-yn-1-yl)-1-(tetrahydro-2H-pyran-2-yl)-1H-pyrazolo[3,4-d]pyrimidine (164 mg, 93% yield) as an orange oil. $^1$H NMR (400 MHz, CDCl$_3$) δ 8.29 (s, 1H), 7.16 (s, 1H), 7.01 (m, 1H), 6.89-6.86 (m, 2H), 5.91 (dd, 1H), 4.54 (s, 2H), 4.08 (m, 4H), 4.02 (m, 1H), 3.69 (m, 1H), 2.95 (m, 4H), 2.47 (m, 1H), 2.22 (s, 3H), 2.03 (m, 1H), 1.82 (m, 1H), 1.67 (m, 2H), 1.51 (m, 1H), 0.78 (s, 9H), 0.00 (s, 6H).

To a solution of 4-[4-(5-chloro-2-methylphenyl)piperazin-1-yl]-3-(3-{[(1,1-dimethylethyl)(dimethyl)silyl]oxy}prop-1-yn-1-yl)-1-(tetrahydro-2H-pyran-2-yl)-1H-pyrazolo[3,4-d]pyrimidine (164 mg, 0.28 mmol) in THF (2 mL) was added tetrabutyl-ammonium fluoride in THF (1.0 M, 340 μL, 0.34 mmol). The mixture was stirred at room temperature for 80 min, then diluted with ethyl acetate, washed with water, and brine, dried over magnesium sulfate, and concentrated. Column chromatography on silica (hexane:ethyl acetate 1:1) afforded 3-[4-[4-(5-chloro-2-methylphenyl)piperazin-1-yl]-1-(tetrahydro-2H-pyran-2-yl)-1H-pyrazolo[3,4-d]pyrimidin-3-yl]prop-2-yn-1-ol (118 mg, 90% yield) as a colorless syrup. $^1$H NMR (400 MHz, CDCl$_3$) δ 8.41 (s, 1H), 7.11 (d, 1H), 6.99 (m, 2H), 6.01 (dd, 1H), 4.54 (s, 2H), 4.16 (m, 4H), 4.09 (m, 1H), 3.79 (m, 1H), 3.03 (m, 4H), 2.71 (br s, 1H), 2.53 (m, 1H), 2.31 (s, 3H), 2.10 (m, 1H), 1.93 (m, 1H), 1.75 (m, 2H), 1.60 (m, 1H).

To a solution of 3-[4-[4-(5-chloro-2-methylphenyl)piperazin-1-yl]-1-(tetrahydro-2H-pyran-2-yl)-1H-pyrazolo[3,4-d]pyrimidin-3-yl]prop-2-yn-1-ol (85 mg, 0.18 mmol) in dichloromethane (4 mL) was added triethylamine (38 μL, 0.27 mmol) and methanesulfonyl chloride (18 μL, 0.23 mmol) at 0° C. The reaction mixture was allowed to warm to room temperature over 1 h before diluting with dichloromethane. The organic solution was washed with 10% citric acid followed by saturated sodium bicarbonate. The organic layer was dried over magnesium sulfate, and concentrated to give 3-[4-[4-(5-chloro-2-methylphenyl)piperazin-1-yl]-1-(tetrahydro-2H-pyran-2-yl)-1H-pyrazolo[3,4-d]-pyrimidin-3-yl]prop-2-yn-1-yl methanesulfonate (86.5 mg, 88% yield) as a white solid. $^1$H NMR (400 MHz, CDCl$_3$) δ 8.40 (s, 1H), 7.11 (m, 1H), 6.98 (m, 2H), 6.02 (d, 1H), 5.09 (s, 2H), 4.18 (m, 4H), 4.13 (m, 1H), 3.79 (m, 1H), 3.09 (s, 3H), 3.04 (m, 4H), 2.54 (m, 1H), 2.33 (s, 3H), 2.13 (m, 1H), 1.92 (m, 1H), 1.77 (m, 2H), 1.63 (m, 1H).

To a solution of 3-[4-[4-(5-chloro-2-methylphenyl)piperazin-1-yl]-1-(tetrahydro-2H-pyran-2-yl)-1H-pyrazolo[3,4-d]pyrimidin-3-yl]prop-2-yn-1-yl methanesulfonate (43 mg, 0.08 mmol) in DMF (1 mL) was added pyrrolidine (33 μL, 0.4 mmol). The mixture was stirred for 1 h at room temperature, and then concentrated to provide 4-[4-(5-chloro-2-methylphenyl)piperazin-1-yl]-3-(3-pyrrolidin-1-ylprop-1-yn-1-yl)-1-(tetrahydro-2H-pyran-2-yl)-1H-pyrazolo[3,4-d]pyrimidine. $^1$H NMR (400 MHz, CDCl$_3$) δ 8.40 (s, 1H), 7.13 (d, 1H), 7.01 (d, 1H), 6.98 (m, 1H), 6.01 (dd, 1H), 4.21 (m, 4H), 4.12 (m, 1H), 3.80 (m, 1H), 3.74 (s, 2H), 3.33 (m, 4H), 3.04 (m, 4H), 2.57 (m, 1H), 2.32 (s, 3H), 2.13 (m, 1H), 2.01 (m, 4H), 1.93 (m, 1H), 1.77 (m, 2H), 1.61 (m, 1H).

A solution of 4-[4-(5-chloro-2-methylphenyl)piperazin-1-yl]-3-(3-pyrrolidin-1-ylprop-1-yn-1-yl)-1-(tetrahydro-2H-pyran-2-yl)-1H-pyrazolo[3,4-d]pyrimidine in methanol (2 mL) and 4M hydrochloric acid in dioxane (2 mL) was stirred at 60° C. for 30 min and then concentrated. Purification by reverse phase HPLC provided 4-[4-(5-chloro-2-methylphenyl)piperazin-1-yl]-3-(3-pyrrolidin-1-ylprop-1-yn-1-yl)-1H-pyrazolo[3,4-d]-pyrimidine trifluoroacetate as a yellow syrup. $^1$H NMR (400 MHz, d$_4$-methanol) δ 8.39 (s, 1H), 7.18 (d, 1H), 7.07 (d, 1H), 7.00 (dd, 1H), 4.54 (s, 2H), 4.32 (m, 4H), 3.53 (br s, 4H), 3.11 (m, 4H), 2.37 (s, 3H), 2.16 (br s, 4H); MS (ESI) for C$_{23}$H$_{25}$ClN$_7$: 436 (MH$^+$).

Using the analogous synthetic techniques and substituting with alternative reagents, the following compounds of the invention were prepared:

N-(3-{4-[4-(5-chloro-2-methylphenyl)piperazin-1-yl]-1H-pyrazolo[3,4-d]pyrimidin-3-yl}prop-2-yn-1-yl)acetamide: $^1$H NMR (400 MHz, d$_6$-DMSO) δ 8.47 (t, 1H), 8.34 (s, 1H), 7.23 (d, 1H), 7.10 (d, 1H), 7.04 (dd, 1H), 4.18 (d, 2H), 4.12 (br s, 4H), 3.04 (m, 4H), 2.31 (s, 3H), 1.77 (s, 3H); MS (ESI) for C$_{21}$H$_{22}$ClN$_7$O: 424 (MH$^+$).

3-{4-[4-(5-chloro-2-methylphenyl)piperazin-1-yl]-1H-pyrazolo[3,4-d]pyrimidin-3-yl}-N,N-diethylprop-2-yn-1-amine trifluoroacetate: $^1$H NMR (400 MHz, d$_6$-DMSO) δ 9.97 (br s, 1H), 8.34 (s, 1H), 7.21 (d, 1H), 7.05 (m, 1H), 7.02 (d, 1H), 4.54 (br s, 2H), 4.14 (m, 4H), 3.26 (m, 4H), 3.03 (m, 4H), 2.30 (s, 3H), 1.26 (t, 6H); MS (ESI) for C$_{23}$H$_{28}$ClN$_7$: 438 (MH$^+$).

3-{4-[4-(5-chloro-2-methylphenyl)piperazin-1-yl]-1H-pyrazolo[3,4-d]pyrimidin-3-yl}prop-2-yn-1-ol: $^1$H NMR (400 MHz, d$_6$-DMSO) δ 8.31 (s, 1H), 7.20 (d, 1H), 7.05 (d, 1H), 7.02 (dd, 1H), 4.37 (s, 2H), 4.11 (m, 4H), 3.04 (m, 4H), 2.29 (s, 3H); MS (ESI) for C$_{19}$H$_{19}$ClN$_6$O: 383 (MH$^+$).

4-[4-(5-chloro-2-methylphenyl)piperazin-1-yl]-3-[3-(4-methylpiperazin-1-yl)prop-1-yn-1-yl]-1H-pyrazolo[3,4-d]pyrimidine trifluoroacetate: $^1$H NMR (400 MHz, d$_4$-methanol) δ 8.47 (s, 1H), 7.20 (d, 1H), 7.08 (d, 1H), 7.02 (dd, 1H), 4.45 (m, 4H), 3.85 (s, 2H), 3.16 (m, 4H), 3.00 (br s, 8H), 2.89 (s, 3H), 2.37 (s, 3H); MS (ESI) for C$_{24}$H$_{28}$ClN$_8$: 465 (MH$^+$).

Example 14

4-[4-(5-chloro-2-methylphenyl)piperazin-1-yl]-3-piperazin-1-yl-1H-pyrazolo[3,4-d]pyrimidine trifluoroacetate To 3-bromo-4-[4-(5-chloro-2-methylphenyl)piperazin-1-yl]-1-(tetrahydro-2H-pyran-2-yl)-1H-pyrazolo[3,4-d]pyrimidine (50 mg, 0.11 mmol) in anhydrous toluene (0.4 mL) was added Pd$_2$(dba)$_3$ (10 mg, 0.011 mmol), 2-(di-t-butylphosphino-1,1'-binaphthyl (10 mg, 0.033 mmol), sodium tert-butoxide (15 mg, 0.15 mmol), and Boc-piperazine (25 mg, 0.13 mmol). The reaction mixture was stirred at 100° C. for 16 h under nitrogen, and then concentrated. Column chromatography on silica (hexanes:ethyl acetate 2:1) provided 1,1-dimethylethyl 4-[4-[4-(5-chloro-2-methylphenyl)piperazin-1-yl]-1-(tetrahydro-2H-pyran-2-yl)-1H-pyrazolo[3,4-d]pyrimidin-3-yl]piperazine-1-carboxylate (14 mg, 21% yield). MS (ESI) for C$_{30}$H$_{41}$ClN$_8$O$_3$: 597 (MH$^+$).

To 1,1-dimethylethyl 4-[4-[4-(5-chloro-2-methylphenyl)piperazin-1-yl]-1-(tetrahydro-2H-pyran-2-yl)-1H-pyrazolo[3,4-d]pyrimidin-3-yl]piperazine-1-carboxylate (14 mg, 0.023 mmol) in methanol (1 mL) was added 4N hydrogen chloride in dioxane (0.11 ml), and the mixture was refluxed for 2 min. Purification by reversed phase HPLC yielded 4-[4-(5-chloro-2-methylphenyl)piperazin-1-yl]-3-piperazin-1-yl-1H-pyrazolo[3,4-d]pyrimidine trifluoroacetate (6 mg, 49% yield) as a white solid. $^1$H NMR (400 MHz, d$_4$-methanol) δ 8.30 (s, 1H), 7.17 (d, 1H), 7.04-7.01 (m, 1H), 6.99 (dd, 1H), 4.16 (br s, 4H), 3.58-3.37 (m, 8H), 3.08-2.96 (m, 4H), 2.34 (s, 3H); MS (ESI) for C$_{20}$H$_{25}$ClN$_8$: 413 (MH$^+$).

Using the same or analogous synthetic techniques and/or substituting with alternative reagents, the following compound of the invention was prepared:

4-[4-(5-chloro-2-methylphenyl)piperazin-1-yl]-3-(4-methylpiperazin-1-yl)-1H-pyrazolo[3,4-d]pyrimidine: $^1$H NMR (400 MHz, d$_4$-methanol) δ 8.29 (s, 1H), 7.16 (d, 1H), 7.03 (m, 1H), 6.99 (dd, 1H), 4.14 (br s, 4H), 3.90-3.79 (m, 2H), 3.65-3.53 (m, 2H), 3.45-3.34 (m, 2H), 3.28-3.16 (m, 2H), 3.06-3.00 (m, 4H), 2.98 (s, 3H), 2.34 (s, 3H); MS (ESI) for C$_{21}$H$_{27}$ClN$_8$: 427 (MH$^+$).

Example 15

2-[(5-chloro-2-methyl-3-{4-[3-(trifluoromethyl)-1H-pyrazolo[3,4-d]pyrimidin-4-yl]piperazin-1-yl}phenyl)oxy]-N,N-diethylethanamine trifluoroacetate A mixture of ethyl 2-cyano-4,4,4-trifluoro-3-oxobutanoate (18.2 g, 78 mmol, EP 1067121A2), tert-butylhydrazine hydrochloride (17.4 g, 140 mmol), trifluoroacetic acid (12.3 mL, 160 mmol), molecular sieves (3A, 28 g) and dimethyl carbonate (165 mL) was stirred at 80° C. for 18 h. The reaction mixture was cooled, diluted with ethyl acetate (200 mL), and filtered. The filtrate was concentrated and ethyl acetate (200 mL) was added. The organic layer was washed with 5% bicarbonate, 5% sodium hydroxide, water and brine (100 mL each), dried over sodium sulfate, and concentrated. Column chromatography on silica (hexanes:ethyl acetate 95:5 to 4:1) gave ethyl 5-amino-1-(1,1-dimethyl-ethyl)-3-(trifluoromethyl)-1H-pyrazole-4-carboxylate (7.3 g, 33% yield); MS (ESI) for $C_{11}H_{16}F_3N_3O$: 280 (MH$^+$).

A mixture of ethyl 5-amino-1-(1,1-dimethylethyl)-3-(trifluoromethyl)-1H-pyrazole-4-carboxylate (16.0, 57 mmol) and ammonium carbonate (5.4 g, 69 mmol) in formamide (48 mL) was stirred at 170° C. for 3 d. The reaction mixture was cooled, diluted with ethyl acetate (200 mL), washed with water and brine (200 mL each), dried over sodium sulfate, and concentrated. Column chromatography on silica (hexanes: ethyl acetate 65:35 to 3:1) provided 1-(1,1-dimethylethyl)-3-(trifluoromethyl)-1H-pyrazolo[3,4-d]pyrimidin-4-ol (7.3 g, 52% yield); MS (ESI) for $C_{10}H_{11}F_3N_4O_2$: 261 (MH$^+$).

DMF (3.0 mL, 38 mmol) was added drop wise to a mixture of 4-hydroxypyrazolopyrimidine (5.0, 19 mmol) and thionyl chloride (50 mL). The resulting mixture was stirred at 75° C. for 2 h. The reaction mixture was cooled, concentrated, and partitioned between aqueous sodium bicarbonate (100 mL) and ethyl acetate (100 mL). The organic layer was washed with water and brine (100 mL each), dried over sodium sulfate, and concentrated. Column chromatography on silica (hexanes:ethyl acetate 95:5) afforded 4-chloro-1-(1,1-dimethylethyl)-3-(trifluoromethyl)-1H-pyrazolo[3,4-d]pyrimidine (5.0 g, 95% yield); $^1$H NMR (400 MHz, CDCl$_3$) δ 8.80 (s, 1H), 1.85 (m, 9H); MS (ESI) for $C_{10}H_{10}ClF_3N_4$: 279 (MH$^+$).

A mixture of 4-chloro-1-(1,1-dimethylethyl)-3-(trifluoromethyl)-1H-pyrazolo[3,4-d]pyrimidine (85 mg, 0.31 mmol), 2-[(5-chloro-2-methyl-3-piperazin-1-ylphenyl)oxy]-N,N-diethylethanamine (200 mg, 0.61 mmol), and triethylamine (0.21 mL, 1.5 mmol), in dioxane (5 mL) was stirred at 75° C. for 18 h. The reaction mixture was cooled, diluted with ethyl acetate (50 mL), washed with water and brine (30 mL each), dried over sodium sulfate, and concentrated. Column chromatography on silica (dichloromethane:methanol:ammonia 95:4:1) gave 2-[(5-chloro-3-{4-[1-(1,1-dimethylethyl)-3-(trifluoromethyl)-1H-pyrazolo[3,4-d]pyrimidin-4-yl]piperazin-1-yl}-2-methylphenyl)oxy]-N,N-diethylethanamine (105 mg, 61% yield). $^1$H NMR (400 MHz, d$_4$-methanol) δ 8.42 (s, 1H), 6.83 (s, 1H), 6.79 (s, 1H), 4.36-4.33 (t, 2H), 3.92-3.89 (m, 4H), 3.68-3.66 (t, 2H), 3.41-3.37 (q, d, 4H), 3.01-2.98 (t, 4H), 2.24 (s, 3H), 1.81 (m, 9H), 1.42-1.38 (t, 6H); MS (ESI) for $C_{27}H_{37}ClF_3N_7O$: 568 (MH$^+$).

A mixture of 2-[(5-chloro-3-{4-[1-(1,1-dimethylethyl)-3-(trifluoromethyl)-1H-pyrazolo[3,4-d]pyrimidin-4-yl]piperazin-1-yl}-2-methylphenyl)oxy]-N,N-diethylethanamine (105 mg, 0.19 mmol) and methanesulfonic acid (1.0 mL) was stirred at 55° C. for 2 h, then poured into ice (10 g), and basified with solid sodium bicarbonate to pH 8. The aqueous layer was extracted with ethyl acetate (3×10 mL). The organic layer was washed with water and brine (20 mL each), dried over sodium sulfate, and concentrated. The residue was purified by reverse phase HPLC to give 2-[(5-chloro-2-methyl-3-{4-[3-(trifluoromethyl)-1H-pyrazolo[3,4-d]pyrimidin-4-yl]piperazin-1-yl}phenyl)oxy]-N,N-diethylethanamine trifluoroacetate (85 mg, 74% yield). $^1$H NMR (400 MHz, d$_4$-methanol) δ 8.40 (s, 1H), 6.74 (s, 1H), 6.71 (s, 1H), 4.11-4.09 (t, 2H), 3.96-3.93 (m, 4H), 3.03-2.99 (m, 6H), 2.79-2.74 (q, 4H), 2.02 (s, 3H), 1.17-1.14 (t, 6H); MS (ESI) for $C_{23}H_{29}ClF_3N_7O$: 512 (MH$^+$).

Using the same or analogous synthetic techniques and/or substituting with alternative reagents, the following compounds of the invention were prepared:

4-(4-{5-Chloro-2-methyl-3-[(2-pyrrolidin-1-ylethyl)oxy]phenyl}piperazin-1-yl)-3-(trifluoromethyl)-1H-pyrazolo[3,4-d]pyrimidine trifluoroacetate: $^1$H NMR (400 MHz, d$_4$-methanol) δ 8.42 (s, 1H), 6.83 (s, 1H), 6.79 (s, 1H), 4.34-4.32 (t, 2H), 3.97-3.93 (m, 4H), 3.69-3.66 (m, 2H), 3.72-3.70 (t, 2H), 3.26-3.23 (m, 2H), 3.02-2.99 (t, 4H), 2.26 (s, 3H), 2.23-2.19 (m, 2H), 2.09-2.05 (m, 2H); MS (ESI) for $C_{23}H_{27}ClF_3N_7O$: 510 (MH$^+$).

4-(4-{5-Chloro-2-methyl-3-[(3-morpholin-4-ylpropyl)oxy]phenyl}piperazin-1-yl)-3-(trifluoromethyl)-1H-pyrazolo[3,4-d]pyrimidine trifluoroacetate: $^1$H NMR (400 MHz, d$_4$-methanol) δ 8.32 (s, 1H), 6.67 (s, 1H), 6.64 (s, 1H), 4.03-4.00 (t, 4H), 3.89-3.85 (m, 4H), 3.70-3.64 (t, 2H), 3.50-3.47 (d, 2H), 3.33-3.29 (d, d, 2H), 3.16-3.11 (t, d, 2H), 2.91-2.89 (t, 4H), 2.22-2.17 (m, 2H), 2.12 (s, 3H); MS (ESI) for $C_{24}H_{29}ClF_3N_7O_2$: 540 (MH$^+$).

4-(4-{5-Chloro-2-methyl-3-[(2-morpholin-4-ylethyl)oxy]phenyl}piperazin-1-yl)-3-(trifluoromethyl)-1H-pyrazolo[3,4-d]pyrimidine trifluoroacetate: $^1$H NMR (400 MHz, d$_4$-methanol) δ 8.41 (s, 1H), 6.83 (s, 1H), 6.79 (s, 1H), 4.39 (t, 2H), 4.10-4.07 (m, 2H), 3.97-3.93 (m, 4H), 3.88 (m, 2H), 3.69 (t, 2H), 3.64-3.61 (m, 2H), 3.36-3.33 (m, 2H), 3.25 (m, 2H), 3.01-2.99 (t, d, 4H), 2.24 (s, 3H); MS (ESI) for $C_{23}H_{27}ClF_3N_7O_2$: 526 (MH$^+$).

4-(4-{5-Chloro-2-methyl-3-[(2-piperidin-1-ylethyl)oxy]phenyl}piperazin-1-yl)-3-(trifluoromethyl)-1H-pyrazolo[3,4-d]pyrimidine hydrochloride: $^1$H NMR (400 MHz, d$_4$-methanol) δ 8.51 (s, 1H), 6.85 (s, 1H), 6.80 (s, 1H), 4.39-4.37 (t, 2H), 4.11-4.07 (m, 4H), 3.68-3.60 (m, 4H), 3.17-3.12 (t, d, 2H), 3.07-3.05 (t, 4H), 2.26 (s, 3H), 2.01-1.97 (m, 2H), 1.87-1.81 (m, 3H), 1.60-1.56 (m, 1H); MS (ESI) for $C_{24}H_{29}ClF_3N_7O$: 524 (MH$^+$).

4-(4-{5-Chloro-2-methyl-3-[(3-pyrrolidin-1-ylpropyl)oxy]phenyl}piperazin-1-yl)-3-(trifluoromethyl)-1H-pyrazolo[3,4-d]pyrimidine trifluoroacetate: $^1$H NMR (400 MHz, β4-methanol) δ 8.41 (s, 1H), 6.76 (s, 1H), 6.73 (s, 1H), 4.12-4.09 (t, 2H), 3.98-3.94 (m, 4H), 3.76-3.70 (m, 2H), 3.46-3.42 (d, d, 2H), 3.18-3.13 (m, 2H), 3.02-2.99 (t, 4H), 2.29-2.19 (m, 7H), 2.09-2.04 (m, 2H); MS (ESI) for $C_{24}H_{29}ClF_3N_7O$: 524 (MH$^+$).

4-(4-{5-Chloro-2-methyl-3-[(3-piperidin-1-ylpropyl)oxy]phenyl}piperazin-1-yl)-3-(trifluoromethyl)-1H-pyrazolo[3,4-d]pyrimidine trifluoroacetate: $^1$H NMR (400 MHz, d$_4$-methanol) δ 8.41 (s, 1H), 6.76 (s, 1H), 6.73 (s, 1H), 4.12-4.09 (t, 2H), 3.98-3.94 (m, 4H), 3.63-3.60 (m, 2H), 3.02-2.98 (m, 6H), 2.31-2.25 (m, 2H), 2.29-2.19 (s, 3H), 2.02-1.96 (m, 2H), 1.90-1.70 (m, 4H), 1.58-1.50 (m, 2H); MS (ESI) for $C_{25}H_{31}ClF_3N_7O$: 538 (MH$^+$).

4-[4-(5-Chloro-2-methyl-3-{[3-(4-methylpiperazin-1-yl)propyl]oxy}phenyl)piperazin-1-yl]-3-(trifluoromethyl)-1H-pyrazolo[3,4-d]pyrimidine trifluoroacetate: $^1$H NMR (400 MHz, d$_4$-methanol) δ 8.41 (s, 1H), 6.74 (s, 1H), 6.71 (s, 1H), 4.11-4.08 (t, 2H), 3.98-3.94 (m, 4H), 3.52-3.36 (m, 8H), 3.26-3.22 (d, d, 2H), 3.01-2.99 (m, 4H), 2.95 (s, 3H), 2.26-2.20 (m, 5H); MS (ESI) for $C_{25}H_{32}ClF_3N_8O$: 553 (MH$^+$).

4-[4-(5-Chloro-3-{[3-(4-ethylpiperazin-1-yl)propyl]oxy}-2-methylphenyl)piperazin-1-yl]-3-(trifluoromethyl)-1H-pyrazolo[3,4-d]pyrimidine hydrochloride: $^1$H NMR (400 MHz, d$_4$-methanol) δ 8.41 (s, 1H), 6.74 (s, 1H), 6.71 (s, 1H), 4.11-4.08 (t, 2H), 3.98-3.94 (m, 4H), 3.52-3.36 (m, 8H), 3.26-3.21 (t, 2H), 3.19-3.17 (d, d, 2H), 3.02-2.99 (m, 4H), 2.22 (m, 5H), 1.39-1.35 (t, 3H); MS (ESI) for $C_{26}H_{34}ClF_3N_8O$: 567 (MH$^+$).

N'-(5-chloro-2-methyl-3-{4-[3-(trifluoromethyl)-1H-pyrazolo[3,4-d]pyrimidin-4-yl]piperazin-1-yl}phenyl)-N,N-dimethylethane-1,2-diamine hydrochloride: $^1$H NMR (400 MHz, d$_4$-methanol) δ 8.50 (s, 1H), 6.58-6.53 (m, 2H), 4.36-

3.79 (br m, 4H), 3.58 (t, 2H), 3.40 (t, 2H), 3.09-2.98 (m, 4H), 2.96 (s, 6H), 2.22 (s, 3H); MS (ESI) for $C_{21}H_{26}ClF_3N_8$: 483 (MH$^+$).

3-[(5-chloro-2-methyl-3-{4-[3-(trifluoromethyl)-1H-pyrazolo[3,4-d]pyrimidin-4-yl]piperazin-1-yl}phenyl)oxy]-N,N-diethylpropan-1-amine hydrochloride: $^1$H NMR (400 MHz, d$_4$-methanol) δ 8.40 (s, 1H), 6.69 (d, 1H), 6.65 (d, 1H), 4.04-3.95 (m, 6H), 3.29 (m, 2H), 2.95 (t, 4H), 2.16 (m, 2H), 2.13 (s, 3H), 1.27 (t, 6H); MS (ESI) for $C_{24}H_{31}ClF_3N_7O$: 526 (MH$^+$).

4-[4-(5-chloro-2-methyl-3-{[2-(4-methylpiperazin-1-yl)ethyl]oxy}phenyl)piperazin-1-yl]-3-(trifluoromethyl)-1H-pyrazolo[3,4-d]pyrimidine hydrochloride: $^1$H NMR (400 MHz, d$_4$-methanol) δ 8.55 (s, 1H), 6.86 (m, 1H), 6.81 (m, 1H), 4.52-4.45 (m, 2H), 4.24-4.14 (m, 4H), 4.09-3.60 (m, 10H), 3.15-3.08 (m, 4H), 3.05 (s, 3H), 2.30 (s, 3H); MS (ESI) for $C_{24}H_{30}ClF_3N_8O$: 539 (MH$^+$).

4-[4-(5-chloro-3-{[2-(4-ethylpiperazin-1-yl)ethyl]oxy}-2-methylphenyl)piperazin-1-yl]-3-(trifluoromethyl)-1H-pyrazolo[3,4-d]pyrimidine hydrochloride: $^1$H NMR (400 MHz, d$_4$-methanol) δ 8.57 (s, 1H), 6.88 (br s, 1H), 6.81 (br s, 1H), 4.55-4.42 (m, 2H), 4.26-4.12 (br s, 4H), 4.11-3.49 (m, 10H), 3.37 (q, 2H), 3.17-3.04 (m, 4H), 2.29 (s, 3H), 1.43 (t, 3H); MS (ESI) for $C_{25}H_{32}ClF_3N_8O$: 553 (MH$^+$).

3-(5-chloro-2-methyl-3-{4-[3-(trifluoromethyl)-1H-pyrazolo[3,4-d]pyrimidin-4-yl]piperazin-1-yl}phenyl)-N,N-diethylpropan-1-amine trifluoroacetate: $^1$H NMR (400 MHz, d$_4$-methanol) δ 8.42 (s, 1H), 7.02 (br s, 1H), 6.97 (br s, 1H), 4.09-3.84 (m, 4H), 3.28-3.15 (m, 6H), 3.02-2.94 (m, 4H), 2.73 (t, 2H), 2.35 (s, 3H), 2.02-1.89 (m, 2H), 1.30 (t, 6H); MS (ESI) for $C_{24}H_{31}ClF_3N_7$: 510 (MH$^+$).

4-[4-(5-chloro-2-methylphenyl)piperazin-1-yl]-3-(trifluoromethyl)-1H-pyrazolo[3,4-d]pyrimidine: $^1$H NMR (400 MHz, d$_4$-methanol) δ 8.30 (s, 1H), 7.06 (d, 1H), 6.91 (d, 1H), 6.88 (d, 1H), 6.86 (d, 1H), 3.86 (t, 4H), 2.92 (t, 4H), 2.24 (s, 3H); MS (ESI) for $C_{17}H_{16}ClF_3N_6$: 399 (MH$^+$).

4-[4-(5-chloro-2-methyl-3-{[(1-methylpiperidin-4-yl)methyl]oxy}phenyl)piperazin-1-yl]-3-(trifluoromethyl)-1H-pyrazolo[3,4-d]pyrimidine hydrochloride: $^1$H NMR (400 MHz, d$_4$-methanol) δ 8.42 (s, 1H), 6.74 (d, 1H), 6.72 (d, 1H), 3.98 (br s, 4H), 3.92 (d, 2H), 3.60 (d, 2H), 3.08 (m, 2H), 3.01 (m, 4H), 2.90 (s, 3H), 2.22 (s, 3H), 2.17 (m, 3H), 1.72 (m, 2H); MS (ESI) for $C_{24}H_{29}ClF_3N_7O$: 524 (MH$^+$).

4-[4-(5-chloro-2-methyl-3-{[2-(1-methylpiperidin-4-yl)ethyl]oxy}phenyl)piperazin-1-yl]-3-(trifluoromethyl)-1H-pyrazolo[3,4-d]pyrimidine: $^1$H NMR (400 MHz, d$_4$-methanol) δ 8.43 (s, 1H), 6.74 (d, 1H), 6.70 (d, 2H), 4.06 (t, 2H), 3.99 (br s, 4H), 3.52 (m, 2H), 3.05-2.98 (m, 6H), 2.87 (s, 3H), 2.21 (s, 3H), 2.11 (m, 2H), 1.91-1.82 (m, 3H), 1.52 (m, 2H); MS (ESI) for $C_{25}H_{31}ClF_3N_7O$: 538 (MH$^+$).

N'-(5-chloro-2-methyl-3-{4-[3-(trifluoromethyl)-1H-pyrazolo[3,4-d]pyrimidin-4-yl]piperazin-1-yl}phenyl)-N,N-diethylethane-1,2-diamine hydrochloride: $^1$H NMR (400 MHz, d$_4$-methanol) δ 8.57 (s, 1H), 6.60 (s, 1H), 6.58 (s, 1H), 4.28-4.14 (br s, 4H), 3.63-3.58 (m, 2H), 3.42-3.38 (m, 2H), 3.36-3.30 (m, 4H), 3.15-3.09 (br s, 4H), 2.24-2.22 (s, 3H), 1.37-1.32 (m, 6H); MS (ESI) for $C_{25}H_{32}ClF_3N_6$: 510 (MH$^+$).

5-chloro-2-methyl-N-(2-pyrrolidin-1-ylethyl)-3-{4-[3-(trifluoromethyl)-1H-pyrazolo[3,4-d]pyrimidin-4-yl]piperazin-1-yl}aniline: $^1$H NMR (400 MHz, d$_4$-methanol) δ 8.58 (s, 1H), 6.58 (s, 2H), 6.58 (s, 1H), 4.28-4.14 (br s, 4H), 3.77-3.70 (m, 2H), 3.61-3.56 (m, 2H), 3.48-3.44 (m, 2H), 3.19-3.09 (m, 6H), 2.25-2.23 (s, 3H), 2.19-2.13 (m, 2H), 2.09-2.01 (m, 3H); MS (ESI) for $C_{23}H_{28}ClF_3N_8$: 509 (MH$^+$).

4-{5-chloro-2-methyl-3-(3-pyrrolidin-1-ylpropyl)phenyl]piperazin-1-yl}-3-(trifluoromethyl)-1H-pyrazolo[3,4-d]pyrimidine hydrochloride: $^1$H NMR (400 MHz, d$_4$-methanol) δ 8.51 (s, 1H), 7.03 (s, 1H), 6.99 (s, 1H), 4.15-4.07 (br s, 4H), 3.69-3.62 (m, 2H), 3.28-3.23 (m, 2H), 3.13-3.02 (m, 6H), 2.77-2.17 (m, 2H), 2.37-2.35 (s, 3H), 2.19-2.12 (m, 4H), 2.04-1.96 (m, 4H); MS (ESI) for $C_{24}H_{29}ClF_3N_7$: 508 (MH$^+$).

4-(4-{5-chloro-2-methyl-3-[3-(4-methylpiperazin-1-yl)propyl]phenyl}piperazin-1-yl)-3-(trifluoromethyl)-1H-pyrazolo[3,4-d]pyrimidine: MS (ESI) for $C_{24}H_{29}ClF_3N_7$: 538 (MH$^+$).

4-{4-[5-chloro-2-methyl-3-(3-piperidin-1-ylpropyl)phenyl]piperazin-1-yl}-3-(trifluoromethyl)-1H-pyrazolo[3,4-d]pyrimidine trifluoroacetate: $^1$H NMR (400 MHz, d$_4$-methanol) δ 8.41 (s, 1H), 7.01 (s, 1H), 6.97 (s, 1H), 4.04-3.91 (br s, 4H), 3.58-3.53 (m, 2H), 3.18-3.13 (m, 2H), 3.02-2.98 (m, 4H), 2.97-2.89 (m, 2H), 2.76-2.70 (m, 2H), 2.37-2.35 (s, 3H), 2.04-1.94 (m, 4H), 1.89-1.82 (m, 2H), 1.80-1.67 (m, 2H); MS (ESI) for $C_{25}H_{31}ClF_3N_7$: 523 (MH$^+$).

Example 16

4-[4-(5-Chloro-2-methylphenyl)piperazin-1-yl]-6-methyl-1H-pyrazolo[3,4-d]pyrimidine 3-Amino-4-pyrazolecarboxamide hemisulfate salt (250 mg, 1.4 mmol.) was taken into 1:1 polyphosphoric acid and glacial acetic acid (2 mL) and the mixture was heated at 120° C. over six hours. The mixture was cooled to room temperature then taken into water (10 mL) and the pH adjusted to approximately 5 by dropwise addition of 50% aqueous sodium hydroxide. The resulting white precipitate was collected by filtration and washed with additional water. The solid was then suspended in methanol and collected by filtration then washed with ethyl ether. Drying in vacuo afforded 6-methyl-1,5-dihydro-pyrazolo[3,4-d]pyrimidin-4-one (154 mg) as a colorless solid. $^1$H-NMR (400 MHz, d$_6$-DMSO): 13.55 (s, 1H), 11.95 (s, 1H), 8.03 (s, 1H), 2.34 (s, 3H).

6-Methyl-1,5-dihydro-pyrazolo[3,4-d]pyrimidin-4-one (134 mg, 0.89 mmol.) was taken into thionyl chloride (3 mL) followed by addition of DMF (0.2 mL) and the mixture was brought to reflux over 30 minutes. The resulting solution was concentrated and the residue partitioned with ethyl acetate and saturated aqueous sodium bicarbonate. The organic phase was washed with brine then dried over anhydrous sodium sulfate, filtered and concentrated to afford a yellow oil. The oil was taken into THF (3 mL) followed by addition of 1-(5-Chloro-2-methylphenyl)-piperazine (390 mg, 1.87 mmol.) and catalytic DMAP then the mixture was brought to reflux over one hour. The resulting suspension was filtered and the filtrate was then concentrated. The residue was then suspended in methanol, filtered again and the resulting methanolic solution purified by preparative reverse phase HPLC. The pure fraction were combined and lyophilized to give 4-[4-(5-chloro-2-methylphenyl)piperazin-1-yl]-6-methyl-1H-pyrazolo[3,4-d]pyrimidine (10.7 mg) as a colorless solid. MS (ESI) for $C_{17}H_{19}ClN_6$: 343 (MH$^+$).

Using the same or analogous synthetic techniques and/or substituting with alternative reagents, the following compounds of the invention were prepared:

4-[4-(5-chloro-2-methylphenyl)piperazin-1-yl]-6-ethyl-1H-pyrazolo[3,4-d]pyrimidine: MS (ESI) for $C_{18}H_{21}ClN_6$: 357 (MH$^+$).

4-[4-(5-chloro-2-methylphenyl)piperazin-1-yl]-6-(1-methylethyl)-1H-pyrazolo[3,4-d]pyrimidine: MS (ESI) for $C_{19}H_{23}ClN_6$: 371 (MH$^+$).

4-[4-(5-chloro-2-methylphenyl)piperazin-1-yl]-3-methyl-6-phenyl-1H-pyrazolo[3,4-d]pyrimidine: $^1$H NMR (400 MHz, d$_6$-DMSO) δ 8.41 (m, 2H), 7.52 (m, 3H), 7.23 (d, 1H), 7.10 (d, 1H), 7.05 (dd, 1H), 4.01 (br s, 4H), 3.08 (m, 4H), 2.62 (s, 3H), 2.32 (s, 3H); MS (ESI) for $C_{23}H_{23}ClN_6$: 419 (MH$^+$).

Example 17

1-(3-chlorophenyl)-1,4-diazepane

A mixture of 1-chloro-3-iodobenzene (240 mg, 1 mmol), homopiperazine (600 mg, 6 mmol), sodium tert-butoxide (135 mg, 1.4 mmol), Pd$_2$(dba)$_3$ (23 mg, 0.025 mmol), and XANTPHOS (29 mg, 0.05 mmol) in dioxane (3 mL) was heated to 60° C. for 6 h. After cooling to room temperature, the mixture was filtered through celite, and the filter cake was rinsed with ethyl acetate. Concentration in vacuo and column chromatography of the residue (dichloromethane:methanol 8:2 to 7:3) gave 1-(3-chlorophenyl)-1,4-diazepane (46 mg, 22% yield) as a yellow-brown film. $^1$H NMR (400 MHz, CDCl$_3$) δ 7.11 (t, 1H), 6.64 (m, 2H), 6.56 (m, 1H), 3.61 (m, 2H), 3.56 (m, 2H), 3.10 (m, 2H), 2.93 (m, 2H), 2.89 (br s, 1H), 2.04-1.98 (m, 2H).

Example 18

2-(3-chlorophenyl)-2,5-diazabicyclo[2.2.1]heptane

A mixture of 3-bromo-1-chlorobenzene (191 mg, 1.0 mmol), 2,5-diazabicyclo[2.2.1]heptane-2-carboxylic acid tert-butyl ester (240 mg, 1.2 mmol), sodium tert-butoxide (135 mg, 1.4 mmol), Pd$_2$(dba)$_3$ (27 mg, 0.03 mmol), and BINAP (56 mg, 0.09 mmol) in toluene (3 mL) was heated to 110° C. for 15 h. After cooling to room temperature, the mixture was filtered through celite, and the filter cake was rinsed with ethyl acetate. The solvents were removed in vacuo. Column chromatography on silica (hexanes:ethyl acetate 4:1) of the residue afforded 5-(3-chlorophenyl)-2,5-diazabicyclo[2.2.1]heptane-2-carboxylic acid tert-butyl ester (240 mg, 78% yield) as a yellow solid. $^1$H NMR (400 MHz, CDCl$_3$, mixture of rotamers) δ 7.10 (q, 1H), 6.65 (d, 1H), 6.50 (m, 1H), 6.40 (d, 1H), 4.62 (s, 0.5H), 4.48 (s, 0.5H), 3.53 (m, 1H), 3.47-3.67 (m, 2H), 3.20-3.08 (dd, 1H), 1.98-1.91 (m, 2H), 1.45 (s, 4.5H), 1.41 (s, 4.5H).

To 5-(3-chlorophenyl)-2,5-diazabicyclo[2.2.1]heptane-2-carboxylic acid tert-butyl ester (240 mg, 0.78 mmol) was added 4NHCl in dioxane (3 mL). The mixture was heated with a heat gun for two minutes, cooled to room temperature, and concentrated to provide 2-(3-chlorophenyl)-2,5-diazabicyclo[2.2.1]heptane hydrochloride as a yellow solid, which was used without further purification. $^1$H NMR (400 MHz, d$_4$-methanol) δ 7.18 (t, 1H), 6.69 (m, 2H), 6.60 (m, 1H), 4.66 (s, 1H), 4.50 (s, 1H), 3.71 (m, 2H), 3.40-3.33 (m, 2H), 2.27 (d, 1H), 2.10 (d, 1H).

Example 19

4-[2-(2-chloro-4-piperazin-1-ylphenoxy)ethyl]morpholine hydrochloride

A mixture of 4-bromo-2-chlorophenol (5.0 g, 24 mmol), cesium carbonate (15.7 g, 48 mmol), and benzyl bromide in DMF (50 mL) was stirred at room temperature for 30 min. Water was added and the resulting mixture was extracted with ether. The organic layer was washed with water and brine, dried over magnesium sulfate, and concentrated. The residue was triturated with hexanes to provide 1-benzyloxy-4-bromo-2-chlorobenzene (5.91 g, 83% yield) as a white solid. $^1$H NMR (400 MHz, CDCl$_3$) δ 7.52 (d, 1H), 7.45-7.27 (m, 6H), 6.84-6.82 (d, 1H), 5.14 (s, 2H).

A mixture of 1-benzyloxy-4-bromo-2-chlorobenzene (300 mg, 1 mmol), piperazine (517 mg, 6 mmol), sodium tert-butoxide (135 mg, 1.4 mmol), Pd$_2$(dba)$_3$ (23 mg, 0.025 mmol), and BINAP (62 mg, 0.1 mmol) in toluene (3 mL) was heated to 110° C. for 14 h. After cooling to room temperature, the mixture was filtered through celite, and the filter cake was rinsed with ethyl acetate. The filtrate was concentrated. Column chromatography of the residue (dichloromethane:methanol 4:1) afforded 1-(4-benzyloxy-3-chlorophenyl)piperazine (147 mg, 48% yield) as a yellow film. $^1$H NMR (400 MHz, CDCl$_3$) δ 7.45 (m, 2H), 7.40-7.35 (m, 2H), 7.30 (m, 1H), 6.98 (d, 1H), 6.88 (d, 1H), 6.73 (dd, 1H), 5.08 (s, 2H), 3.03-2.98 (m, 8H), 1.73 (br s, 1H).

A mixture of 1-(4-benzyloxy-3-chlorophenyl)piperazine (147 mg, 0.48 mmol) in trifluoroacetic acid (1 mL) was stirred at 65° C. for 2 h, and then concentrated. The residue was dissolved in ethyl acetate, and washed with saturated sodium bicarbonate. The aqueous layer was extracted with ethyl acetate. The combined organic layers were dried over magnesium sulfate, and concentrated to give 2-chloro-4-piperazin-1-yl-phenol as a brown sticky film, which was used without further purification. $^1$H NMR (400 MHz, d$_4$-methanol) δ 7.12 (m, 1H), 6.86 (m, 2H), 3.34 (m, 4H), 3.25 (m, 4H).

A solution of 2-chloro-4-piperazin-1-yl-phenol (0.47 mmol) and Boc-anhydride (110 mg, 0.5 mmol) in THF (5 mL) was stirred at room temperature for 3 d. Concentration and column chromatography on silica (hexanes:ethyl acetate 3:2) provided 1,1-dimethylethyl 4-(3-chloro-4-hydroxyphenyl)-piperazine-1-carboxylate (112 mg, 75% yield) as a yellow sticky film. $^1$H NMR (400 MHz, d$_4$-methanol) δ 6.95 (m, 1H), 6.85-6.79 (m, 2H), 3.53 (m, 4H), 2.97-2.94 (m, 4H), 1.47 (S, 9H).

To a mixture of 1,1-dimethylethyl 4-(3-chloro-4-hydroxyphenyl)-piperazine-1-carboxylate (56 mg, 0.18 mmol) and cesium carbonate (176 mg, 0.54 mmol) in DMF (1.8 mL) was added N-(2-chloroethyl)-morpholine hydrochloride (67 mg, 0.36 mmol). The suspension was stirred at 60° C. for 4 h, and then cooled to room temperature. Water and ethyl acetate were added, and the layers were separated. The organic phase was washed with brine, dried over magnesium sulfate, and concentrated to provide 1,1-dimethylethyl 4-[3-chloro-4-(2-morpholin-4-yl-ethoxy)phenyl]piperazine-1-carboxylate (68 mg, 89% yield) as an orange oil. $^1$H NMR (400 MHz, CDCl$_3$) δ 6.97 (d, 1H), 6.88 (d, 1H), 6.78 (dd, 1H), 4.12 (t, 2H), 3.73 (m, 4H), 3.56 (m, 4H), 3.01 (m, 4H), 2.86 (t, 2H), 2.63 (m, 4H), 1.48 (s, 9H).

A solution of 1,1-dimethylethyl 4-[3-chloro-4-(2-morpholin-4-yl-ethoxy)phenyl]piperazine-1-carboxylate (68 mg, 0.16 mmol) in 4N hydrochloric acid in dioxane was refluxed for 2 min, and then concentrated to give 4-[2-(2-chloro-4-piperazin-1-ylphenoxy)ethyl]morpholine hydrochloride as a yellow film. $^1$H NMR (400 MHz, d$_4$-methanol) δ 7.38 (m, 1H), 7.22 (m, 2H), 4.50 (m, 2H), 4.08 (m, 2H), 3.92-3.85 (m, 2H), 3.72-3.66 (m, 4H), 3.55-3.49 (m, 8H), 3.42-3.35 (m, 2H).

Example 20

1,1-dimethylethyl 4-(3-chlorophenyl)-3-{[(2-morpholin-4-ylethyl)amino]carbonyl}piperazine-1-carboxylate To 1-(1,1-dimethylethyl) 3-methyl piperazine-1,3-dicarboxylate (1.00 g, 4.09 mmol) in dry toluene (15 mL) was added 3-bromo-chlorobenzene (653 mg, 3.41 mmol), Pd$_2$(dba)$_3$ (93.0 mg, 0.102 mmol), BINAP (191 mg, 0.307 mmol), and cesium carbonate (1.11 g, 4.77 mmol). The reaction mixture was stirred at 100° C. for 42 h, then cooled to room temperature and filtered through celite. The filter cake was washed with ethanol, and the filtrate was concentrated. Column chromatography on silica (hexanes:ethyl acetate 3:1) provided 1-(1,1-dimethylethyl) 3-methyl 4-(3-chlorophenyl)piperazine-1,3-dicarboxylate (310 mg, 21% yield) as a colorless oil. $^1$H NMR (400 MHz, CDCl$_3$) δ 7.20-7.13 (t, 1H), 6.84-6.79 (m, 2H), 6.73-6.78 (d, 1H), 4.63-4.50 (br s, 1H), 4.41-4.32 (br s, 1H), 4.24-4.02 (br s, 2H), 3.71-3.65 (s, 3H), 3.55-3.46 (br s, 1H), 3.42-3.26 (br s, 1H), 3.16-2.97 (br s, 1H), 1.49-1.42 (s, 9H); MS (ESI) for $C_{17}H_{23}ClN_2O_4$: 355 (MH$^+$).

To 1-(1,1-dimethylethyl) 3-methyl 4-(3-chlorophenyl)piperazine-1,3-dicarboxylate (184 mg, 0.519 mmol) in methanol (6 mL) was added 1M potassium hydroxide (3 mL). The reaction mixture was stirred at 50° C. for 5 h. The pH was adjusted to 5, and the mixture was extracted with ethyl acetate, dried over sodium sulfate, and concentrated to provide 1-(3-chlorophenyl)-4-{[(1,1-dimethylethyl)oxy]carbonyl}piperazine-2-carboxylic acid (159 mg, 76% yield) as a colorless oil. MS (ESI) for $C_{16}H_{21}ClN_2O_4$: 341 (MH$^+$).

To 1-(3-chlorophenyl)-4-{[(1,1-dimethylethyl)oxy]carbonyl}piperazine-2-carboxylic acid (67 mg, 0.291 mmol) in DMF (4 mL) was added 2-morpholin-4-yl-ethylamine (379 mg, 2.91 mmol), HATU (111 mg, 0.291 mmol), HOAt (48 mg, 0.349 mmol), and N-methyl morpholine (0.170 ml, 1.45 mmol). The reaction mixture was stirred at 25° C. for 21 h. Water and saturated sodium bicarbonate were added, and the solution was extracted with diethyl ether. The organic layer was washed with brine, dried over sodium sulfate, and concentrated. The residue was suspended in acetonitrile and filtered. The filtrate was concentrated to provide 1,1-dimethylethyl 4-(3-chlorophenyl)-3-{[(2-morpholin-4-ylethyl)amino]carbonyl}piperazine-1-carboxylate (81 mg, 62% yield) as a colorless oil. MS (ESI) for $C_{22}H_{33}ClN_4O_4$: 453 (MH$^+$).

To 1,1-dimethylethyl 4-(3-chlorophenyl)-3-{[(2-morpholin-4-ylethyl)amino]carbonyl}piperazine-1-carboxylate (81 mg, 0.18 mmol) in methanol (5 mL) was added 4N hydrochloric acid in dioxane (0.1 mL). The reaction mixture was refluxed for 2 min, and then concentrated to provide 1-(3-chlorophenyl)-N-(2-morpholin-4-ylethyl)piperazine-2-carboxamide hydrochloride (69 mg, 100% yield) as a colorless oil. MS (ESI) for $C_{17}H_{25}ClN_4O_2$: 353 (MH$^+$).

Using the same or analogous synthetic techniques and/or substitution with alternative reagents, the following compounds of the invention were prepared:

1-(3-chlorophenyl)-N-(1-methylpiperidin-4-yl)piperazine-2-carboxamide: MS (ESI) for $C_{17}H_{25}ClN_4O$: 337 (MH$^+$).

[1-(3-chlorophenyl)piperazin-2-yl]methanol: MS (ESI) for $C_{11}H_{15}ClN_2O$: 227 (MH$^+$).

1-(3-chlorophenyl)-N-[2-(dimethylamino)ethyl]piperazine-2-carboxamide: MS (ESI) for $C_{15}H_{23}ClN_4O$: 311 (MH$^+$).

1-(3-chlorophenyl)-N-methylpiperazine-2-carboxamide: MS (ESI) for $C_{12}H_{16}ClN_3O$: 254 (MH$^+$).

methyl 4-(3-chlorophenyl)piperazine-2-carboxylate: MS (ESI) for $C_{12}H_{15}ClN_2O_2$: 255 (MH$^+$).

4-(3-chlorophenyl)-N-methylpiperazine-2-carboxamide: MS (ESI) for $C_{12}H_{16}ClN_3O$: 254 (MH$^+$).

Example 21

4-[4-(5-chloro-2-methylphenyl)piperazin-1-yl]-3-(3-methylbut-2-en-1-yl)-1H-pyrazolo[3,4-d]pyrimidine hydrochloride A mixture of 3-bromo-4-[4-(5-chloro-2-methylphenyl)piperazin-1-yl]-1H-pyrazolo[3,4-d]pyrimidine (20 mg, 0.050 mmol), 3-methyl-2-butenyltributylstannane (19 mg, 0.055 mmol), [1,1'-bis(diphenylphosphino)ferrocene]dichloropalladium(II) complex with dichlormethane (8.0 mg, 0.010 mmol), and hexamethylphosphoramide (1 mL) was de-gassed with nitrogen for 5 min, and then stirred at 140° C. for 18 h. The reaction mixture was cooled, and diluted with ethyl acetate (10 mL). The organic layer was washed with water (3×5 mL), and brine (5 mL), dried over sodium sulfate, and concentrated. The residue was purified by reversed phase HPLC to give a powder, which was azoetroped with a mixture of 4M hydrogen chloride in dioxane:methanol 95:5 (3×1 mL) to give 4-[4-(5-chloro-2-methylphenyl)piperazin-1-yl]-3-(3-methylbut-2-en-1-yl)-1H-pyrazolo[3,4-d]pyrimidine hydrochloride (3.1 mg, 16% yield). $^1$H NMR (400 MHz, d$_4$-methanol) δ 8.39 (s, 1H), 7.18 (d, 1H), 7.03 (d, 1H), 7.00 (d, d, 1H), 5.35 (t, 1H), 4.17-4.08 (m, 4H), 3.84 (d, 1H), 3.07-3.02 (m, 4H), 2.34 (s, 3H), 1.78 (s, 3H), 1.75 (s, 3H); MS (ESI) for $C_{21}H_{25}ClN_6$: 397 (MH$^+$).

Example 22

[5-chloro-3-[4-(3-ethyl-1H-pyrazolo[3,4-d]pyrimidin-4-yl)piperazin-1-yl]-2-(methyloxy)phenyl]methanol To a degassed solution of methyl 3-bromo-5-chloro-2-(methyloxy)benzoate (1.57 g, 5.64 mmol) in toluene (60 mL) was added cesium carbonate (2.57 g, 7.89 mmol), BINAP (351 mg, 0.564 mmol), tris(dibenzylideneacetone)dipalladium(0) (130 mg, 0.141 mmol), and Boc-piperazine (1.4 g, 7.33 mmol). The mixture was refluxed for 24 h, then cooled to room temperature, and filtered through celite. The filtrate was concentrated and the residue was purified by column chromatography on silica (hexanes:ethyl acetate 4:1) to afford of 1,1-dimethylethyl 4-{5-chloro-2-(methyloxy)-3-[(methyloxy)carbonyl]phenyl}piperazine-1-carboxylate (1.13 g, 52% yield) as a white solid. $^1$H NMR (400 MHz, CDCl$_3$) δ 7.37 (d, 1H), 6.97 (d, 1H), 3.90 (s, 3H), 3.87 (s, 3H), 3.58-3.56 (m, 4H), 3.06-3.03 (m, 4H), 1.48 (s, 9H); MS (ESI) for $C_{18}H_{25}ClN_2O_5$: 385 (MH$^+$).

A solution of 1,1-dimethylethyl-4-{5-chloro-2-(methyloxy)-3-[(methyloxy)carbonyl]phenyl}piperazine-1-carboxylate (300 mg, 0.78 mmol) in THF (8 mL) was cooled to 0° C., and lithium aluminum hydride (1.17 mL, 1.17 mmol) was added. The solution was stirred at 0° C. for 1 h, followed by the addition of water (150 μL), 15% sodium hydroxide (150 μL), and finally water (300 μL). The mixture was stirred at 0° C. for 10 min, then filtered through celite and concentrated. Column chromatography on silica (hexanes:ethyl acetate 3:2) gave 1,1-dimethylethyl-4-[5-chloro-3-(hydroxymethyl)-2-(methyloxy)phenyl]piperazine-1-carboxylate (264 mg, 95% yield) as a white solid. $^1$H NMR (400 MHz, CDCl$_3$) δ 7.00 (d, 1H), 6.82 (d, 1H), 4.65 (d, 2H), 3.87 (s, 3H), 3.60-3.57 (m, 4H), 3.05-3.02 (m, 4H), 1.48 (s, 9H); MS (ESI) for $C_{17}H_{25}ClN_2O_4$: 357 (MH$^+$).

A solution of 1,1-dimethylethyl-4-[5-chloro-3-(hydroxymethyl)-2-(methyloxy)phenyl]piperazine-1-carboxylate (40 mg, 0.11 mmol) in dioxane (2 mL) and 4N hydrochloric acid in dioxane (1 mL) was refluxed for 3 min, and then concentrated. The solid residue was dissolved in THF (5 mL), and triethylamine (50 μl, 0.34 mmol) and 4-chloro-3-ethyl-1H-pyrazolo[3,4-d]pyrimidine (20 mg, 0.11 mmol) were added. The solution was stirred at 50° C. for 24 h, then cooled to room temperature and concentrated. Column chromatography on silica (dichloromethane:methanol 95:5 to 9:1) afforded [5-chloro-3-[4-(3-ethyl-1H-pyrazolo[3,4-d]pyrimidin-4-yl)piperazin-1-yl]-2-(methyloxy)phenyl]methanol (7.3 mg, 16% yield) as a white solid. $^1$H NMR (400 MHz, CDCl$_3$) δ 3.31 (s, 1H), 8.30 (s, 1H), 7.04 (d, 1H), 6.88 (d, 1H), 5.19 (t, 1H), 4.49 (d, 2H), 3.85-3.78 (m, 7H), 3.21-3.16 (m, 4H), 2.97 (q, 2H), 1.29 (t, 3H); MS (ESI) for C$_{19}$H$_{24}$ClN$_6$O$_2$: 403 (MH$^+$).

Using the same or analogous synthetic techniques and/or substituting with alternative reagents, the following compound of the invention was prepared:

methyl 5-chloro-3-[4-(3-ethyl-1H-pyrazolo[3,4-d]pyrimidin-4-yl)piperazin-1-yl]-2-(methyloxy)benzoate: $^1$H NMR (400 MHz, CDCl$_3$) δ 13.35 (s, 1H), 8.30 (s, 1H), 7.22 (d, 1H), 7.19 (d, 1H), 3.85-3.81 (m, 10H), 3.23-3.20 (m, 4H), 2.97 (q, 2H), 1.30 (t, 3H); MS (ESI) for C$_{20}$H$_{23}$ClN$_6$O$_3$; 431 (MH$^+$).

Example 23

5-chloro-N-[2-(dimethylamino)ethyl]-3-[4-(3-ethyl-1H-pyrazolo[3,4-d]pyrimidin-4-yl)piperazin-1-yl]-2-(methyloxy)benzamide To a solution of 1,1-dimethylethyl-4-{5-chloro-2-(methyloxy)-3-[(methyloxy)-carbonyl]phenyl}piperazine-1-carboxylate (Example 22, 290 mg, 0.75 mmol) in methanol (6 mL) was added 1N aqueous potassium hydroxide (3.75 mL, 3.75 mmol). The solution was stirred at 60° C. for 15 h, then cooled to 0° C. and acidified to pH 2 using aqueous 1N hydrochloric acid. The solution was diluted with water, and extracted with ethyl acetate. The combined organic layers were washed with brine, dried over sodium sulfate, and concentrated to afford 5-chloro-3-(4-{[(1,1-dimethylethyl)oxy]carbonyl}piperazin-1-yl)-2-(methyloxy)benzoic acid (268 mg, 96% yield) as a yellow solid. $^1$H NMR (400 MHz, d$_4$-methanol) δ 7.26 (br s, 1H), 7.08 (d, 1H), 3.88 (s, 3H), 3.61-3.57 (m, 4H), 3.06-3.03 (m, 4H), 1.48 (s, 9H); MS (ESI) for C$_{17}$H$_{23}$ClN$_2$O$_5$: 393 (M+Na$^+$).

To a solution of 5-chloro-3-(4-{[(1,1-dimethylethyl)oxy]carbonyl}piperazin-1-yl)-2-(methyloxy)benzoic acid (95 mg, 0.26 mmol) in DMF (5 mL) was added N,N-dimethylethylenediamine (25 μl, 0.23 mmol), triethylamine (75 μl, 0.51 mmol), and HATU (146 mg, 0.38 mmol). The solution was stirred at room temperature for 17 h, and then partitioned between ethyl acetate and 5% aqueous lithium chloride. The organic layer was washed with brine, dried over sodium sulfate, and concentrated. Column chromatography on silica (dichloromethane:methanol 95:5) provided 1,1-dimethylethyl 4-[5-chloro-3-({[2-(dimethylamino)ethyl]amino}carbonyl)-2-(methyloxy)phenyl]piperazine-1-carboxylate (108 mg, 96% yield) as a white solid. $^1$H NMR (400 MHz, CDCl$_3$) δ 8.63 (br s, 1H), 7.71 (d, 1H), 7.00 (d, 1H), 3.93 (s, 3H), 3.66-3.63 (m, 2H), 3.62-3.58 (m, 4H), 3.04-3.01 (m, 4H), 2.90-2.87 (m, 2H), 2.58 (s, 6H), 1.49 (s, 9H); MS (ESI) for C$_{21}$H$_{33}$ClN$_4$O$_4$: 441 (MH$^+$).

A solution of 1,1-dimethylethyl 4-[5-chloro-3-({[2-(dimethylamino)ethyl]amino}carbonyl)-2-(methyloxy)phenyl]piperazine-1-carboxylate (108 mg, 0.25 mmol) in dioxane (2 mL) and 4N hydrochloric acid in dioxane (1 mL) was refluxed for 3 min and then concentrated. The residue was dissolved in THF (3 mL), and triethylamine (103 μl, 0.75 mmol) and 4-chloro-3-ethyl-1H-pyrazolo[3,4-d]pyrimidine (45 mg, 0.25 mmol) were added. The mixture was stirred at 50° C. for 24 h, then cooled to room temperature and concentrated. The residue was diluted with sodium bicarbonate, and the aqueous layer was extracted with ethyl acetate. The combined organic layers were washed with brine, dried over sodium sulfate, and concentrated. Column chromatography on silica (dichloromethane:methanol 85:15) yielded 5-chloro-N-[2-(dimethylamino)ethyl]-3-[4-(3-ethyl-1H-pyrazolo[3,4-d]pyrimidin-4-yl)piperazin-1-yl]-2-(methyloxy)benzamide (15 mg, 13% yield) as a white solid. $^1$H NMR (400 MHz, d$_6$-DMSO) δ 13.32 (br s, 1H), 8.37-8.34 (m, 1H), 8.30 (s, 1H), 7.22 (d, 1H), 7.12 (d, 1H), 3.85-3.81 (m, 7H), 3.22-3.20 (m, 4H), 2.39 (q, 2H), 2.19 (s, 6H), 1.99 (t, 3H); MS (ESI) for C$_{23}$H$_{31}$ClN$_8$O$_2$: 488 (MH$^+$).

Using the same or analogous synthetic techniques and/or substituting with alternative reagents, the following compounds of the invention were prepared:

4-(4-{5-chloro-2-(methyloxy)-3-[(4-methylpiperazin-1-yl)carbonyl]phenyl}piperazin-1-yl)-3-ethyl-1H-pyrazolo[3,4-d]pyrimidine: $^1$H NMR (400 MHz, d$_6$-DMSO) δ 13.31 (br s, 1H), 8.30 (s, 1H), 7.03 (d, 1H), 6.87 (d, 1H), 3.85-3.75 (m, 7H), 3.64-3.58 (m, 2H), 3.18-3.10 (m, 4H), 2.96 (q, 2H), 2.36-2.30 (m, 2H), 2.23-2.19 (m, 5H), 1.30 (t, 3H); MS (ESI) for C$_{24}$H$_{31}$ClN$_8$O$_2$: 499 (MH$^+$).

2-(dimethylamino)ethyl 5-chloro-3-[4-(3-ethyl-1H-pyrazolo[3,4-d]pyrimidin-4-yl)piperazin-1-yl]-2-(methyloxy)benzoate: $^1$H NMR (400 MHz, d$_6$-DMSO) δ 13.32 (br s, 1H), 8.30 (s, 1H), 7.19 (m, 2H), 4.30 (t, 2H), 3.84-3.80 (m, 7H), 3.25-3.20 (m, 4H), 2.99 (q, 2H), 2.58 (t, 2H), 2.19 (s, 6H), 1.29 (t, 3H); MS (ESI) for C$_{23}$H$_{30}$ClN$_7$O$_3$: 488 (MH$^+$).

Example 24

1-[5-chloro-3-[4-(3-ethyl-1H-pyrazolo[3,4-d]pyrimidin-4-yl)piperazin-1-yl]-2-(methyloxy)phenyl]-N,N-dimethylmethanamine To a solution of 1,1-dimethylethyl-4-[5-chloro-3-(hydroxymethyl)-2-(methyloxy)phenyl]piperazine-1-carboxylate (82 mg, 0.23 mmol) in dichloromethane (5 mL) was added Dess-Martin periodinane (117 mg, 0.28 mmol). The solution was stirred at room temperature for 1 h, followed by the addition of a 10% aqueous sodium thiosulfate pentahydrate solution (10 mL) and saturated sodium bicarbonate (10 mL). The mixture was stirred at room temperature for 15 minutes, the layers were separated, and the aqueous layer was extracted with more dichloromethane. The combined organic layers were washed with brine, dried over sodium sulfate, and concentrated. Column chromatography on silica (hexanes:ethyl acetate 4:1) afforded 1,1-dimethylethyl 4-[5-chloro-3-formyl-2-(methoxy)phenyl]piperazine-1-carboxylate (69 mg, 85% yield) as a yellow oil. $^1$H NMR (400 MHz, CDCl$_3$) δ 10.35 (s, 1H), 7.44 (d, 1H), 7.08 (d, 1H), 3.97 (s, 3H), 3.63-3.60 (m, 4H), 3.09-3.06 (m, 4H), 1.49 (s, 9H); MS (ESI) for C$_{17}$H$_{23}$ClN$_2$O$_4$: 377 (M+Na$^+$).

To a solution of 1,1-dimethylethyl 4-[5-chloro-3-formyl-2-(methoxy)phenyl]piperazine-1-carboxylate (95 mg, 0.27 mmol) in ethanol (2 mL) was added triethylamine (75 Al, 0.54 mmol), dimethylamine hydrochloride (44 mg, 0.54 mmol), and Titanium(IV) isopropoxide (160 μl, 0.54 mmol). The mixture was stirred at room temperature for 15 h. Sodium borohydride (16 mg, 0.42 mmol) was added, and the mixture was stirred at room temperature for additional 3 h. The mixture was quenched by the addition of a 2N ammonia solution (3 mL), and the resulting precipitate was filtered and washed with dichloromethane. The filtrate was partitioned between water and dichloromethane, and the aqueous layer was extracted with dichloromethane. The organic layer was washed with brine, dried over sodium sulfate, and concentrated to give 1,1-dimethylethyl 4-[5-chloro-3-[(dimethylamino)methyl]-2-(methoxy)phenyl]piperazine-1-carboxylate (59 mg, 57% yield) as a white solid. $^1$H NMR (400 MHz, CDCl$_3$) δ 7.01 (d, 1H), 6.75 (d, 1H), 3.80 (s, 3H), 3.60-3.52 (m, 4H), 3.38 (s, 2H), 3.06-2.99 (m, 4H), 2.24 (s, 6H), 1.48 (s, 9H); MS (ESI) for C$_{19}$H$_{30}$ClN$_3$O$_3$: 384 (MH$^+$).

To a solution of 1,1-dimethylethyl 4-[5-chloro-3-[(dimethylamino)methyl]-2-(methoxy)phenyl]piperazine-1-carboxylate (59 mg, 0.15 mmol) in dioxane (2 mL) was added 4N hydrochloric acid in dioxane (1 mL). The solution was refluxed for 2 min, and then concentrated. The residue was dissolved in THF (5 mL) and triethylamine (65 µl, 0.46 mmol) and 4-chloro-3-ethyl-1H-pyrazolo[3,4-d]pyrimidine (28 mg, 0.15 mmol) were added. The solution was stirred at 50° C. for 24 h, cooled to room temperature and concentrated. The residue was added into saturated sodium bicarbonate, and extracted with ethyl acetate. The organic layer was washed with brine, dried over sodium sulfate, and concentrated. Column chromatography on silica (dichloromethane:methanol 85:15) yielded 1-[5-chloro-3-[4-(3-ethyl-1H-pyrazolo[3,4-d]pyrimidin-4-yl)piperazin-1-yl]-2-(methyloxy)phenyl]-N,N-dimethylmethanamine (21 mg, 33% yield) as a white solid. $^1$H NMR (400 MHz, $d_6$-DMSO) δ 13.31 (br s, 1H), 8.30 (s, 1H), 6.99 (d, 1H), 6.89 (d, 1H), 3.82-3.78 (m, 7H), 3.37 (s, 2H), 3.22-3.17 (m, 4H), 2.97 (q, 2H), 2.16 (s, 6H), 1.30 (t, 3H); MS (ESI) for $C_{21}H_{28}ClN_7O$: 430 (MH$^+$).

Using the same or analogous synthetic techniques and/or substituting with alternative reagents, the following compound of the invention was prepared:

N'-{[5-chloro-3-[4-(3-ethyl-1H-pyrazolo[3,4-d]pyrimidin-4-yl)piperazin-1-yl]-2-(methyloxy)phenyl]methyl}-N,N-dimethylethane-1,2-diamine: $^1$H NMR (400 MHz, CD$_3$OD) δ 8.30 (s, 1H), 7.02 (d, 1H), 6.93 (d, 1H), 3.97-3.93 (m, 7H), 3.76 (s, 2H), 3.27-3.24 (m, 4H), 3.06 (q, 2H), 2.69 (t, 2H), 2.48 (t, 2H), 2.22 (s, 6H), 1.38 (t, 3H); MS (ESI) for $C_{23}H_{33}ClN_8O$: 474 (MH$^+$).

Example 25

1-[5-chloro-2-methyl-4-(methyloxy)phenyl]piperazine trifluoroacetate

A mixture of 2-chloro-5-methyl-4-nitrosophenol (11.6 g, 67.9 mmol, M. E. Falugh, T. A. Crowell, J. A. Clemens, B. D. Sawyer, *J. Med. Chem.* 1979, 22, 63-69), benzyl bromide (11.6 g, 67.9 mmol), and potassium carbonate (14.1 g, 102.2 mmol) in DMSO was stirred at 60° C. for 6 h. The reaction mixture was partitioned between water and ethyl acetate, filtered through celite, and the layers were separated. The organic layer was washed with saturated sodium bicarbonate, water, and brine, dried over sodium sulfate, and concentrated. Column chromatography on silica (hexanes:ethyl acetate 97:3) afforded 1-chloro-4-methyl-5-nitroso-2-[(phenylmethyl)oxy]benzene (1.55 g, 9% yield).

A mixture of 1-chloro-4-methyl-5-nitroso-2-[(phenylmethyl)oxy]benzene (1.55 g, 5.92 mmol) and tin(II) chloride (5.05 g, 22.38 mmol) in ethanol was refluxed for 4 h. The reaction mixture was concentrated and the residue partitioned between ethyl acetate and saturated sodium bicarbonate. The layers were separated, the organic layer was washed with water, and brine, dried over sodium sulfate, and concentrated. Column chromatography on silica (hexanes:ethyl acetate 9:1) gave 1-chloro-4-methyl-2-[(phenyl-methyl)oxy]aniline (1.32 g, 90% yield).

A mixture of 1-chloro-4-methyl-2-[(phenylmethyl)oxy]aniline (1.10 g, 4.44 mmol), bis(2-chloroethyl)amine hydrochloride (0.79 g, 4.43 mmol), and potassium carbonate (0.61 g, 4.42 mmol) in diglyme was refluxed for 18 h. The reaction mixture was diluted with hexanes, decanted, and concentrated. Column chromatography on silica (dichloromethane:methanol 95:5 to 92:9) provided 1-{5-chloro-2-methyl-4-[(phenyl-methyl)oxy]phenyl}piperazine (0.23 g, 16% yield).

A solution of 1-{5-chloro-2-methyl-4-[(phenylmethyl)oxy]phenyl}piperazine (0.23 mg, 0.73 mmol) in trifluoroacetic acid (3 mL) was refluxed for 3 h and then concentrated. The residue was dissolved in ethyl acetate, treated with activated charcoal, and filtered. Concentration gave 2-chloro-5-methyl-4-piperazine-1-ylphenol (159 mg, 96% yield).

A solution of 2-chloro-5-methyl-4-piperazine-1-ylphenol (49 mg, 0.22 mmol) and Boc-anhydride (48 mg, 0.22 mmol) in ethyl acetate was stirred at 50° C. for 2 h. Concentration and column chromatography on silica (dichloromethane:methanol 95:5 to 9:1) afforded 1,1-dimethylethyl 4-(5-chloro-4-hydroxy-2-methylphenyl)piperazine 1-carboxylate (49 mg, 68% yield).

A mixture of 1,1-dimethylethyl 4(5-chloro-4-hydroxy-2-methylphenyl)piperazine-1-carboxylate (16 mg, 0.05 mmol), methyl iodide (14 mg, 0.10 mmol), and cesium carbonate (32 mg, 0.10 mmol) in DMF was stirred at 60° C. for 5 h. The reaction mixture was diluted with ethyl acetate, washed with water, 1N sodium hydroxide, and water, dried over sodium sulfate, and concentrated. The residue was dissolved in dichloromethane/trifluoroacetic acid/water (75:20:5) and stirred at room temperature for 12 h. Concentration provided 1-[5-chloro-2-methyl-4-(methyloxy)-phenyl]piperazine trifluoroacetate (8 mg, 47% yield), which was used without further purification.

Using the same or analogous synthetic techniques and/or substituting with alternative reagents, the following compounds of the invention were prepared:

3-[(2-chloro-5-methyl-4-piperazin-1-ylphenyl)oxy]-N,N-dimethylpropan-1-amine

2-[(2-chloro-5-methyl-4-piperazin-1-ylphenyl)oxy]-N,N-dimethylethanamine

Example 26

2-{[5-chloro-2-(methyloxy)-3-piperazin-1-ylphenyl]oxy}-N,N-dimethylethanamine

To a solution of methyl 3-bromo-5-chloro-2-(methyloxy)benzoate (2.86 g, 10.6 mmol) in THF (30 mL) was added methanol (620 µL, 15.3 mmol) followed by 2 M lithium borohydride in THF (7.7 mL, 15.4 mmol). The resulting mixture was heated to 50° C. for 2 h. The residual hydride was quenched with 1M hydrochloric acid at 0° C. The mixture was diluted with ethyl acetate and neutralized with sodium bicarbonate. The layers were separated, the organic layer was dried over magnesium sulfate, and concentrated to give [3-bromo-5-chloro-2-(methyloxy)phenyl]methanol as a white solid. $^1$H NMR (400 MHz, CDCl$_3$) δ 7.47 (d, 1H), 7.34 (d, 1H), 4.71 (d, 2H), 3.85 (s, 3H), 2.03 (t, 1H).

A biphasic mixture of [3-bromo-5-chloro-2-(methyloxy)phenyl]methanol, potassium bromide (122 mg, 1.02 mmol), and TEMPO (16 mg, 0.10 mmol) in dichloro-methane (25 mL) and water (10 mL) was cooled to 0° C. A solution of bleach saturated with sodium bicarbonate (5% sodium hypochlorite, 18.7 mL, 12.5 mmol) was added, and the mixture was stirred for 20 min. Water was then added followed by dichloromethane. The layers were separated, and the aqueous layer was extracted with dichloromethane. The organic extracts were combined, dried over magnesium sulfate, and concentrated to afford 3-bromo-5-chloro-2-(methyloxy)benzaldehyde (2.2 g, 87% yield over 2 steps) as a pale yellow solid. $^1$H NMR (400 MHz, CDCl$_3$) δ 10.26 (s, 2H), 7.78 (d, 1H), 7.75 (d, 1H), 3.97 (s, 3H).

A mixture of 3-bromo-5-chloro-2-(methyloxy)benzaldehyde (1.22 g, 4.9 mmol), and 3-chloroperbenzoic acid (2.4 g, 9.8 mmol) in dichloromethane (20 mL) was refluxed for 26 h, and then concentrated. The residue was dissolved in ethyl acetate, washed twice with saturated sodium bicarbonate, dried over magnesium sulfate, and concentrated. The residue was dissolved in methanol, and 1M potassium hydroxide (5 mL) was added. The mixture was stirred for 1 h at room temperature, and then acidified with 1M hydrochloric acid (5 mL). The methanol was removed in vacuo, and the resulting mixture was extracted with ethyl acetate. The organic extracts were dried with magnesium sulfate, and concentrated. Silica gel column chromatography (hexanes:ethyl acetate 4:1) provided 3-bromo-5-chloro-2-(methyloxy)phenol (123 mg, 11% yield) as a colorless oil. $^1$H NMR (400 MHz, CDCl$_3$) δ 7.08 (d, 1H), 6.94 (d, 1H), 3.89 (s, 3H).

To a solution of 3-bromo-5-chloro-2-(methyloxy)phenol (123 mg, 0.52 mmol) in DMF (1 mL) was added cesium carbonate (678 mg, 2.08 mmol) and 2-chloro-N,N-dimethylethylamine hydrochloride (150 mg, 1.04 mmol). The mixture was stirred at room temperature for 4 h and then at 70° C. for additional 2 h. After cooling to room temperature, water and ethyl acetate were added. The layers were separated, and the organic layer was washed with brine, dried over sodium sulfate, and concentrated to give crude 2-{[3-bromo-5-chloro-2-(methyloxy)phenyl]oxy}-N,N-dimethylethanamine as a yellow film, which was used without further purification. $^1$H NMR (400 MHz, CDCl$_3$) δ 7.14 (d, 1H), 6.86 (d, 1H), 4.09 (t, 2H), 3.84 (s, 3H), 2.78 (t, 2H), 2.35 (s, 6H).

To a solution of crude 2-{[3-bromo-5-chloro-2-(methyloxy)phenyl]oxy}-N,N-dimethylethanamine in toluene (2 mL) was added tri(dibenzylideneacetone)dipalladium(0) (12 mg, 0.013 mmol), BINAP (16 mg, 0.026 mmol), sodium tert-butoxide (70 mg, 0.73 mmol), and piperazine (270 mg, 3.12 mmol). The resulting mixture was refluxed for 5 h. After cooling to room temperature, the mixture was filtered through celite, and the filter cake was rinsed with ethyl acetate. The filtrate was concentrated and the residue purified by column chromatography on silica (dichloromethane:methanol:aqueous ammonia 80:19:1) to provide 2-{[5-chloro-2-(methyloxy)-3-piperazin-1-ylphenyl]oxy}-N,N-dimethylethanamine (84.3 mg, 52% yield for 2 steps) as a yellow film. $^1$H NMR (400 MHz, CDCl$_3$) δ 6.57 (d, 1H), 6.50 (d, 1H), 4.05 (t, 2H), 3.79 (s, 3H), 3.02 (m, 8H), 2.75 (t, 2H), 2.34 (s, 6H); MS (ESI) for C$_{15}$H$_{24}$ClN$_3$O$_2$: 314 (MH$^+$).

Example 27

3-(5-chloro-2-methyl-3-piperazin-1-ylphenyl)-N,N-dimethylprop-2-yn-1-amine hydrochloride A mixture of 5-chloro-1-iodo-2-methyl-3-nitrobenzene (3.0 g, 10.1 mmol) and tin(II) chloride dihydrate (9.1 g, 40.4 mmol) in acetic acid (10 mL) was stirred for 1 h at room temperature, and was then diluted with ether. The mixture was cooled to 0° C. and 50% aqueous sodium hydroxide was added slowly. A clumpy white solid formed, and was removed by filtration. The filtrate was concentrated and the residue purified by column chromatography on silica (hexane:ethyl acetate 4:1) to provide 5-chloro-3-iodo-2-methylaniline (1.81 g, 67% yield) as a pale yellow solid. $^1$H NMR (400 MHz, CDCl$_3$) δ 7.25 (d, 1H), 6.64 (d, 1H), 3.78 (br s, 2H), 2.28 (s, 3H).

To a solution of 5-chloro-3-iodo-2-methylaniline (1.32 g, 4.9 mmol) in diglyme (5 mL) was added potassium carbonate (677 mg, 4.9 mmol) and bis(2-chloroethyl)amine hydrochloride (875 mg, 4.9 mmol). The mixture was refluxed for 24 h and then cooled to room temperature. Water and ethyl acetate were added. The layers were separated, the organic layer was dried over sodium sulfate, filtered, and concentrated. Column chromatography on silica (dichloromethane:methanol 4:1) provided 1-(5-chloro-3-iodo-2-methylphenyl)piperazine as a white solid (660 mg, 40% yield). $^1$H NMR (400 MHz, CDCl$_3$) δ 7.56 (d, 1H), 6.97 (d, 1H), 3.03 (m, 4H), 2.83 (m, 4H), 2.39 (s, 3H), 1.73 (br s, 1H); MS (ESI) for C$_{11}$H$_{14}$ClIN$_2$: 337 (MH$^+$).

A mixture of 1-(5-chloro-3-iodo-2-methylphenyl)piperazine (660 mg, 2.0 mmol) and Boc-anhydride (437 mg, 2.0 mmol) in THF (20 mL) was stirred at room temperature for 15 h, and then concentrated to give 1,1-dimethylethyl 4-(5-chloro-3-iodo-2-methylphenyl)piperazine-1-carboxylate (784 mg, 92% yield) as a pale yellow syrup. $^1$H NMR (400 MHz, CDCl$_3$) δ 7.56 (d, 1H), 6.93 (d, 1H), 3.55 (br s, 4H), 2.80 (m, 4H), 2.38 (s, 3H), 1.48 (s, 9H).

To a solution of 1,1-dimethylethyl 4-(5-chloro-3-iodo-2-methylphenyl)piperazine-1-carboxylate (106 mg, 0.24 mmol) in THF (1 mL) was added bis(triphenylphosphine)palladium(II) chloride (35 mg, 0.012 mmol), 3-dimethylamino-1-propyne (40 μL, 0.36 mmol), triethylamine (50 μL, 0.36 mmol), and copper(I) iodide (5 mg, 0.024 mmol). The mixture was stirred at room temperature for 20 h, and then concentrated. Column chromatography on silica (dichloromethane:methanol 95:5) provided 1,1-dimethylethyl 4-{5-chloro-3-[3-(dimethylamino)prop-1-yn-1-yl]-2-methylphenyl}piperazine-1-carboxylate (41.1 mg, 44% yield) as a yellow film. $^1$H NMR (400 MHz, CDCl$_3$) δ 7.14 (d, 1H), 6.89 (d, 1H), 3.56 (br s, 4H), 3.52 (s, 2H), 2.80 (m, 4H), 2.37 (s, 6H), 2.36 (s, 3H), 1.48 (s, 9H); MS (ESI) for C$_{21}$H$_{30}$ClN$_3$O$_2$: 392 (MH$^+$).

A mixture of 1,1-dimethylethyl 4-{5-chloro-3-[3-(dimethylamino)prop-1-yn-1-yl]-2-methylphenyl}piperazine-1-carboxylate (41.1 mg, 0.105 mmol) in methanol (1 mL) and 4N hydrochloric acid in dioxane (1 mL) was refluxed for 2 min and then concentrated to provide 3-(5-chloro-2-methyl-3-piperazin-1-ylphenyl)-N,N-dimethylprop-2-yn-1-amine hydrochloride as a solid. MS (ESI) for C$_{16}$H$_{22}$ClN$_3$: 292 (MH$^+$).

Example 28

N'-(5-chloro-2-methyl-3-piperazin-1-ylphenyl)-N,N-dimethylethane-1,2-diamine hydrochloride To a solution of 1,1-dimethylethyl 4-(5-chloro-3-iodo-2-methylphenyl)piperazine-1-carboxylate (92 mg, 0.21 mmol) in dioxane (1 mL) was added sodium tert-butoxide (28 mg, 0.29 mmol), tri(dibenzylideneacetone)dipalladium(0) (6 mg, 0.006 mmol), XANTPHOS (8 mg, 0.013 mmol), and N,N-dimethylethylenediamine (28 μL, 0.25 mmol). The mixture was refluxed for 5 h, then cooled to room temperature and concentrated. Column chromatography on silica (dichloromethane:methanol 9:1) gave 1,1-dimethylethyl 4-(5-chloro-3-{[2-(dimethylamino)ethyl]amino}-2-methylphenyl)-piperazine-1-carboxylate (33.3 mg, 0.084 mmol, 40% yield) as a yellow film. $^1$H NMR (400 MHz, CDCl$_3$) δ 6.43 (d, 1H), 6.38 (d, 1H), 4.43 (br s, 1H), 3.56 (br s, 4H), 3.15 (m, 2H), 2.79 (br s, 4H), 2.62 (m, 2H), 2.28 (s, 6H), 2.07 (s, 3H), 1.48 (s, 9H); MS (ESI) for C$_{20}$H$_{33}$ClN$_4$O$_2$: 397 (MH$^+$).

A solution of 1,1-dimethylethyl 4-(5-chloro-3-{[2-(dimethylamino)ethyl]amino}-2-methylphenyl)piperazine-1-carboxylate (33.3 mg, 0.084 mmol) in methanol (1 mL) and 4N hydrochloric acid in dioxane (1 mL) was refluxed for 2 min and then concentrated to provide N'-(5-chloro-2-methyl-3-piperazin-1-ylphenyl)-N,N-dimethylethane-1,2-diamine hydrochloride as a solid. MS (ESI) for C$_{15}$H$_{25}$ClN$_4$: 297 (MH$^+$).

Using the analogous synthetic techniques and substituting with alternative reagents, the following compounds of the invention were prepared:

N'-(5-chloro-2-methyl-3-piperazin-1-ylphenyl)-N-methyl-N-(1-methylethyl)ethane-1,2-diamine: MS (ESI) for $C_{17}H_{29}ClN_4$: 325 (MH$^+$).

N'-(5-chloro-2-methyl-3-piperazin-1-ylphenyl)-N-ethyl-N-methylethane-1,2-diamine: MS (ESI) for $C_{16}H_{27}ClN_4$: 311 (MH$^+$).

1-(3-bromo-2-chloro-5-fluorophenyl)piperazine: MS (ESI) for $C_{10}H_{11}BrClFN_2$: 295 (MH$^+$)

2-chloro-5-fluoro-3-piperazin-1-yl-N-(2-pyrrolidin-1-ylethyl)aniline: MS (ESI) for $C_{16}H_{24}ClFN_4$: 327 (MH$^+$).

N-(5-chloro-2-methyl-3-piperazin-1-ylphenyl)-N,N',N'-trimethylethane-1,2-diamine: MS (ESI) for $C_{16}H_{27}ClN_4$: 311 (MH$^+$).

5-bromo-2-methyl-3-piperazin-1-yl-N-(2-pyrrolidin-1-ylethyl)aniline hydrochloride: MS (ESI) for $C_{17}H_{27}BrN_4$: 368 (MH$^+$).

5-chloro-2-methyl-3-piperazin-1-yl-N-(2-pyrrolidin-1-ylethyl)aniline hydrochloride: MS (ESI) for $C_{17}H_{27}ClN_4$: 323 (MH$^+$).

Example 29

3-(5-chloro-2-methyl-3-piperazin-1-ylphenyl)-N,N-diethylpropan-1-amine hydrochloride To a solution 1,1-dimethylethyl 4-(5-chloro-3-iodo-2-methylphenyl)piperazine-1-carboxylate (111 mg, 0.25 mmol) in DMF (0.5 mL) was added tetrabutylammonium chloride (70 mg, 0.25 mmol), sodium bicarbonate (53 mg, 0.63 mmol), palladium(II) acetate (1 mg, 0.005 mmol), and allylalcohol (26 μL, 0.38 mmol). The resulting mixture was heated to 50° C. for 4 h before cooling to room temperature. Brine and ethyl acetate were added, the organic layer was dried over magnesium sulfate, and concentrated. Column chromatography on silica (hexane:ethyl acetate 4:1) afforded 1,1-dimethylethyl 4-[5-chloro-2-methyl-3-(3-oxopropyl)phenyl]piperazine-1-carboxylate (63.0 mg, 69% yield) as a colorless film. $^1$H NMR (400 MHz, CDCl$_3$) δ 9.82 (m, 1H), 6.88-6.85 (m, 2H), 3.56 (br s, 4H), 2.91 (t, 2H), 2.78 (m, 4H), 2.73 (m, 2H), 2.22 (s, 3H), 1.48 (s, 9H).

To a solution of 1,1-dimethylethyl 4-[5-chloro-2-methyl-3-(3-oxopropyl)phenyl]piperazine-1-carboxylate (31 mg, 0.085 mmol) in 1,2-dichloroethane (1 mL) was added diethylamine (44 μL, 0.43 mmol) and sodium triacetoxyborohydride (36 mg, 0.17 mmol). The mixture was stirred for 45 min at room temperature. The residual hydride was quenched with 1N hydrochloric acid, and water and dichloromethane were added. The mixture was neutralized with sodium bicarbonate. The organic layer was dried over magnesium sulfate, and concentrated to provide 1,1-dimethylethyl 4-{5-chloro-3-[3-(diethylamino)propyl]-2-methylphenyl}piperazine-1-carboxylate (27.5 mg, 76% yield) as a colorless film. $^1$H NMR (400 MHz, CDCl$_3$) δ 6.92 (d, 1H), 6.89 (d, 1H), 3.56 (br s, 4H), 2.79 (br s, 4H), 2.60-2.49 (m, 8H), 2.22 (s, 3H), 1.70 (m, 2H), 1.49 (s, 9H), 1.03 (t, 6H).

A solution of 1,1-dimethylethyl 4-{5-chloro-3-[3-(diethylamino)propyl]-2-methylphenyl}piperazine-1-carboxylate (27.5 mg, 0.065 mmol) in methanol (1 mL) and 4N hydrochloric acid in dioxane (1 mL) was refluxed for 4 min and then concentrated to provide 3-(5-chloro-2-methyl-3-piperazin-1-ylphenyl)-N,N-diethylpropan-1-amine hydrochloride as a solid. MS (ESI) for $C_{18}H_{30}ClN_3$: 324 (MH$^+$).

Using the analogous synthetic techniques and substituting with alternative reagents, the following compounds of the invention were prepared:

1-[5-chloro-2-methyl-3-(3-pyrrolidin-1-ylpropyl)phenyl]piperazine: MS (ESI) for $C_{18}H_{28}ClN_3$: 295 (MH$^+$).

1-[3-(5-chloro-2-methyl-3-piperazin-1-ylphenyl)propyl]-4-methylpiperazine hydrochloride: MS (ESI) for $C_{19}H_{31}ClN_4$: 351 (MH$^+$).

Example 30

2-[(5-chloro-2-methyl-3-piperazin-1-ylphenyl)oxy]-N,N-dimethylethanamine hydrochloride To a solution of 1,1-dimethylethyl 4-(5-chloro-3-iodo-2-methylphenyl)piperazine-1-carboxylate (384 mg, 0.88 mmol) in DMSO (5 mL) was added potassium acetate (259 mg, 2.64 mmol), bis(pinacolato)diboron (226 mg, 0.97 mmol), and [1,1'-bis(diphenylphosphino)ferrocene]dichloropalladium(II) (72 mg, 0.088 mmol). The mixture was stirred at 80° C. for 24 h, and cooled to room temperature. Water and ethyl acetate were added, and the suspension was filtered through celite. The layers were separated, the organic layer was washed with brine, dried over magnesium sulfate, and concentrated. Column chromatography on silica (hexane:ethyl acetate 9:1) provided 1,1-dimethylethyl 4-[5-chloro-2-methyl-3-(4,4,5,5-tetramethyl-1,3,2-dioxaborolan-2-yl)phenyl]piperazine-1-carboxylate (185 mg, 48% yield) as a pale yellow oil. $^1$H NMR (400 MHz, CDCl$_3$) δ 7.43 (d, 1H), 7.01 (d, 1H), 3.55 (br s, 4H), 2.79 (m, 4H), 2.44 (s, 3H), 1.48 (s, 9H), 1.34 (s, 12H).

To a solution of 1,1-dimethylethyl 4-[5-chloro-2-methyl-3-(4,4,5,5-tetramethyl-1,3,2-dioxaborolan-2-yl)phenyl]piperazine-1-carboxylate (185 mg, 0.42 mmol) in THF (5 mL) was added 7.5 M sodium hydroxide (170 μL, 1.26 mmol) and 30% hydrogen peroxide solution (242 μL, 2.52 mmol) at 0° C. The mixture was stirred for 30 min before adding 10% citric acid and ethyl acetate. The layers were separated, the organic layer was dried over magnesium sulfate, and concentrated to give 1,1-dimethylethyl 4-(5-chloro-3-hydroxy-2-methylphenyl)piperazine-1-carboxylate (139 mg, 100% yield) as a yellow solid. $^1$H NMR (400 MHz, CDCl$_3$) δ 6.61 (d, 1H), 6.53 (d, 1H), 6.23 (br s, 1H), 3.56 (br s, 4H), 2.79 (m, 4H), 2.13 (s, 3H), 2.13 (s, 3H), 1.49 (s, 9H).

To a solution of 1,1-dimethylethyl 4-(5-chloro-3-hydroxy-2-methylphenyl)piperazine-1-carboxylate (45 mg, 0.122 mmol) in DMF was added 2-chloro-N,N-dimethylethylamine hydrochloride (35 mg, 0.244 mmol) and cesium carbonate (159 mg, 0.488 mmol). The mixture was stirred at room temperature for 16 h. Water was added and the resulting aqueous mixture was extracted twice with ethyl acetate. The organic extracts were combined, washed with water and brine, dried over magnesium sulfate, and concentrated to afford 1,1-dimethylethyl 4-(5-chloro-3-{[2-(dimethylamino)ethyl]oxy}-2-methylphenyl)piperazine-1-carboxylate as a colorless film which was used without further purification. $^1$H NMR (400 MHz, CDCl$_3$) δ 6.61 (d, 1H), 6.59 (d, 1H), 4.06 (t, 2H), 3.55 (br s, 4H), 2.80 (m, 6H), 2.39 (s, 6H), 2.11 (s, 3H), 1.48 (s, 9H).

A solution of 1,1-dimethylethyl 4-(5-chloro-3-{[2-(dimethylamino)ethyl]oxy}-2-methylphenyl)piperazine-1-carboxylate in methanol (1 mL) and 4N hydrochloric acid in dioxane (1 mL) was refluxed for 4 min and then concentrated to provide 2-[(5-chloro-2-methyl-3-piperazin-1-ylphenyl)oxy]-N,N-dimethylethanamine hydrochloride as a solid. MS (ESI) for $C_{15}H_{24}ClN_3O$: 298 (MH$^+$).

Using the analogous synthetic techniques and substituting with alternative reagents, the following compounds of the invention were prepared:

1-[5-chloro-2-methyl-3-(methyloxy)phenyl]piperazine: MS (ESI) for $C_{12}H_{17}ClN_2O$: 241 (MH+).

2-[(5-chloro-2-methyl-3-piperazin-1-ylphenyl)oxy]-N,N-diethylethanamine: MS (ESI) for $C_{17}H_{28}ClN_3O$: 326 (MH+).

1-{5-chloro-2-methyl-3-[(2-pyrrolidin-1-ylethyl)oxy]phenyl}piperazine: MS (ESI) for $C_{17}H_{26}ClN_3O$: 324 (MH+).

4-{2-[(5-chloro-2-methyl-3-piperazin-1-ylphenyl)oxy]ethyl}morpholine: MS (ESI) for $C_{17}H_{26}ClN_3O_2$: 340 (MH+).

1-{5-chloro-2-methyl-3-[(2-piperidin-1-ylethyl)oxy]phenyl}piperazine: MS (ESI) for $C_{18}H_{28}ClN_3O$: 338 (MH+).

1-{2-[(5-chloro-2-methyl-3-piperazin-1-ylphenyl)oxy]ethyl}-4-ethylpiperazine: MS (ESI) for $C_{19}H_{31}ClN_4O$: 367 (MH+).

4-{3-[(5-chloro-2-methyl-3-piperazin-1-ylphenyl)oxy]propyl}morpholine: MS (ESI) for $C_{18}H_{28}ClN_3O_2$: 354 (MH+).

1-{5-chloro-2-methyl-3-[(3-pyrrolidin-1-ylpropyl)oxy]phenyl}piperazine: MS (ESI) for $C_{18}H_{28}ClN_3O$: 338 (MH+).

1-{3-[(5-chloro-2-methyl-3-piperazin-1-ylphenyl)oxy]propyl}-4-methylpiperazine: MS (ESI) for $C_{19}H_{31}CN_4O$: 367 (MH+).

1-{5-chloro-2-methyl-3-[(3-piperidin-1-ylpropyl)oxy]phenyl}piperazine: MS (ESI) for $C_{19}H_{30}ClN_3O$: 352 (MH+).

1-{3-[(5-chloro-2-methyl-3-piperazin-1-ylphenyl)oxy]propyl}-4-ethylpiperazine: MS (ESI) for $C_{20}H_{33}ClN_4O$: 381 (MH+).

3-[(5-chloro-2-methyl-3-piperazin-1-ylphenyl)oxy]-N,N-diethylpropan-1-amine: MS (ESI) for $C_{18}H_{30}ClN_3O$: 340 (MH+).

1-{2-[(5-chloro-2-methyl-3-piperazin-1-ylphenyl)oxy]ethyl}-4-methylpiperazine hydrochloride: MS (ESI) for $C_{18}H_{29}ClN_4O$: 353 (MH+).

Example 31

N,N-diethyl-2-[(3-piperazin-1-ylphenyl)oxy]ethanamine hydrochloride

A mixture of 3-hydroxyphenylpiperazine (0.41 g, 2.25 mmol) and Boc-anhydride (0.49 g, 2.25 mmol) in dry THF (15 mL) was stirred at room temperature for 5 h. The reaction mixture was concentrated to provide 1,1-dimethylethyl 4-(3-hydroxyphenyl)piperazine-1-carboxylate (100% yield) as a beige solid. MS (ESI) for $C_{15}H_{22}N_2O_3$: 223 (M-56).

A mixture of 1,1-dimethylethyl 4-(3-hydroxyphenyl)piperazine-1-carboxylate (0.13 g, 0.46 mmol), potassium carbonate (256 mg, 1.9 mmol), and 2-(diethylamino)ethyl chloride hydrochloride (0.16 g, 0.92 mmol) in DMF (3 mL) was stirred at 110° C. for 1 h. The reaction mixture was poured into ice water, and extracted several times with ether. The organic layer was washed with water, dried over sodium sulfate, and concentrated to give crude 1,1-dimethylethyl 4-(3-{[2-(diethylamino)ethyl]oxy}phenyl)piperazine-1-carboxylate. MS (ESI) for $C_{21}H_{35}N_3O_3$: 378 (MH+).

A solution of 1,1-dimethylethyl 4-(3-{[2-(diethylamino)ethyl]oxy}phenyl)piperazine-1-carboxylate (0.17 g, 0.45 mmol) in MeOH (2 mL) and 4N hydrochloric acid in dioxane (2 mL) was refluxed for 1 min. The reaction mixture was concentrated, the residue was triturated with ether, and dried to afford N,N-diethyl-2-[(3-piperazin-1-ylphenyl)oxy]ethanamine hydrochloride (100% yield) as an oil. MS (ESI) for $C_{16}H_{27}N_3O$: 278 (MH+).

Example 32

N,N-diethyl-2-[(2-methyl-3-piperazin-1-ylphenyl)oxy]ethanamine hydrochloride

A mixture of 2-methyl-3-nitrophenol (672 mg, 4.4 mmol), cesium carbonate (2.1 g, 6.44 mmol), and benzyl bromide (751 mg, 4.4 mmol) in DMF (6 mL) was stirred at room temperature for 3 h. The reaction mixture was poured into ice water. The light yellow precipitation was filtered off, washed several times with water, and dried, to provide 1-nitro-2-methyl-3-[(phenylmethyl)oxy]benzene (930 mg, 87% yield). ¹HNMR (400 MHz, $d_4$-methanol): δ 7.47 (d, 1H), 7.45 (s, 1H), 7.40 (s, 1H), 7.39 (d, 1H), 7.37 (d, 1H), 7.34 (m, 1H), 7.32 (s, 1H), 7.29 (d, 1H), 4.90 (s, 2H), 2.35 (s, 3H).

To a solution of 1-nitro-2-methyl-3-[(phenylmethyl)oxy]benzene (0.92 g, 3.8 mmol) in ethyl acetate (50 mL) was added tin(II) chloride monohydrate (3.5 g, 15.2 mmol) and the reaction mixture was stirred at 70° C. for 5 h. The reaction mixture was cooled to room temperature, diluted with ether (50 mL), and sodium bicarbonate was added until pH 8. The semi-solid byproduct was filtered off, washed with ethyl acetate, the organic layer was dried with sodium sulfate, and concentrated. Trituration with ether gave 2-methyl-3-[(phenylmethyl)oxy]aniline (0.35 g, 44% yield) as a light yellow solid. MS (ESI) for $C_{14}H_{15}NO$: 214 (MH+).

A mixture of 2-methyl-3-[(phenylmethyl)oxy]aniline (0.34 g, 1.6 mmol), potassium carbonate (0.44 g, 3.2 mmol), and bis(2-chloroethyl)amine hydrochloride (1.6 mmol) diglyme (5 mL) was refluxed for 4 h. The reaction mixture was cooled to room temperature, water was added, and the pH of the aqueous layer was adjusted to pH 13. The aqueous layer was extracted with ethyl acetate (3×20 mL), dried with sodium sulfate, and concentrated to provide 1-{2-methyl-3-[(phenylmethyl)oxy]phenyl}piperazine (0.43 g, 96% yield) as a dark oil. MS (ESI) for $C_{18}H_{22}N_2O$: 283 (MH+).

A mixture of 1-{2-methyl-3-[(phenylmethyl)oxy]phenyl}piperazine (0.42 g 1.5 mmol) and Boc-anhydride (0.33 g, 1.5 mmol) in THF (10 mL) was stirred at room temperature for 30 h. The reaction mixture was concentrated, diluted with ethyl acetate (30 ml), the organic layer was washed with water, brine, dried with sodium sulfate, and concentrated. Column chromatography on silica provided 1,1-dimethylethyl 4-{2-methyl-3-[(phenylmethyl)oxy]phenyl}piperazine-1-carboxylate (0.18 g, 32% yield). MS (ESI) for $C_{23}H_{30}N_2O_3$: 384 (MH+) and 327 (MH-56).

To a solution of 1,1-dimethylethyl 4-{2-methyl-3-[(phenylmethyl)oxy]-phenyl}piperazine-1-carboxylate (0.18 g, 0.5 mmol) in ethanol (15 mL) was added palladium on carbon (0.11 g, 10%, contains 50% water), and the reaction mixture was stirred under an hydrogen atmosphere for 15 h. The reaction mixture was filtered through celite, and the filter cake was washed with ethanol. The filtrate was concentrated to give 1,1-dimethylethyl 4-(3-hydroxy-2-methylphenyl)piperazine-1-carboxylate (0.075 g, 54% yield). MS (ESI) for $C_{16}H_{24}N_2O_3$: 293 (MH+).

A mixture of 1,1-dimethylethyl 4-(3-hydroxy-2-methylphenyl)piperazine-1-carboxylate (0.07 g, 0.24 mmol), potassium carbonate (0.134 g, 0.96 mmol), and 2-(diethylamino)ethylchloride hydrochloride (0.083 g, 0.48 mmol) in DMF (2 mL) was stirred at 100° C. for 1 h. The reaction mixture was cooled to room temperature, poured into ice water, and extracted with ethyl acetate (3×20 ml). The organic layer was dried with sodium sulfate, and concentrated to afford 1,1-dimethylethyl 4-(3-{[2-(diethylamino)ethyl]oxy}-2-methylphenyl)piperazine-1-carboxylate (0.07 g, 76% yield). MS (ESI) for $C_{22}H_{37}N_3O_3$: 392 (MH+).

A solution of 1,1-dimethylethyl 4-(3-{[2-(diethylamino)ethyl]oxy}-2-methylphenyl)piperazine-1-carboxylate (0.07 g, 0.18 mmol) in MeOH (2 mL) and 4N hydrochloric acid in dioxane (2 mL) was refluxed for 1 min. The reaction mixture was concentrated to give N,N-diethyl-2-[(2-methyl-3-piperazin-1-ylphenyl)oxy]ethanamine hydrochloride (0.04 g, 77% yield), which was used without further purification. MS (ESI) for $C_{17}H_{29}N_3O$: 292 (MH$^+$).

Example 33

5-(ethylsulfonyl)-2-methyl-3-piperazin-1-yl-N-(2-pyrrolidin-1-ylethyl)aniline hydrochloride To a solution of 3,5-dibromo-4-methylphenol (5.24 g, 19.70 mmol) in DMF (30 mL) was added sodium hydride (60% in mineral oil, 0.79 g, 19.75 mmol) at room temperature under nitrogen. The resulting mixture was stirred at 60° C. for 15 min, cooled to room temperature, and dimethylthiocarbamoyl chloride (2.30 g, 18.61 mmol) was added. The resulting mixture was stirred at 60° C. for 1 h, and then diluted with ethyl acetate (100 mL). The organic layer was washed with 1N sodium hydroxide (2×50 mL), water (50 mL), 5% lithium chloride (50 mL), and brine (50 mL), dried with sodium sulfate, and concentrated. Column chromatography on silica (hexanes:ethyl acetate 9:1) afforded O-(3,5-dibromo-4-methylphenyl)dimethylthiocarbamate (5.11 g, 78% yield) as a colorless solid. $^1$H NMR (400 MHz, CDCl$_3$) δ 7.28 (s, 2H), 3.44 (s, 3H), 3.32 (s, 3H), 2.55 (s, 3H).

O-(3,5-dibromo-4-methylphenyl)dimethylthiocarbamate (4.00 g, 11.33 mmol) was stirred at 200° C. for 23 h under nitrogen. Column chromatography on silica (hexanes:ethyl acetate 9:1) gave S-(3,5-dibromo-4-methylphenyl)dimethylthiocarbamate (3.05 g, 76% yield) as a colorless solid. $^1$H NMR (400 MHz, CDCl$_3$) δ 7.64 (s, 2H), 3.07 (br s, 3H), 3.03 (br s, 3H), 2.57 (s, 3H).

A solution of S-(3,5-dibromo-4-methylphenyl)dimethylthiocarbamate (3.73 g, 10.56 mmol) in methanol (50 mL) and 2N sodium hydroxide (20 mL) was refluxed for 90 min. The reaction mixture was diluted with water (100 mL), acidified with 1N hydrochloric acid to pH 3, and then extracted with ethyl acetate (100 mL). The organic layer was washed with water (50 mL), and brine (50 mL), dried with sodium sulfate, and concentrated to give 3,5-dibromo-4-methylbenzenethiol (2.85 g, 96% yield) as a colorless solid. $^1$H NMR (400 MHz, d$_6$-DMSO) δ 7.61 (s, 2H), 6.94 (s, 1H), 2.43 (s, 3H).

A mixture of 3,5-dibromo-4-methylbenzenethiol (0.88 g, 3.12 mmol), cesium carbonate (2.03 g, 6.24 mmol), and ethyl iodide (0.72 g, 4.63 mmol) in DMF (7 mL) mixture was stirred at 60° C. for 1 h, and then diluted with ethyl acetate (100 mL). The organic layer was washed with water (30 mL), 5% lithium chloride (2×30 mL), and brine (30 mL), dried with sodium sulfate, and concentrated to afford 1,3-dibromo-5-(ethylthio)-2-methylbenzene (0.90 g, 93% yield) as a pale yellow oil. $^1$H NMR (400 MHz, CDCl$_3$) δ 7.54 (s, 2H), 2.92 (q, 2H), 2.52 (s, 3H), 1.31 (t, 3H).

To a solution of 1,3-dibromo-5-(ethylthio)-2-methylbenzene (0.88 g, 2.84 mmol) in dichloromethane (30 mL) was added m-chloroperbenzoic acid (70%, 2.80 g) at 0° C. The ice batch was removed and the resulting mixture was stirred at room temperate for 5 h. The mixture was diluted with ethyl acetate (200 mL), washed with saturated sodium bicarbonate (3×50 mL), and brine (30 mL), dried with sodium sulfate, and concentrated. Column chromatography on silica (hexanes:ethyl acetate 9:1) provided 1,3-dibromo-5-(ethylsulfonyl)-2-methylbenzene (0.57 g, 59% yield) as a colorless solid. $^1$H NMR (400 MHz, CDCl$_3$) δ 8.03 (s, 2H), 3.14 (q, 2H), 2.66 (s, 3H), 1.31 (t, 3H).

A mixture of 1,3-dibromo-5-(ethylsulfonyl)-2-methylbenzene (400 mg, 1.17 mmol), Boc-piperazine (218 mg, 1.17 mmol), sodium tert-butoxide (160 mg, 1.66 mmol), Pd$_2$(dba)$_3$ (55 mg, 0.06 mmol), and BINAP (110 mg, 0.18 mmol) in toluene (5 mL) was stirred at 100° C. for 17 h. Column chromatography of the mixture on silica (hexanes:ethyl acetate 4:1) gave 1,1-dimethylethyl 4-[3-bromo-5-(ethylsulfonyl)-2-methylphenyl]piperazine-1-carboxylate (184 mg, 35% yield) as a yellow solid. $^1$H NMR (400 MHz, CDCl$_3$) δ 7.82 (d, 3H), 7.43 (d, 1H), 3.60 (br s, 4H), 3.11 (q, 2H), 2.18 (m, 4H), 2.46 (s, 3H), 1.49 (s, 9H), 1.29 (t, 3H).

A mixture of 1,1-dimethylethyl 4-[3-bromo-5-(ethylsulfonyl)-2-methylphenyl]-piperazine-1-carboxylate (220 mg, 0.49 mmol), 1-(2-aminoethyl)pyrrolidine (90 mg, 0.79 mmol), sodium tert-butoxide (95 mg, 0.98 mmol), Pd$_2$(dba)$_3$ (22 mg, 0.02 mmol), and BINAP (46 mg, 0.07 mmol) in toluene (3 mL) was stirred in a sealed pressure vessel at 100° C. for 2 h. Column chromatography of the mixture on silica (dichloromethane:methanol 95:5) afforded 1,1-dimethylethyl 4-{5-(ethylsulfonyl)-2-methyl-3-[(2-pyrrolidin-1-ylethyl)amino]phenyl}piperazine-1-carboxylate (158 mg, 67% yield) as a yellow oil. $^1$H NMR (400 MHz, d$_4$-methanol) δ 6.95 (d, 1H), 6.88 (d, 1H), 3.58 (br s, 4H), 3.52 (t, 2H), 3.30 (m, 4H), 3.09 (br s, 4H), 2.84 (br s, 4H), 2.23 (s, 3H), 1.99 (m, 4H), 1.48 (s, 9H), 1.21 (t, 3H); MS (ESI) for $C_{24}H_{10}N_4O_4S$: 481 (MH$^+$).

A mixture of 1,1-dimethylethyl 4-{5-(ethylsulfonyl)-2-methyl-3-[(2-pyrrolidin-1-ylethyl)amino]phenyl}piperazine-1-carboxylate (155 mg, 0.32 mmol), methanol (5 mL), and 4N hydrochloric acid in dioxane (5 mL) was refluxed for 1 min. The mixture was concentrated to 5-(ethylsulfonyl)-2-methyl-3-piperazin-1-yl-N-(2-pyrrolidin-1-ylethyl)-aniline hydrochloride (170 mg, 100% yield) which was used without further purification. MS (ESI) for $C_{19}H_{32}N_4O_2S$: 381 (MH$^+$).

Using the same or analogous synthetic techniques and/or substituting with alternative reagents, the following compound of the invention was prepared:

2-methyl-5-(methylsulfonyl)-3-piperazin-1-yl-N-(2-pyrrolidin-1-ylethyl)aniline hydrochloride: MS (ESI) for $C_{18}H_{30}N_4O_2S$: 367 (MH$^+$).

Example 34

5-bromo-2-methyl-3-piperazin-1-yl-N-(2-pyrrolidin-1-ylethyl)aniline hydrochloride A mixture of 3,5-dibromo-4-methylbenzoic acid (6.3 g, 21.4 mmol), potassium carbonate (4.4 g, 32.1 mmol), and benzyl bromide (3.7 g, 21.7 mmol) in acetone (100 mL) was refluxed for 3 h. The resulting mixture was partitioned between ethyl acetate (300 mL) and water (100 mL). The organic layer was washed with water (2×100 mL), and brine (100 mL), dried with sodium sulfate, and concentrated to give phenylmethyl 3,5-dibromo-4-methylbenzoate (7.5 g, 91% yield) as a pale yellow solid. $^1$H NMR (400 MHz, CDCl$_3$) δ 8.18 (s, 2H), 7.41 (m, 5H), 5.35 (s, 2H), 2.62 (s, 3H).

A mixture of phenylmethyl 3,5-dibromo-4-methylbenzoate (7.50 mg, 19.53 mmol), Boc-piperazine (3.64 g, 19.53 mmol), cesium carbonate (8.91 g, 27.34 mmol), Pd$_2$(dba)$_3$ (0.89 g, 0.98 mmol), and BINAP (1.82 g, 2.93 mmol) in toluene (100 mL) was stirred at 100° C. for 16 h. The reaction mixture was filtered through celite and concentrated. Column chromatography on silica (hexanes:ethyl acetate 9:1) gave 1,1-dimethylethyl 4-(3-bromo-2-methyl-5-{[(phenylmethyl)oxy]carbonyl}phenyl)piperazine-1-carboxylate (4.04, 42% yield) as a yellow solid. $^1$H NMR (400 MHz, CDCl$_3$) δ 8.00 (d, 1H), 7.64 (d, 1H), 7.40 (m, 5H), 5.35 (s, 2H), 3.58 (br s, 4H), 2.85 (m, 4H), 2.43 (s, 3H), 1.49 (s, 9H).

A mixture of 1,1-dimethylethyl 4-(3-bromo-2-methyl-5-{[(phenylmethyl)-oxy]carbonyl}phenyl)piperazine-1-carboxylate (2.10 g, 4.29 mmol), 1-(2-aminoethyl)pyrrolidine (0.74 g, 6.44 mmol), cesium carbonate (2.80 g, 8.58 mmol), Pd$_2$(dba)$_3$ (0.20 g, 0.21 mmol), and BINAP (0.40 g, 0.64 mmol) in toluene (40 mL) was stirred at 100° C. for 16 h. The reaction mixture was filtered through celite and concentrated. Column chromatography on silica (dichloromethane:methanol 95:5 to 90:10) afforded 1,1-dimethylethyl 4-{2-methyl-5-{[(phenylmethyl)oxy]carbonyl}-3-[(2-pyrrolidin-1-ylethyl)amino]phenyl}piperazine-1-carboxylate (0.91 g, 41% yield) as a brown foam. $^1$H NMR (400 MHz, CDCl$_3$) δ 7.40 (m, 5H), 7.20 (d, 1H), 7.13 (d, 1H), 5.35 (s, 2H), 4.41 (s, 1H), 3.58 (br s, 4H), 3.26 (m, 2H), 2.83 (br s, 4H), 2.79 (t, 2H), 2.53 (m, 4H), 2.15 (s, 3H), 1.77 (m, 4H), 1.49 (s, 9H).

A solution of 1,1-dimethylethyl 4-{2-methyl-5-{[(phenylmethyl)-oxy]carbonyl}-3-[(2-pyrrolidin-1-ylethyl)amino]phenyl}piperazine-1-carboxylate (3.94 g, 7.54 mmol) in dichloromethane (30 mL) and trifluoroacetic acid (30 mL) was stirred at room temperature for 90 min and then concentrated. Dichloromethane (60 mL) and diiso-propylethylamine (10 mL) was added to the residue, and the resulting solution was cooled to 0° C. Trifluoroacetic anhydride (3.56 g, 16.95 mmol) was added dropwise, and the mixture was stirred at 0° C. for 30 min and then at room temperature for 1 h. The reaction mixture was diluted with ethyl acetate (300 mL), washed with water (100 mL), saturated sodium bicarbonate (100 mL), water (100 mL), and brine (100 mL), dried with sodium sulfate, and concentrated. Column chromatography on silica (dichloromethane:methanol 97:3) provided phenylmethyl 4-methyl-3-[(2-pyrrolidin-1-ylethyl)(trifluoroacetyl)amino]-5-[4-(trifluoroacetyl)piperazin-1-yl]benzoate (3.60 g, 78% yield) as a yellow foam. $^1$H NMR (400 MHz, CDCl$_3$) δ 7.79 (s, 1H), 7.76 (s, 1H), 7.40 (m, 5H), 5.39 (d, 1H), 5.34 (d, 1H), 4.43 (m, 1H), 3.80 (br s, 4H), 3.13 (m, 1H), 2.99 (m, 4H), 2.72 (m, 1H), 2.61 (m, 1H), 2.46 (m, 4H), 2.27 (s, 3H), 1.68 (br s, 4H).

A mixture of phenylmethyl 4-methyl-3-[(2-pyrrolidin-1-ylethyl)(trifluoro-acetyl)amino]-5-[4-(trifluoroacetyl)piperazin-1-yl]benzoate (3.60 g, 5.86 mmol) and palladium on carbon (0.60 g, 10%, contains 50% water) was stirred under an hydrogen atmosphere for 3 h. The reaction mixture was filtered through celite, and concentrated to give 4-methyl-3-[(2-pyrrolidin-1-ylethyl)(trifluoroacetyl)amino]-5-[4-(trifluoroacetyl)-piperazin-1-yl]benzoic acid (3.13 g, 100% yield) as yellow semisolid. $^1$H NMR (400 MHz, CDCl$_3$) δ 7.91 (s, 1H), 7.61 (s, 1H), 4.48 (m, 1H), 3.68 (br s, 4H), 3.51 (m, 2H), 3.25 (br s, 4H), 2.90 (m, 5H), 2.16 (s, 3H), 2.06 (m, 4H).

A solution of 4-methyl-3-[(2-pyrrolidin-1-ylethyl)(trifluoroacetyl)amino]-5-[4-(trifluoroacetyl)piperazin-1-yl]benzoic acid (0.98 g, 1.87 mmol) and pyridine (0.15 g, 1.85 mmol) in dichloromethane (10 mL) was cooled to 0° C., and cyanuric fluoride (0.27 g, 2.01 mmol) was added dropwise. The mixture was stirred at 0° C. for 2.5 h, and then partitioned between dichloromethane (20 mL) and water (30 mL). The aqueous layer was extracted with more dichloromethane (2×20 mL), dried with sodium sulfate, and concentrated to afford 4-methyl-3-[(2-pyrrolidin-1-ylethyl)(trifluoroacetyl)amino]-5-[4-(trifluoroacetyl)piperazin-1-yl]benzoyl fluoride (1.05 g, 100% yield) as a yellow foam. MS (ESI) for C$_{22}$H$_{25}$F$_7$N$_4$O$_3$: 527 (MH$^+$).

A solution of 4-methyl-3-[(2-pyrrolidin-1-ylethyl)(trifluoroacetyl)amino]-5-[4-(trifluoroacetyl)piperazin-1-yl]benzoyl fluoride (1.05 g, 1.87 mmol) in dichloromethane (20 mL) was cooled to 0° C., and sodium azide (1.20 g, 18.46 mmol) was added. The mixture was stirred at 0° C. for 3 h, and then partitioned between ethyl acetate (50 mL) and water (50 mL). The aqueous layer was extracted with more ethyl acetate (2×50 mL), washed with brine (50 mL), dried with sodium sulfate, and concentrated to give 4-methyl-3-[(2-pyrrolidin-1-ylethyl)(trifluoroacetyl)amino]-5-[4-(trifluoroacetyl)piperazin-1-yl]-benzoyl azide (0.88 g, 85% yield) as a yellow foam. $^1$H NMR (400 MHz, CDCl$_3$) δ 7.72 (s, 1H), 7.69 (s, 1H), 4.45 (m, 1H), 3.87 (br s, 2H), 3.80 (m, 4H), 3.01 (m, 4H), 2.76 (br s, 4H), 2.29 (s, 3H), 1.88 (br s, 4H).

A solution of tert-butanol (2 mL) in toluene (20 mL) was heated to 100° C., and a solution of 4-methyl-3-[(2-pyrrolidin-1-ylethyl)(trifluoroacetyl)amino]-5-[4-(trifluoroacetyl)piperazin-1-yl]benzoyl azide (0.88 g, 1.60 mmol) and tert-butanol (2 mL) in toluene (20 mL) was added at that temperature. The mixture was stirred at 100° C. for 2 h, and then concentrated. Column chromatography on silica (dichloromethane:methanol 95:5) provided 1,1-dimethylethyl {4-methyl-3-[(2-pyrrolidin-1-ylethyl)(trifluoro-acetyl)amino]-5-[4-(trifluoroacetyl)piperazin-1-yl]phenyl}carbamate (0.42 g, 44% yield) as a yellow foam. $^1$H NMR (400 MHz, d$_4$-methanol) δ 7.26 (s, 1H), 7.18 (s, 1H), 4.39 (m, 1H), 3.82 (br s, 2H), 3.22 (m, 1H), 2.96 (m, 4H), 2.80 (m, 1H), 2.70 (m, 1H), 2.61 (m, 4H), 2.17 (s, 3H), 1.80 (m, 4H), 1.51 (s, 9H).

A solution of 1,1-dimethylethyl {4-methyl-3-[(2-pyrrolidin-1-ylethyl)-(trifluoroacetyl)amino]-5-[4-(trifluoroacetyl)piperazin-1-yl]phenyl}carbamate (0.42 g, 0.71 mmol) in dichloromethane (5 mL) and trifluoroacetic acid (5 mL) was stirred at room temperature for 3.5 h, and then concentrated. The residue was dissolved in ethyl acetate (50 mL), and washed with saturated sodium bicarbonate (50 mL). The aqueous layer was further extracted with ethyl acetate (2×30 mL), the combined organic layers were washed with brine (50 mL), dried with sodium sulfate, and concentrated. Column chromatography on silica (dichloromethane:methanol 95:5) gave N-{5-amino-2-methyl-3-[4-(trifluoro-acetyl)piperazin-1-yl]phenyl}-2,2,2-trifluoro-N-(2-pyrrolidin-1-ylethyl)acetamide (0.23 g, 66% yield) as a yellow glass. $^1$H NMR (400 MHz, d$_4$-methanol) δ 6.55 (d, 1H), 6.39 (s, 1H), 4.35 (m, 1H), 3.80 (br s, 4H), 3.18 (m, 1H), 2.93 (m, 4H), 2.77 (m, 1H), 2.68 (m, 1H), 2.58 (m, 4H), 2.08 (s, 3H), 1.80 (m, 4H).

A mixture of copper(II) bromide (120 mg, 0.54 mmol) and tert-butyl nitrite (76 mg, 0.66 mmol) in acetonitrile (8 mL) was cooled to 0° C., and a solution of N-{5-amino-2-methyl-3-[4-(trifluoroacetyl)piperazin-1-yl]phenyl}-2,2,2-trifluoro-N-(2-pyrrolidin-1-ylethyl)acetamide (220 mg, 0.44 mmol) in acetonitrile (2 mL) was added dropwise. The mixture was stirred at room temperature for 2 h, and then added into 1N hydrochloric acid (100 mL). The aqueous layer was extracted with ethyl acetate (3×30 mL), washed with brine (30 mL), dried with sodium sulfate, and concentrated. Purification by reverse phase HPLC afforded N-{5-bromo-2-methyl-3-[4-(trifluoroacetyl)piperazin-1-yl]phenyl}-2,2,2-trifluoro-N-(2-pyrrolidin-1-ylethyl)acetamide (42 mg, 17% yield) as a yellow oil. MS (ESI) for C$_{21}$H$_{25}$BrF$_6$N$_4$O$_2$: 559, 561 (MH$^+$).

A mixture of N-{5-bromo-2-methyl-3-[4-(trifluoroacetyl)piperazin-1-yl]-phenyl}-2,2,2-trifluoro-N-(2-pyrrolidin-1-ylethyl)acetamide (42 mg, 0.08 mmol) and potassium carbonate (100 mg, 0.72 mmol) in methanol (5 mL) and water (0.5 mL) was stirred at 60° C. for 19 h, then concentrated and azeotroped with 2-propanol (2×5 mL) to give crude 5-bromo-2-methyl-3-piperazin-1-yl-N-(2-pyrrolidin-1-ylethyl)aniline hydrochloride, which was used without further purification. MS (ESI) for $C_{17}H_{27}BrN_4$: 367, 369 (MH$^+$).

Example 35

2-[(3-chloro-5-piperazin-1-ylphenyl)oxy]-N,N-diethylethanamine trifluoroacetate

A mixture of dichlorophenol (2.30 g, 14 mmol), cesium carbonate (7.00 g, 21 mmol), and benzyl bromide (2.43 g, 14 mmol) in DMF (20 mL) was stirred at room temperature for 4 h. The reaction mixture was poured into ice water, and extracted several times with ether. The organic layer was dried with sodium sulfate, and concentrated to provide 1,3-dichloro-5-[(phenylmethyl)oxy]benzene (100% yield). $^1$H NMR (CDCl$_3$): δ 6.97 (s, 1H), 6.88 (m, 2H), 5.03 (s, 2H).

A mixture of 1,3-dichloro-5-[(phenylmethyl)oxy]benzene (0.56 g, 2.2 mmol), Boc-piperazine (0.5 g, 2.64 mmol), sodium tert-butoxide (0.30 g, 3.12 mmol), Pd(dba)$_3$ (0.02 g, 1 mol %), and 2-(di-tert-butylphosphino)biphenyl (0.03 g, 4 mol %) in toluene (4 ml), was stirred at 90° C. for 15 h. Column chromatography on silica (ethyl acetate:hexanes 1:8) afforded 1,1-dimethyl 4-{3-chloro-5[(phenylmethyl)oxy]phenyl}piperazine-1-carboxylate (0.70 g, 78% yield). MS (ESI) for $C_{22}H_{27}ClN_2O_3$: 347 (M-56).

A solution of 1,1-dimethylethyl 4-{3-chloro-5-[(phenylmethyl)oxy]phenyl}piperazine-1-carboxylate (190 mg, 0.47 mmol) in trifluoroacetic acid (4 mL) was refluxed for 5 h. The reaction mixture was concentrated to give 3-chloro-5-piperazin-1-ylphenol (98 mg, 98% yield). MS (ESI) for $C_{10}H_{13}ClN_2O$: 213 (MH$^+$).

A solution of 3-chloro-5-piperazin-1-ylphenol (98 mg, 0.46 mmol) and Boc-anhydride (101 mg, 0.46 mmol) in THF (4 mL) was stirred at room temperature for 48 h. The reaction mixture was concentrated, the residue was dissolved in ethyl acetate, washed with water, and brine, dried with sodium sulfate, and concentrated to provide 1,1-di-methylethyl 4-(3-chloro-5-hydroxyphenyl)piperazine-1-carboxylate (150 mg, 100% yield). MS (ESI) for $C_{15}H_{21}ClN_2O_3$: 257 (M-56).

A mixture of 1,1-dimethylethyl 4-(3-chloro-5-hydroxyphenyl)piperazine-1-carboxylate (150 mg, 0.46 mmol), potassium carbonate (0.26 g, 1.84 mmol), and 2-(diethylamino)ethyl chloride hydrochloride (160 mg, 0.92 mmol) in DMF (3 mL) was stirred at 100° C. for 6 h. The reaction mixture was poured into ice water, and extracted several times with ethyl acetate. The organic layer was washed with water, brine, dried with sodium sulfate, and concentrated to give 1,1-dimethylethyl 4-(3-chloro-5-{[2-(diethylamino)ethyl]oxy}phenyl)piperazine-1-carboxylate yield (73 mg, 38% yield). MS (ESI) for $C_{21}H_{34}ClN_3O_3$: 412 (MH$^+$).

A solution of 1,1-dimethylethyl 4-(3-chloro-5{[2-(diethylamino)ethyl]oxy}phenyl)piperazine-1-carboxylate (73 mg, 0.18 mmol) in trifluoroacetic acid (4 mL) was stirred at room temperature for 30 min. The reaction mixture was concentrated, and the residue was dissolved in ethyl acetate. The organic layer was washed with saturated sodium bicarbonate, water, dried with sodium sulfate, and concentrated to afford 2-[(3-chloro-5-piperazin-1-ylphenyl)oxy]-N,N-diethylethanamine trifluoroacetate (100% yield). MS (ESI) for $C_{16}H_{26}ClN_3O$: 312 (MH$^+$).

Using the analogous synthetic techniques and substituting with alternative reagents, the following compound of the invention was prepared:

1-[3-chloro-5-(methyloxy)phenyl]piperazine: MS (ESI) for $C_{11}H_{15}ClN_2O$: 228 (MH$^+$).

Example 36

5-[(2-ethylbutyl)oxy]-2-methyl-3-piperazin-1-yl-N-(2-pyrrolidin-1-ylethyl)aniline hydrochloride A mixture of 3,5 dibromo-4-methylphenol (250 mg, 0.94 mmol), cesium carbonate (919 mg, 2.82 mmol) and 3-(bromomethyl)pentane (197 µl, 1.41 mmol) were stirred in DMF (5 mL) at 60° C. for 16 h under nitrogen. The reaction mixture was diluted with ethyl acetate (50 mL), washed with water (20 mL), 5% lithium chloride (20 mL), and brine (20 mL), dried over sodium sulfate, and concentrated to give 1,3-dibromo-5-[(2-ethylbutyl)oxy]-2-methylbenzene (300 mg, 91% yield) as a colorless oil. $^1$H NMR (400 MHz, CDCl$_3$) δ 7.10-7.08 (br s, 2H), 3.80-3.77 (m, 2H), 2.48 (s, 3H), 1.69-1.57 (m, 1H), 1.51-1.36 (m, 4H), 0.92 (t, 6H).

To 1,3-dibromo-5-[(2-ethylbutyl)oxy]-2-methylbenzene (289 mg, 0.83 mmol) in dry toluene (3 mL) was added Pd$_2$(dba)$_3$ (76 mg, 0.083 mmol), BINAP (154 mg, 0.25 mmol), sodium tert-butoxide (109 mg, 1.16 mmol), and Boc-piperazine (163 mg, 0.87 mmol). The reaction mixture was stirred at 110° C. for 16 h under nitrogen, cooled to room temperature, diluted with ethyl acetate (30 mL), filtered, and concentrated. Column chromatography on silica (hexanes:ethyl acetate 95:5) provided 1,1-dimethylethyl 4-{3-bromo-5-[(2-ethylbutyl)oxy]-2-methylphenyl}piperazine-1-carboxylate (200 mg, 53% yield) as a yellow oil. $^1$H NMR (400 MHz, CDCl$_3$) δ 6.87 (d, 1H), 6.52 (d, 1H), 3.78 (d, 2H), 3.64-3.47 (br m, 4H), 2.86-2.75 (br m, 4H), 2.30 (s, 3H), 1.68-1.59 (m, 1H), 1.51-1.38 (m, 13H), 0.92 (t, 6H).

To 1,1-dimethylethyl 4-{3-bromo-5-[(2-ethylbutyl)oxy]-2-methylphenyl}piperazine-1-carboxylate (193 mg, 0.42 mmol) in anhydrous toluene (2 mL) was added Pd$_2$(dba)$_3$ (39 mg, 0.042 mmol), BINAP (79 mg, 0.13 mmol), sodium tert-butoxide (56 mg, 0.59 mmol) and 1-(2-aminoethyl)pyrrolidine (64 µl, 0.51 mmol). The reaction mixture was refluxed for 4 h under nitrogen, diluted with ethyl acetate (20 mL), filtered and concentrated. Column chromatography on silica (dichloromethane:methanol 94:6) gave 1,1-dimethylethyl 4-{5-[(2-ethylbutyl)oxy]-2-methyl-3-[(2-pyrrolidin-1-ylethyl)amino]phenyl}piperazine-1-carboxylate (147 mg, 53% yield) as a yellow oil. $^1$H NMR (400 MHz, CDCl$_3$) δ 6.06 (d, 1H), 6.01 (d, 1H), 3.81 (d, 2H), 3.73-3.35 (br m, 4H), 3.34-3.22 (m, 2H), 2.94-2.73 (m, 6H), 2.72-2.53 (m, 4H), 2.05 (s, 3H), 1.83 (m, 4H), 1.72-1.56 (m, 1H), 1.55-1.35 (m, 13H), 0.93 (t, 6H); MS (ESI) for $C_{28}H_{48}N_4O_3$: 489 (MH$^+$).

A solution of 1,1-dimethylethyl 4-{5-[(2-ethylbutyl)oxy]-2-methyl-3-[(2-pyrrolidin-1-ylethyl)amino]phenyl}piperazine-1-carboxylate (141 mg, 0.29 mmol) in methanol (2 mL) and 4N hydrogen chloride in dioxane (0.3 ml) was refluxed for 2 min, and then concentrated to yield 5-[(2-ethylbutyl)oxy]-2-methyl-3-piperazin-1-yl-N-(2-pyrrolidin-1-ylethyl)aniline hydrochloride (130 mg, 99% yield). MS (ESI) for $C_{23}H_{40}N_4O$: 389 (MH$^+$).

Using the same or analogous synthetic techniques and/or substituting with alternative reagents, the following compounds of the invention were prepared:

2-methyl-5-[(2-methylpropyl)oxy]-3-piperazin-1-yl-N-(2-pyrrolidin-1-ylethyl)aniline hydrochloride: MS (ESI) for $C_{21}H_{36}N_4O$: 361 (MH$^+$).

5-(butyloxy)-2-methyl-3-piperazin-1-yl-N-(2-pyrrolidin-1-ylethyl)aniline hydrochloride: MS (ESI) for $C_{21}H_{36}N_4O$: 361 (MH$^+$).

5-[(2,2-dimethylpropyl)oxy]-2-methyl-3-piperazin-1-yl-N-(2-pyrrolidin-1-ylethyl)aniline hydrochloride: MS (ESI) for $C_{22}H_{38}N_4O$: 375 (MH$^+$).

2-methyl-3-piperazin-1-yl-N-(2-pyrrolidin-1-ylethyl)-5-[(tetrahydrofuran-2-ylmethyl)oxy]aniline hydrochloride: MS (ESI) for $C_{22}H_{36}N_4O_2$: 389 (MH$^+$).

2-methyl-5-{[2-(methyloxy)ethyl]oxy}-3-piperazin-1-yl-N-(2-pyrrolidin-1-ylethyl)aniline hydrochloride: MS (ESI) for $C_{20}H_{34}N_4O_2$: 363 (MH$^+$).

5-{[(2,2-difluorocyclopropyl)methyl]oxy}-2-methyl-3-piperazin-1-yl-N-(2-pyrrolidin-1-ylethyl)aniline hydrochloride: MS (ESI) for $C_{21}H_{32}F_2N_4O$: 395 (MH$^+$).

5-[(cyclopropylmethyl)oxy]-2-methyl-3-piperazin-1-yl-N-(2-pyrrolidin-1-ylethyl)aniline hydrochloride: MS (ESI) for $C_{21}H_{34}N_4O$: 359 (MH$^+$).

2-methyl-5-[(3-methylbutyl)oxy]-3-piperazin-1-yl-N-(2-pyrrolidin-1-ylethyl)aniline hydrochloride: MS (ESI) for $C_{22}H_{38}N_4O$: 375 (MH$^+$).

5-[(cyclohexylmethyl)oxy]-2-methyl-3-piperazin-1-yl-N-(2-pyrrolidin-1-ylethyl)aniline hydrochloride: MS (ESI) for $C_{24}H_{40}N_4O$: 401 (MH$^+$).

5-[(cyclopentylmethyl)oxy]-2-methyl-3-piperazin-1-yl-N-(2-pyrrolidin-1-ylethyl)aniline: MS (ESI) for $C_{23}H_{38}N_{40}$: 387 (MH$^+$).

2-methyl-5-[(phenylmethyl)oxy]-3-piperazin-1-yl-N-(2-pyrrolidin-1-ylethyl)aniline: MS (ESI) for $C_{24}H_{34}N_4O$: 395 (MH$^+$).

5-[(cyclobutylmethyl)oxy]-2-methyl-3-piperazin-1-yl-N-(2-pyrrolidin-1-ylethyl)aniline hydrochloride: MS (ESI) for $C_{22}H_{36}N_4O$: 373 (MH$^+$).

5-(ethyloxy)-2-methyl-3-piperazin-1-yl-N-(2-pyrrolidin-1-ylethyl)aniline hydrochloride: MS (ESI) for $C_{19}H_{32}N_4O$: 333 (MH$^+$).

2-methyl-5-[(1-methylethyl)oxy]-3-piperazin-1-yl-N-(2-pyrrolidin-1-ylethyl)aniline hydrochloride: MS (ESI) for $C_{20}H_{34}N_4O$: 347 (MH$^+$).

2-methyl-3-piperazin-1-yl-5-(propyloxy)-N-(2-pyrrolidin-1-ylethyl)aniline hydrochloride: MS (ESI) for $C_{20}H_{34}N_4O$: 347 (MH$^+$).

2-methyl-3-piperazin-1-yl-N-(2-pyrrolidin-1-ylethyl)-5-[(3,3,3-trifluoropropyl)oxy]aniline hydrochloride: MS (ESI) for $C_{20}H_{31}F_3N_4O$: 401 (MH$^+$).

Example 37

3-bromo-4-methyl-N-phenyl-5-piperazin-1-ylbenzamide hydrochloride

To 1,1-dimethylethyl 4-{3-bromo-2-methyl-5-[(methyloxy)carbonyl]phenyl}piperazine-1-carboxylate (1.05 g, 2.54 mmol) in methanol (10 mL) and water (3 mL) was added potassium hydroxide (713 mg, 12.7 mmol). The reaction mixture was stirred at 60° C. for 2 hours. The pH was adjusted to 5 with 10% citric acid, and the mixture was extracted with ethyl acetate. The organic layer was dried over magnesium sulfate, and concentrated to give 3-bromo-5-(4-{[(1,1-dimethylethyl)oxy]carbonyl}piperazin-1-yl)-4-methylbenzoic acid (849 mg, 84% yield) as a white solid. MS (ESI) for $C_{17}H_{23}BrN_2O_4$: 400 (MH$^+$).

To 3-bromo-5-(4-{[(1,1-dimethylethyl)oxy]carbonyl}piperazin-1-yl)-4-methylbenzoic acid (25 mg, 0.06 mmol) in DMF (3 mL) was added aniline (58 mg, 0.63 mmol), HATU (24 mg, 0.06 mmol), HOAT (11 mg, 0.08 mmol), and N-methyl morpholine (34 mg, 0.31 mmol). The reaction mixture was stirred at room temperature for 17 h, and then diluted with water. The pH was adjusted to 10 with saturated sodium bicarbonate. The mixture was extracted with diethyl ether, the organic layer was dried over magnesium sulfate, and concentrated to provide 1,1-dimethylethyl 4-{3-bromo-2-methyl-5-[(phenylamino)carbonyl]phenyl}piperazine-1-carboxylate (30 mg, 100% yield) as a colorless oil. MS (ESI) for $C_{23}H_{28}BrN_3O_3$: 475 (MH$^+$).

To 1,1-dimethylethyl 4-{3-bromo-2-methyl-5-[(phenylamino)carbonyl]phenyl}piperazine-1-carboxylate (106 mg, 0.22 mmol) in methanol (5 mL) was added 4N hydrochloric acid in dioxane (1 mL). The reaction mixture was refluxed for 3 min, and then concentrated to yield 3-bromo-4-methyl-N-phenyl-5-piperazin-1-ylbenzamide hydrochloride (84 mg, 100% yield) as a colorless oil. MS (ESI) for $C_{18}H_{20}BrN_3O$: 375 (MH$^+$).

Example 38

1-{4-methyl-3-piperazin-1-yl-5-[(2-pyrrolidin-1-ylethyl)amino]phenyl}butan-1-one hydrochloride To methyl-3,5 dibromo-4-methylbenzoate (7.13 g, 23.2 mmol) in dry toluene (90 mL) was added $Pd_2(dba)_3$ (1.06 g, 1.16 mmol), BINAP (2.17 g, 3.48 mmol), cesium carbonate (10.6 g, 32.5 mmol) and Boc-piperazine (4.36 g, 23.2 mmol). The reaction mixture was stirred at 110° C. for 16 h under nitrogen, cooled to room temperature, diluted with ethyl acetate (300 mL), filtered and concentrated. Column chromatography on silica (hexanes:ethyl acetate 9:1) provided 1,1-dimethylethyl 4-{3-bromo-2-methyl-5-[(methyloxy)carbonyl]phenyl}piperazine-1-carboxylate (5.5 g, 57% yield) as a light yellow oil. MS (ESI) for $C_{18}H_{25}BrN_2O_4$: 313 (MH$^+$-100).

To 1,1-dimethylethyl 4-{3-bromo-2-methyl-5-[(methyloxy)carbonyl]phenyl}piperazine-1-carboxylate (5.5 g, 13.3 mmol) in dry toluene (50 mL) was added $Pd_2(dba)_3$ (610 mg, 0.66 mmol), BINAP (1.24 g, 2.0 mmol), cesium carbonate (6.06 g, 18.6 mmol) and 1-(2-aminoethyl)pyrrolidine (2.02 mL, 16.0 mmol). The reaction mixture was stirred at 100° C. for 16 h under nitrogen, diluted with ethyl acetate (200 mL), filtered and concentrated. Column chromatography on silica (dichloromethane:methanol 93:7) afforded 1,1-dimethylethyl 4-{2-methyl-5-[(methyloxy)carbonyl]-3-[(2-pyrrolidin-1-ylethyl)amino]phenyl}piperazine-1-carboxylate (3.0 g, 50% yield) as an orange solid. MS (ESI) for $C_{24}H_{38}N_4O_4$: 447 (MH$^+$).

To 1,1-dimethylethyl 4-{2-methyl-5-[(methyloxy)carbonyl]-3-[(2-pyrrolidin-1-ylethyl)amino]phenyl}piperazine-1-carboxylate (2.6 g, 5.8 mmol) in methanol (12 mL) was added 4N sodium hydroxide (4.4 ml, 17.5 mmol), and the reaction mixture was stirred at room temperature for 16 h. To the solution was added 1.5N hydrogen chloride until pH 4, and the water layer was extracted with chloroform (2×100 mL). The combined organic layers were washed with brine (2×50 mL), dried over sodium sulfate, and concentrated to yield 3-(4-{[(1,1-dimethylethyl)oxy]carbonyl}piperazin-1-yl)-4-methyl-5-[(2-pyrrolidin-1-ylethyl)amino]benzoic acid (2.5 g, 99% yield). MS (ESI) for $C_{23}H_{36}N_4O_4$: 433 (MH$^+$).

To 3-(4-{[(1,1-dimethylethyl)oxy]carbonyl}piperazin-1-yl)-4-methyl-5-[(2-pyrrolidin-1-ylethyl)amino]benzoic acid (1.5 g, 3.47 mmol) in dry DMF (9 mL) was added N-methyl morpholine (1.53 mL, 13.90 mmol), N,O-dimethylhydroxylamine hydrochloride (406 mg, 4.16 mmol), HATU (1.32 g, 3.47 mmol) and HOAt (570 mg, 4.16 mmol). The reaction mixture was stirred at room temperature for 16 h, and then partitioned between ethyl acetate (100 mL) and water (50 mL). The organic layer was washed with 5% lithium chloride (50 mL), brine (50 mL), dried over sodium sulfate and concentrated. Column chromatography on silica (dichloromethane:methanol 93:7) gave 1,1-dimethylethyl 4-{2-methyl-5-{[methyl(methyloxy)amino]carbonyl}-3-[(2- pyrrolidin-1-ylethyl)amino]-phenyl}piperazine-1-carboxylate (919 mg, 56% yield). MS (ESI) for $C_{25}H_{41}N_5O_4$: 476 (MH$^+$).

A solution of 1,1-dimethylethyl 4-{2-methyl-5-{[methyl(methyloxy)amino]carbonyl}-3-[(2-pyrrolidin-1-ylethyl)amino]phenyl}piperazine-1-carboxylate (300 mg, 0.63 mmol) in anhydrous THF (3 mL) was cooled to 0° C., and a 2M solution of propylmagnesium bromide in THF (1.6 ml, 3.16 mmol) was slowly added. The reaction mixture was allowed to warm to room temperature and stirred for 3 h. The solution was cooled again to 0° C. and 1.5N hydrogen chloride was added until pH 2. Then, saturated sodium bicarbonate was added until basic pH. The water layer was extracted with ethyl acetate (2×50 mL), washed with brine (50 mL), dried over sodium sulfate, and concentrated. Column chromatography on silica (dichloromethane:methanol 95:5) yielded 1,1-dimethylethyl 4-{5-butanoyl-2-methyl-3-[(2-pyrrolidin-1-ylethyl)amino]phenyl}piperazine-1-carboxylate (196 mg, 68% yield). MS (ESI) for $C_{26}H_{42}N_4O_3$: 459 (MH$^+$).

A mixture of 1,1-dimethylethyl 4-{5-butanoyl-2-methyl-3-[(2-pyrrolidin-1-ylethyl)amino]phenyl}piperazine-1-carboxylate (30 mg, 0.07 mmol) in methanol (2 mL) and 4N hydrogen chloride in dioxane (0.2 ml) was refluxed for 2 min, and then concentrated to afford 1-{4-methyl-3-piperazin-1-yl-5-[(2-pyrrolidin-1-ylethyl)amino]phenyl}butan-1-one hydrochloride (28 mg, 99% yield). MS (ESI) for $C_{21}H_{34}N_4O$: 359 (MH$^+$).

Using the same or analogous synthetic techniques and/or substituting with alternative reagents, the following compounds of the invention were prepared:

1-{4-methyl-3-piperazin-1-yl-5-[(2-pyrrolidin-1-ylethyl)amino]phenyl}pentan-1-one hydrochloride: MS (ESI) for $C_{22}H_{36}N_4O$: 373 (MH$^+$).

{4-methyl-3-piperazin-1-yl-5-[(2-pyrrolidin-1-ylethyl)amino]phenyl}(phenyl)methanone hydrochloride: MS (ESI) for $C_{24}H_{32}N_4O$: 393 (MH$^+$).

1-{4-methyl-3-piperazin-1-yl-5-[(2-pyrrolidin-1-ylethyl)amino]phenyl}propan-1-one hydrochloride: MS (ESI) for $C_{20}H_{32}N_4O$: 345 (MH$^+$).

1-{4-methyl-3-piperazin-1-yl-5-[(2-pyrrolidin-1-ylethyl)amino]phenyl}ethanone hydrochloride: MS (ESI) for $C_{19}H_{30}N_4O$: 331 (MH$^+$).

4,4,4-trifluoro-1-{4-methyl-3-piperazin-1-yl-5-[(2-pyrrolidin-1-ylethyl)amino]-phenyl}butan-1-one hydrochloride: MS (ESI) for $C_{21}H_{31}F_3N_4O$: 413 (MH$^+$).

cyclopropyl{4-methyl-3-piperazin-1-yl-5-[(2-pyrrolidin-1-ylethyl)amino]-phenyl}methanone hydrochloride: MS (ESI) for $C_{21}H_{32}N_4O$: 395 (MH$^+$).

Example 39

5-(3,3-dimethylbutyl)-2-methyl-3-piperazin-1-yl-N-(2-pyrrolidin-1-ylethyl)aniline hydrochloride To 3,5-dibromo-4-methylphenol (19.0 g, 71.4 mmol) in toluene (200 mL) was added 1,1-dimethylethyl piperazine-1-carboxylate (11.9 g, 63.9 mmol), Pd$_2$(dba)$_3$ (1.63 g, 1.8 mmol), sodium tert-butoxide (19.3 g, 201 mmol), and BINAP (4.40 g, 7.1 mmol). The reaction mixture was heated to 110° C. in a sealed tube for 16 h, and then partitioned between with water and ethyl acetate. The organic layer was diluted with ether, filtered, dried over sodium sulfate, and concentrated. Column chromatography on silica (hexanes:ethyl acetate 8:2) provided 1,1-dimethylethyl 4-(3-bromo-5-hydroxy-2-methylphenyl)-piperazine-1-carboxylate (9.75 g, 41.1% yield) as a white solid. MS (ESI) for $C_{16}H_{23}BrN_2O_3$: 372 (MH$^+$).

To 1,1-dimethylethyl 4-(3-bromo-5-hydroxy-2-methylphenyl)piperazine-1-carboxylate (990 mg, 2.67 mmol) in toluene (5 mL) was added 2-pyrrolidin-1-yl-ethylamine (623 mg, 5.33 mmol), sodium tert-butoxide (512 mg, 5.33 mmol), Pd$_2$(dba)$_3$ (123 mg, 0.13 mmol), and 2-(di-t-butylphosphino)biphenyl (159 mg, 0.53 mmol). The reaction mixture was stirred at 110° C. for 16 h, and filtered through celite. The filtrate was diluted with water, extracted with ethyl acetate, dried over sodium sulfate, and concentrated to give 1,1-dimethylethyl 4-{5-hydroxy-2-methyl-3-[(2-pyrrolidin-1-ylethyl)amino]phenyl}piperazine-1-carboxylate (1.08 g, 100% yield) as a brown oil, which was used without further purification. MS (ESI) for $C_{22}H_{36}N_4O_3$: 405 (MH$^+$).

To 1,1-dimethylethyl 4-{5-hydroxy-2-methyl-3-[(2-pyrrolidin-1-ylethyl)amino]phenyl}piperazine-1-carboxylate (1.08 g, 2.67 mmol) in methylene chloride (10 mL), was added triethylamine (540 mg, 5.34 mmol), and triflic anhydride (829 mg, 2.94 mmol) at −78° C. The reaction mixture was stirred at −78° C. for 30 min and then at room temperature for 16 h. The reaction was quenched with water, extracted with methylene chloride, dried over sodium sulfate, and concentrated. Column chromatography on silica (dichloromethane:methanol 9:1) afforded 1,1-dimethylethyl 4-(2-methyl-3-[(2-pyrrolidin-1-ylethyl)amino]-5-{[(trifluoromethyl)sulfonyl]oxy}phenyl)piperazine-1-carboxylate (873 mg, 61% yield) as a light brown oil. MS (ESI) for $C_{23}H_{35}F_3N_4O_5S$: 537 (MH$^+$).

To 1,1-dimethylethyl 4-(2-methyl-3-[(2-pyrrolidin-1-ylethyl)amino]-5-{[(trifluoromethyl)sulfonyl]oxy}phenyl)piperazine-1-carboxylate (256 mg, 0.48 mmol) in DMF (3 mL) was added 3,3-dimethyl-but-1-yne (588 mg, 7.16 mmol), PdCl$_2$(PPh$_3$)$_2$ (50 mg, 0.07 mmol), copper(I) iodide (41 mg, 0.22 mmol), and triethylamine (965 mg, 9.54 mmol). The reaction mixture was stirred in a sealed tube at 100° C. for 16 h, and filtered. The filtrate was diluted with water, extracted with ethyl acetate, dried over sodium sulfate, and concentrated. Column chromatography on silica (dichloromethane:methanol 9:1) provided 1,1-dimethylethyl 4-{5-(3,3-dimethylbut-1-yn-1-yl)-2-methyl-3-[(2-pyrrolidin-1-ylethyl)amino]phenyl}piperazine-1-carboxylate (224 mg, 100% yield) as a pink oil. MS (ESI) for $C_{28}H_{44}N_4O_2$: 469 (MH$^+$).

To a solution of 1,1-dimethylethyl 4-{5-(3,3-dimethylbut-1-yn-1-yl)-2-methyl-3-[(2-pyrrolidin-1-ylethyl)amino]phenyl}piperazine-1-carboxylate (200 mg, 0.43 mmol) in ethyl acetate (40 mL) and glacial acetic acid (4 mL) was added palladium on carbon (100 mg, 10%, contains 50% water), and the reaction mixture was stirred under an hydrogen atmosphere for 3 h. The reaction mixture was filtered through celite, and concentrated. The filtrate was diluted with water, the pH adjusted to 10, and extracted with ethyl acetate. The organic layer was dried over sodium sulfate, and concentrated to give 1,1-dimethylethyl 4-{5-(3,3-dimethylbutyl)-2-methyl-3-[(2-pyrrolidin-1-ylethyl)amino]phenyl}piperazine-1-carboxylate (202 mg, 100% yield) as a light tan oil. MS (ESI) for $C_{28}R_{48}N_4O_2$: 473 (MH$^+$).

To 1,1-dimethylethyl 4-{5-(3,3-dimethylbutyl)-2-methyl-3-[(2-pyrrolidin-1-ylethyl)amino]phenyl}piperazine-1-carboxylate (210 mg, 0.44 mmol) in methanol (5 mL) was added 4N hydrochloric acid in dioxane (1 mL). The reaction mixture was refluxed for 3 min and then concentrated to provide 5-(3,3-dimethylbutyl)-2-methyl-3-piperazin-1-yl-N-(2-pyrrolidin-1-ylethyl)aniline hydrochloride (166 mg, 100% yield) as a colorless oil. MS (ESI) for $C_{23}H_{40}N_4$: 373 (MH$^+$).

Using the same or analogous synthetic techniques and/or substitution with alternative reagents, the following compounds of the invention were prepared:

2-methyl-5-(phenylethynyl)-3-piperazin-1-yl-N-(2-pyrrolidin-1-ylethyl)aniline: MS (ESI) for $C_{25}H_{32}N_4$: 389 (MH$^+$).

5-ethynyl-2-methyl-3-piperazin-1-yl-N-(2-pyrrolidin-1-ylethyl)aniline: MS (ESI) for $C_{19}H_{28}N_4$: 313 (MH$^+$).

5-(3,3-dimethylbut-1-yn-1-yl)-2-methyl-3-piperazin-1-yl-N-(2-pyrrolidin-1-ylethyl)aniline: MS (ESI) for $C_{23}H_{36}N_4$: 369 (MH$^+$).

5-ethyl-2-methyl-3-piperazin-1-yl-N-(2-pyrrolidin-1-ylethyl)aniline: MS (ESI) for $C_{19}H_{32}N_4$: 317 (MH$^+$).

2-methyl-3-piperazin-1-yl-N-(2-pyrrolidin-1-ylethyl)-5-[2-(trimethylsilyl)ethyl]aniline: MS (ESI) for $C_{22}H_{40}N_4Si$: 389 (MH$^+$).

2-methyl-5-(2-phenylethyl)-3-piperazin-1-yl-N-(2-pyrrolidin-1-ylethyl)aniline: MS (ESI) for $C_{25}H_{36}N_4$: 393 (MH$^+$).

Example 40

2-Methyl-5-(3-phenyl-1,2,4-oxadiazol-5-yl)-3-piperazin-1-yl-N-(2-pyrrolidin-1-ylethyl)aniline hydrochloride To a solution of 3,5-dibromo-4-methylbenzoic acid (500 mg, 1.70 mmol) in DMF (10 mL) was added HATU (951 mg, 2.50 mmol), benzamidineoxime (272 mg, 2.00 mmol) and diisopropylethylamine (505 mg, 3.90 mmol). The reaction mixture was stirred at room temperature for 3 h, then diluted with ethyl acetate (100 mL), washed with saturated sodium bicarbonate (50 mL), 5% lithium chloride (2×50 mL), and brine (50 mL), dried over sodium sulfate, and concentrated. Column chromatography on silica (hexanes:ethyl acetate 4:1) afforded N'-{[(3,5-dibromo-4-methylphenyl)carbonyl]oxy}-benzenecarboximidamide (630 mg, 90% yield) as a yellow solid. $^1$H NMR (400 MHz, $d_6$-DMSO) δ 8.39 (s, 2H), 7.75 (m, 2H), 7.50 (m, 3H), 7.16 (s, 2H), 2.60 (s, 3H).

To a solution of N'-{[(3,5-dibromo-4-methylphenyl)carbonyl]oxy}benzene-carboximidamide (620 mg, 1.50 mmol) in THF (10 mL) was added a 1.0 M solution of tetrabutylammonium fluoride in THF (1.50 mL). The reaction mixture was stirred at room temperature for 17 h, then diluted with ethyl acetate (100 mL), washed with water (50 mL), and brine (50 mL), dried over sodium sulfate, and concentrated. Trituration with ethyl acetate provided 5-(3,5-dibromo-4-methylphenyl)-3-phenyl-1,2,4-oxadiazole (311 mg, 52% yield) as a colorless solid. $^1$H NMR (400 MHz, $d_6$-DMSO) δ 8.36 (s, 2H), 8.11 (m, 2H), 7.62 (m, 3H), 2.63 (s, 3H).

A mixture of 5-(3,5-dibromo-4-methylphenyl)-3-phenyl-1,2,4-oxadiazole (162 mg, 0.41 mmol), Boc-piperazine (76 mg, 0.41 mmol), sodium tert-butoxide (56 mg, 0.58 mmol), Pd$_2$(dba)$_3$ (19 mg, 0.02 mmol), and BINAP (38 mg, 0.06 mmol) in toluene (4 mL) was stirred at 110° C. for 16 h. Column chromatography of the mixture on silica (hexanes:ethyl acetate 9:1) gave 1,1-dimethylethyl 4-[3-bromo-2-methyl-5-(3-phenyl-1,2,4-oxa-diazol-5-yl)phenyl]piperazine-1-carboxylate (76 mg, 37% yield) as a colorless solid. $^1$H NMR (400 MHz, CDCl$_3$) δ 8.17 (m, 3H), 7.78 (s, 1H), 7.53 (m, 3H), 3.63 (br s, 4H), 2.95 (m, 4H), 2.49 (s, 3H), 1.50 (s, 9H).

A mixture of 1,1-dimethylethyl 4-[3-bromo-2-methyl-5-(3-phenyl-1,2,4-oxadiazol-5-yl)phenyl]piperazine-1-carboxylate (111 mg, 0.22 mmol), 1-(2-aminoethyl)pyrrolidine (51 mg, 0.45 mmol), sodium tert-butoxide (49 mg, 0.51 mmol), Pd$_2$(dba)$_3$ (15 mg, 0.02 mmol), and BINAP (30 mg, 0.05 mmol) in toluene (4 mL) was stirred in a sealed pressure vessel at 100° C. for 12 h. Column chromatography of the mixture on silica (dichloromethane:methanol 95:5) gave 1,1-dimethylethyl 4-{2-methyl-5-(3-phenyl-1,2,4-oxadiazol-5-yl)-3-[(2-pyrrolidin-1-ylethyl)amino]phenyl}piperazine-1-carboxylate (27 mg, 23% yield) as a yellow oil. $^1$H NMR (400 MHz, $d_4$-methanol) δ 8.13 (m, 2H), 7.95 (m, 1H), 7.55 (m, 2H), 7.34 (s, 1H), 7.27 (s, 1H), 3.61 (m, 4H), 3.19 (br s, 4H), 2.90 (br s, 4H), 2.26 (s, 3H), 2.02 (m, 4H), 1.50 (s, 9H); MS (ESI) for $C_{30}H_{40}N_6O$: 533 (MH$^+$).

A mixture of 1,1-dimethylethyl 4-{2-methyl-5-(3-phenyl-1,2,4-oxadiazol-5-yl)-3-[(2-pyrrolidin-1-ylethyl)amino]phenyl}piperazine-1-carboxylate (27 mg, 0.05 mmol), methanol (2 mL), and 4N hydrochloric acid in dioxane (2 mL) was refluxed for 1 min. The mixture was concentrated to give 2-Methyl-5-(3-phenyl-1,2,4-oxadiazol-5-yl)-3-piperazin-1-yl-N-(2-pyrrolidin-1-ylethyl)aniline hydrochloride (31 mg, 100% yield) as a yellow oil, which was used without further purification. MS (ESI) for $C_{25}H_{32}N_6O$: 433 (MH$^+$).

Using the same or analogous synthetic techniques and/or substituting with alternative reagents, the following compound of the invention was prepared:

2-Methyl-5-(3-methyl-1,2,4-oxadiazol-5-yl)-3-piperazin-1-yl-N-(2-pyrrolidin-1-ylethyl)aniline hydrochloride: MS (ESI) for $C_{20}H_{30}N_6O$: 371 (MH$^+$).

Example 41

1-{3-piperazin-1-yl-5-[(2-pyrrolidin-1-ylethyl)amino]phenyl}butan-1-one hydrochloride To 1,1-dimethylethyl 4-{3-bromo-5-[(methyloxy)carbonyl]phenyl}piperazine-1-carboxylate (2.65 g, 6.64 mmol) in toluene (70 mL) was added 2-pyrrolidin-1-yl-ethyl-amine (1.55 g, 13.3 mmol), cesium carbonate (8.65 g, 26.5 mmol), Pd$_2$(dba)$_3$ (486 mg, 0.531 mmol), and BINAP (992 mg, 1.59 mmol). The reaction mixture was stirred at 110° C. in a sealed tube for 16 h, filtered, and concentrated. Column chromatography on silica (dichloromethane:methanol 9:1) gave 1,1-dimethylethyl 4-{3-[(methyloxy)carbonyl]-5-[(2-pyrrolidin-1-ylethyl)amino]phenyl}piperazine-1-carboxylate (1.53 g, 53% yield) as a tan oil. MS (ESI) for $C_{23}H_{36}N_4O_4$: 433 (MH$^+$).

To 1,1-dimethylethyl 4-{3-[(methyloxy)carbonyl]-5-[(2-pyrrolidin-1-ylethyl)amino]phenyl}piperazine-1-carboxylate (924 mg, 2.13 mmol) in methanol (10 mL) and water (3 mL), was added potassium hydroxide (600 mg, 10.7 mmol). The reaction mixture was stirred at 60° C. for 1 h. The pH was adjusted to 4 with 10% citric acid. The reaction mixture was extracted with chloroform, and concentrated to provide 3-(4-{[(1,1-dimethylethyl)oxy]carbonyl}piperazin-1-yl)-5-[(2-pyrrolidin-1-ylethyl)amino]benzoic acid (262 mg, 29% yield) as a white solid. MS (ESI) for $C_{22}H_{34}N_4O_4$: 419 (MH$^+$).

To 3-(4-{[(1,1-dimethylethyl)oxy]carbonyl}piperazin-1-yl)-5-[(2-pyrrolidin-1-ylethyl)amino]benzoic acid (802 mg, 1.92 mmol), in DMF (5 mL) was added O,N-dimethyl-hydroxylamine (224 mg, 2.30 mmol), HATU (730 mg, 1.92 mmol), HOAT (313 mg, 2.30 mmol), and N-methyl morpholine (583 mg, 5.76 mmol). The reaction mixture was stirred at 60° C. for 22 h, diluted with water, and extracted with ethyl acetate. The organic layer was washed with brine, dried over sodium sulfate, and concentrated. Column chromatography on silica (dichloromethane:methanol 92:8) gave 1,1-dimethyl-ethyl 4-{3-{[methyl(methyloxy)amino]carbonyl}-5-[(2-pyrrolidin-1-ylethyl)amino]-phenyl}piperazine-1-carboxylate (316 mg, 36% yield) as an orange solid. MS (ESI) for $C_{24}H_{39}N_5O_4$: 462 (MH$^+$).

To 1,1-dimethylethyl 4-{3-{[methyl(methyloxy)amino]carbonyl}-5-[(2-pyrrolidin-1-ylethyl)amino]phenyl}piperazine-1-carboxylate (150 mg, 0.33 mmol) in anhydrous THF (2 mL) was added propyl magnesium bromide (240 mg, 1.63 mmol). The reaction mixture was stirred at 0° C. for 10 min, and then at room temperature for 2 h. Excess Grignard reagent was quenched with 1N aqueous hydrogen chloride. The pH was adjusted to 10 with sodium bicarbonate, and the aqueous layer was extracted with ethyl acetate. The organic layer was washed with brine, dried over sodium sulfate, and concentrated. Column chromatography on silica (dichloromethane:methanol 93:7) provided 1,1-dimethylethyl 4-{3-butanoyl-5-[(2-pyrrolidin-1-ylethyl)amino]phenyl}-piperazine-1-carboxylate (20 mg, 14% yield) as a white solid. MS (ESI) for $C_{25}H_{40}N_4O_3$: 445 (MH$^+$).

To 1,1-dimethylethyl 4-{3-butanoyl-5-[(2-pyrrolidin-1-ylethyl)amino]phenyl}piperazine-1-carboxylate (45 mg, 0.10 mmol) in methanol (5 mL) was added 4N hydrogen chloride in dioxane (1 mL). The reaction mixture was refluxed for 3 min, and then concentrated to give 1-{3-piperazin-1-yl-5-[(2-pyrrolidin-1-ylethyl)amino]phenyl}butan-1-one hydrochloride (35 mg, 100% yield) as a clear oil. MS (ESI) for $C_{20}H_{32}N_4O$: 345 (MH$^+$).

Example 42

3-Bromo-4-{4-[5-chloro-2-methyl-3-(3-pyrrolidin-1-yl-propyl)-phenyl]-piperazin-1-yl}-1H-pyrazolo[3,4-d]pyrimidine To a 50 mL recovery flask was added 4-(5-chloro-3-iodo-2-methyl-phenyl)-piperazine-1-carboxylic acid tert-butyl ester (1.25 g, 2.87 mmol, 1.0 eq.), tetra-n-butylammonium chloride (799 mg, 2.87 mmol, 1.0 eq.), sodium bicarbonate (604 mg, 7.18 mmol, 2.5 eq.), palladium (II) acetate (13 mg, 0.02 eq.), and DMF (10 mL). Allyl alcohol (295 µL, 4.31 mmol, 1.5 eq.) was added and the reaction was heated at 50° C. for 4 h. The reaction mixture was filtered through Celite and the Celite cake was rinsed with EtOAc. The organic phase was washed with water (50 mL), 10% aq LiCl (2×50 mL), and saturated aq. sodium chloride (50 mL). The combined aqueous phases were extracted with EtOAc (2×50 mL). The organic phases were combined and dried over anhydrous $Na_2SO_4$, filtered, and concentrated to give black oil. The crude material was purified via column chromatography (20% EtOAc/Hex) to give 4-[5-chloro-2-methyl-3-(3-oxo-propyl)-phenyl]-piperazine-1-carboxylic acid tert-butyl ester as yellow oil (489 mg, 47%).

To a 25 mL recovery flask was added 4-[5-chloro-2-methyl-3-(3-oxo-propyl)-phenyl]-piperazine-1-carboxylic acid tert-butyl ester (240 mg, 0.655 mmol, 1.0 eq.), pyrrolidine (274 µL, 3.28 mmol, 5.0 eq.), and 1,2-dichloroethane (5 mL). Upon stirring, NaBH(OAc)$_3$ (278 mg, 1.31 mmol, 2.0 eq.) was added and the reaction was stirred at room temperature for 1 h. 1N HCl (2 mL) was added and the reaction mixture was diluted with water (50 mL) and EtOAc (50 mL). The organic phase was washed with saturated aq. NaHCO$_3$ (30 mL) and saturated aq. NaCl (30 mL). The combined aqueous phases were extracted with EtOAc (2×50 mL). The organic phases were combined and dried over anhydrous $Na_2SO_4$, filtered, and concentrated to give 4-[5-chloro-2-methyl-3-(3-pyrrolidin-1-yl-propyl)-phenyl]-piperazine-1-carboxylic acid tert-butyl ester as a gray paste that was used in the next step without further purification.

To a 25 mL recovery flask was added 4-[5-chloro-2-methyl-3-(3-pyrrolidin-1-yl-propyl)-phenyl]-piperazine-1-carboxylic acid tert-butyl ester (278 mg, 0.665 mol, 1.0 eq.) and methanol (3 mL). 4N HCl/dioxane (4 mL) was added and the reaction was stirred for 2 h at room temperature. LC/MS analysis indicated that the deprotection was complete, whereupon the reaction was concentrated and placed on high vacuum. The crude material of 1-[5-chloro-2-methyl-3-(3-pyrrolidin-1-yl-propyl)-phenyl]-piperazine was used in the next reaction without further purification.

To a 25 mL recovery flask was added 1-[5-chloro-2-methyl-3-(3-pyrrolidin-1-yl-propyl)-phenyl]-piperazine dihydrochloride (280 mg, 0.713 mmol, 1.1 eq.), 3-bromo-1-(tetrahydro-pyran-2-yl)-1H-pyrazolo[3,4-d]pyrimidin-4-ol (193 mg, 0.648 mmol, 1.0 eq.), N-methylmorpholine (285 µL, 2.59 mmol, 4.0 eq.), and DMF (5 mL). With stirring, PyBOP (506 mg, 0.972 mmol, 1.5 eq.) was added whereupon the reaction was heated at 80° C. overnight. The reaction mixture was diluted with H$_2$O (50 mL) and EtOAc (50 mL). The organic phase was washed with 10% aq. LiCl (2×30 mL) saturated aq. NaCl (30 mL). The combined aqueous phases were extracted with EtOAc (2×50 mL). The organic phases were combined and dried over anhydrous $Na_2SO_4$, filtered, and concentrated. The crude material was purified via column chromatography (1% to 4% CH$_3$OH/CH$_2$Cl$_2$) to give 3-bromo-4-{4-[5-chloro-2-methyl-3-(3-pyrrolidin-1-yl-propyl)-phenyl]-piperazin-1-yl}-1-(tetrahydro-pyran-2-yl)-1H-pyrazolo[3,4-d]pyrimidine as a white solid (186 mg).

3-Bromo-4-{4-[5-chloro-2-methyl-3-(3-pyrrolidin-1-yl-propyl)phenyl]piperazin-1-yl}-1H-pyrazolo[3,4-d]pyrimidine. To a 25 mL recovery flask was added 3-bromo-4-{4-[5-chloro-2-methyl-3-(3-pyrrolidin-1-yl-propyl)-phenyl]-piperazin-1-yl}-1-(tetrahydro-pyran-2-yl)-1H-pyrazolo[3,4-d]pyrimidine (186 mg, 0.309 mol, 1.0 eq.) and methanol (7.5 mL). 4N HCl/dioxane (2.5 mL) was added and the reaction was stirred for 30 min at room temperature. LC/MS analysis indicated that the deprotection was complete, whereupon the reaction was concentrated and placed on high vacuum. The crude material was purified via reverse-phase HPLC to give pure product, 3-bromo-4-{4-[5-chloro-2-methyl-3-(3-pyrrolidin-1-ylpropyl)phenyl]piperazin-1-yl}-1H-pyrazolo[3,4-d]pyrimidine as the TFA salt (60 mg, 31%). $^1$H NMR (400 MHz, d$_6$-DMSO) δ 10.55 (br s, 1H), 8.38 (s, 1H), 7.04 (s, 1H), 7.00 (s, 1H), 3.54-3.50 (m, 2H), 3.17-3.12 (m, 2H), 3.02-2.94 (m, 6H), 2.67-2.63 (t, 2H), 2.54 (s, 2H), 2.27 (s, 3H), 1.98-1.85 (m, 6H). MS (ESI) for $C_{23}H_{29}BrClN_7$: 518 (MH$^+$).

Using the same or analogous synthetic techniques and/or substituting with alternative reagents, the following compounds of the invention were prepared:

3-{3-[4-(3-Bromo-1H-pyrazolo[3,4-d]pyrimidin-4-yl)piperazin-1-yl]-5-chloro-2-methylphenyl}-N,N-diethylpropan-1-amine: $^1$H NMR (400 MHz, d$_6$-DMSO) δ 10.03 (br s, 1H), 8.38 (s, 1H), 7.07 (d, 1H), 7.00 (d, 1H), 3.14-3.05 (m, 6H), 3.02-3.00 (m, 4H), 2.66-2.62 (t, 2H), 2.27 (s, 3H), 1.89 (m, 2H), 1.20 (t, 6H). MS (ESI) for $C_{23}H_{31}BrClN_7$: 520 (MH$^+$).

3-Bromo-4-{4-[5-chloro-2-methyl-3-(3-morpholin-4-yl-propyl)phenyl]piperazin-1-yl}-1H-pyrazolo[3,4-d]pyrimidine: $^1$H NMR (400 MHz, d$_6$-DMSO) δ 10.61 (br. s, 1H), 8.39 (s, 1H), 7.04 (s, 1H), 7.00 (s, 1H), 3.98 (d, 4H), 3.75 (t, 2H), 3.49 (m, 2H), 3.31 (m, 2H), 3.13 (m, 2H), 3.09 (m, 2H), 3.01 (m, 4H), 2.63 (t, 2H), 2.28 (s, 3H), 1.97 (m, 2H). MS (ESI) for $C_{23}H_{29}BrClN_7O$: 536 (MH$^+$).

3-Bromo-4-(4-{5-chloro-2-methyl-3-[3-(4-methylpiperazin-1-yl)propyl]phenyl}piperazin-1-yl)-1H-pyrazolo[3,4-d]pyrimidine: $^1$H NMR (400 MHz, d$_6$-DMSO) δ 11.43 (br. s, 1H), 8.36 (s, 1H), 6.99 (s, 1H) 7.02 (s, 1H), 3.95 (m, 4H), 3.79 (m, 2H), 3.67 (m, 2H), 3.52 (m, 2H), 3.35 (m, 2H), 3.19 (m, 2H), 3.01 (m, 4H), 2.83 (s, 3H), 2.64 (m, 2H), 2.28 (s, 3H), 1.98 (m, 2H). MS (ESI) for $C_{24}H_{32}BrClN_8$: 549 (MH$^+$).

3-Bromo-4-{4-[5-chloro-2-methyl-3-(3-piperidin-1-yl-propyl)phenyl]piperazin-1-yl}-1H-pyrazolo[3,4-d]pyrimidine: $^1$H NMR (400 MHz, d$_6$-DMSO) δ 10.01 (br. s, 1H), 8.40 (s, 1H), 7.07 (s, 1H), 7.02 (s, 1H), 3.98 (m, 4H), 3.43 (d, 2H), 3.09 (m, 2H), 3.04 (m, 4H), 2.85 (m, 2H), 2.62 (t, 2H), 2.28 (s, 3H), 1.96 (m, 2H), 1.79 (m, 2H), 1.71 (m, 2H), 1.39 (m, 2H). MS (ESI) for $C_{24}H_{31}BrClN_7$: 534 (MH$^+$).

4-{4-[5-Chloro-2-methyl-3-(3-pyrrolidin-1-ylpropyl)phenyl]piperazin-1-yl}-1H-pyrazolo[3,4-d]pyrimidine: $^1$H NMR (400 MHz, d$_6$-DMSO) δ 9.43 (br. s, 1H), 8.19 (s, 1H), 6.99 (s, 1H), 6.96 (s, 1H), 4.03 (m, 2H), 3.31 (m, 2H), 3.10 (m, 2H), 2.93 (m, 4H), 2.58 (m, 2H), 2.43 (m, 2H), 2.40 (m, 2H), 2.21 (m, 3H), 1.93 (m, 2H), 1.81 (m, 4H). MS (ESI) for $C_{23}H_{30}ClN_7$: 440 (MH$^+$).

3-Bromo-4-{4-[5-fluoro-2-methyl-3-(3-pyrrolidin-1-ylpropyl)phenyl]piperazin-1-yl}-1H-pyrazolo[3,4-d]pyrimidine: $^1$H NMR (400 MHz, d$_6$-DMSO) δ 9.80 (br. s, 1H), 8.89 (s, 1H), 6.72 (m, 2H), 3.88 (m, 4H), 3.08 (m, 2H), 2.92 (m, 6H), 2.57 (m, 2H), 2.39 (m, 2H), 2.17 (s, 3H), 1.92 (m, 2H), 1.79 (m, 4H). MS (ESI) for $C_{23}H_{29}BrFN_7$: 504 (MH$^+$).

3-Bromo-4-{4-[4-methyl-3-(3-pyrrolidin-1-ylpropyl)phenyl]piperazin-1-yl}-1H-pyrazolo[3,4-d]pyrimidine. MS (ESI) for $C_{23}H_{30}BrN_7$: 486 (MH$^+$).

(2E)-3-(4-{4-[5-Chloro-2-methyl-3-(3-pyrrolidin-1-ylpropyl)phenyl]piperazin-1-yl}-1H-pyrazolo[3,4-d]pyrimidin-3-yl)prop-2-enoic acid: $^1$H NMR (400 MHz, d$_6$-DMSO) δ 9.51 (br. s, 1H), 8.47 (s, 1H), 7.72 (d, 1H), 7.05 (s, 1H), 6.98 (s, 1H), 6.60 (d, 1H), 3.80 (m, 4H), 3.52 (m, 4H), 3.19 (m, 2H), 3.0 (m, 4H), 2.63 (m, 2H), 2.25 (s, 3H), 2.02 (m, 2H), 1.86 (m, 4H). MS (ESI) for $C_{26}H_{32}ClN_7O_2$: 510 (MH$^+$).

3-(4-{4-[5-Chloro-2-methyl-3-(3-pyrrolidin-1-ylpropyl)phenyl]piperazin-1-yl}-1H-pyrazolo[3,4-d]pyrimidin-3-yl)prop-2-yn-1-ol: $^1$H NMR (400 MHz, d$_6$-DMSO) δ 9.51 (br. s, 1H), 8.32 (s, 1H), 7.05 (s, 1H), 7.02 (s, 1H), 4.40 (s, 2H), 4.13 (m, 2H), 3.50 (m, 2H), 3.20 (m, 2H), 3.02 (m, 6H), 2.65 (m, 2H), 2.28 (s, 3H), 2.03 (m, 2H), 1.89 (m, 4H). MS (ESI) for $C_{26}H_{32}ClN_7O$: 494 (MH$^+$).

Example 43

3-Bromo-4-{4-[5-Chloro-2-methyl-3-(2-pyrrolidin-1-yl-ethoxy)-phenyl]-piperazin-1-yl}-1H-pyrazolo[3,4-d]pyrimidine 4-(5-Chloro-3-iodo-2-methyl-phenyl)-piperazine-1-carboxylic acid tert-butyl ester was synthesized as in a previous procedure.

To a pressure vessels was added 4-(5-chloro-3-iodo-2-methyl-phenyl)-Boc piperazine (4.0 g, 9.2 mmol), dry DMSO (18.0 mL), potassium acetate (2.7 g mg, 27.6 mmol), bis-(pinacolato)diboron (2.5 mg, 10.1 mmol), and Pd(dppf)Cl$_2$ dichloromethane complex (751 mg, 0.92 mmol). The reaction was sealed and heated to 80° C. overnight. The reaction was then cooled to rt, filtered through celite, and flushed with EtOAc. The combined organic flushes were washed with water, brine, and dried with Na$_2$SO$_4$, and concentrated. Column chromatography on silica gel with 10:90 EtOAc:hexanes gave 2.3 g of 4-[5-chloro-2-methyl-3-(4,4,5,5-tetramethyl-[1,3,2]dioxaborolan-2-yl)-phenyl]-piperazine-1-carboxylic acid tert-butyl ester as an oil that crystallizes to 4-[5-chloro-2-methyl-3-(4,4,5,5-tetramethyl-[1,3,2]dioxaborolan-2-yl)-phenyl]-piperazine-1-carboxylic acid tert-butyl ester as a white solid (57% yield). $^1$H NMR (400 MHz, CDCl$_3$) δ 7.49 (d, 1H), 7.05 (d, 1H), 3.60 (br s, 4H), 2.85 (br m, 4H), 2.42 (s, 3H), 1.50 (s, 9H), 1.4-1.2 (s, 12H). MS (ESI) for $C_{22}H_{34}BClN_2O_4$: 437 (MH$^+$).

To a round bottom flask cooled to 0° C. was added 4-[5-chloro-2-Methyl-3-(4,4,5,5-tetramethyl-[1,3,2]dioxaborolan-2-yl)-phenyl]-piperazine-1-carboxylic acid tert-butyl ester (2.3 g, 5.3 mmol), THF (50.0 mL), 12.5M NaOH (1.25 mL, 15.8 mmol), and 30% aq H$_2$O$_2$ (3.03 mL mg, 31.6 mmol). The reaction was stirred at 0° C. for 30 min (or until complete) before quenching with 10% citric acid and EtOAc. The reaction was partitioned, and the EtOAc layer was dried with Na$_2$SO$_4$, and concentrated to obtain 4-(5-chloro-3-Hydroxy-2-methyl-phenyl)-piperazine-1-carboxylic acid tert-butyl ester as a white solid (1.8 g, 100% yield). $^1$H NMR (400 MHz, CDCl$_3$) δ 6.62 (d, 1H), 6.58 (d, 1H), 6.22 (br s, 1H), 3.60 (br s, 4H), 2.80 (br m, 4H), 2.18 (s, 3H), 1.50 (s, 9H). MS (ESI) for $C_{16}H_{23}BClN_2O_3$: 327 (MH$^+$).

To a round bottom flask was added 4-(5-chloro-3-hydroxy-2-methyl-phenyl)-piperazine-1-carboxylic acid tert-butyl ester (150 mg, 0.46 mmol), DMF (4.0 mL), 1-(2-chloroethyl pyrrolidine) HCl (156 mg, 0.92 mmol), and Cs$_2$CO$_3$ (598 mg, 1.84 mmol). The reaction was stirred at 60° C. for 5 hr (or until complete) before quenching with 10% LiCl and EtOAc. The reaction was partitioned, and the EtOAc layer was dried with Na$_2$SO$_4$, and concentrated to obtain 4-[5-chloro-2-methyl-3-(2-pyrrolidin-1-yl-ethoxy)-phenyl]-piperazine-1-carboxylic acid tert-butyl ester as a brown oil (279 mg, 100% yield) which was taken to the next step without further purification. $^1$H NMR, (400 MHz, CDCl$_3$) δ 6.62 (br d, 2H), 4.10 (t, 2H), 3.80 (br s, 4H), 2.80 (br t, 4H), 2.60 (m, 4H), 2.18 (s, 3H), 1.80 (br m, 4H), 1.50 (s, 9H). MS (ESI) for $C_{22}H_{34}BClN_3O_3$: 424 (MH$^+$).

3-Bromo-4-{4-[5-chloro-2-methyl-3-(2-pyrrolidin-1-yl-ethoxy)-phenyl]-piperazin-1-yl}-1H-pyrazolo[3,4-d]pyrimidine: To a round bottom flask was added 4-[5-chloro-2-methyl-3-(2-pyrrolidin-1-yl-ethoxy)-phenyl]-piperazine-1-carboxylic acid tert-butyl ester (279 mg, 0.65 mmol), MeOH (4.0 mL), and 4M HCl in dioxane. The reaction was stirred at RT for 1 hr (or until complete) before concentrating to obtain free-base as brown oil. The brown oil was dissolved in DMF (4.0 mL) before adding N-methylmorpholine (0.31 mL, 2.8 mmol), PyBop (436 mg, 0.84 mmol), and 3-bromo-1-(tetrahydro-pyran-2-yl)-1H-pyrazolo[3,4-d]pyrimidin-4-ol (229 mg, 0.77 mmol). The reaction was heated to 60° C. overnight. The reaction was then quenched with 50 mL EtOAc and 5 mL 10% LiCl, partitioned, dried with Na$_2$SO$_4$, concentrated and columned with 90:10 EtOAc:hexane to give 3-bromo-4-{4-[5-chloro-2-methyl-3-(2-pyrrolidin-1-yl-ethoxy)-phenyl]-piperazin-1-yl}-1H-pyrazolo[3,4-d]pyrimidine. The THP group was removed by dissolving in MeOH (7.5 mL) and 4M HCl in dioxanes (2.5 mL), and heating to 60° C. for 15 min. The reaction was concentrated and prep purified, and then converted to the HCl salt to give 65 mg of 3-bromo-4-{4-[5-chloro-2-methyl-3-(2-pyrrolidin-1-yl-ethoxy)-phenyl]-piperazin-1-yl}-1H-pyrazolo[3,4-d]pyrimidine (65 mg). $^1$H NMR (400 MHz, d$_6$-DMSO) δ 11.3 (br s, 1H), 8.40 (s, 1H), 6.81 (d, 2H), 4.20 (t, 2H), 4.0 (br s, 4H), 3.60 (br q, 4H), 3.00 (m, 6H), 2.18 (s, 3H), 1.80-2.0 (br m, 4H). MS (ESI) for $C_{22}H_{27}BrClN_7O$: 518 (MH$^+$).

Using the same or analogous synthetic techniques and/or substituting with alternative reagents, the following compounds of the invention were prepared:

(2-{3-[4-(3-Bromo-1H-pyrazolo[3,4-d]pyrimidin-4-yl)-piperazin-1-yl]-5-chloro-2-methyl-phenoxy}-ethyl)-diethyl-amine: $^1$H NMR (400 MHz, d$_6$-DMSO) δ 10.7 (br s, 1H), 8.40 (s, 1H), 6.81 (d, 2H), 4.20 (buried t, 2H), 3.8 (br q, 2H), 3.20 (m, 4H), 3.00 (br t, 4H), 2.18 (s, 3H), 1.25 (t, 6H). MS (ESI) for $C_{22}H_{29}BrClN_7O$: 520 (MH$^+$).

3-Bromo-4-{4-[5-chloro-2-methyl-3-(2-piperidin-1-yl-ethoxy)-phenyl]-piperazin-1-yl}-1H-pyrazolo[3,4-d]pyrimidine: $^1$H NMR (400 MHz, d$_6$-DMSO) δ 9.9 (br s, 1H), 8.40 (s, 1H), 6.81 (d, 2H), 4.40 (t; 2H), 4.0 (br s, 4H), 3.6 (m, 4H), 3.00 (m, 8H), 2.18 (s, 3H), 1.80 (m, 6H). MS (ESI) for $C_{23}H_{29}BrClN_7O$: 532 (MH$^+$).

3-Bromo-4-{4-[5-chloro-2-methyl-3-(2-morpholin-4-yl-ethoxy)-phenyl]-piperazin-1-yl}-1H-pyrazolo[3,4-d]pyrimidine: $^1$H NMR (400 MHz, $d_6$-DMSO) δ 10.8 (br s, 1H), 8.40 (s, 1H), 6.81 (d, 2H), 4.40 (br t, 1H), 4.0 (br m, 4H), 3.8 (t, 2H), 3.4 (m, 6H), 3.00 (m, 4H), 2.18 (s, 3H), 1.80 (m, 4H). MS (ESI) for $C_{22}H_{27}BrClN_7O_2$: 536 (MH$^+$).

3-Bromo-4-{4-[5-chloro-2-methyl-3-(3-piperidin-1-yl-propoxy)-phenyl]-piperazin-1-yl}-1H-pyrazolo[3,4-d]pyrimidine: $^1$H NMR (400 MHz, $d_6$-DMSO) δ 9.4 (br s, 1H), 8.40 (s, 1H), 6.81 (d, 2H), 4.15 (br t, 2H), 4.0 (br s, 4H), 3.2 (m, 2H), 3.0 (br s, 4H), 2.8 (m, 4H), 2.18 (s, 3H), 1.80 (m, 4H). MS (ESI) for $C_{24}H_{31}BrClN_7O$: 548 (MH$^+$).

3-Bromo-4-{4-[5-chloro-2-methyl-3-(3-morpholin-4-yl-propoxy)-phenyl]-piperazin-1-yl}-1H-pyrazolo[3,4-d]pyrimidine: $^1$H NMR (400 MHz, $d_6$-DMSO) δ 10.5 (br s, 1H), 8.40 (s, 1H), 6.81 (d, 2H), 4.15 (br t, 2H), 4.0 (br m, 4H), 3.8 (t, 2H), 3.21 (m, 2H), 3.0 (m, 8H), 2.18 (s, 3H), 1.80 (m, 4H). MS (ESI) for $C_{23}H_{29}BrClN_7O_2$: 548 (MH$^+$).

3-Bromo-4-{4-[4-methyl-3-(2-pyrrolidin-1-yl-ethoxy)-phenyl]-piperazin-1-yl}-1H-pyrazolo[3,4-d]pyrimidine: $^1$H NMR (400 MHz, $d_6$-DMSO) δ 10.4 (br s, 1H), 8.40 (s, 1H), 7.05 (d, 1H), 6.75 (s, 1H), 6.6 (d, 1H), 4.15 (br t, 2H), 4.0 (br s, 4H), 3.2 (m, 4H), 2.18 (s, 3H), 1.80 (m, 4H). MS (ESI) for $C_{22}H_{28}BrN_7O$: 486 (MH$^+$).

4-{4-[4-Methyl-3-(2-pyrrolidin-1-yl-ethoxy)-phenyl]-piperazin-1-yl}-1H-pyrazolo[3,4-d]pyrimidine: $^1$H NMR (400 MHz, $d_6$-DMSO) δ 7.9, 7.4 (d, 1H), 7.05 (d, 1H), 6.75 (s, 1H), 6.6 (d, 1H), 4.20 (br t, 2H), 4.0 (br s, 4H), 3.2 (m, 4H), 2.18 (s, 3H), 1.80 (m, 4H). MS (ESI) for $C_{22}H_{29}N_7O$: 406 (MH$^+$).

3-Methyl-4-{4-[4-methyl-3-(2-pyrrolidin-1-yl-ethoxy)-phenyl]-piperazin-1-yl}-1H-pyrazolo[3,4-d]pyrimidine: $^1$H NMR (400 MHz, $d_6$-DMSO) δ 8.5 (s, 1H), 7.9, 7.4 (d, 1H), 7.05 (d, 1H), 6.75 (s, 1H), 6.6 (d, 1H), 4.20 (br t, 2H), 4.0 (br s, 4H), 3.2 (m, 4H), 2.8 (m, 4H), 2.18 (s, 3H), 1.80 (m, 4H). MS (ESI) for $C_{23}H_{32}N_7O$: 422 (MH$^+$).

4-{4-[5-Chloro-2-methyl-3-(2-pyrrolidin-1-yl-ethoxy)-phenyl]-piperazin-1-yl}-1H-pyrazolo[3,4-d]pyrimidine: $^1$H NMR (400 MHz, $d_6$-DMSO) δ 10.6 (br s, 1H), 6.8 (d, 2H), 4.40 (br t, 2H), 4.10 (br s, 4H), 3.8 (m, 4H), 3.2 (m, 4H), 2.18 (s, 3H), 1.80 (m, 4H). MS (ESI) for $C_{22}H_{25}ClN_7O$: 442 (MH$^+$).

4-{4-[5-Chloro-2-methyl-3-(2-pyrrolidin-1-yl-ethoxy)-phenyl]-piperazin-1-yl}-3-methyl-1H-pyrazolo[3,4-d]pyrimidine: $^1$H NMR (400 MHz, $d_6$-DMSO) δ 10.9 (br s, 1H), 8.6 (br s, 1H), 6.8 (d, 2H), 4.20 (br t, 2H), 4.10 (br s, 4H), 3.8 (m, 4H), 3.2 (m, 8H), 2.80 (br s, 2H), 2.18 (s, 3H), 1.80 (m, 4H). MS (ESI) for $C_{23}H_{30}ClN_7O$: 456 (MH$^+$).

Example 44

3-[4-(3-Bromo-1H-pyrazolo[3,4-d]pyrimidin-4-yl) piperazin-1-yl]-5-chloro-2-methyl-N-(2-pyrrolidin-1-ylethyl)aniline To a 15 mL pressure vessel was added 4-(5-chloro-3-iodo-2-methyl-phenyl)-piperazine-1-carboxylic acid tert-butyl ester (450 mg, 1.03 mmol, 1.0 eq.), Xant phos (36 mg, 0.062 mmol, 0.06 eq.), 2-pyrrolidinoethylamine (157 μL, 1.24 mmol, 1.2 eq.), and dioxane (4 mL). The suspension was bubbled with $N_2$ upon which $Pd_2(dba)_3$ (28 mg, 0.031 mmol, 0.03 eq.) and sodium tert-butoxide (139 mg, 1.44 mmol, 1.4 eq.) was added. The vessel was sealed and heated at 100° C. overnight. The crude reaction mixture was concentrated and chromatographed (3% to 10% $CH_3OH/CH_2Cl_2$) to afford pure product 4-[5-chloro-2-methyl-3-(2-pyrrolidin-1-yl-ethylamino)-phenyl]-piperazine-1-carboxylic acid tert-butyl ester as an oil (312 mg, 72%).

To a 25 mL recovery flask was added 4-[5-chloro-2-methyl-3-(2-pyrrolidin-1-yl-ethylamino)-phenyl]-piperazine-1-carboxylic acid tert-butyl ester (308 mg, 0.729 mol, 1.0 eq.) and $CH_3OH$ (4 mL). 4N HCl/dioxane (4 mL) was added and the reaction was stirred for 2 h at room temperature. LC/MS analysis indicated that the deprotection was complete, whereupon the reaction was concentrated and placed on high vacuum. The crude material of (5-chloro-2-methyl-3-piperazin-1-yl-phenyl)-(2-pyrrolidin-1-yl-ethyl)-amine was used in the next reaction without further purification.

To a 25 mL recovery flask was added (5-chloro-2-methyl-3-piperazin-1-yl-phenyl)-(2-pyrrolidin-1-yl-ethyl)-amine dihydrochloride (287 mg, 0.728 mmol, 1.1 eq.), 3-bromo-1-(tetrahydro-pyran-2-yl)-1H-pyrazolo[3,4-d]pyrimidin-4-ol (197 mg, 0.662 mmol, 1.0 eq.), N-methylmorpholine (364 μL, 3.31 mmol, 5.0 eq.), and DMF (7 mL). With stirring, PyBOP (689 mg, 1.32 mmol, 2.0 eq.) was added whereupon the reaction was heated at 80° C. overnight. The reaction mixture was diluted with $H_2O$ (50 mL) and EtOAc (50 mL). The organic phase was washed with 10% aq. LiCl (4×30 mL) saturated aq. NaCl (30 mL). The combined aqueous phases were extracted with EtOAc (2×50 mL). The organic phases were combined and dried over anhydrous $Na_2SO_4$, filtered, and concentrated. The crude material of (3-{4-[3-bromo-1-(tetrahydro-pyran-2-yl)-1H-pyrazolo[3,4-d]pyrimidin-4-yl]-piperazin-1-yl}-5-chloro-2-methyl-phenyl)-(2-pyrrolidin-1-yl-ethyl)-amine was purified via column chromatography (2% to 5% $CH_3OH/CH_2Cl_2$) to give a white solid (470 mg).

3-[4-(3-Bromo-1H-pyrazolo[3,4-d]pyrimidin-4-yl)piperazin-1-yl]-5-chloro-2-methyl-N-(2-pyrrolidin-1-ylethyl) aniline: To a 25 mL recovery flask was added (3-{4-[3-bromo-1-(tetrahydro-pyran-2-yl)-1H-pyrazolo[3,4-d] pyrimidin-4-yl]-piperazin-1-yl}-5-chloro-2-methyl-phenyl)-(2-pyrrolidin-1-yl-ethyl)-amine (438 mg, 0.727 mol, 1.0 eq.) and methanol (5 mL). 4N HCl/dioxane (5 mL) was added and the reaction was stirred for 30 min at room temperature. LC/MS analysis indicated that the deprotection was complete, whereupon the reaction was concentrated and placed on high vacuum. The crude material was purified via reverse-phase HPLC to give pure product 3-[4-(3-bromo-1H-pyrazolo[3,4-d]pyrimidin-4-yl)piperazin-1-yl]-5-chloro-2-methyl-N-(2-pyrrolidin-1-ylethyl)aniline as the TFA salt (60 mg, 13%). $^1$H NMR (400 MHz, $d_6$-DMSO) δ10.76 (br s, 1H), 8.38 (s, 1H), 6.47 (d, 2H), 3.96 (br s, 3H), 3.61 (m, 2H), 3.51-3.48 (m, 2H), 3.34-3.31 (m, 2H), 3.03-2.97 (m, 6H), 2.12 (s, 3H), 2.01-1.96 (m, 2H), 1.90-1.87 (m, 2H). MS (ESI) for $C_{22}H_{28}BrClN_8$: 521 (MH$^+$).

Using the same or analogous synthetic techniques and/or substituting with alternative reagents, the following compounds of the invention were prepared:

N'-{3-[4-(3-Bromo-1H-pyrazolo[3,4-d]pyrimidin-4-yl)piperazin-1-yl]-5-chloro-2-methylphenyl}-N,N-diethyl-ethane-1,2-diamine: $^1$H NMR (400 MHz, $d_6$-DMSO) δ 10.43 (br s, 1H), 8.38 (s, 1H), 6.50 (s, 1H), 6.46 (s, 1H), 3.96 (m, 4H), 3.52 (t, 2H), 3.22-3.16 (m, 6H), 2.97 (m, 4H), 2.10 (s, 3H), 1.22 (t, 6H). MS (ESI) for $C_{22}H_{30}BrClN_8$: 523 (MH$^+$).

5-Chloro-2-methyl-3-[4-(1H-pyrazolo[3,4-d]pyrimidin-4-yl)piperazin-1-yl]-N-(2-pyrrolidin-1-ylethyl)aniline: $^1$H NMR (400 MHz, $d_6$-DMSO) δ 10.64 (s, 1H), 8.55 (s, 1H), 6.48 (d, 1H), 6.43 (s, 1H), 4.19 (m, 4H), 3.51 (t, 2H), 3.34-3.31 (2H), 2.98 (m, 6H), 2.14 (s, 3H), 2.00 (m, 2H), 1.89 (m, 2H). MS (ESI) for $C_{22}H_{29}ClN_8$: 441 (MH$^+$).

5-Chloro-2-methyl-3-[4-(3-methyl-1H-pyrazolo[3,4-d]pyrimidin-4-yl)piperazin-1-yl]-N-(2-pyrrolidin-1-ylethyl)

aniline: ¹H NMR (400 MHz, d₆-DMSO) δ 10.96 (s, 1H), 8.57 (s, 1H), 6.46 (d, 1H), 6.40 (d, 1H), 3.59 (m, 2H), 3.49 (m, 2H), 3.30 (m, 2H), 2.98 (m, 6H), 2.76 (s, 3H), 2.14 (s, 3H), 2.00 (m, 2H), 1.89 (m, 2H). MS (ESI) for $C_{23}H_{31}ClN_8$: 455 (MH⁺).

5-[4-(3-Bromo-1H-pyrazolo[3,4-d]pyrimidin-4-yl)piperazin-1-yl]-2-methyl-N-(2-pyrrolidin-1-ylethyl)aniline: ¹H NMR (400 MHz, d₆-DMSO) δ 10.14 (br s, 1H), 8.40 (d, 1H), 6.94 (m, 1H), 6.50 (m, 2H), 4.02 (m, 4H), 3.34 (m, 4H), 3.05 (m, 2H), 2.07 (m, 3H), 2.01 (m, 2H), 1.89 (m, 2H). MS (ESI) for $C_{22}H_{29}BrClN_8$: 485 (MH⁺).

3-[4-(3-Bromo-1H-pyrazolo[3,4-d]pyrimidin-4-yl)piperazin-1-yl]-5-fluoro-2-methyl-N-(2-pyrrolidin-1-ylethyl)aniline: ¹H NMR (400 MHz, d₆-DMSO) δ 10.33 (br s, 1H), 8.37 (s, 1H), 6.27 (td, 2H), 3.95 (m, 4H), 3.46 (t, 4H), 3.31 (m, 2H), 3.02 (m, 2H), 2.95 (m, 3H), 2.09 (s, 3H), 2.00 (m, 2H), 1.89 (m, 2H). MS (ESI) for $C_{22}H_{28}BrFN_8$: 505 (MH⁺).

3-Bromo-4-(4-pyridin-2-ylpiperazin-1-yl)-1H-pyrazolo[3,4-d]pyrimidine: ¹H NMR (400 MHz, d₆-DMSO) δ 8.40 (s, 1H), 8.07-8.05 (m, 2H), 7.43 (d, 1H), 7.00 (t, 1H), 4.07-4.04 (m, 4H), 3.97-3.94 (m, 4H). MS (ESI) for $C_{14}H_{14}BrN_7$: 360 (MH⁺).

3-Bromo-4-[4-(2,4-dimethylphenyl)piperazin-1-yl]-1H-pyrazolo[3,4-d]pyrimidine: ¹H NMR (400 MHz, d₆-DMSO) δ 8.36 (s, 1H), 7.00 (s, 1H), 6.95 (s, 1H), 3.94 (m, 4H), 2.97 (t, 4H), 2.27 (s, 3H), 2.22 (s, 3H). MS (ESI) for $C_{17}H_{19}BrN_6$: 389 (MH⁺).

3-Bromo-4-{4-[3-(methyloxy)phenyl]piperazin-1-yl}-1H-pyrazolo[3,4-d]pyrimidine: ¹H NMR (400 MHz, d₆-DMSO) δ 8.44 (s, 1H), 7.29 (t, 1H), 6.98-6.95 (m, 2H), 6.68 (d, 1H), 4.14 (m, 4H), 3.77 (s, 3H), 3.54 (t, 4H). MS (ESI) for $C_{16}H_{17}BrN_6O$: 391 (MH⁺).

3-Bromo-4-{4-[2-(methyloxy)phenyl]piperazin-1-yl}-1H-pyrazolo[3,4-d]pyrimidine: ¹H NMR (400 MHz, d₆-DMSO) δ 8.37 (s, 1H), 7.00-6.97 (m, 2H), 6.92-6.90 (m, 1H), 3.96 (m, 4H), 3.82 (s, 3H), 3.18 (m, 4H). MS (ESI) for $C_{16}H_{17}BrN_6O$: 391 (MH⁺).

3-[4-(3-Ethyl-1H-pyrazolo[3,4-d]pyrimidin-4-yl)piperazin-1-yl]-5-fluoro-2-methyl-N-(2-pyrrolidin-1-ylethyl)aniline: ¹H NMR (400 MHz, d₆-DMSO) δ 11.10 (s, 1H), 8.57 (s, 1H), 6.30 (dd, 1H), 6.21, (dd, 1H), 4.13 (br s, 4H), 3.49-3.48 (m, 2H), 3.51-3.48 (m, 2H), 3.32-3.29 (m, 2H), 3.15-3.10 (m, 2H), 3.00-2.96 (m, 6H), 2.12 (s, 3H), 2.02-1.97 (m, 2H), 1.91-1.87 (m, 2H), 1.31 (t, 3H). MS (ESI) for $C_{24}H_{33}FN_8$: 453 (MH⁺).

5-Fluoro-2-methyl-N-(2-pyrrolidin-1-ylethyl)-3-{4-[3-(trifluoromethyl)-1H-pyrazolo[3,4-d]pyrimidin-4-yl]piperazin-1-yl}aniline: ¹H NMR (400 MHz, d₆-DMSO) HCl salt δ 10.49 (br s, 1H), 8.48 (s, 1H), 6.28 (dd, 1H), 6.21 (dd, 1H), 3.84 (m, 4H), 3.61-3.59 (m, 2H), 3.48 (t, 2H), 3.32-3.29 (m, 2H), 3.02 (m, 2H), 2.89 (m, 4H), 2.09 (s, 3H), 2.03-1.97 (m, 2H), 1.93-1.87 (m, 2H). MS (ESI) for $C_{23}H_{28}F_4N_8$: 493 (MH⁺).

3-[4-(3-Bromo-1H-pyrazolo[3,4-d]pyrimidin-4-yl)piperazin-1-yl]-N—[(cyclopropylmethyl)oxy]-4-methyl-5-[(2-pyrrolidin-1-ylethyl)amino]benzamide: ¹H NMR (400 MHz, CDCl₃) δ 8.42 (s, 1H), 7.26 (s, 1H), 6.90 (s, 1H), 6.81 (s, 1H), 4.47 (s, 1H), 4.12 (s, 1H), 3.87 (s, 2H), 3.33 (s, 2H), 3.06 (s, 4H), 2.86 (s, 2H), 2.64 (s, 4H), 2.15 (s, 3H), 2.05 (s, 1H), 1.83 (s, 4H), 1.26-1.20 (m, 2H), 0.60 (s, 2H), 0.33 (s, 2H). MS (ESI) for $C_{27}H_{36}BrN_9O_2$: 600 (MH⁺).

Example 45

3-[4-(3-Bromo-1H-pyrazolo[3,4-d]pyrimidin-4-yl)piperazin-1-yl]-4-methyl-N-phenyl-5-[(2-pyrrolidin-1-ylethyl)amino]benzamide To 4-[5-carboxy-2-methyl-3-(2-pyrrolidin-1-yl-ethylamino)-phenyl]-piperazine-1-carboxylic acid tert-butyl ester (118 mg, 0.27 mmol) in DMF (3 mL) was added triethylamine (82 mg, 0.81 mmol), HOBT (93 mg, 0.68 mmol), EDCI (136 mg, 0.68 mmol) and phenylamine (46 mg, 0.49 mmol). After heating the reaction mixture at 70° C. for 1 hour the reaction was cooled to room temperature. Ethyl Acetate was added and the organic layer was washed twice with water (50 ml), once with 1N HCl (50 ml), twice with 5% LiCl (50 ml), and once with brine (50 ml). The organic layer was dried over sodium sulfate and the solvent was removed to yield 4-[2-methyl-5-phenylcarbamoyl-3-(2-pyrrolidin-1-yl-ethylamino)-phenyl]-piperazine-1-carboxylic acid tert-butyl ester (133 mg, 96% yield). ¹H NMR (400 MHz, d₆-DMSO) δ 8.91 (s, 1H), 7.89 (d, 2H), 7.35 (t, 2H), 7.14 (m, 3H), 6.74 (d, 1H), 4.60 (m, 1H), 3.86 (m, 3H), 3.58 (br, s, 1H), 3.24 (t, 3H), 2.84 (m, 6H), 2.17 (s, 3H), 2.10 (m, 5H), 1.49 (s, 9H), 1.28 (m, 3H), 0.90 (t, 1H). MS (ESI) for $C_{29}H_{41}N_5O_3$: 508 (MH⁺).

To 4-[2-methyl-5-phenylcarbamoyl-3-(2-pyrrolidin-1-ylethylamino)-phenyl]-piperazine-1-carboxylic acid tert-butyl ester (106.1 mg, 0.21 mmol) in THF (3 mL) was added excess triethylamine and 3-Bromo-4-chloro-1H-pyrazolo[3,4-d]pyrimidine (60 mg, 0.25 mmol. The reaction was heated to reflux for 1 hour upon which the reaction was cooled to room temperature. Water 50 ml was added and the product was extracted into ethyl acetate (50 ml). After extraction the organic layer was washed once with water (50 ml) and once with brine (50 ml). The organic layer was dried over sodium sulfate and the solvent removed under vacuum. Purification was carried out by column chromatography starting with straight DCM then a 5% MeOH/DCM solution and ending with a 10% MeOH/DCM solution. The product of 3-[4-(3-bromo-1H-pyrazolo[3,4-d]pyrimidin-4-yl)piperazin-1-yl]-4-methyl-N-phenyl-5-[(2-pyrrolidin-1-ylethyl)amino]benzamide was isolated and precipitated out of hexane (59.7 mg, 46% yield). ¹H NMR (400 MHz, d₆-DMSO) δ 10.88 (br, s, 1H), 10.15 (s, 1H), 8.41 (s, 1H), 7.78 (d, 2H), 7.34 (m, 3H), 7.08 (m, 3H), 4.07 (br, s, 3H), 3.64 (m, 4H), 3.38 (m, 2H), 3.07 (m, 6H), 2.24 (s, 3H), 2.01 (m, 2H), 1.88 (m, 2H). MS (ESI) for $C_{29}H_{34}BrN_9O$: 602 (MH⁻).

Using the same or analogous synthetic techniques and/or substituting with alternative reagents, the following compounds of the invention were prepared:

3-[4-(3-Bromo-1H-pyrazolo[3,4-d]pyrimidin-4-yl)piperazin-1-yl]-N,N,4-trimethyl-5-[(2-pyrrolidin-1-ylethyl)amino]benzamide. ¹H NMR (400 MHz, d₆-DMSO) δ 8.49 (s, 1H), 6.62 (s, 1H), 6.58 (s, 1H), 3.78 (m, 1H), 3.65 (s, 1H), 3.61 (t, 1H), 3.22 (s, 6H), 3.09 (br, s, 4H), 3.02 (br, s, 4H), 2.30 (s, 3H), 2.18 (m, 2H), 2.05 (m, 3H), 1.29, (t, 2H), 0.91 (t, 2H). MS (ESI) for $C_{25}H_{34}BrN_9O$: 556 (MH⁺).

3-[4-(3-Bromo-1H-pyrazolo[3,4-d]pyrimidin-4-yl)piperazin-1-yl]-2-methyl-5-(pyrrolidin-1-ylcarbonyl)-N-(2-pyrrolidin-1-ylethyl)aniline. ¹H NMR (400 MHz, d₆-DMSO) δ 14.18 (br, s, 1H), 10.42 (br, s, 1H), 8.38 (s, 1H), 6.58 (s, 1H), 6.38 (s, 1H), 3.61 (m, 3H), 3.51 (t, 2H), 3.42 (m, 4H), 3.33 (m, 3H), 2.99 (br, s, 7H), 2.17 (s, 3H), 2.01 (m, 2H), 1.83 (m, 4H), 1.76 (m, 3H). MS (ESI) for $C_{27}H_{36}BrN_9O$: 582 (MH⁺).

3-[4-(3-Bromo-1H-pyrazolo[3,4-d]pyrimidin-4-yl)piperazin-1-yl]-N,4-dimethyl-5-[(2-pyrrolidin-1-ylethyl)amino]benzamide. ¹H NMR (400 MHz, d₆-DMSO) δ 8.36 (s, 1H), 8.26 (m, 1H), 6.92 (s, 1H), 6.85 (s, 1H), 4.91 (t, 1H), 3.96 (br, s, 3H), 3.22 (m, 4H), 2.98 (m, 4H), 2.75 (d, 3H), 2.58 (m, 4H), 2.10 (s, 3H), 1.72 (m, 4H), 1.23 (m, 2H). MS (ESI) for $C_{24}H_{32}BrN_9O$: 542 (MH⁺).

3-[4-(3-Bromo-1H-pyrazolo[3,4-d]pyrimidin-4-yl)piperazin-1-yl]-N-(4-chlorophenyl)-4-methyl-5-[(2-pyrrolidin-1-ylethyl)amino]benzamide. ¹H NMR (400 MHz, d₆-DMSO) δ 10.11 (s, 1H), 8.37 (s, 1H), 7.81 (d, 2H), 7.41 (d, 2H), 7.06 (s, 1H), 6.97 (s, 1H), 4.03 (m, 3H), 3.45 (m, 2H), 3.03 (m, 10H), 2.18 (s, 3H), 1.84 (m, 5H), 1.17 (m, 2H). MS (ESI) for $C_{29}H_{33}BrClN_9O$: 638 (MH$^+$).

3-[4-(3-Bromo-1H-pyrazolo[3,4-d]pyrimidin-4-yl)piperazin-1-yl]-N-(2-chlorophenyl)-4-methyl-5-[(2-pyrrolidin-1-ylethyl)amino]benzamide. $^1$H NMR (400 MHz, d$_6$-DMSO) δ 10.14 (s, 1H), 8.45 (s, 1H), 7.87 (s, 2H), 7.62 (d, 1H), 7.39 (t, 1H), 7.12 (d, 1H), 7.03 (s, 1H), 6.91 (s, 1H), 5.09 (m, 1H), 3.99 (m, 3H), 3.33 (m, 5H), 3.06 (m, 5H), 2.85 (m, 2H), 2.69 (m, 3H), 2.18 (s, 3H), 1.76 (m, 4H). MS (ESI) for $C_{29}H_{33}BrClN_9O$: 638 (MH$^+$).

Methyl-3-bromo-5-[4-(3-bromo-1H-pyrazolo[3,4-d]pyrimidin-4-yl)piperazin-1-yl]-4-methylbenzoate. $^1$H NMR (400 MHz, d$_6$-DMSO) δ 14.08 (br, s, 1H), 8.38 (s, 1H), 7.85 (s, 1H), 7.61 (s, 1H), 3.97 (br, s, 4H), 3.85 (s, 3H), 3.08 (br, s, 4H), 2.46 (s, 3H). MS (ESI) for $C_{18}H_{18}Br_2N_6O_2$: 511 (MH$^+$).

Methyl-3-[4-(3-bromo-1H-pyrazolo[3,4-d]pyrimidin-4-yl)piperazin-1-yl]-4-methyl-5-[(2-pyrrolidin-1-ylethyl)amino]benzoate. $^1$H NMR (400 MHz, CDCl$_3$) δ 8.45 (s, 1H), 7.22 (s, 1H), 7.11 (s, 1H), 4.50 (br, s, 1H), 3.89 (s, 3H), 3.33 (m, 2H), 3.08 (m, 4H), 2.87 (m, 2H), 2.62 (m, 4H), 2.02 (s, 3H), 1.82 (m, 4H), 1.28 (m, 4H), 0.88 (t, 3H). MS (ESI) for $C_{24}H_3BrN_8O_2$: 543 (MH$^+$).

3-[4-(3-Bromo-1H-pyrazolo[3,4-d]pyrimidin-4-yl)piperazin-1-yl]-4-methyl-N-(1-methylethyl)-5-[(2-pyrrolidin-1-ylethyl)amino]benzamide. $^1$H NMR (400 MHz, d$_6$-DMSO) δ 8.35 (s, 1H), 8.00 (d, 1H), 6.84 (s, 1H), 6.92 (s, 1H), 4.89 (m, 1H), 4.06 (m, 1H), 4.00 (m, 4H), 3.26 (m, 2H), 2.96 (m, 4H), 2.77 (m, 2H), 2.61 (m, 4H), 2.10 (s, 3H), 1.72 (m, 4H), 1.13 (d, 6H). MS (ESI) for $C_{26}H_{36}BrN_9O$: 570 (MH$^+$).

3-[4-(3-Bromo-1H-pyrazolo[3,4-d]pyrimidin-4-yl)piperazin-1-yl]-N,4-dimethyl-N-(1-methylethyl)-5-[(2-pyrrolidin-1-ylethyl)amino]benzamide. $^1$H NMR (400 MHz, CDCl$_3$) δ 8.41 (s, 1H), 6.50 (s, 1H), 6.40 (s, 1H), 4.49 (m, 1H), 4.06 (m, 3H), 3.28 (m, 2H), 3.05 (m, 4H), 2.86 (m, 4H), 2.62 (m, 3H), 2.17 (s, 3H), 1.83 (m, 4H), 1.19 (m, 8H), 0.88 (m, 2H). MS (ESI) for $C_{27}H_{38}BrN_9O$: 584 (MH$^+$).

3-[4-(3-Bromo-1H-pyrazolo[3,4-d]pyrimidin-4-yl)-2-oxopiperazin-1-yl]-4-methyl-N-phenylbenzamide: $^1$H NMR (400 MHz, d$_6$-DMSO) δ 14.18 (br s, 1H), 10.21 (s, 1H), 8.43 (s, 1H), 7.88 (m, 2H), 7.75 (m, 2H), 7.46 (m, 1H), 7.35 (m, 2H), 7.12 (m, 1H), 4.59 (m, 2H), 4.42 (m, 1H), 4.25 (m, 1H), 3.95 (m, 1H), 3.68 (m, 1H), 2.21 (s, 3H). MS (ESI) for $C_{23}H_{20}BrN_7O_2$: 506 (MH$^+$).

3-[4-(3-Bromo-1H-pyrazolo[3,4-d]pyrimidin-4-yl)piperazin-1-yl]-N-(1,1-dimethylethyl)-4-methyl-5-[(2-pyrrolidin-1-ylethyl)amino]benzamide: $^1$H NMR (400 MHz, d$_6$-DMSO) δ 8.37 (s, 1H), 7.52 (s, 1H), 6.87 (s, 1H), 6.79 (s, 1H), 4.86 (m, 1H), 3.26 (m, 6H), 2.99 (m, 4H), 2.72 (m, 2H), 2.55 (m, 4H), 2.10 (s, 3H), 1.72 (m, 4H), 1.36 (s, 9H). MS (ESI) for $C_{27}H_{38}BrN_9O$: 584 (MH$^+$).

3-[4-(3-Bromo-1H-pyrazolo[3,4-d]pyrimidin-4-yl)piperazin-1-yl]-4-methyl-N-pyridin-3-yl-5-[(2-pyrrolidin-1-ylethyl)amino]benzamide: $^1$H NMR (400 MHz, d$_6$-DMSO) δ 10.21 (s, 1H), 8.89 (s, 1H), 8.36 (d, 1H), 8.29 (d, 1H), 8.14 (d, 1H), 7.38 (m, 1H), 7.06 (s, 1H), 6.97 (s, 1H), 4.98 (m, 1H), 3.28 (m, 4H), 3.04 (m, 4H), 2.98 (m, 2H), 2.69 (m, 2H), 2.51 (m, 4H), 2.15 (s, 3H), 1.70 (m, 4H). MS (ESI) for $C_{28}H_{33}BrN_{10}O$: 605 (MH$^+$).

3-[4-(3-Bromo-1H-pyrazolo[3,4-d]pyrimidin-4-yl)piperazin-1-yl]-N-ethyl-4-methyl-5-[(2-pyrrolidin-1-ylethyl)amino]benzamide: $^1$H NMR (400 MHz, d$_6$-DMSO) δ 8.34 (s, 1H), 8.28 (m, 1H), 6.91 (s, 1H), 6.84 (s, 1H), 4.86 (m, 1H), 3.24 (m, 6H), 2.97 (br s, 6H), 2.71 (t, 2H), 2.54 (br s, 4H), 2.10 (s, 3H), 1.71 (br s, 4H), 1.08 (t, 3H). MS (ESI) for $C_{25}H_{34}BrN_9O$: 556 (MH$^+$).

3-[4-(3-Bromo-1H-pyrazolo[3,4-d]pyrimidin-4-yl)piperazin-1-yl]-5-{[2-(dimethylamino)ethyl]amino}-4-methyl-N-phenylbenzamide: $^1$H NMR (400 MHz, d$_6$-DMSO) δ 10.02 (s, 1H), 8.32 (s, 1H), 7.66 (d, 2H), 7.32 (t, 2H), 7.07 (t, 1H), 7.01 (s, 1H), 6.91 (s, 1H), 4.90 (m, 1H), 3.52 (m, 4H), 3.25 (m, 2H), 3.00 (br s, 4H), 2.63 (m, 2H), 2.28 (s, 6H), 2.12 (s, 3H). MS (ESI) for $C_{27}H_{32}BrN_9O$: 578 (MH$^+$).

3-[4-(3-Bromo-1H-pyrazolo[3,4-d]pyrimidin-4-yl)piperazin-1-yl]-5-{[2-(dimethylamino)ethyl]amino}-4-methyl-N-(1-methylethyl)benzamide: $^1$H NMR (400 MHz, d$_6$-DMSO) δ 8.32 (s, 1H), 8.06 (d, 1H), 6.90 (s, 1H), 6.82 (s, 1H), 4.82 (m, 1H), 4.03 (m, 1H), 3.21 (m, 4H), 2.95 (m, 4H), 2.90 (m, 2H), 2.61 (t, 2H), 2.27 (s, 6H), 2.08 (s, 3H), 1.11 (d, 6H). MS (ESI) for $C_{24}H_{34}BrN_9O$: 544 (MH$^+$).

3-[4-(3-Bromo-1H-pyrazolo[3,4-d]pyrimidin-4-yl)piperazin-1-yl]-4-methyl-5-[(2-pyrrolidin-1-ylethyl)amino]benzoic acid: $^1$H NMR (400 MHz, d$_6$-DMSO) δ 9.58 (br s, 1H), 8.33 (s, 1H), 7.06 (s, 1H), 6.95 (s, 1H), 3.76 (br s, 4H), 3.59 (m, 2H), 3.46 (m, 2H), 3.35 (br s, 2H), 3.03 (m, 2H), 2.96 (br s, 4H), 2.15 (s, 3H), 2.00 (m, 2H), 1.85 (m, 2H). MS (ESI) for $C_{23}H_{29}BrN_8O$: 529 (MH$^+$).

3-[(2S)-4-(3-Bromo-1H-pyrazolo[3,4-d]pyrimidin-4-yl)-2-methylpiperazin-1-yl]-4-methyl-N-phenylbenzamide: $^1$H NMR (400 MHz, d$_6$-DMSO) δ 10.1 (s, 1H), 8.37 (s, 1H), 7.81 (s, 1H), 7.72 (m, 3H), 7.37 (m, 3H), 7.10 (t, 1H), 4.48 (d, 1H), 4.36 (d, 1H), 3.58 (m, 1H), 3.47 (m, 1H), 3.23 (m, 1H), 3.10 (m, 1H), 2.88 (m, 1H), 2.40 (s, 3H), 0.86 (d, 3H). MS (ESI) for $C_{24}H_{24}BrN_7O$: 506 (MH$^+$).

3-[(2S)-4-(3-Bromo-1H-pyrazolo[3,4-d]pyrimidin-4-yl)-2-methylpiperazin-1-yl]-4-methyl-N-(phenylmethyl)benzamide: $^1$H NMR (400 MHz, d$_6$-DMSO) δ 9.01 (t, 1H), 8.37 (s, 1H), 7.76 (s, 1H), 7.63 (d, 1H), 7.31 (m, 5H), 7.23 (m, 1H), 4.47 (m, 3H), 4.34 (m, 1H), 3.56 (m, 1H), 3.41 (m, 1H), 3.20 (m, 1H), 3.05 (m, 1H), 2.82 (t, 1H), 2.37 (s, 3H), 0.83 (d, 3H). MS (ESI) for $C_{25}H_{26}BrN_7O$: 520 (MH$^+$).

3-[(2R)-4-(3-Bromo-1H-pyrazolo[3,4-d]pyrimidin-4-yl)-2-(hydroxymethyl)piperazin-1-yl]-4-methyl-N-phenylbenzamide: $^1$H NMR (400 MHz, d$_6$-DMSO) δ 10.1 (s, 1H), 8.34 (s, 1H), 7.81 (m, 1H), 7.70 (m, 4H), 7.33 (m, 4H), 7.08 (m, 1H), 4.60 (m, 1H), 4.48 (m, 1H), 4.17 (m, 1H), 3.73 (m, 2H), 3.52 (m, 2H), 3.20 (m, 3H), 2.95 (m, 1H), 2.68 (m, 1H). MS (ESI) for $C_{24}H_{24}BrN_7O_2$: 522 (MH$^+$).

Methyl-3-[4-(3-bromo-1H-pyrazolo[3,4-d]pyrimidin-4-yl)piperazin-1-yl]-4-methylbenzoate: $^1$H NMR (400 MHz, CDCl$_3$) δ 11.97 (1H, Br s), 8.45 (1H, s), 7.73 (1H, s), 7.72-7.70 (1H, d), 7.29-7.26 (1H, d), 4.10 (4H, m), 3.90 (3H, s), 3.15-3.02 (4H, m), 2.43 (3H, s). MS (ESI) for $C_{18}H_{19}BrN_6O_2$: 433 (MH$^+$).

3-[4-(3-Bromo-1H-pyrazolo[3,4-d]pyrimidin-4-yl)piperazin-1-yl]-4-methylbenzoic acid: $^1$H NMR (400 MHz, d$_6$-DMSO) δ 14.07 (1H, Br s), 12.84 (1H, Br s), 8.38 (1H, s), 7.60-7.57 (2H, m), 7.34-7.32 (1H, d), 3.95 (4H, m), 3.07-3.05 (4H, m), 2.38 (3H, s). MS (ESI) for $C_{17}H_{17}BrN_6O_2$: 417 (MH$^+$).

3-[4-(3-Bromo-1H-pyrazolo[3,4-d]pyrimidin-4-yl)piperazin-1-yl]-4-methyl-N-phenylbenzamide: $^1$H NMR (400 MHz, d$_6$-DMSO) δ 14.11 (1H, Br s), 10.13 (1H, s), 8.38 (1H, s), 7.73-7.71 (2H, d), 7.61-7.59 (2H, m), 7.34-7.30 (3H, m), 7.09-7.05 (1H, t), 3.98 (4H, m), 3.11-3.09 (4H, m), 2.39 (3H, s). MS (ESI) for $C_{23}H_{22}BrN_7O$: 492 (MH$^+$).

3-[4-(3-Bromo-1H-pyrazolo[3,4-d]pyrimidin-4-yl)piperazin-1-yl]-N,4-dimethylbenzamide: $^1$H NMR (400 MHz, d$_6$-DMSO) δ 14.07 (1H, Br s), 8.38 (1H, s), 8.37-8.35 (1H, m), 7.53 (1H, s), 7.48-7.46 (1H, d), 7.28-7.26 (1H, d), 3.97 (4H, m), 3.06-3.04 (4H, m), 2.76-2.75 (3H, d), 2.08 (3H, s). MS (ESI) for $C_{18}H_{20}BrN_7O$: 430 (MH$^+$).

3-[4-(3-Bromo-1H-pyrazolo[3,4-d]pyrimidin-4-yl)piperazin-1-yl]-N,N,4-trimethylbenzamide: $^1$H NMR (400 MHz, d$_6$-DMSO) δ 14.07 (1H, Br s), 8.37 (1H, s), 7.26-7.24 (1H, d), 7.06 (1H, s), 7.03-7.01 (1H, d), 3.95 (4H, m), 3.06-3.04 (4H, m), 2.95 (3H, s), 2.91 (3H, s), 2.34 (3H, s). MS (ESI) for C$_{19}$H$_{22}$BrN$_7$O: 444 (MH$^+$).

3-[4-(3-Chloro-1H-pyrazolo[3,4-d]pyrimidin-4-yl)piperazin-1-yl]-4-methyl-N-(2-methylpropyl)benzamide: $^1$H NMR (400 MHz, d$_6$-DMSO) δ 13.96 (1H, Br s), 8.41-8.38 (1H, t), 8.37 (1H, s), 7.54 (1H, s), 7.51-7.49 (1H, d), 7.28-7.26 (1H, d), 4.01 (4H, m), 3.07-3.04 (6H, m), 1.84-1.80 (1H, m), 0.88-0.86 (6H, d). MS (ESI) for C$_{21}$H$_{26}$ClN$_7$O: 428 (MH$^+$).

3-[4-(3-Bromo-1H-pyrazolo[3,4-d]pyrimidin-4-yl)piperazin-1-yl]-N-[2-(dimethylamino)ethyl]-4-methylbenzamide: $^1$H NMR (400 MHz, d$_6$-DMSO) δ 14.75 (1H, Br s), 8.38 (1H, s), 8.37-8.29 (1H, t), 7.54 (1H, s), 7.50-7.47 (1H, d), 7.28-7.26 (1H, d), 3.97 (4H, m), 3.36 (2H, t), 3.05-3.04 (4H, m), 2.40 (2H, t), 2.36 (3H, s), 2.19 (6H, s). MS (ESI) for C$_{21}$H$_{27}$BrN$_8$O: 487 (MH$^+$).

Example 46

3-Bromo-4-{4-[4-methyl-2'-(2-pyrrolidin-1-yl-ethoxy)-biphenyl-3-yl]-piperazin-1-yl}-1H-pyrazolo[3,4-d]pyrimidine 4-Bromo-1-methyl-2-nitro-benzene (3.76 g, 17.4 mmol), 2-benzyloxyphenylboronic acid (7.91 g, 34.7 mmol), and K$_3$PO$_4$ (13.1 g, 61.7 mmol) were combined in dry THF (20 mls) and the mixture sparged with N$_2$ for 1 min. Biphenyl-2-yl-dicyclohexyl-phosphane (574 mg, 1.6 mmol) and palladium(II) acetate (206 mg, 0.92 mmol) were then added and the mixture was stirred under N$_2$ overnight at room temperature. The reaction was partitioned between H$_2$O and EtOAc and the biphasic mixture was filtered through Celite with washing with H$_2$O and EtOAc. The filtrate was transferred to a separatory funnel, the phases were separated and the organic phase was further washed with 1N HCl (3×), H$_2$O (1×), 1N NaOH (3×), sat'd NaCl (1×), dried (Na$_2$SO$_4$), and conc'd in vacuo. The crude product was purified by flash chromatography (100% hexanes, followed by 5% EtOAc in hexanes) to give 2'-benzyloxy-4-methyl-3-nitro-biphenyl (5.51 g, 99%). $^1$H NMR (400 MHz, CDCl$_3$) δ 8.26 (d, 1H), 7.70 (dd, 1H), 7.35 (complex multiplet, 8H), 7.05 (m, 2H), 5.11 (s, 2H), 2.63 (s, 3H).

2'-Benzyloxy-4-methyl-3-nitro-biphenyl (5.51 g, 17.2 mmol), toluene (50 mls), H$_2$O (50 mls), iron powder (5.0 g, 89.5 mmol), and ammonium formate (10.0 g, 158 mmol) were combined and heated to reflux overnight. The cooled reaction mixture was filtered through Celite with washing with H$_2$O and EtOAc. The filtrate was transferred to a separatory funnel and the phases were separated. The aqueous phase was further extracted with EtOAc (1×). The combined EtOAc extractions were washed with H$_2$O (1×), sat'd NaCl (1×), dried (Na$_2$SO$_4$), and concentrated in vacuo. The crude product was purified by flash chromatography (9:1 hexane: EtOAc, followed by 4:1 hexane:EtOAc) to give 2'-benzyloxy-4-methyl-biphenyl-3-ylamine (3.99 g, 80%). $^1$H NMR (400 MHz, CDCl$_3$) δ 7.36 (m, 4H), 7.26 (m, 3H), 7.10 (d, 1H), 6.98 (complex multiplet, 4H), 5.08 (s, 2H), 3.57 (br. s, 2H), 2.20 (s, 3H). MS (ESI) for C$_{20}$H$_{19}$NO: 290 (MH$^+$).

2'-Benzyloxy-4-methyl-biphenyl-3-ylamine (3.99 g, 13.8 mmol), bis-(2-chloro-ethyl)-amine hydrochloride (2.50 g, 14.0 mmol), K$_2$CO$_3$ (1.93 g, 13.9 mmol), and diglyme (25 mls) were combined and the mixture stirred at 145° C. overnight. The cooled reaction mixture was diluted with 1N HCl and EtOAc and stirred vigorously for several minutes. The resulting solid was washed with H$_2$O and EtOAc and dried under vacuum to give crude 1-(2'-benzyloxy-4-methyl-biphenyl-3-yl)-piperazine hydrochloride (5.60 g, 103%) which was used in the next reaction without further purification. $^1$H NMR (400 MHz, CDCl$_3$) δ 10.22 (br. s, 1H), 7.76 (s, 1H), 7.47 (d, 1H), 7.27 (complex multiplet, 8H), 7.03 (m, 2H), 5.04 (s, 2H), 3.96 (br. m, 4H), 3.75 (br. m, 4H), 2.64 (s, 3H). MS (ESI) for C$_{24}$H$_{26}$N$_2$O: 359 (MH$^+$).

1-(2'-Benzyloxy-4-methyl-biphenyl-3-yl)-piperazine hydrochloride (5.60 g, 14.2 mmol) was dissolved in dioxane (40 mls) and 5N NaOH (8 mls), to which was added Boc anhydride (3.72 g, 17.0 mmol) and the mixture stirred at room temperature overnight. The reaction mixture was diluted with EtOAc and washed with H$_2$O (1×), sat'd NaCl (1×), dried (Na$_2$SO$_4$), and conc'd in vacuo. The crude product was purified by flash chromatography (5% EtOAc in hexanes) followed by a second purification by flash chromatography (5% ether in hexanes) to give 4-(2'-benzyloxy-4-methyl-biphenyl-3-yl)-piperazine-1-carboxylic acid tert-butyl ester (2.84 g, 45%). $^1$H NMR (400 MHz, CDCl$_3$) δ 7.31 (m, 8H), 7.20 (m, 2H), 7.04 (m, 2H), 5.06 (s, 2H), 3.51 (m, 4H), 2.73 (m, 4H), 2.32 (s, 2H), 1.50 (s, 9H). MS (ESI) for C$_{29}$H$_{34}$N$_2$O$_3$: 459 (MH$^+$).

4-(2'-Benzyloxy-4-methyl-biphenyl-3-yl)-piperazine-1-carboxylic acid tert-butyl ester (2.84 g, 6.2 mmol), methanol (10 ml), ethyl acetate (10 ml), acetic acid (few drops) and 10% Pd/C (0.200 g) were agitated under hydrogen gas (40 psi) for 2 days. The mixture was diluted with methanol (200 ml) and ethyl acetate (100 ml), and heated to reflux, filtered through Celite and concentrated to give 4-(2'-hydroxy-4-methyl-biphenyl-3-yl)-piperazine-1-carboxylic acid tert-butyl ester (1.98 g, 88%). $^1$H NMR (400 MHz, CDCl$_3$) δ 7.31 (d, 1H), 7.22 (m, 2H), 7.11 (d, 1H), 7.07 (s, 1H), 6.98 (m, 2H), 5.27 (br. s, 1H), 3.61 (m 4H), 2.91 (m, 4H), 2.38 (s, 3H), 1.48 (s, 9H). MS (ESI) for C$_{22}$H$_{28}$N$_2$O$_3$: 369 (MH$^+$).

4-(2'-Hydroxy-4-methyl-biphenyl-3-yl)-piperazine-1-carboxylic acid tert-butyl ester (552 mgs, 1.5 mmol), K$_2$CO$_3$ (622 mgs, 4.5 mmol), and 1-(2-chloro-ethyl)-pyrrolidine hydrochloride (273 mgs, 1.6 mmol) were combined in DMA (10 mls) and stirred at room temperature overnight. The reaction had proceeded only slightly at room temperature, so it was heated at 60 C overnight to drive it to completion. The cooled reaction was partitioned between 1N HCl and EtOAc. The phases were separated and the organic phase was further extracted with 1N HCl (2×). The combined aqueous extractions were washed with EtOAc (1×), then basified with ice-cold 10N NaOH and the resulting basic aqueous mixture extracted with EtOAc (3×). The combined EtOAc extractions were washed with sat'd NaCl (1×), dried (Na$_2$SO$_4$), and conc'd in vacuo. The crude product was purified by flash chromatography (2% Et$_3$N in EtOAc) to give 4-[4-methyl-2'-(2-pyrrolidin-1-yl-ethoxy)-biphenyl-3-yl]-piperazine-1-carboxylic acid tert-butyl ester (511 mg, 73%). $^1$H NMR (400 MHz, CDCl$_3$) δ 7.31 (m, 2H), 7.18 (m, 3H), 7.00 (m, 2H), 4.10 (t, 2H), 3.58 (m, 4H), 2.88 (m, 4H), 2.83 (t, 2H), 2.52 (m, 4H), 2.34 (s, 3H), 1.75 (m, 4H), 1.49 (s, 9H). MS (ESI) for C$_{28}$H$_{39}$N$_3$O$_3$: 466 (MH$^+$).

4-[4-Methyl-2'-(2-pyrrolidin-1-yl-ethoxy)-biphenyl-3-yl]-piperazine-1-carboxylic acid tert-butyl ester (261 mgs, 0.56 mmol) was dissolved in DCM (5 mls) to which was added TFA (5 mls) and the mixture stirred at room temperature for 2 hrs. The reaction mixture was concentrated in vacuo and dried under high vacuum for several hrs to give 1-[4-methyl-2'-(2-pyrrolidin-1-yl-ethoxy)-biphenyl-3-yl]-piperazine trifluoroacetate (100%). MS (ESI) for C$_{23}$H$_{31}$N$_3$O: 366 (MH$^+$).

3-Bromo-4-{4-[4-methyl-2'-(2-pyrrolidin-1-yl-ethoxy)-biphenyl-3-yl]-piperazin-1-yl}-1H-pyrazolo[3,4-d]pyrimidine. 1-[4-Methyl-2'-(2-pyrrolidin-1-yl-ethoxy)-biphenyl-3-yl]-piperazine, di-TFA salt (0.56 mmol), Et$_3$N (600 µl, 4.3 mmol), dry THF (10 mls), and 3-bromo-4-chloro-1H-pyrazolo[3,4-d]pyrimidine (146 mgs, 0.62 mmol) were combined and stirred at 40 C overnight. The cooled reaction was diluted with EtOAc and washed with H$_2$O (1×), sat'd NaHCO$_3$ (2×), sat'd NaCl (1×), dried (Na$_2$SO$_4$), and conc'd in vacuo. The crude material was purified by flash chromatography (2.5% MeOH, 0.5% Et$_3$N in DCM), followed by purification by preparative HPLC (solvent A=0.05% ammonium acetate in H$_2$O, Solvent B=100% AcCN). Lyophilization of the pure HPLC fractions gave 3-bromo-4-{4-[4-methyl-2'-(2-pyrrolidin-1-yl-ethoxy)-biphenyl-3-yl]-piperazin-1-yl}-1H-pyrazolo[3,4-d]pyrimidine as the 0.5 AcOH salt (118 mg, 37%). $^1$H NMR (400 MHz, d$_6$-DMSO) δ 8.36 (s, 1H), 7.30 (complex multiplet, 4H), 7.12 (m, 2H), 7.02 (t, 1H), 4.12 (t, 2H), 3.98 (m, 4H), 3.06 (m, 4H), 2.92 (m, 2H), 2.58 (m, 4H), 2.35 (s, 3H), 1.91 (s, 1.5H, 0.5 AcOH), 1.62 (m, 4H). MS (ESI) for C$_{28}$H$_{32}$BrN$_7$O: 562 (MH$^+$).

Using the same or analogous synthetic techniques and/or substituting with alternative reagents, the following compound of the invention was prepared:

1-(3-{5-[4-(3-Bromo-1H-pyrazolo[3,4-d]pyrimidin-4-yl)piperazin-1-yl]-4-methylbiphenyl-3-yl}propyl)pyridinium.
$^1$H NMR (400 MHz, d$_6$-DMSO) δ 9.14 (d, 2H), 8.59 (t, 1H), 8.22 (s, 1H), 8.14 (t, 2H), 7.64 (d, 2H), 7.45 (t, 2H), 7.34 (t, 1H), 7.20 (s, 2H), 4.73 (t, 2H), 3.86 (m, 2H), 3.07 (m, 4H), 2.73 (t, 2H), 2.30 (m, 4H), 1.80 (s, 3H). MS (ESI) for C$_{30}$H$_{31}$BrN$_7$: 568 (MH$^+$).

Example 47

3-Bromo-4-(4-{3'-fluoro-4-methyl-2'-[(2-pyrrolidin-1-ylethyl)oxy]biphenyl-3-yl}piperazin-1-yl)-1H-pyrazolo[3,4-d]pyrimidine To a 150 mL pressure vessel was added 4-bromo-2-nitrotoluene (4.85 g, 22.4 mmol, 1.0 eq.), 3-fluoro-2-methoxyphenylboronic acid (4.20 g, 24.7 mmol, 1.1 eq.), Pd(dppf)$_2$Cl$_2$ (CH$_2$Cl$_2$ complex, 917 mg, 2.24 mmol, 0.1 eq.), sodium carbonate (7.14 g, 67.4 mmol, 3.0 eq.), H$_2$O (40 mL), and toluene (40 mL). The vessel was sealed and heated at 88° C. overnight. GC/MS analysis indicated product is present as the major component. The reaction mixture was cooled and filtered through Celite, followed by a rinse of EtOAc. The organic phase was washed with H$_2$O (100 mL) and saturated aq. NaCl (100 mL). The combined aqueous phases were extracted with EtOAc (2×100 mL). The organic phases were combined and dried over anhydrous Na$_2$SO$_4$, filtered, and concentrated to give black oil. The crude material was purified via column chromatography to afford 3-fluoro-2-methoxy-4'-methyl-3'-nitro-biphenyl as orange oil which later solidified upon standing (5.18 g, 88%).

To a 500 mL recovery flask was added 3-fluoro-2-methoxy-4'-methyl-3'-nitro-biphenyl (5.14 g, 19.6 mmol, 1.0 eq.) and CH$_2$Cl$_2$ (150 mL). Upon stirring, BBr$_3$ (1.0 M in CH$_2$Cl$_2$, 58.6 mL, 58.6 mmol, 3.0 eq.) was added. Upon addition, the reaction mixture color turns light orange to dark red. After stirring for 1 h, the reaction color becomes lighter red. The reaction was stirred for 4 h at room temperature whereupon CH$_3$OH was added to quench any excess BBr$_3$. The reaction was concentrated and then taken up in CH$_2$Cl$_2$. The organic phase was washed with H$_2$O (100 mL) and saturated aq. NaCl (100 mL). The combined aqueous phases were extracted with CH$_2$Cl$_2$ (2×100 mL). The organic phases were combined and dried over anhydrous Na$_2$SO$_4$, filtered, and concentrated to give a brown solid. The solid was suspended in 10% EtOAc/Hex. The insoluble material was filtered to give 3-fluoro-4'-methyl-3'-nitro-biphenyl-2-ol as a tan solid. (4.08 g, 84%).

To a 150 mL pressure vessel was added 3-fluoro-4'-methyl-3'-nitro-biphenyl-2-ol (1.00 g, 4.04 mmol, 1.0 eq.), Cs$_2$CO$_3$ (3.69 g, 11.3 mmol, 2.8 eq.), 1-(2-chloroethyl)-pyrrolidine hydrochloride (894 mg, 5.26 mmol, 1.3 eq.), and DMF (40 mL). The vessel was sealed and heated at 70° C. overnight. The reaction mixture was cooled and was diluted with EtOAc (150 mL) and 10% aq. LiCl (50 mL). The organic phase was washed with 10% aq. LiCl (2×75 mL) and saturated aq. NaCl (1×50 mL). The combined aqueous phases were extracted with EtOAc (2×75 mL). The combined organic phases were dried over anhydrous Na$_2$SO$_4$, filtered, and concentrated to give brown oil. The crude material was purified via column chromatography (3% CH$_3$OH/CH$_2$Cl$_2$) to afford pure product 1-[2-(3-fluoro-4'-methyl-3'-nitro-biphenyl-2-yloxy)-ethyl]-pyrrolidine as light-brown oil (1.39 g, 100%).

To a 50 mL recovery flask was added 1-[2-(3-fluoro-4'-methyl-3'-nitro-biphenyl-2-yloxy)-ethyl]-pyrrolidine (1.39 g, 4.04 mmol, 1.0 eq.), AcOH (8 mL), and tin (II) chloride dihydrate (3.64 g, 16.1 mmol, 4.0 eq.). The reaction was stirred vigorously at room temperature. After 3 h, LC/MS shows approximately 1:1 ratio of starting material to product. The reaction mixture was heated at 75° C. overnight, which drove the reaction to completion. The reaction mixture was cooled and poured into a 250 mL Erlenmeyer flask containing H$_2$O (100 mL). 4N NaOH was added until the solution became alkaline. The thick mixture was extracted with Et$_2$O (5×75 mL). The organic phase was dried over Na$_2$SO$_4$, filtered, and concentrated to afford 3'-fluoro-4-methyl-2'-(2-pyrrolidin-1-yl-ethoxy)-biphenyl-3-ylamine as a brown oil which was used in the next reaction without further purification (1.25 g, 98%).

To a 48 mL pressure vessel was added 3'-fluoro-4-methyl-2'-(2-pyrrolidin-1-yl-ethoxy)-biphenyl-3-ylamine (333 mg, 1.06 mmol, 1.0 eq.), bis-(2-chloroethyl)amine hydrochloride (189 mg, 1.06 mmol, 1.0 eq.), K$_2$CO$_3$ (146 mg, 1.06 mmol, 1.0 eq.), and diglyme (10 mL). The vessel was sealed and heated at 145° C. overnight. The reaction was cooled and diluted with H$_2$O (30 mL) and EtOAc (50 mL). The organic phase was washed with H$_2$O (30 mL), saturated aq. NaHCO$_3$ (30 mL), and brine (30 mL). The combined aqueous phases were extracted with EtOAc (4×30 mL). The combined organic phases were dried over anhydrous Na$_2$SO$_4$, filtered, and concentrated to give black oil which still contained a large amount of diglyme. The crude mixture was purified by column chromatography (20% CH$_3$OH/CH$_2$Cl$_2$ to 20% CH$_3$OH/CH$_2$Cl$_2$ with 1% Et$_3$N) to afford 1-[3'-fluoro-4-methyl-2'-(2-pyrrolidin-1-yl-ethoxy)-biphenyl-3-yl]-piperazine as black oil (257 mg, 62%).

3-Bromo-4-(4-{3'-fluoro-4-methyl-2'-[(2-pyrrolidin-1-ylethyl)oxy]biphenyl-3-yl}piperazin-1-yl)-1H-pyrazolo[3,4-d]pyrimidine: To a 50 mL recovery flask was added 1-[3'-fluoro-4-methyl-2'-(2-pyrrolidin-1-yl-ethoxy)-biphenyl-3-yl]-piperazine (255 mg, 0.665 mmol, 1.0 eq.), isopropanol (8 mL), i-Pr$_2$NEt (348 µL, 1.99 mmol, 3.0 eq.). Upon stirring, chloropyrimidine 7 (155 mg, 0.665 mmol, 1.0 eq.) was added and the reaction was heated at 65° C. for 1 h and overnight while cooling to room temperature. The reaction mixture was concentrated and then redissolved in EtOAc (100 mL). The organic phase was washed with H$_2$O (2×50 mL) and brine (1×50 mL). The combined aqueous phases were extracted with EtOAc (2×50 mL). The organic phases were combined and dried over anhydrous Na$_2$SO$_4$, filtered, and concentrated to give a brown solid. Column chromatography (3% to 10%

CH₃OH(CH₂Cl₂) afforded 3-bromo-4-(4-{3'-fluoro-4-methyl-2'-[(2-pyrrolidin-1-ylethyl)oxy]biphenyl-3-yl}piperazin-1-yl)-1H-pyrazolo[3,4-d]pyrimidine as an off-white solid (160 mg, 41%). ¹H NMR (400 MHz, d₆-DMSO) δ 10.29 (br s, 1H), 8.38 (s, 1H), 7.36-7.17 (m, 6H), 4.11 (t, 2H), 3.98 (m, 4H), 3.36-3.33 (m, 4H), 3.11-3.09 (m, 4H), 2.97-2.92 (m, 2H), 2.38 (s, 3H), 1.92 (m, 2H), 1.80 (m, 2H). MS (ESI) for $C_{28}H_{31}FBrN_7O$: 582 (MH⁺).

Using the same or analogous synthetic techniques and/or substituting with alternative reagents, the following compounds of the invention were prepared:

5-[4-(3-Bromo-1H-pyrazolo[3,4-d]pyrimidin-4-yl)piperazin-1-yl]-4-methyl-N-(2-pyrrolidin-1-ylethyl)biphenyl-3-amine. ¹H NMR (400 MHz, d₆-DMSO) δ 8.69 (s, 1H), 8.36 (s, 1H), 7.61 (m, 2H), 7.41 (m, 1H), 7.31 (m, 1H), 6.68 (s, 1H), 6.61 (s, 1H), 4.97 (m, 1H), 3.98 (m, 3H), 3.25 (m, 2H), 3.03 (m, 3H), 2.91 (br, s, 1), 2.76 (m, 3H), 2.57 (m, 4H), 2.13 (s, 2H), 1.19 (s, 2H), 1.78 (m, 3H). MS (ESI) for $C_{28}H_{33}BrN_8$: 560 (MH⁺).

3-[4-(3-Bromo-1H-pyrazolo[3,4-d]pyrimidin-4-yl)piperazin-1-yl]-2-methyl-N-(2-pyrrolidin-1-ylethyl)-5-(1,3-thiazol-2-yl)aniline. ¹H NMR (400 MHz, d₆-DMSO) δ 8.38 (s, 1H), 7.76 (d, 2H), 7.71 (d, 1H), 6.99 (s, 1H), 6.92 (s, 1H), 6.61 (s, 1H), 5.07 (t, 1H), 4.01 (m, 3H), 2.73 (m, 4H), 2.67 (m, 2H), 2.55 (m, 4H), 2.45 (m, 2H), 2.13 (d, 3H), 2.07 (s, 2H), 1.75 (m, 3H). MS (ESI) for $C_{25}H_{30}BrN_9S$: 568 (MH⁺).

1-[3-Bromo-1H-pyrazolo[3,4-d]pyrimidin-4-yl]-4-[2-methyl-4-[[3-(2-pyrrolidin-1-yletoxy)]phenyl]phenyl]piperazine: ¹H-NMR, (400 MHz CDCl₃) δ 8.45 (s, 1H), 7.22-7.33 (m, 4H), 7.13 (d, J=8 Hz, 1H), 7.08 (m, 1H), 6.86 (dd, J=1.5, J=8 Hz), 4.20 (t, J=6 Hz, 2H), 4.10 (m, 4H), 3.15 (m, 4H), 2.98 (t, J=6 Hz, 2H), 2.70 (m, 4H), 2.40 (s, 3H), 1.84 (m, 4H). MS (ESI) for $C_{28}H_{32}BrN_7O$: 564 (MH⁺).

3-Bromo-4-(4-{4-methyl-2'-[(3-morpholin-4-ylpropyl)oxy]biphenyl-3-yl}piperazin-1-yl)-1H-pyrazolo[3,4-d]pyrimidine: ¹H NMR (400 MHz, d₆-DMSO) δ 8.36 (s, 1H), 7.26 (m, 4H), 7.09 (m, 2H), 7.00 (t, 1H), 4.00 (m, 6H), 3.44 (m, 4H), 3.07 (m, 4H), 2.35 (m, 5H), 2.25 (br s, 4H), 1.81 (m, 2H). MS (ESI) for $C_{29}H_{34}BrN_7O_2$: 592 (MH⁺).

3-Bromo-4-(4-{4-methyl-2'-[(2-morpholin-4-ylethyl)oxy]biphenyl-3-yl}piperazin-1-yl)-1H-pyrazolo[3,4-d]pyrimidine: ¹H NMR (400 MHz, d₆-DMSO) δ 8.37 (s, 1H), 7.26 (m, 4H), 7.13 (dd, 2H), 7.01 (t, 1H), 4.09 (m, 2H), 3.98 (m, 4H), 3.49 (m, 4H), 3.07 (m, 4H), 2.62 (m, 2H), 2.35 (br s, 7H). MS (ESI) for $C_{28}H_{32}BrN_7O_2$: 578 (MH⁺).

3-({3'-[4-(3-Bromo-1H-pyrazolo[3,4-d]pyrimidin-4-yl)piperazin-1-yl]-4'-methylbiphenyl-2-yl}oxy)-N,N-dimethylpropan-1-amine: ¹H NMR (400 MHz, d₆-DMSO) δ 10.7 (s, 1H), 8.40 (s, 1H), 7.28 (m, 3H), 7.23 (s, 1H), 7.18 (d, 1H), 7.11 (d, 1H), 7.03 (t, 1H), 5.40 (m, 4H), 4.06 (m, 4H), 3.15 (s, 3H), 3.07 (m, 2H), 2.68 (m, 5H), 2.39 (s, 3H), 2.09 (m, 2H). MS (ESI) for $C_{27}H_{32}BrN_7O$: 551 (MH⁺).

1-[2-({3'-[4-(3-Bromo-1H-pyrazolo[3,4-d]pyrimidin-4-yl)piperazin-1-yl]-4'-methylbiphenyl-2-yl}oxy)ethyl]pyrrolidine-2,5-dione: ¹H NMR (400 MHz, d₆-DMSO) δ 8.35 (s, 1H), 7.30 (m, 2H), 7.20 (d, 1H), 7.12 (s, 1H), 7.04 (m, 3H), 4.10 (t, 2H), 3.97 (m, 4H), 3.69 (t, 2H), 3.35 (m, 4H), 3.09 (m, 4H), 2.35 (s, 3H). MS (ESI) for $C_{28}H_{28}BrN_7O_3$: 591 (MH⁺).

3-Bromo-4-(4-{4-chloro-2'-[(2-pyrrolidin-1-ylethyl)oxy]biphenyl-3-yl}piperazin-1-yl)-1H-pyrazolo[3,4-d]pyrimidine: ¹H NMR (400 MHz, d₆-DMSO) δ 9.6 (br s, 1H), 8.38 (s, 1H), 7.49 (d, 1H), 7.42 (m, 2H), 7.28 (d, 1H), 7.20 (m, 1H), 7.10 (t, 1H), 4.70 (t, 2H), 3.98 (br q, 4H), 3.55 (br q, 2H), 3.45 (m, 2H), 3.22 (br q, 2H), 1.89 (br m, 2H), 1.75 (br m, 2H). MS (ESI) for $C_{27}H_{29}BrClN_7O$: 582 (MH⁺).

3-Bromo-4-(4-{4-chloro-4'-fluoro-2'-[(2-pyrrolidin-1-ylethyl)oxy]biphenyl-3-yl}piperazin-1-yl)-1H-pyrazolo[3,4-d]pyrimidine: ¹H NMR (400 MHz, d₆-DMSO) δ 10.0 (br s, 1H), 8.37 (s, 1H), 7.49 (d, 1H), 7.40 (t, 1H), 7.25 (s, 1H), 7.18 (dt, 2H), 6.94 (dt, 1H), 4.35 (t, 2H), 3.98 (br s, 4H), 3.41 (m, 4H), 3.21 (br s, 4H), 2.93 (br q, 2H), 1.90 (br m, 2H), 1.75 (br m, 2H). MS (ESI) for $C_{27}H_{28}BrClFN_7O$: 600 (MH⁺).

Example 48

6-[4-(3-Bromo-1H-pyrazolo[3,4-d]pyrimidin-4-yl)-piperazin-1-yl]-3,5-difluoro-N4-(3-methyl-butyl)-N2-(2-pyrrolidin-1-yl-ethyl)-pyridine-2,4-diamine To 2,3,4,5,6-pentafluoro-pyridine (770 mg, 4.55 mmol) in dichloromethane (3 mL) was added 3-methyl-butylamine (530 uL, 4.55 mmol) slowly. After the reaction mixture was stirred at r.t. for 1 hr, it was concentrated to yield (3-methyl-butyl)-(2,3,5,6-tetrafluoro-pyridin-4-yl)-amine and used for next reaction. MS (ESI) for $C_{10}H_{12}F_4N_2$: 237 (MH⁺).

The mixture of (3-methyl-butyl)-(2,3,5,6-tetrafluoro-pyridin-4-yl)-amine and Boc-piperazine (4.35 mmol) was heated at 110° C. for overnight. The product 4-[3,5,6-trifluoro-4-(3-methyl-butylamino)-pyridin-2-yl]-piperazine-1-carboxylic acid tert-butyl ester was purified by column chromatography (624 mg). MS (ESI) for $C_{19}H_{29}F_3N_4O_2$: 401 (MH⁻).

The mixture of 4-[3,5,6-trifluoro-4-(3-methyl-butylamino)-pyridin-2-yl]-piperazine-1-carboxylic acid tert-butyl ester (122 mg) and 2-amino-ethyl pyrrolidine (700 uL, 40 eq.) in sealed tube was heated at 130° C. for 3 days. The product 4-[3,5-difluoro-4-(3-methyl-butylamino)-6-(2-pyrrolidin-1-yl-ethylamino)-pyridin-2-yl]-piperazine-1-carboxylic acid tert-butyl ester was purified by column chromatography (91 mg). MS (ESI) for $C_{25}H_{42}F_2N_6O_2$: 497 (MH⁺).

4-[3,5-Difluoro-4-(3-methyl-butylamino)-6-(2-pyrrolidin-1-yl-ethylamino)-pyridin-2-yl]-piperazine-1-carboxylic acid tert-butyl ester (4, 91 mg, 0.18 mmol) was treated with 4N—HCl-dioxane (2 mL) in methanol (2mL) at r.t. for 1 hr. and gave 3,5-difluoro-N4-(3-methyl-butyl)-6-piperazin-1-yl-N2-(2-pyrrolidin-1-yl-ethyl)-pyridine-2,4-diamine hydrochloride. MS (ESI) for $C_{20}H_{34}F_2N_6$: 397 (MH⁺).

To the crude 3,5-difluoro-N4-(3-methyl-butyl)-6-piperazin-1-yl-N2-(2-pyrrolidin-1-yl-ethyl)-pyridine-2,4-diamine hydrochloride in THF (3 mL), 3-bromo-4-chloro-1H-pyrazolo[3,4-d]pyrimidine (43 mg, 0.18 mmol), and triethylamine (150 uL, 1.1 mmol) were added. The mixture was heated at 60° C. for 2 hrs. After concentrated, the product was purified by HPLC and gave to 6-[4-(3-bromo-1H-pyrazolo[3,4-d]pyrimidin-4-yl)-piperazin-1-yl]-3,5-difluoro-N4-(3-methyl-butyl)-N2-(2-pyrrolidin-1-yl-ethyl)-pyridine-2,4-diamine. ¹H-NMR (400 MHz, CDCl₃) δ 8.4 (s, 1H), 4.98 (br s. 1H), 4.04 (m, 4H), 3.58 (m, 2H), 3.48 (m, 4H), 3.42 (m, 2H), 2.84 (m, 2H), 2.73 (br s, 4H), 1.85 (s, 4H), 1.68 (m, 1H), 1.49 (m, 2H), 0.94 (d, 6H). MS (ESI) for $C_{25}H_{35}BrF_2N_{10}$: 595 (MH⁺).

Using the same or analogous synthetic techniques and/or substituting with alternative reagents, the following compound of the invention was prepared:

2-[4-(3-Bromo-1H-pyrazolo[3,4-d]pyrimidin-4-yl)piperazin-1-yl]-3,5,6-trifluoro-N-(3-methylbutyl)pyridin-4-amine: ¹H-NMR (400 MHz, CDCl₃) δ 12.69 (br s, 1H), 8.44 (s, 1H), 4.18 (s, 1H), 4.03 (m, 4H), 3.53 (m, 4H), 3.48 (m, 2H), 1.72 (m, 1H), 1.53 (m, 2H), 0.94 (m, 6H). MS (ESI) for $C_{19}H_{22}BrF_3N_8$: 501 (MH⁺).

Example 49

[3-[4-(3-Bromo-1H-pyrazolo[3,4-d]pyrimidin-4-yl)-piperazin-1-yl]-5-(1,1-difluoro-butyl)-2-methyl-phenyl]-(2-pyrrolidin-1-yl-ethyl)-amine To a round bottom flask was added 1-(3,5-dibromo-4-methyl-phenyl)-butane-1-one (1.0 g, 3.1 mmol), 1,2- ethanedithiol (0.52 mL, 6.2 mmol), and boron trifluoride acetic acid complex (0.43 mL, 3.1 mmol). The reaction was stirred vigorously at r.t. for 30 min before diluting with hexanes (20 mL). The organic solution was washed (3×20 mL) with saturated NaHCO$_3$, 15% NaOH, and finally with brine. The organic layer was dried with Na$_2$SO$_4$, and concentrated. Column chromatography with 10:90 EtOAc:Hexanes gave 2-(3,5-dibromo-4-methyl-phenyl)-2-propyl-[1,3]dithiolane as a clear oil that solidified upon standing (1.14 g, 90% yield). $^1$H NMR (400 MHz, CDCl$_3$) δ 7.82 (s, 2H), 3.40 (m, 2H), 3.20 (m, 2H), 2.58 (s, 3H), 2.25 (m, 2H), 1.30 (m, 2H), 0.90 (t, 3H).

To an oven dried round bottom flask was added dry 1,3-dibromo-5,5-dimethylhydantoin (360 mg, 1.26 mmol), CH$_2$Cl$_2$ (2.5 mL), and hydrogen fluoride pyridine (0.62 mL, 2.73 mmol). The mixture was cooled to −78° C. before adding dropwise a solution of 2-(3,5-Dibromo-4-methyl-phenyl)-2-propyl-[1,3]dithiolane (500 mg, 1.26 mmol) in 0.5 mL dry CH$_2$Cl$_2$. The reaction changed from yellow to orange to red in color. After 30 min at −78° C., the reaction was filtered through a 50 mL polypropylene/polyethylene column packed with basic alumina. The column was rinsed with hexanes and then CH$_2$Cl$_2$. The combined organics were concentrated and columned with EtOAc:hexane (5:95) to give 1,3-dibromo-5-(1,1-difluoro-butyl)-2-methyl-benzene as an oil (240 mg, 70% yield). $^1$H NMR (400 MHz, CDCl$_3$) δ 7.60 (m, 2H), 2.60 (m, 3H), 2.05 (m, 2H), 1.42 (m, 2H), 0.95 (t, 3H).

To a sealed tube was added 1,3-dibromo-5-(1,1-difluoro-butyl)-2-methyl-benzene (235 mg, 0.68 mmol), toluene (3.0 mL), Boc-piperazine (115 mg, 0.62 mmol), NaOtBu (91.0 mg, 0.95 mmol), and BINAP (42.0 mg, 0.068 mmol). The reaction was purged with nitrogen before adding Pd$_2$(dba)$_3$ (15.0 mg, 0.017 mmol). The tube was sealed and heated to 110° C. overnight. The reaction was then cooled to r.t., filtered through celite, rinsed with EtOAc, and concentrated. Column purification with 10:90 EtOAc:hexane gave 4-[3-bromo-5-(1,1-difluoro-butyl)-2-methyl-phenyl]-piperazine-1-carboxylic acid tert-butyl ester (200 mg, 66% yield). $^1$H NMR (400 MHz, CDCl$_3$) δ 7.40 (s, 1H), 7.00 (s, 1H), 3.60 (br s, 4H), 2.82 (br t, 4H), 2.40 (s, 3H), 2.05 (m, 2H), 1.50 (s, 9H), 1.45 (m, 2H), 0.95 (t, 3H).

To a sealed tube was added 4-[3-bromo-5-(1,1-difluoro-butyl)-2-methyl-phenyl]-piperazine-1-carboxylic acid tert-butyl ester (200 mg, 0.44 mmol), dioxane (5.0 mL), NaOtBu (68.0 mg, 0.72 mmol), and xantphos (25.0 mg, 0.044 mmol). The reaction was purged with nitrogen before adding Pd$_2$(dba)$_3$ (20.0 mg, 0.022 mmol). The tube was sealed and stirred at RT for 10 min before adding 1-(2-aminoethyl)-pyrrolidine (75 mg, 0.66 mmol), sealed and heated to 100° C. overnight. The reaction was then cooled to r.t., filtered through celite, rinsed with MeOH, and concentrated. Column purification with MeOH:CH$_2$Cl$_2$ (7:93) gave 4-5-(1,1-difluoro-butyl)-2-methyl-3-(2-pyrrolidin-1-yl-ethylamino)-phenyl]-piperazine-1-carboxylic acid tert-butyl ester (130 mg, 62% yield). $^1$H NMR (400 MHz, d$_6$-DMSO) δ 6.42 (d, 2H), 4.95 (br s, 1H), 3.60 (s, 2H), 3.20 (m, 4H), 2.70 (m, 4H), 2.15 (m, 2H), 2.01 (s, 3H), 1.70 (br s, 4H), 1.42 (s, 9H), 1.40 (m, 2H), 0.93 (t, 3H). MS (ESI) for C$_{26}$H$_{42}$F$_2$N$_4$O$_2$: 481 (MH$^+$).

[3-[4-(3-Bromo-1H-pyrazolo[3,4-d]pyrimidin-4-yl)-piperazin-1-yl]-5-(1,1-difluoro-butyl)-2-methyl-phenyl]-(2-pyrrolidin-1-yl-ethyl)-amine: To a round bottom flask was added 4-5-(1,1-difluoro-butyl)-2-methyl-3-(2-pyrrolidin-1-yl-ethylamino)-phenyl]-piperazine-1-carboxylic acid tert-butyl ester (130 mg, 0.27 mmol), dry methanol (3.0 mL) and 4N HCl in dioxane (3.0 mL). The reaction was stirred at RT for 1 hr, then concentrated to remove trace HCl. The residue was then dissolved in THF (5.0 mL), and triethyl amine (0.156 mL, 1.08 mmol), before adding 3-bromo-4-chloro-1H-pyrazolo[3,4-d]pyrimidine (63.0 mg, 0.27 mmol). The reaction was stirred at 65° C. for 30 min, concentrated and prep purified to give the TFA salt of [3-[4-(3-bromo-1H-pyrazolo[3,4-d]pyrimidin-4-yl)-piperazin-1-yl]-5-(1,1-difluoro-butyl)-2-methyl-phenyl]-(2-pyrrolidin-1-yl-ethyl)-amine. The salt was converted to the HCl salt by adding excess 4N HCl and lyophilizing in H$_2$O/CH$_3$CN to give [3-[4-(3-bromo-1H-pyrazolo[3,4-d]pyrimidin-4-yl)-piperazin-1-yl]-5-(1,1-difluoro-butyl)-2-methyl-phenyl]-(2-pyrrolidin-1-yl-ethyl)-amine as a white solid (101 mg, 64% yield): $^1$H NMR (400 MHz, d$_6$-DMSO) δ 9.60 (br s, 1H), 8.40 (s, 1H), 6.60 (d, 2H), 3.45 (m, 4H), 3.40 (m, 4H), 3.00 (m, 6H), 2.20 (s, 3H), 2.10 (m, 4H), 1.95 (m, 2H), 1.40 (m, 2H), 0.95 (t, 3H). MS (ESI) for C$_{26}$H$_{35}$BrF$_2$N$_9$: 577 (MH$^+$).

Using the same or analogous synthetic techniques and/or substituting with alternative reagents, the following compound of the invention was prepared:

1-{3-[4-(3-Bromo-1H-pyrazolo[3,4-d]pyrimidin-4-yl)piperazin-1-yl]-4-methyl-5-[(2-pyrrolidin-1-ylethyl)amino]phenyl}butan-1-ol: $^1$H NMR (400 MHz, d$_6$-DMSO) δ 8.36 (s, 1H), 6.47 (s, 1H), 6.38 (s, 1H), 4.39 (m, 1H), 3.95 (br, 3H), 3.62 (br, 2H), 3.43 (m, 2H), 3.36 (m, 2H), 3.08 (br, 2H), 2.94 (s, 4H), 2.10 (s, 3H), 1.95 (br, 5H), 1.52 (m, 2H), 1.45 (m, 1H), 1.25 (m, 1H), 0.86 (t, 3H). MS (ESI) for C$_{26}$H$_{37}$BrN$_8$O: 557 (MH$^+$).

Example 50

3-[4-(3-Bromo-1H-pyrazolo[3,4-d]pyrimidin-4-yl) piperazin-1-yl]-5-[(ethyloxy)methyl]-2-methyl-N-(2-pyrrolidin-1-ylethyl)aniline To a 500 mL recovery flask was added methyl 3,5-dibromo-4-methylbenzoate (26 g, 84.4 mmol, 1.0 eq.), anhydrous ethanol (300 mL), and NaBH$_4$ (9.58 g, 253 mmol, 3.0 eq.). The reaction was stirred at reflux overnight. TLC analysis indicated that the reaction was complete. The reaction was concentrated and chromatographed (10% EtOAc/Hex) to give (3,5-dibromo-4-methyl-phenyl)-methanol as a white solid (17.2 g, 73%).

To a 50 mL recovery flask was added (3,5-dibromo-4-methyl-phenyl)-methanol (0.50 g, 1.78 mmol, 1.0 eq.) and DMF (15 mL). NaH (60% dispersion in mineral oil, 143 mg, 3.57 mmol, 2.0 eq.) was added and the mixture was stirred at 70° C. for 5 min. Bromoethane (400 μL, 5.36 mmol, 3.0 eq.) was added and the reaction was stirred overnight at 70° C. The reaction mixture was diluted with EtOAc (100 mL) and the organic phase was washed with 10% aq. LiCl (2×50 mL) and saturated aq. sodium chloride (50 mL). The combined aqueous phases were extracted with EtOAc (2×50 mL). The combined organic phases were dried over anhydrous Na$_2$SO$_4$, filtered, and concentrated. The crude oil was purified via column chromatography (5% EtOAc/Hex) to give 1,3-dibromo-5-ethoxymethyl-2-methyl-benzene as yellow oil (410 mg, 75%).

To a 48 mL pressure vessel was added 1,3-dibromo-5-ethoxymethyl-2-methyl-benzene (1.24 g, 4.02 mmol, 1.0 eq.), Boc-piperazine (675 mg, 3.62 mmol, 0.9 eq.), BINAP (250 mg, 0.402 mmol, 0.1 eq.), and toluene (15 mL). The suspension was bubbled with N$_2$ upon which Pd$_2$(dba)$_3$ (92 mg, 0.0100 mmol, 0.025 eq.) and sodium tert-butoxide (542 mg, 5.64 mmol, 1.4 eq.) was added. The vessel was sealed and heated at 110° C. overnight. The crude mixture was filtered through Celite and the Celite cake was rinsed with EtOAc. The filtrate was concentrated and chromatographed (5% to 15% EtOAc/Hex) to afford 4-(3-bromo-5-ethoxymethyl-2-methyl-phenyl)-piperazine-1-carboxylic acid tert-butyl ester as yellow oil (1.01 g, 61%).

To a 75 mL pressure vessel was added 4-(3-bromo-5-ethoxymethyl-2-methyl-phenyl)-piperazine-1-carboxylic acid tert-butyl ester (1.00 g, 2.42 mmol, 1.0 eq.), XantPHOS (84 mg, 0.145 mmol, 0.06 eq.), 2-pyrrolidinoethylamine (457 µL, 3.63 mmol, 1.5 eq.), and dioxane (25 mL). The suspension was bubbled with $N_2$ upon which $Pd_2(dba)_3$ (66 mg, 0.0725 mmol, 0.03 eq.) and sodium tert-butoxide (349 mg, 3.63 mmol, 1.5 eq.) was added. The vessel was sealed and heated at 100° C. overnight. The crude mixture was filtered through Celite and the Celite cake was rinsed with EtOAc. The filtrate was concentrated and chromatographed (5%-15% $CH_3OH/CH_2Cl_2$) to afford 4-[5-ethoxymethyl-2-methyl-3-(2-pyrrolidin-1-yl-ethylamino)-phenyl]-piperazine-1-carboxylic acid tert-butyl ester as bronze oil (535 mg, 49%).

To a 50 mL recovery flask was added 4-[5-ethoxymethyl-2-methyl-3-(2-pyrrolidin-1-yl-ethylamino)-phenyl]-piperazine-1-carboxylic acid tert-butyl ester (535 mg, 1.20 mol, 1.0 eq.) and methanol (8 mL). 4N HCl/dioxane (8 mL) was added and the reaction was stirred for 2 h at room temperature. LC/MS analysis indicated that the deprotection was complete, whereupon the reaction was concentrated and placed on high vacuum. The crude material of (5-ethoxymethyl-2-methyl-3-piperazin-1-yl-phenyl)-(2-pyrrolidin-1-yl-ethyl)-amine was used in the next reaction without further purification.

3-[4-(3-Bromo-1H-pyrazolo[3,4-d]pyrimidin-4-yl)piperazin-1-yl]-5-[(ethyloxy)methyl]-2-methyl-N-(2-pyrrolidin-1-ylethyl)aniline: To a 50 mL recovery flask was added (5-ethoxymethyl-2-methyl-3-piperazin-1-yl-phenyl)-(2-pyrrolidin-1-yl-ethyl)-amine (502 mg, 1.20 mmol, 1.0 eq.), isopropanol (15 mL), i-Pr$_2$NEt (1.04 mL, 5.98 mmol, 5.0 eq.). Upon stirring, 3-bromo-4-chloro-1H-pyrazolo[3,4-d]pyrimidine (279 mg, 1.20 mmol, 1.0 eq.) was added and the reaction was heated at 65° C. for 1 h. The reaction mixture was concentrated and then redissolved in EtOAc (100 mL). The organic phase was washed with $H_2O$ (2×50 mL) and brine (1×50 mL). The combined aqueous phases were extracted with EtOAc (2×50 mL). The organic phases were combined and dried over anhydrous Na$_2$SO$_4$, filtered, and concentrated to give light-brown oil. Column chromatography (5% to 15% CH$_3$OH/CH$_2$Cl$_2$) afforded pure product 3-[4-(3-bromo-1H-pyrazolo[3,4-d]pyrimidin-4-yl)piperazin-1-yl]-5-[(ethyloxy)methyl]-2-methyl-N-(2-pyrrolidin-1-ylethyl)aniline as a light yellow oil (277 mg, 43%). $^1$H NMR (400 MHz, d$_6$-DMSO) δ 11.18 (br s, 1H), 8.42 (s, 1H), 6.62 (s, 1H), 6.59 (s, 1H), 4.37 (s, 2H), 4.09 (br s, 3H), 3.60 (m, 2H), 3.54 (t, 2H), 3.47 (q, 2H), 3.38 (m, 2H), 3.12 (m, 3H), 3.04 (m, 2H), 2.24 (s, 3H), 2.00 (m, 2H), 1.91 (m, 2H), 1.14 (t, 3H). MS (ESI) for C$_{25}$H$_{35}$BrN$_8$O: 545 (MH$^+$).

Using the same or analogous synthetic techniques and/or substituting with alternative reagents, the following compound of the invention was prepared:

3-[4-(3-Bromo-1H-pyrazolo[3,4-d]pyrimidin-4-yl)piperazin-1-yl]-2-methyl-N-(2-pyrrolidin-1-ylethyl)-5-{[(2,2,2-trifluoroethyl)oxy]methyl}aniline:

The key intermediate of 1,3-dibromo-2-methyl-5-(2,2,2-trifluoro-ethoxymethyl)-benzene was synthesized by following method and further reactions were the same as the previous section.

To a 200 mL recovery flask was added (3,5-dibromo-4-methyl-phenyl)-methanol (1.50 g, 5.36 mmol, 1.0 eq.) and azodicarbonyldipiperidine (2.70 g, 10.7 mmol, 2.0 eq.). Benzene (60 mL) was added and the mixture was stirred at room temperature. Tri-n-butylphosphine (2.64 mL, 10.7 mmol, 2.0 eq.) was added at the reaction mixture was stirred for 10 minutes whereupon 2,2,2-trifluoroethanol (3.85 mL, 53.6 mmol, 10.0 eq.) was added. The reaction was stirred for 6 hours at room temperature. TLC analysis at 2 h and 6 h indicated the reaction progression had slowed and therefore the reaction was concentrated and chromatographed (100% CH$_2$Cl$_2$) to afford the product 1,3-dibromo-2-methyl-5-(2,2,2-trifluoro-ethoxymethyl)-benzene as a white solid (1.11 g, 57%, 79% based on recovered starting material).

To a 50 mL recovery flask was added [2-methyl-3-piperazin-1-yl-5-(2,2,2-trifluoro-ethoxymethyl)-phenyl]-(2-pyrrolidin-1-yl-ethyl)-amine dihydrochloride (570 mg, 1.20 mmol, 1.0 eq.), isopropanol (15 mL), i-Pr$_2$NEt (1.05 mL, 6.02 mmol, 5.0 eq.). Upon stirring, 3-Bromo-4-chloro-1H-pyrazolo[3,4-d]pyrimidine (281 mg, 1.20 mmol, 1.0 eq.) was added and the reaction was heated at 65° C. for 1 h. The reaction mixture was concentrated and then redissolved in EtOAc (100 mL). The organic phase was washed with water (2×50 mL) and brine (1×50 mL). The combined aqueous phases were extracted with EtOAc (2×50 mL). The organic phases were combined and dried over anhydrous Na$_2$SO$_4$, filtered, and concentrated to give light-brown oil. Column chromatography (3% to 15% CH$_3$OH/CH$_2$Cl$_2$) afforded 3-[4-(3-bromo-1H-pyrazolo[3,4-d]pyrimidin-4-yl)piperazin-1-yl]-2-methyl-N-(2-pyrrolidin-1-ylethyl)-5-{[(2,2,2-trifluoroethyl)oxy]methyl}aniline as a light yellow oil (258 mg, 36%). $^1$H NMR (400 MHz, d$_6$-DMSO) δ 11.00 (br s, 1H), 8.40 (s, 1H), 6.55 (s, 1H), 6.52 (s, 1H), 4.56 (s, 2H), 4.09-4.02 (m, 5H), 3.59 (m, 2H), 3.51 (t, 2H), 3.34 (m, 2H), 3.04 (m, 6H), 2.19 (s, 3H), 2.00 (m, 2H), 1.90 (m, 2H). MS (ESI) for C$_{25}$H$_{32}$BrF$_3$N$_9$O: 599 (MH$^+$).

Example 51

[3-[4-(3-Bromo-1H-pyrazolo[3,4-d]pyrimidin-4-yl]-piperazin-1-yl]-5-(2,3-difluoro-2-fluoromethyl-propoxy)-2-methyl-phenyl]-(2-pyrrolidin-1-yl-ethyl)-amine To a pressure vessel was added 3,5-dibromo-4-methyl phenol (12.0 g, 45 mmol), dry DMF (80 mL), cesium carbonate (35.4 g, 108.6 mmol), and 2-(Bromomethyl)-1,2,3-trifluoropropane (11.2 g, 58 mmol). The reaction was sealed and heated to 80° C. overnight. The reaction was then cooled to r.t. then partitioned between EtOAc and water. The organic layer was washed with brine, dried with Na$_2$SO$_4$, and concentrated. Column chromatography on silica gel with 5:95 EtOAc:hexanes gave 15 g of 1,3-dibromo-5-(2,3-difluoro-2-fluoromethyl-propoxy)-2-methyl-benzene as a white solid (89% yield). $^1$H NMR (400 MHz, CDCl$_3$) δ 7.10 (s, 2H), 4.70 (dd, 4H), 4.2 (d, 2H), 2.44 (s, 3H). MS (ESI) for C$_{11}$H$_{11}$Br$_2$F$_3$O: 375 (MH$^+$).

To a pressure vessel was added pure trifluoro ether 1,3-dibromo-5-(2,3-difluoro-2-fluoromethyl-propoxy)-2-methyl-benzene (15.0 g, 40 mmol), toluene (100 mL), Boc piperazine (6.7 g, 36.0 mmol), sodium t-butoxide (5.35 g, 56.0 mmol), and BINAP (2.49 g, 4.0 mmol). The vessel was then purged with N$_2$ before adding Pd$_2$(dba)$_3$ (915 mg, 1.0 mmol), sealed and heated to 110° C. overnight. The reaction was then cooled to r.t., filtered through celite, rinsed with EtOAc and concentrated. Column chromatography on silica gel with 10:90' EtOAc:hexane gave 12.7 g of 4-[3-bromo-5-(2,3-difluoro-2-fluoromethyl-propoxy)-2-methyl-phenyl]-piperazine-1-carboxylic acid t-butyl ester as a pale yellow solid (67% yield). $^1$H NMR (400 MHz, CDCl$_3$) δ 6.90 (s, 1H), 6.60 (s, 1H), 4.75 (dd, 4H), 4.2 (d, 2H), 3.60 (br s, 4H), 2.81 (br s, 4H), 2.34 (s, 3H), 1.45 (s, 9H). MS (ESI) for $C_{20}H_{28}BrF_3N_2O_3$: 481 (MH$^+$).

To a pressure vessel was added 4-[3-bromo-5-(2,3-difluoro-2-fluoromethyl-propoxy)-2-methyl-phenyl]-piperazine-1-carboxylic acid t-butyl ester (6.8 g, 14.2 mmol), dry dioxane (100 mL), sodium t-butoxide (2.2 g, 22.7 mmol), and Xantphos (821 mg, 1.4 mmol). The reaction was purged with N$_2$ before adding Pd$_2$(dba)$_3$ (649 mg, 0.71 mmol). The reaction was stirred at rt for 5 min before adding 1-(2-aminoethyl pyrrolidine) (2.7 mL, 21.3 mmol). The reaction was then sealed and stirred at 90° C. overnight. The reaction was cooled to rt, filtered through celite, rinsed with methanol, concentrated and column purified with silica gel and 10:90 MeOH:CH$_2$Cl$_2$ to give 4-[5-(2,3-difluoro-2-fluoromethyl-propoxy)-2-methyl-3-(2-pyrrolidin-1-yl-ethylamino)-phenyl]-piperazine-1-carboxylic acid t-butyl ester as a brown solid (6.2 g, 85% yield). $^1$H NMR (400 MHz, d$_6$-DMSO) δ 6.00 (d, 2H), 4.80 (m, 4H), 4.2 (d, 2H), 3.50 (br s, 4H), 3.19 (q, 2H), 2.72 (br s, 4H), 2.70 (t, 2H), 2.44 (m, 4H), 2.00 (s, 3H), 1.70 (br s, 4H), 1.45 (s, 9H). MS (ESI) for $C_{26}H_{41}F_3N_4O_3$: 515 (MH$^+$).

[3-[4-(3-Bromo-1H-pyrazolo[3,4-d]pyrimidin-4-yl]-piperazin-1-yl]-5-(2,3-difluoro-2-fluoromethyl-propoxy)-2-methyl-phenyl]-(2-pyrrolidin-1-yl-ethyl)-amine: To a round bottom flask was added 4-[5-(2,3-difluoro-2-fluoromethyl-propoxy)-2-methyl-3-(2-pyrrolidin-1-yl-ethylamino)-phenyl]-piperazine-1-carboxylic acid t-butyl ester (6.2 g, 12.0 mmol), dry MeOH (35 mL) and 4N HCl in dioxane (35 mL). The reaction was stirred at rt for 1 hr or until complete as monitored by LC/MS. The reaction was then concentrated, and placed on high vacuum for 1 hr before carrying onto the next step without further purification.

To the round bottom flask containing [5-(2,3-difluoro-2-fluoromethyl-propoxy)-2-methyl-3-piperazin-1-yl-phenyl]-(2-pyrrolidin-1-yl-ethyl)-amine was added in order: THF (60 mL), triethyl amine (6.9 mL, 48.0 mmol), and 3-bromo-4-chloro-1H-pyrazolo[3,4-d]pyrimidine (2.8 g, 12.0 mmol). The reaction was stirred at 65° C. for 1 hr or until complete as monitored by LC/MS. The reaction was then concentrated before adding EtOAc (200 mL). The organic layer was washed with saturated NaHCO$_3$ (2×), water, brine, and then dried with Na$_2$SO$_4$ before concentrating. Column purification with silica gel and a gradient of 5:95 to 15:85 MeOH:CH$_2$Cl$_2$ gave [3-[4-(3-bromo-1H-pyrazolo[3,4-d]pyrimidin-4-yl]-piperazin-1-yl]-5-(2,3-difluoro-2-fluoromethyl-propoxy)-2-methyl-phenyl]-(2-pyrrolidin-1-yl-ethyl)-amine (5.41 g, 73% yield). Conversion to the HCl salt was achieved by dissolving [3-[4-(3-bromo-1H-pyrazolo[3,4-d]pyrimidin-4-yl]-piperazin-1-yl]-5-(2,3-difluoro-2-fluoromethyl-propoxy)-2-methyl-phenyl]-(2-pyrrolidin-1-yl-ethyl)-amine in 1:1 water:acetonitrile and adding 1.0 eq. of 4N HCl, and lyophilizing. The HCl salt was then lyophilized again with water-acetonitrile. $^1$H NMR (400 MHz, d$_6$-DMSO) δ 10.90 (br s, 1H), 8.20 (s, 1H), 6.19 (d, 2H), 4.85 (d sextet, 4H), 4.25 (d, 2H), 4.00 (br s, 4H), 3.80 (br s, 2H), 3.75 (br t, 2H), 3.25 (br s, 2H), 3.00 (br s, 4H), 2.10 (s, 3H), 1.95 (br m, 4H). MS (ESI) for $C_{26}H_{34}BrF_3N_8O$: 609 (MH$^+$).

Using the same or analogous synthetic techniques and/or substituting with alternative reagents, the following compounds of the invention were prepared:

{3-[4-(3-Bromo-1H-pyrazolo[3,4-d]pyrimidin-4-yl]-piperazin-1-yl]-5-isobutoxy-2-methyl-phenyl}-2-pyrrolidin-1-yl-ethyl)-amine: $^1$H NMR (400 MHz, d$_6$-DMSO) δ 10.85 (br s, 1H), 8.40 (s, 1H), 6.12 (d, 2H), 3.7 (d, 2H), 3.62 (br s, 2H), 3.45 (br t, 2H), 3.22 (br s, 4H), 3.00 (br s, 8H), 2.18 (s, 3H), 1.80 (m, 4H), 1.00 (d, 6H). MS (ESI) for $C_{26}H_{37}BrN_8O$: 557 (MH$^+$).

N'-{3-[4-(3-Bromo-1H-pyrazolo[3,4-d]pyrimidin-4-yl]-piperazin-1-yl]-5-isobutoxy-2-methyl-phenyl}-N,N-diethyl-ethane-1,2-diamine: $^1$H NMR (400 MHz, d$_6$-DMSO) δ 12.2 (br s, 1H), 10.20 (br s, 1H), 8.20 (s, 1H), 6.12 (d, 2H), 3.80 (d, 2H), 3.22 (m, 5H), 3.00 (br s, 2H), 2.18 (s, 3H), 1.90 (m, 1H), 1.25 (t, 6H), 1.00 (d, 6H). MS (ESI) for $C_{26}H_{39}BrN_8O$: 558 (MH$^+$).

N'-{3-[4-(3-Bromo-1H-pyrazolo[3,4-d]pyrimidin-4-yl]-piperazin-1-yl]-5-isobutoxy-2-methyl-phenyl}-N,N-methyl-ethane-1,2-diamine: $^1$H NMR (400 MHz, d$_6$-DMSO) δ 12.2 (br s, 1H), 10.20 (br s, 1H), 8.40 (s, 1H), 6.02 (d, 2H), 3.70 (d, 2H), 3.60 (t, 2H), 3.30 (t, 2H), 3.00 (br s, 4H), 2.80 (s, 6H), 2.18 (s, 3H), 1.90 (m, 1H), 1.00 (d, 6H). MS (ESI) for $C_{24}H_{35}BrN_8O$: 531 (MH$^+$).

[3-[4-(3-Bromo-1H-pyrazolo[3,4-d]pyrimidin-4-yl]-piperazin-1-yl]-5-(2-fluoro-2-methyl-propoxy)-2-methyl-phenyl]-2-pyrrolidin-1-yl-ethyl)-amine: $^1$H NMR (400 MHz, d$_6$-DMSO) δ 10.60 (br s, 1H), 8.40 (s, 1H), 6.12 (d, 2H), 4.0 (d, 4H), 3.60 (m, 4H), 3.00 (m, 8H), 2.18 (s, 3H), 1.80 (m, 4H), 1.40 (d, 6H). MS (ESI) for $C_{26}H_{36}BrFN_8O$: 555 (MH$^+$).

N'-[3-[4-(3-Bromo-1H-pyrazolo[3,4-d]pyrimidin-4-yl]-piperazin-1-yl]-5-(2-fluoro-2-methyl-propoxy)-2-methyl-phenyl]-N,N-dimethyl-ethane-diamine: $^1$H NMR (400 MHz, d$_6$-DMSO) δ 10.80 (br s, 1H), 8.40 (s, 1H), 6.12 (d, 2H), 4.0 (d, 4H), 3.30 (t, 2H), 3.00 (s, 2H), 2.80 (s, 6H), 2.18 (s, 3H), 1.40 (d, 6H). MS (ESI) for $C_{24}H_{34}BrFN_8O$: 549 (MH$^+$).

N'-[3-[4-(3-Bromo-1H-pyrazolo[3,4-d]pyrimidin-4-yl]-piperazin-1-yl]-5-(2,3-difluoro-2-fluoromethylpropoxy)-2-methyl-phenyl]-N,N-dimethyl-ethane-1,2diamine: $^1$H NMR (400 MHz, d$_6$-DMSO) δ 10.80 (br s, 1H), 8.40 (s, 1H), 6.19 (d, 2H), 4.90 (dq, 2H), 4.80 (dq, 2H), 4.25 (d, 2H), 4.00 (br s, 4H), 3.50 (t, 2H), 3.23 (t, 2H), 3.00 (br s, 4H), 2.80 (s, 6H), 2.12 (s, 3H). MS (ESI) for $C_{24}H_{32}BrF_3N_8O$: 585 (MH$^+$).

3-Bromo-4-{4-[5-(2,3-difluoro-2-fluoromethyl-propoxy)-2-methyl-3-(3-pyrrolidin-1-yl-propyl)-phenyl]-piperazin-1-yl}-1H-pyrazolo[3,4-d]pyrimidine: $^1$H NMR (400 MHz, d$_6$-DMSO) δ 10.60 (br s, 1H), 8.40 (s, 1H), 6.60 (s, 2H), 4.90 (dq, 2H), 4.85 (dq, 2H), 4.25 (d, 2H), 3.80 (m, 6H), 3.19 (m, 2H), 3.00 (br m, 6H), 2.80 (m, 2H), 2.20 (s, 3H), 1.95 (m, 6H). MS (ESI) for $C_{27}H_{35}BrF_3N_7O$: 610 (MH$^+$).

3-Bromo-4-{4-[5-isobutoxy-2-methyl-3-(3-pyrrolidin-1-yl-propyl)-phenyl]-piperazin-1-yl}-1H-pyrazolo[3,4-d]pyrimidine: $^1$H NMR (400 MHz, d$_6$-DMSO) δ 10.23 (br s, 1H), 8.40 (s, 1H), 6.60 (d, 2H), 4.00 (br s, 4H), 3.70 (d, 2H), 3.20 (m, 2H), 3.00 (br s, 6H), 2.60 (m, 2H), 2.20 (s, 3H), 1.95 (m, 6H). MS (ESI) for $C_{27}H_{38}BrN_7O$: 556 (MH$^+$).

3-Bromo-4-{4-[3-Bromo-5-(2,3-difluoro-2-fluoromethyl-propoxy)-2-methyl-phenyl]-piperazin-1-yl}-1H-pyrazolo[3,4-d]pyrimidine: $^1$H NMR (400 MHz, d$_6$-DMSO) δ 8.40 (s, 1H), 7.05 (s, 1H), 6.80 (s, 1H), 4.90 (dq, 2H), 4.85 (dq, 2H), 4.32 (d, 2H), 4.00 (br s, 4H), 3.00 (br s, 4H), 2.20 (s, 3H). MS (ESI) for $C_{20}H_{21}Br_2F_3N_6O$: 579 (MH$^+$).

4-{4-[3-Bromo-5-(2,3-difluoro-2-fluoromethyl-propoxy)-2-methyl-phenyl]-piperazin-1-yl}-3-ethyl-1H-pyrazolo[3,4-d]pyrimidine: $^1$H NMR (400 MHz, d$_6$-DMSO) δ 8.40 (br s, 1H), 7.05 (s, 1H), 6.79 (s, 1H), 4.90 (dq, 2H), 4.85 (dq, 2H), 4.32 (d, 2H), 4.00 (br s, 4H), 3.00 (br s, 6H), 2.20 (s, 3H), 1.4 (t, 3H). MS (ESI) for $C_{22}H_{26}BrN_6O$: 526 (MH$^+$).

{3-[4-(3-Bromo-1H-pyrazolo[3,4-d]pyrimidin-4-yl]-piperazin-1-yl]-5-difluoromethoxy-2-methyl-phenyl}-(2-pyrrolidin-1-yl-ethyl)-amine: $^1$H NMR (400 MHz, d$_6$-DMSO) δ 8.40 (s, 1H), 7.25 (t, 1H), 6.25 (d, 2H), 4.00 (br s, 4H), 3.60 (m, 2H), 3.45 (t, 2H), 3.31 ((br t, 2H), 3.00 (br s, 6H), 2.18 (s, 3H), 1.95 (m, 4H). MS (ESI) for $C_{23}H_{29}BrF_2N_8O$: 551 (MH$^+$).

{3-[4-(3-Bromo-1H-pyrazolo[3,4-d]pyrimidin-4-yl]-piperazin-1-yl]-5-difluoromethoxymethyl-2-methyl-phenyl}-

(2-pyrrolidin-1-yl-ethyl)-amine: $^1$H NMR (400 MHz, d$_6$-DMSO) δ 10.95 (br s, 1H), 8.40 (s, 1H), 6.80 (t, 1H), 6.60 (d, 2H), 4.00 (br s, 4H), 3.60 (m, 2H), 3.55 (m, 2H), 3.39 (m, 2H), 3.00 (br s, 6H), 2.18 (s, 3H), 1.95 (m, 4H). MS (ESI) for C$_{24}$H$_{31}$BrF$_2$N$_8$O: 565 (MH$^+$).

3-Bromo-4-{4-[5-(2,3-difluoro-2-fluoromethyl-propoxy)-2-methyl-phenyl]-piperazin-1-yl}-1H-pyrazolo[3,4-d]pyrimidine: $^1$H NMR (400 MHz, d$_6$-DMSO) δ 8.40 (s, 1H), 7.15 (d, 1H), 6.70 (s, 1H), 6.65 (dd, 2H), 4.90 (dq, 2H), 4.85 (dq, 2H), 4.32 (d, 2H), 4.00 (br s, 4H), 3.00 (br s, 4H), 2.20 (s, 3H). MS (ESI) for C$_{20}$H$_{22}$F$_3$BrN$_6$O: 579 (MH$^+$).

[3-[4-(3-Bromo-1H-pyrazolo[3,4-d]pyrimidin-4-yl]-piperazin-1-yl]-4-methyl-5-(2-pyrrolidin-1-yl-ethylamino)-phenyl]-methanol: $^1$H NMR (400 MHz, d$_6$-DMSO) δ 10.95 (br s, 1H), 8.20 (s, 1H), 6.60 (d, 2H), 4.50 (s, 2H), 3.80 (m, 8H), 3.10 (br s, 6H), 2.18 (s, 3H), 1.99 (m, 4H). MS (ESI) for C$_{23}$H$_{31}$BrN$_8$O: 515 (MH$^+$).

5-{[2,3-Difluoro-2-(fluoromethyl)propyl]oxy}-3-[4-(3-ethyl-1H-pyrazolo[3,4-d]pyrimidin-4-yl)piperazin-1-yl]-2-methyl-N-(2-pyrrolidin-1-ylethyl)aniline: $^1$H NMR (400 MHz, d$_6$-DMSO) δ 9.58 (br s, 1H), 8.37 (br s, 1H), 6.08 (dd, 2H), 4.78 (m, 4H), 4.23 (d, 4H), 3.90 (br s, 4H), 3.65 (br s, 2H), 3.44 (t, 2H), 3.35 (br s, 2H), 3.01 (br m, 4H), 2.91 (br s, 4H), 2.06 (s, 3H), 1.89 (m, 4H), 1.29 (t, 3H). MS (ESI) for C$_{28}$H$_{39}$F$_3$N$_8$O: 561 (MH$^+$).

3-[4-(3-Bromo-1H-pyrazolo[3,4-d]pyrimidin-4-yl)piperazin-1-yl]-2-methyl-N-(2-pyrrolidin-1-ylethyl)-5-[(2,2,2-trifluoroethyl)oxy]aniline: $^1$H NMR (400 MHz, d$_6$-DMSO) δ 8.38 (s, 1H), 6.10 (s, 1H), 6.03 (s, 1H), 4.88 (t, 2H), 4.66 (q, 2H), 3.93 (m, 4H), 3.34 (m, 2H), 3.19 (q, 2H), 2.95 (q, 2H), 2.95 (m, 4H), 2.68 (t, 3H), 2.01 (s, 3H), 1.7 (m, 4H). MS (ESI) for C24H30BrF3N8O: 585 (MH$^+$).

Example 52

4-[4-(3-Bromo-5-chloro-2-methyl-phenyl)-piperazin-1-yl]-1H-pyrazolo[3,4-d]-pyrimidin-6-ylamine To a round bottom flask cooled to −78° C. was added 2-amino-4,6-dichloro-5-formyl-pyrimidine (576 mg, 3.0 mmol), dry THF (30.0 mL), DIEA (0.96 mL, 6.0 mmol), and 1-(5-chloro-2-methyl-phenyl)piperazine (630 mg, 3.0 mmol). The reaction was then warmed to rt, and stirred for 3 hr. The yellow precipitate was then filtered out, and the supernatant containing crude product was then concentrated to give crude 2-amino-4-chloro-6-[4-(5-chloro-2-methyl-phenyl)-piperazin-1-yl]-pyrimidine-5-carbaldehyde (1.0 g, 90% yield). $^1$H NMR, (400 MHz, d$_6$-DMSO) δ 9.88 (s, 1H), 7.65 (d, 2H), 7.20 (d, 1H), 7.00 (d, 1H), 3.62 (m, 4H), 2.98 (m, 4H), 2.42 (s, 3H), 2.20 (s, 3H). MS (ESI) for C$_{16}$H$_{17}$Cl$_2$N$_5$O: 366 (MH$^+$).

To a round bottom flask was added 2-amino-4-chloro-6-[4-(5-chloro-2-methyl-phenyl)-piperazin-1-yl]-pyrimidine-5-carbaldehyde (364 mg, 1.0 mmol), isopropanol (6.0 mL), and hydrazine (0.080 mL, 1.4 mmol). The reaction was heated to 80° C. overnight in a sealed tube before cooling to RT. Product precipitated out of the reaction mixture as a white solid, was filtered, rinsed with iPrOH and dried to give 4-[4-(5-chloro-2-methyl-phenyl)-piperazin-1-yl]-1H-pyrazolo[3,4-d]-pyrimidin-6-ylamine (220 mg, 64% yield): $^1$H NMR (400 MHz, d$_6$-DMSO) δ 12.80 (br s, 1H), 8.82 (s, 1H), 7.25 (d, 1H), 7.10 (m, 2H), 4.19 (m, 4H), 3.00 (br s, 4H), 2.30 (s, 3H). MS (ESI) for C$_{16}$H$_{18}$ClN$_7$: 344 (MH$^+$).

Example 53

4-[4-(3-bromo-5-chloro-2-methyl-phenyl)-piperazin-1-yl]-1H-pyrazolo[3,4-d]-pyrimidin-6-ylamine 4-[4-(3-Bromo-5-chloro-2-methyl-phenyl)-piperazin-1-yl]-1H-pyrazolo[3,4-d]-pyrimidin-6-ylamine: To a sealed tube was added 4-[4-(5-Chloro-2-methyl-phenyl)-piperazin-1-yl]-1H-pyrazolo[3,4-d]-pyrimidin-6-ylamine (85 mg, 0.25 mmol), water (1.5 mL), and bromine (0.014 mL, 0.27 mmol). The reaction was heated to 110° C. overnight in a sealed tube. Three compounds were detected by LC/MS: major portion was starting material, second one was unidentified, and third one was the desired product. The reaction was cooled to r.t. The brown precipitate was filtered and rinsed with water and purified by prep-HPLC to give 4-[4-(3-bromo-5-chloro-2-methyl-phenyl)-piperazin-1-yl]-1H-pyrazolo[3,4-d]-pyrimidin-6-ylamine (6.0 mg, 1.4%): $^1$H NMR (400 MHz, d$_6$-DMSO) δ 12.70 (br s, 1H), 8.82 (s, 1H), 7.61 (s, 1H), 7.23 (s, 1H), 4.19 (m, 4H), 3.00 (br s, 4H), 2.30 (s, 3H). MS (ESI) for C$_{16}$H$_{17}$BrClN$_7$: 422 (MH$^+$).

Example 54

(2E)-3-[4-(4-{5-{[2,3-Difluoro-2-(fluoromethyl) propyl]oxy}-2-methyl-3-[(2-pyrrolidin-1-ylethyl) amino]phenyl}piperazin-1-yl)-1H-pyrazolo[3,4-d] pyrimidin-3-yl]prop-2-enoic acid To a round bottom flask was added 4-[5-(2,3-difluoro-2-fluoromethyl-propoxy)-2-methyl-3-(2-pyrrolidin-1-yl-ethylamino)-phenyl]-piperazine-1-carboxylic acid tert-butyl ester (539 mg, 1.04 mmol), dry MeOH (2.0 mL) and 4N HCl in dioxane (2.0 mL). The reaction was stirred at RT for 1 hr, then concentrated to remove trace HCl. The residue was then dissolved in THF (20.0 mL), and triethyl amine (0.69 mL, 4.8 mmol), before adding 3-bromo-1-(tetrahydro-pyran-2-yl)-4-[1,2,4]triazol-1-yl-1H-pyrazolo[3,4-d]pyrimidine (420.0 mg, 1.2 mmol). The reaction was then stirred at 65° C. overnight, concentrated, extract with EtOAc and water, washed with saturated NaHCO$_3$, brine, and dried with Na$_2$SO$_4$, concentrated and columned with 20:80 CH$_2$Cl$_2$ to give [3-{4-[3-bromo-1-(tetrahydro-pyran-2-yl)-1H-pyrazolo[3,4-d]-pyrimidin-4-yl}-5-(2,3-difluoro-2-fluoromethyl-propxy)-2-methyl-phenyl]-(2-pyrrolidin-1-yl-ethyl)-amine as a pale yellow solid (509 mg, 61% yield). $^1$H NMR, (400 MHz, d$_6$-DMSO) δ 8.40 (s, 1H), 6.08 (d, 2H), 5.90 (dd, 1H), 4.80 (m, 5H), 4.22 (d, 2H), 3.98 (m, 4H), 3.68 (m, 1H), 3.19 (q, 2H), 2.98 (br s, 4H), 2.40 (dq, 2H), 2.0 (m, 5H), 1.80-1.60 (m, 8H). MS (ESI) for C$_{31}$H$_{42}$BrF$_3$N$_8$O$_2$: 695 (MH$^+$).

To a sealed tube was added [3-{4-[3-bromo-1-(tetrahydro-pyran-2-yl)-1H-pyrazolo[3,4-d]-pyrimidin-4-yl}-5-(2,3-difluoro-2-fluoromethyl-propxy)-2-methyl-phenyl]-(2-pyrrolidin-1-yl-ethyl)-amine (130 mg, 0.19 mmol), DMF (3.0 mL), triethylamine (0.23 mL, 1.9 mmol), CuI (12 mg, 0.06 mmol), and tert-butyldimethyl-(2-propynyloxy)-silane (0.11 mL, 0.56 mmol). The reaction mixture was purged with nitrogen before adding Pd(PPh$_3$)$_4$ (23 mg, 0.02 mmol). The tube was sealed and heated to 105° C. overnight and cooled to RT, filtered through celite, rinsed with MeOH and columned with 5:95 MeOH:CH$_2$Cl$_2$ to give [3-{4-[3-[3-(tert-butyl-dimethyl-silanyloxy)-prop-1-ynyl]-1-(tetrahydro-pyran-2-yl)-1H-pyrazolo[3,4-d]pyrimidin-4-yl)-piperazin-1-yl}-5-(2,3-difluoro-2-fluoromethyl-propoxy)-2-methyl-phenyl]-(2-pyrrolidin-1-yl-ethyl)-amine (113 mg, 65% yield). MS (ESI) for C$_{40}$H$_{59}$F$_3$N$_8$O$_3$Si: 785 (MH$^+$).

To a round bottom flask was added [3-{4-[3-[3-(tert-butyl-dimethyl-silanyloxy)-prop-1-ynyl]-1-(tetrahydro-pyran-2-yl)-1H-pyrazolo[3,4-d]pyrimidin-4-yl)-piperazin-1-yl}-5-(2,3-difluoro-2-fluoromethyl-propoxy)-2-methyl-phenyl]-(2-pyrolidin-1-yl-ethyl)-amine (113 mg, 0.14 mmol), MeOH (2.0 mL), and 4N HCl in dioxane (2.0 mL). The reaction was stirred at RT for 15 min, concentrated, prep purified and converted to the HCl salt to give 3-(4-{4-[5-(2,3-difluoro-2- fluoromethyl-propxy)-2-methyl-3-(2-pyrrolidin-1-yl-ethylamino)-phenyl]-piperazin-1-yl}-1H-pyrazolo[3,4-d]pyrimidin-3-yl)-prop-2-yn-1-ol as a white solid (48.0 mg, 65% yield): $^1$H NMR (400 MHz, d$_6$-DMSO) δ 10.60 (br s, 1H), 8.40 (br s, 1H), 6.10 (d, 2H), 4.83 (dq, 4H), 4.79 (dq, 4H), 4.40 (s, 1H), 4.30 (d, 2H), 3.60 (m, 6H), 3.35 (br s, 4H), 3.00 (br s, 6H), 2.05 (s, 3H), 1.95 (m, 4H). MS (ESI) for C$_{29}$H$_{37}$F$_3$N$_8$O$_2$: 587 (MH$^+$).

Example 55

(2E)-3-[4-(4-{5-{[2,3-Difluoro-2-(fluoromethyl) propyl]oxy}-2-methyl-3-[(2-pyrrolidin-1-ylethyl) amino]phenyl}piperazin-1-yl)-1H-pyrazolo[3,4-d] pyrimidin-3-yl]prop-2-enoic acid To a sealed tube was added [3-{4-[3-bromo-1-(tetrahydro-pyran-2-yl)-1H-pyrazolo[3,4-d]pyrimidin-4-yl]-piperazin-1-yl}-5-(2,3-difluoro-2-fluoromethyl-propoxy)-2-methyl-phenyl]-(2-pyrrolidin-1-yl-ethyl)-amine (250 mg, 0.36 mmol), DMF (3.0 mL), potassium phosphate tribasic (382 mg, 1.8 mmol), and t-butyl acrylate (0.29 mL, 1.44 mmol). The reaction mixture was purged with nitrogen before adding Pd(dppf)Cl$_2$CH$_2$Cl$_2$ (59 mg, 0.072 mmol). The tube was sealed and heated to 120° C. overnight and cooled to RT, filtered through celite, rinsed with MeOH and concentrated to give crude 3-[4-{4-[5-(2,3-difluoro-2-fluoromethyl-propoxy)-2-methyl-3-(2-pyrrolidin-1-yl-ethylamino)-phenyl]-piperazin-1-yl}-1-(tetrahydro-pyran-2-yl)-1H-pyrazolo[3,4-d]pyrimidin-3-yl]-acrylic acid tert-butyl ester which was carried to the next step without further purification. MS (ESI) for C$_{38}$H$_{53}$F$_3$N$_8$O$_4$: 743 (MH$^+$).

To a round bottom flask was added 3-[4-{4-[5-(2,3-difluoro-2-fluoromethyl-propoxy)-2-methyl-3-(2-pyrrolidin-1-yl)-1-yl-(tetrahydro-pyran-2-yl)-1H-pyrazolo[3,4-d]pyrimidin-3-yl]-acrylic acid tert-butyl ester (250 mg, 0.33 mmol), CH$_2$Cl$_2$ (2.0 mL), and TFA (2.0 mL). The reaction was stirred at r.t. for 2 hr, concentrated, prep purified and converted to the HCl salt to give (2E)-3-[4-(4{5-{[2,3-difluoro-2-(fluoromethyl)propyl]oxy}-2-methyl-3-[(2-pyrrolidin-1-ylethyl) amino]phenyl}piperazin-1-yl)-1H-pyrazolo[3,4-d]pyrimidin-3-yl]prop-2-enoic acid as a yellow solid (102.0 mg, 51% yield over two steps): $^1$H NMR (400 MHz, d$_6$-DMSO) δ 9.42 (br s, 1H), 7.75 (d, 2H), 6.60 (d, 2H), 4.80 (m, 4H), 4.22 (d, 2H), 3.00 (m, 8H), 2.05 (s, 3H), 1.95 (m, 4H). MS (ESI) for C$_{29}$H$_{37}$F$_3$N$_8$O$_3$: 603 (MH$^+$).

Using the same or analogous synthetic techniques and/or substituting with alternative reagents, the following compounds of the invention were prepared:

4-[4-(3-Bromo-1H-pyrazolo[3,4-d]pyrimidin-4-yl)piperazin-1-yl]-2-methylquinoline. $^1$H NMR (400 MHz, d$_6$-DMSO) δ 8.40 (s, 1H), 8.08 (d, 1H), 7.88 (d, 1H), 7.68 (t, 1H), 7.52 (t, 1H), 6.98 (s, 1H), 4.10 (m, 4H), 3.35 (m, 4H), 2.58 (s, 3H). MS (ESI) for C$_9$H$_{18}$BrN$_7$: 424 (MH$^+$).

3-Bromo-4-[4-(3,5-dichlorophenyl)piperazin-1-yl]-1H-pyrazolo[3,4-d]pyrimidine: MS (ESI) for C$_{15}$H$_{13}$BrCl$_2$N$_6$: 429 (MH$^+$).

3-[4-[4-(3-Bromo-1H-pyrazolo[3,4-d]pyrimidin-4-yl) piperazin-1-yl]-1-methyl-6-(trifluoromethyl)-1H-benzimidazol-2-yl]propan-1-ol: $^1$H NMR (400 MHz, CDCl$_3$) δ 8.42 (s, 1H), 7.24 (s, 1H), 6.89 (s, 1H), 4.19 (m, 4H), 3.86 ((q, 2H), 3.79 (s, 3H), 3.70 (m, 4H), 3.12 (t, 2H), 2.20 (m, 2H). MS ESI) for C$_{21}$H$_{22}$BrF$_3$N$_8$O: 541 (MH$^+$).

3-[4-(3-Bromo-1H-pyrazolo[3,4-d]pyrimidin-4-yl)piperazin-1-yl]-2-methyl-N-(2-pyrrolidin-1-ylethyl)-5-[4,4,4-trifluoro-1,1-bis(methyloxy)butyl]aniline $^1$H NMR (400 MHz, d$_6$-DMSO) δ 8.33 (s, 1H), 6.45 (s, 1H), 6.38 (s, 1H), 4.8 (br. 1H), 3.9 (br. 4H), 3.15 (q, 2H), 3.05 (s, 6H), 2.91 (br. 4H), 2.61 (t, 2H), 2.45 (m, 4H), 2.04 (s, 3H), 2.00 (m, 2H), 1.8 (m, 2H), 1.67 (br. 4H). MS (ESI) for C$_{28}$H$_{39}$BrF$_3$N$_9$O$_2$: 657 (MH$^+$).

3-Bromo-4-{4-[4-(trifluoromethyl)pyridin-2-yl]piperazin-1-yl}-1H-pyrazolo[3,4-d]pyrimidine: $^1$H NMR (400 MHz, d$_6$-DMSO) δ 14.12 (br. s, 1H), 8.38 (m, 2H), 7.19 (br s, 1H), 6.95 (br d, J=5.2 Hz, 1H), 3.95 (m, 4H), 3.84 (m, 4H). MS (ESI) for C$_{15}$H$_{13}$BrF$_3$N$_7$: 430 (MH$^+$).

3-Bromo-4-{4-[4-(trifluoromethyl)pyrimidin-2-yl]piperazin-1-yl}-1H-pyrazolo[3,4-d]pyrimidine: $^1$H NMR (400 MHz, d$_6$-DMSO) δ 14.10 (br. s, 1H), 8.75 (d, J=4.8 Hz, 1H), 8.38 (s, 1H), 7.10 (d, J=4.8 Hz, 1H), 3.99 (m, 4H), 3.92 (m, 4H). MS (ESI) for C$_{14}$H$_{12}$BrF$_3$N$_8$: 431 (MH$^+$).

2-({3-[4-(3-Bromo-1H-pyrazolo[3,4-d]pyrimidin-4-yl) piperazin-1-yl]pyrazin-2-yl}oxy)-N,N-dimethylethanamine: $^1$H NMR (400 MHz, d$_6$-DMSO) δ 14.10 (br s, 1H), 8.38 (s, 1H), 7.87 (d, J=2.9 Hz, 1H), 7.68 (d, J=2.9 Hz, 1H), 4.66 (m, 2H), 3.92 (4H), 3.67 (m, 4H), 3.61 (m, 2H), 2.91 (m, 6H). MS (ESI) for C$_{17}$H$_{22}$BrN$_9$O: 430 (MH$^+$).

3-Bromo-4-{4-[3-(methyloxy)pyrazin-2-yl]piperazin-1-yl}-1H-pyrazolo[3,4-d]pyrimidine: $^1$H NMR (400 MHz, d$_6$-DMSO) δ 14.20 (s, 1H), 8.37 (s, 1H), 7.80 (d, J=2.7 Hz, 1H), 7.67 (d, J=2.9 Hz, 1H), 3.94 (s, 3H), 3.92 (m, 4H), 3.65 (m, 4H). MS (ESI) for C$_{14}$H$_{15}$BrN$_8$O: 391 (MH$^+$).

4-(3-Bromo-1H-pyrazolo[3,4-d]pyrimidin-4-yl)-1-(5-chloro-2-methylphenyl)piperazin-2-one: $^1$H NMR (400 MHz, d$_6$-DMSO) δ 14.12 (br s, 1H), 8.42 (s, 1H), 7.43 (br s, 1H), 7.34 (m, 2H), 4.56 (m, 2H), 4.38 (m, 1H), 4.21 (m, 1H), 3.87 (m, 1H), 3.63 (m, 1H), 2.12 (s, 3H). MS (ESI) for C$_{16}$H$_{14}$BrClN$_6$O: 421 (MH$^+$).

3-({6-[4-(3-Bromo-1H-pyrazolo[3,4-d]pyrimidin-4-yl) piperazin-1-yl]-2-chloro-5-methylpyrimidin-4-yl}oxy)-N, N-diethylpropan-1-amine: $^1$H NMR (400 MHz, CDCl$_3$) δ 8.37 (s, 1H), 4.40 (t, 2H), 4.10 (m, 4H), 3.64 (m, 4H), 3.17 (m, 6H), 2.33 (m, 2H), 2.25 (s, 3H), 1.38 (t, 6H). MS (ESI) for C$_{21}$H$_{29}$BrClN$_9$O: 538 (MH$^+$).

3-({4-[4-(3-Bromo-1H-pyrazolo[3,4-d]pyrimidin-4-yl) piperazin-1-yl]-6-chloro-5-methylpyrimidin-2-yl}oxy)-N, N-diethylpropan-1-amine: $^1$H NMR (400 MHz, d$_6$-DMSO) δ 8.37 (s, 1H), 4.35 (t, 2H), 3.91 (m, 4H), 3.56 (m, 4H), 3.08 (m, 6H), 2.07 (m, 5H), 1.15 (m, 6H). MS (ESI) for C$_{21}$H$_{29}$BrClN$_9$O: 538 (MH$^+$).

3-[4-(3-Bromo-1H-pyrazolo[3,4-d]pyrimidin-4-yl)piperazin-1-yl]-2-methyl-5-(5-methyl-1,2,4-oxadiazol-3-yl)-N-(2-pyrrolidin-1-ylethyl)aniline: $^1$H NMR (400 MHz, d$_6$-DMSO) δ 8.38 (s, 1H), 7.05 (s, 1H), 6.99 (s, 1H), 5.09 (t, 1H), 3.97 (br s, 8H), 3.24 (m, 2H), 3.02 (br s, 4H), 2.69 (t, 2H), 2.64 (s, 3H), 2.14 (s, 3H), 1.71 (m, 4H). MS (ESI) for C$_{25}$H$_{31}$BrN$_{10}$O: 567 (MH$^+$).

3-Bromo-4-[(3S)-4-(5-chloro-2-methylphenyl)-3-methylpiperazin-1-yl]-1H-pyrazolo[3,4-d]pyrimidine: $^1$H NMR (400 MHz, d$_6$-DMSO) δ 8.36 (s, 1H), 7.25 (m, 2H), 7.11 (dd, 1H), 4.38 (d, 1H), 4.28 (d, 1H), 3.56 (m, 1H), 3.38 (m, 1H), 3.23 (m, 1H), 3.07 (m, 1H), 2.80 (m, 1H), 2.29 (s, 3H), 0.84 (d, 3H). MS (ESI) for C$_{17}$H$_{18}$BrClN$_6$: 421 (MH$^+$).

3-Bromo-4-[(3R)-4-(5-chloro-2-methylphenyl)-3-methylpiperazin-1-yl]-1H-pyrazolo[3,4-d]pyrimidine: $^1$H NMR (400 MHz, CDCl$_3$) δ 12.2 (s, 1H), 8.41 (s, 1H), 7.09 (m, 3H), 4.57 (m, 1H), 4.48 (m, 1H), 3.60 (m, 1H), 3.33 (m, 1H), 3.28 (m, 1H), 3.06 (m, 1H), 2.88 (m, 1H), 2.32 (s, 3H), 0.94 (d, 3H). MS (ESI) for C$_{17}$H$_{18}$BrClN$_6$: 421 (MH$^+$).

2-({3-[4-(3-Bromo-1H-pyrazolo[3,4-d]pyrimidin-4-yl) piperazin-1-yl]phenyl}oxy)-N-ethylacetamide: $^1$H NMR (400 MHz, CDCl$_3$) δ 11.92 (br s, 1H), 8.42 (s, 1H), 7.21-7.19 (m, 1H), 6.65-6.63 (m, 1H), 6.56 (m, 1H), 6.52 (s, 1H), 6.45-6.43 (m, 1H), 4.48 (s, 2H), 4.09-4.06 (m, 4H), 3.41-3.40 (m, 6H), 1.21-1.18 (t, 3H). MS (ESI) for $C_{19}H_{22}BrN_7O_2$: 460 (MH$^+$).

2-[4-(3-Bromo-1H-pyrazolo[3,4-d]pyrimidin-4-yl)piperazin-1-yl]-N,N-dimethylpyrimidin-4-amine: $^1$H NMR (400 MHz, CDCl$_3$) δ 12.10 (br s, 1H), 8.40 (s, 1H), 7.91-7.89 (d, 1H), 5.82-5.80 (d, 1H), 3.99-3.96 (m, 8H), 3.47 (m, 4H), 1.20-1.17 (t, 6H). MS (ESI) for $C_{17}H_{22}BrN_9$: 432 (MH$^+$).

3-Bromo-4-[4-(3-{[(3-methylphenyl)methyl]oxy}phenyl)piperazin-1-yl]-1H-pyrazolo[3,4-d]pyrimidine: $^1$H NMR (400 MHz, CDCl$_3$) δ 11.35 (br s, 1H), 8.39 (s, 1H), 7.39-7.37 (m, 1H), 7.25-7.23; (m, 1H), 7.22-7.19 (m, 2H), 6.94 (s, 4H), 4.99 (s, 2H), 4.09-4.06 (m, 4H), 3.28-3.25 (m, 4H), 2.37 (s, 3H). MS (ESI) for $C_{23}H_{23}BrN_6O$: 479 (MH$^+$).

3-Bromo-4-(4-{3-[(2-piperidin-1-ylethyl)oxy]phenyl}piperazin-1-yl)-1H-pyrazolo[3,4-d]pyrimidine: $^1$H NMR (400 MHz, CDCl$_3$) δ 8.43 (s, 1H), 6.94-6.92 (d, 2H), 6.87-6.84 (d, 2H), 4.09-4.07 (m, 6H), 3.27-3.25 (m, 4H), 2.78-2.75 (t, 2H), 2.52 (m, 4H), 1.64-1.59 (m, 4H), 1.45 (m, 2H). MS (ESI) for $C_{22}H_{28}BrN_7O$: 486 (MH$^+$).

3-Bromo-4-(4-(4-furan-2-ylpyrimidin-2-yl)piperazin-1-yl]-1H-pyrazolo[3,4-d]pyrimidine: $^1$H NMR (400 MHz, CDCl$_3$) δ 11.56 (br s, 1H), 8.44 (s, 1H), 8.40-8.39 (d, 1H), 7.58-7.58 (m, 1H), 7.22-7.21 (m, 1H), 6.94-6.93 (d, 1H), 6.57-6.56 (m, 1H), 4.11-4.09 (m, 4H), 4.05-4.03 (m, 4H). MS (ESI) for $C_{17}H_{15}BrN_8O$: 427 (MH$^+$).

6-{2-[4-(3-Bromo-1H-pyrazolo[3,4-d]pyrimidin-4-yl)piperazin-1-yl]pyrimidin-4-yl}-2H-1,4-benzoxazin-3(4H)-one: $^1$H NMR (400 MHz, d$_6$-DMSO) δ 14.10 (br s, 1H), 10.85 (s, 1H), 8.46-8.44 (d, 1H), 8.38 (s, 1H), 7.79 (s, 1H), 7.74-7.71 (d, 1H), 7.14-7.13 (d, 1H), 7.07-7.05 (d, 1H), 4.66 (s, 2H), 4.05 (m, 4H), 3.94-3.92 (m, 4H). MS (ESI) for $C_{21}H_{18}BrN_9O_2$: 508 (MH$^+$).

2-({3-[4-(3-Bromo-1H-pyrazolo[3,4-d]pyrimidin-4-yl)piperazin-1-yl]phenyl}oxy)-N-cyclopropylacetamide: $^1$H NMR (400 MHz, CDCl$_3$) δ 8.32 (s, 1H), 7.25-7.21 (m, 1H), 6.68 (br s, 1H), 6.65-6.63 (m, 1H), 6.51-6.47 (m, 2H), 4.50 (s, 2H), 4.36-4.33 (m, 4H), 3.45-3.42 (m, 4H), 2.81-2.78 (m, 1H), 0.88-0.83 (m, 2H), 0.61-0.57 (m, 2H). MS (ESI) for $C_{20}H_{22}BrN_7O_2$: 472 (MH$^+$).

3-Bromo-4-(4-{3-[(2-piperidin-1-ylethyl)oxy]pyrazin-2-yl}piperazin-1-yl)-1H-pyrazolo[3,4-d]pyrimidine: $^1$H NMR (400 MHz, CDCl$_3$) δ 12.48 (br s, 1H), 8.28 (s, 1H), 7.82-7.81 (d, 1H), 7.60-7.59 (m, 1H), 4.86-4.84 (t, 2H), 4.26-4.23 (m, 4H), 3.79-3.72 (m, 6H), 3.51-3.48 (t, 2H), 2.77-2.71 (m, 4H), 2.06-1.98 (m, 2H), 1.91-1.89 (m, 2H). MS (ESI) for $C_{20}H_{26}BrN_9O$: 488 (MH$^+$).

3-Bromo-4-[4-(2,4-dichlorophenyl)piperazin-1-yl]-1H-pyrazolo[3,4-d]pyrimidine: $^1$H NMR (400 MHz, d$_6$-DMSO) δ 8.35 (s, 1H), 7.57 (d, 1H), 7.37 (dd, 1H), 7.21 (d, 1H), 3.94 (t, 4H), 3.14 (t, 4H). MS (ESI) for $C_{15}H_{13}BrCl_2N_6$: 427 (MH$^+$)

4-{4-[3,5-Bis-(methyloxy)phenyl]piperazin-1-yl}-3-bromo-1H-pyrazolo[3,4-d]pyrimidine: $^1$H NMR (400 MHz, d$_6$-DMSO) δ 8.35 (s, 1H), 6.19 (d, 2H), 6.02 (t, 1H), 3.94 (t, 4H), 3.70 (s, 6H), 3.36 (t, 4H). MS (ESI) for $C_{17}H_{19}BrN_6O_2$: 419 (MH$^+$).

3-Bromo-4-[4-(3,4-dimethylphenyl)piperazin-1-yl]-1H-pyrazolo[3,4-d]pyrimidine: $^1$H NMR (400 MHz, d$_6$-DMSO) δ 8.35 (s, 1H), 6.98 (d, 1H), 6.84 (d, 1H), 6.74 (d, 1H), 3.91 (br s, 4H), 3.28 (br s, 4H), 2.18 (s, 3H), 2.12 (s, 3H). MS (ESI) for $C_{17}H_{19}BrN_6$: 387 (MH$^+$).

3-Bromo-4-[4-(4-nitrophenyl)piperazin-1-yl]-1H-pyrazolo[3,4-d]pyrimidine: $^1$H NMR (400 MHz, d$_6$-DMSO) δ 8.35 (s, 1H), 8.07 (d, 2H), 7.05 (d, 2H), 3.96 (t, 4H), 3.71 (t, 4H). MS (ESI) for $C_{15}H_{14}BrN_7O_2$: 404 (MH$^+$).

3-Bromo-4-[4-(2,6-dimethylphenyl)piperazin-1-yl]-1H-pyrazolo[3,4-d]pyrimidine: $^1$H NMR (400 MHz, d$_6$-DMSO) δ 8.33 (s, 1H), 6.97 (m, 3H), 3.91 (t, 4H), 3.18 (t, 4H), 2.39 (s, 6H). MS (ESI) for $C_{17}H_{19}BrN_6$: 387 (MH$^+$).

3-Bromo-4-{4-[4-(ethyloxy)phenyl]piperazin-1-yl}-1H-pyrazolo[3,4-d]pyrimidine: $^1$H NMR (400 MHz, d$_6$-DMSO) δ 8.35 (s, 1H), 6.97 (d, 2H), 6.84 (d, 2H), 3.95 (m, 4H), 3.25 (br t, 4H), 1.29 (t, 3H). MS (ESI) for $C_{17}H_{19}BrN_6O$: 403 (MH$^+$).

3-Bromo-4-[4-(2-ethylphenyl)piperazin-1-yl]-1H-pyrazolo[3,4-d]pyrimidine: $^1$H NMR (400 MHz, d$_6$-DMSO) δ 8.35 (s, 1H), 7.23 (dd, 1H), 7.14 (m, 2H), 7.04 (dt, 1H), 3.95 (br s, 4H), 2.99 (t, 4H), 2.73 (q, 2H), 1.22 (t, 3H). MS (ESI) for $C_{17}H_{19}BrN_6$: 387 (MH$^+$).

3-Bromo-4-[4-(2-nitrophenyl)piperazin-1-yl]-1H-pyrazolo[3,4-d]pyrimidine: $^1$H NMR (400 MHz, d$_6$-DMSO) δ 8.35 (s, 1H), 7.84 (dd, 1H), 7.60 (dt, 1H), 7.38 (dd, 1H), 7.15 (dt, 1H), 3.92 (t, 4H), 3.22 (t, 4H). MS (ESI) for $C_{15}H_{14}BrN_7O_2$: 404 (MH$^+$).

2-[4-(3-Bromo-1H-pyrazolo[3,4-d]pyrimidin-4-yl)piperazin-1-yl]benzonitrile: $^1$H NMR (400 MHz, d$_6$-DMSO) δ 8.36 (s, 1H), 7.73 (d, 1H), 7.61 (t, 1H), 7.22 (d, 1H), 7.12 (t, 1H), 3.98 (br s, 4H), 3.33 (br s, 4H). MS (ESI) for $C_{16}H_{14}BrN_7$: 384 (MH$^+$).

4-[4-(3-Bromo-1H-pyrazolo[3,4-d]pyrimidin-4-yl)piperazin-1-yl]benzonitrile: $^1$H NMR (400 MHz, d$_6$-DMSO) δ 8.35 (s, 1H), 7.60 (d, 2H), 7.05 (d, 2H), 3.93 (t, 4H), 3.58 (t, 4H). MS (ESI) for $C_{16}H_{14}BrN_7$: 384 (MH$^+$).

3-Bromo-4-{4-[4-(trifluoromethyl)phenyl]piperazin-1-yl}-1H-pyrazolo[3,4-d]pyrimidine: $^1$H NMR (400 MHz, d$_6$-DMSO) δ 8.36 (s, 1H), 7.25 (d, 2H), 7.11 (d, 2H), 3.94 (t, 4H), 3.50 (t, 4H). MS (ESI) for $C_{16}H_{14}BrF_3N_6$: 427 (MH$^+$).

3-Bromo-4-(4-{4-[(phenylmethyl)oxy]phenyl}piperazin-1-yl)-1H-pyrazolo[3,4-d]pyrimidine: $^1$H NMR (400 MHz, d$_6$-DMSO) δ 8.36 (s, 1H), 7.40 (m, 5H), 6.95 (q, 4H), 5.04 (s, 2H), 3.93 (t, 4H), 3.46 (t, 4H). MS (ESI) for $C_{22}H_{21}BrN_6O$: 465 (MH$^+$).

2-[4-(3-Bromo-1H-pyrazolo[3,4-d]pyrimidin-4-yl)piperazin-1-yl]pyridine-3-carbonitrile: $^1$H NMR (400 MHz, d$_6$-DMSO) δ 8.42 (dd, 1H), 8.35 (s, 1H), 8.09 (dd, 1H), 6.96 (q, 1H), 3.93 (m, 4H), 3.46 (m, 4H). MS (ESI) for $C_{15}H_{13}BrN_8$: 385 (MH$^+$).

3-Bromo-4-[4-(2,3-dichlorophenyl)piperazin-1-yl]-1H-pyrazolo[3,4-d]pyrimidine: $^1$H NMR (400 MHz, d$_6$-DMSO) δ 8.37 (s, 1H), 7.34 (m, 2H), 7.22 (m, 1H), 3.97 (t, 4H), 3.17 (t, 4H). MS (ESI) for $C_{15}H_{13}BrCl_2N_6$: 427 (MH$^+$).

3-Bromo-4-{4-[2-(trifluoromethyl)phenyl]piperazin-1-yl}-1H-pyrazolo[3,4-d]pyrimidine: $^1$H NMR (400 MHz, d$_6$-DMSO) δ 8.37 (s, 1H), 7.68 (m, 3H), 7.37 (m, 1H), 3.94 (br m, 4H), 3.05 (t, 4H). MS (ESI) for $C_{16}H_{14}BrF_3N_6$: 427 (MH$^+$).

2-({3-[4-(3-Bromo-1H-pyrazolo[3,4-d]pyrimidin-4-yl)piperazin-1-yl]phenyl}oxy)-N,N-diethylethanamine: $^1$H NMR (400 MHz, d$_6$-DMSO) δ 9.40 (br s, 1H), 8.35 (s, 1H), 7.16 (t, 1H), 6.64 (d, 1H), 6.58 (s, 1H), 6.45 (d, 1H), 4.28 (t, 2H), 3.92 (br s, 2H), 3.49 (d, 4H), 3.35 (br s, 4H), 3.21 (q, 4H), 1.23 (t, 6H). MS (ESI) for $C_{21}H_{28}BrN_7O$: 474 (MH$^+$).

3-[4-(3-Bromo-1H-pyrazolo[3,4-d]pyrimidin-4-yl)piperazin-1-yl]-2-methyl-5-(methyloxy)-N-(2-pyrrolidin-1-ylethyl)aniline: $^1$H NMR (400 MHz, d$_6$-DMSO) δ 9.40 (br s, 1H), 8.36 (s, 1H), 6.06 (d, 1H), 5.99 (d, 1H), 3.85 (br m, 4H), 3.69 (s, 3H), 3.62 (br m, 4H), 3.43 (t, 2H), 3.35 (m, 2H), 3.05 (br s, 4H), 2.94 (br s, 4H), 2.05 (s, 3H), 1.85 (br m, 4H). MS (ESI) for $C_{23}H_{31}BrN_8O$: 515 (MH$^+$).

3-Bromo-4-[4-(3',4',6-trifluoro-4-methylbiphenyl-3-yl)piperazin-1-yl]-1H-pyrazolo[3,4-d]pyrimidine: $^1$H NMR (400 MHz, d$_6$-DMSO) δ 8.37 (s, 1H), 7.63 (m, 1H), 7.52 (m, 1H), 7.42 (br m, 1H), 7.20 (d, 1H), 7.18 (s, 1H), 3.96 (br s, 4H), 3.07 (t, 4H), 2.36 (s, 3H). MS (ESI) for $C_{22}H_{18}BrF_3N_6$: 503 (MH$^+$).

3-Bromo-4-[4-(3,4-dichlorophenyl)piperazin-1-yl]-1H-pyrazolo[3,4-d]pyrimidine: MS (ESI) for $C_{15}H_{13}BrCl_2N_6$: 428 (MH$^+$).

3-Bromo-4-[4-(3,4-difluorophenyl)piperazin-1-yl]-1H-pyrazolo[3,4-d]pyrimidine: MS (ESI) for $C_{15}H_{13}BrF_2N_6$: 394 (MH$^+$).

3-Bromo-4-[4-(3-chloro-4-fluorophenyl)piperazin-1-yl]-1H-pyrazolo[3,4-d]pyrimidine: $^1$H NMR (400 MHz, $d_6$-DMSO) δ 8.39 (s, 1H), 7.29 (t, 1H), 7.19 (m, 1H), 7.02 (m, 1H), 3.92 (t, 4H), 3.33 (t, 4H). MS (ESI) for $C_{15}H_{13}BrClFN_6$: 412 (MH$^+$).

1-{4-[4-(3-Bromo-1H-pyrazolo[3,4-d]pyrimidin-4-yl)piperazin-1-yl]phenyl}ethanone: MS (ESI) for $C_{17}H_{17}BrN_6O$: 403 (MH$^+$).

3-Bromo-4-[4-(2,5-dichlorophenyl)piperazin-1-yl]-1H-pyrazolo[3,4-d]pyrimidine: $^1$H NMR (400 MHz, $d_6$-DMSO) δ 8.39 (s, 1H), 7.49 (d, 1H), 7.26 (d, 1H), 7.16 (dd, 1H), 3.95 (m, 4H), 3.20 (m, 4H). MS (ESI) for $C_{15}H_{13}BrCl_2N_6$: 428 (MH$^+$).

4-{4-[2,4-Bis(methyloxy)phenyl]piperazin-1-yl}-3-bromo-1H-pyrazolo[3,4-d]pyrimidine: MS (ESI) for $C_{17}H_{19}BrN_6O_2$: 421 (MH$^+$).

3-Bromo-4-(4-pyrazin-2-ylpiperazin-1-yl)-1H-pyrazolo[3,4-d]pyrimidine: MS (ESI) for $C_{13}H_{13}BrN_8$: 361 (MH$^+$).

3-Bromo-4-(4-pyrimidin-2-ylpiperazin-1-yl)-1H-pyrazolo[3,4-d]pyrimidine: MS (ESI) for $C_{13}H_{13}BrN_8$: 361 (MH$^+$).

4-[4-(3-Bromo-1H-pyrazolo[3,4-d]pyrimidin-4-yl)piperazin-1-yl]-2-(trifluoromethyl)quinoline: $^1$H NMR (400 MHz, $d_6$-DMSO) δ 8.39 (s, 1H) 8.21 (d, 1H), 8.09 (d, 1H), 7.84 (t, 3H), 7.73 (t, 3H), 7.34 (s, 1H), 4.11 (m, 4H), 3.54 (m, 4H). MS (ESI) for $C_{19}H_{15}BrF_3N_7$: 480 (MH$^+$).

3-[4-(3-Bromo-1H-pyrazolo[3,4-d]pyrimidin-4-yl)piperazin-1-yl]pyrazine-2-carbonitrile: MS (ESI) for $C_{14}H_{12}BrN_9$: 386 (MH$^+$).

3-Bromo-4-[4-(3-chlorophenyl)piperazin-1-yl]-1H-pyrazolo[3,4-d]pyrimidine: $^1$H NMR (400 MHz, $d_6$-DMSO) δ 8.38 (s, 1H), 7.22 (t, 1H), 7.01 (s, 1H), 6.97 (d, 1H), 6.81 (d, 1H), 3.91 (t, 4H), 3.40 (t, 4H). MS (ESI) for $C_{15}H_{14}BrClN_6$: 395 (MH$^+$).

3-Bromo-4-{4-[3-(trifluoromethyl)pyridin-2-yl]piperazin-1-yl}-1H-pyrazolo[3,4-d]pyrimidine: MS (ESI) for $C_{15}H_{13}BrF_3N_7$: 429 (MH$^+$).

3-Bromo-4-{4-[3-chloro-5-(trifluoromethyl)pyridin-2-yl]piperazin-1-yl}-1H-pyrazolo[3,4-d]pyrimidine: MS (ESI) for $C_{15}H_{12}BrClF_3N_7$: 464 (MH$^+$).

3-Bromo-4-(4-phenylpiperazin-1-yl)-1H-pyrazolo[3,4-d]pyrimidine: $^1$H NMR (400 MHz, $d_6$-DMSO) δ 8.38 (s, 1H), 7.24 (t, 2H), 7.02 (d, 2H), 6.83 (t, 1H), 3.94 (t, 4H), 3.37 (t, 4H). MS (ESI) for $C_{15}H_{15}BrN_6$: 360 (MH$^+$).

3-Bromo-4-[4-(4-fluorophenyl)piperazin-1-yl]-1H-pyrazolo[3,4-d]pyrimidine: MS (ESI) for $C_{15}H_{14}BrFN_6$: 378 (MH$^+$).

3-Bromo-4-[4-(4-chlorophenyl)piperazin-1-yl]-1H-pyrazolo[3,4-d]pyrimidine: MS (ESI) for $C_{15}H_{14}BrClN_6$: 395 (MH$^+$).

3-Bromo-4-{4-[3-(trifluoromethyl)phenyl]piperazin-1-yl}-1H-pyrazolo[3,4-d]pyrimidine: $^1$H NMR (400 MHz, $d_6$-DMSO) δ 8.38 (s, 1H), 7.42 (t, 1H), 7.29 (d, 1H), 7.25 (s, 1H), 7.11 (d, 1H), 3.94 (m, 4H), 3.43 (m, 4H). MS (ESI) for $C_{16}H_{14}BrF_3N_6$: 430 (MH$^+$).

3-Bromo-4-[4-(4-bromophenyl)piperazin-1-yl]-1H-pyrazolo[3,4-d]pyrimidine: MS (ESI) for $C_{15}H_{14}Br_2N_6$: 439 (MH$^+$).

3-Bromo-4-[3-methyl-4-(3-methylphenyl)piperazin-1-yl]-1H-pyrazolo[3,4-d]pyrimidine: $^1$H NMR (400 MHz, $d_6$-DMSO) δ 8.39 (s, 1H), 7.20 (m, 1H), 6.92 (m, 2H), 6.76 (m, 1H), 4.30 (m, 2H), 4.11 (m, 2H), 3.52 (m, 2H), 3.40 (m, 1H), 2.38 (s, 3H), 0.94 (d, 3H). MS (ESI) for $C_{17}H_{19}BrN_6$: 388 (MH$^+$).

Additional examples of compounds that were made according to the methods and procedures described above are set forth in Table 1. Each of these compounds are further aspects of this invention.

Assays

For assay of activity, generally p70S6K and/or AktK, or a compound according to the invention is non-diffusably bound to an insoluble support having isolated sample-receiving areas (e.g., a microtiter plate, an array, etc.). The insoluble support may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Exemplary methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

One measure of inhibition is $K_i$. For compounds with $IC_{50}$'s less than 1 μM, the $K_i$ or $K_d$ is defined as the dissociation rate constant for the interaction of the agent with a p70S6K and/or AktK. Exemplary compositions have $K_i$'s of, for example, less than about 100 μM, less than about 10 μM, less than about 1 μM, and further for example having $K_i$'s of less than about 100 nM, and still further, for example, less than about 10 nM. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate data (i.e. compound concentration) are fitted to the equation:

where V is the observed rate, $V_{max}$, is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Exemplary compounds have $GI_{50}$'s of, for example, less than about 1 μM, less than about 10 μM, less than about 1 μM, and further, for example, having $GI_{50}$'s of less than about 100 nM, still further having $GI_{50}$'s of less than about 10 nM. Measurement of $GI_{50}$ is done using a cell proliferation assay.

Tyrosine kinase activity is determined by 1) measurement of kinase-dependent ATP consumption by in the presence of a generic substrate such as polyglutamine, tyrosine (pEY), by luciferase/luciferin-mediated chemiluminescence or; 2) incorporation of radioactive phosphate derived from $^{33}$P-ATP into a generic substrate which has been adsorbed onto the well surface of polystyrene microtiter plates. Phosphorylated substrate products are quantified by scintillation spectrometry.

Luciferase-Coupled Chemiluminescence Assay Protocol

Kinase activity is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP and kinase in a 20 uL volume. The reaction mixture was incubated at ambient temperature for 3 hrs. For p70S6K and/or AktK, 2.5-5 nM of the enzyme was pre-incubated with compound in 20 mM Tris pH 7.5, 10 mM MgCl2, 0.03% TX-100, and 1 mM DTT for 30 minutes at room temperature. Following the kinase reaction, a 20 µL aliquot of luciferase-luciferin mix was added and the chemiluminescence signal measured using a Victor$^2$ plate reader (Perkin Elmer). The luciferase-luciferin mix contained 50 mM HEPES, pH 7.8, 67 mM oxalic acid (pH 7.8), 5 (or 50) mM DTT, 0.4% Triton X-100, 0.25 mg/mL coenzyme A, 63 µM AMP, 28 µg/1 mL luciferin and 40,000 units/mL luciferase. Total ATP consumption was limited to 25-60% and the IC$_{50}$ values correlate well with those determined by radiometric assays.

$^{33}$P-Phosphoryl Transfer Kinase Assay Protocol II

Direct p70S6K and/or AktK activity was measured as incorporated $^{33}$P in the method described below. Reactions were performed in a 96-well polypropylene V-bottom plate. Samples were incubated for 30 minutes and then transferred to a 96-well P81 Unifilter plate (Whatman). Each reaction contained 50 nM p70S6 and/or Akt kinase with 5 uM ATP and $^{33}$P-γ-ATP (3.3 µCi/nmol) in 20 mM Tris pH 7.5, 10 mM MgCl2, 0.03% TX-100, and 1 mM DTT. Plates were washed 10 times with 0.075% phosphoric acid. 100 ul of scintillation fluid was added and incorporated $^{33}$P was measured by liquid scintillation spectrometry using a MicroBeta scintillation counter (Perkin Elmer).

Structure Activity Relationships

Table 1 shows structure activity relationship data for selected compounds of the invention. Inhibition is indicated as IC$_{50}$ with following key: A=IC$_{50}$ less than 100 nM, B=IC$_{50}$ greater than 100 nM, but less than or equal to 1000 nM, C=IC$_{50}$ greater than 1000 nM, but less than 10,000 mM, D=IC$_{50}$ 10,000 nM or greater. An empty cell indicates lack of data only.

TABLE 1

| Entry | Name | P70S6K IC50 | AKT-1 IC50 |
|---|---|---|---|
| 1 | 3-(azetidin-3-ylidenemethyl)-4-[4-(5-chloro-2-methylphenyl)piperazin-1-yl]-1H-pyrazolo[3,4-d]pyrimidine | C | C |
| 2 | 4-[4-(5-chloro-2-methylphenyl)piperazin-1-yl]-3-(3-fluoropyridin-4-yl)-1H-pyrazolo[3,4-d]pyrimidine | A | D |
| 3 | 4-[4-(5-chloro-2-methylphenyl)piperazin-1-yl]-3-(3-chloropyridin-4-yl)-1H-pyrazolo[3,4-d]pyrimidine | A | D |
| 4 | 2-({5-chloro-3-[4-(3-ethyl-1H-pyrazolo[3,4-d]pyrimidin-4-yl)piperazin-1-yl]-2-methylphenyl}oxy)-N,N-dimethylethanamine | A | C |
| 5 | 2-({5-chloro-3-[4-(3-ethyl-1H-pyrazolo[3,4-d]pyrimidin-4-yl)piperazin-1-yl]-2-methylphenyl}oxy)-N,N-diethylethanamine | A | C |
| 6 | 4-(4-{5-chloro-2-methyl-3-[(2-pyrrolidin-1-ylethyl)oxy]phenyl}piperazin-1-yl)-3-ethyl-1H-pyrazolo[3,4-d]pyrimidine | A | C |
| 7 | 4-[4-(5-chloro-2-methylphenyl)piperazin-1-yl]-3-piperazin-1-yl-1H-pyrazolo[3,4-d]pyrimidine | B | C |
| 8 | N-(3-{4-[4-(5-chloro-2-methylphenyl)piperazin-1-yl]-1H-pyrazolo[3,4-d]pyrimidin-3-yl}prop-2-yn-1-yl)acetamide | A | C |
| 9 | N,N-diethyl-2-({3-[4-(3-ethyl-1H-pyrazolo[3,4-d]pyrimidin-4-yl)piperazin-1-yl]phenyl}oxy)ethanamine | C | C |
| 10 | 3-{3-[4-(3-bromo-1H-pyrazolo[3,4-d]pyrimidin-4-yl)piperazin-1-yl]-5-chloro-2-methylphenyl}-N,N-diethylpropan-1-amine | A | A |
| 11 | 3-bromo-4-{4-[5-chloro-2-methyl-3-(3-pyrrolidin-1-ylpropyl)phenyl]piperazin-1-yl}-1H-pyrazolo[3,4-d]pyrimidine | A | A |
| 12 | 3-bromo-4-(4-{5-chloro-2-methyl-3-[(2-pyrrolidin-1-ylethyl)oxy]phenyl}piperazin-1-yl)-1H-pyrazolo[3,4-d]pyrimidine | A | B |
| 13 | 2-({3-[4-(3-bromo-1H-pyrazolo[3,4-d]pyrimidin-4-yl)piperazin-1-yl]-5-chloro-2-methylphenyl}oxy)-N,N-diethylethanamine | A | B |
| 14 | 4-[4-(5-chloro-2-methyl-3-{[2-(1-methylpiperidin-4-yl)ethyl]oxy}phenyl)piperazin-1-yl]-3-ethyl-1H-pyrazolo[3,4-d]pyrimidine | A | C |
| 15 | 5-chloro-3-[4-(3-ethyl-1H-pyrazolo[3,4-d]pyrimidin-4-yl)piperazin-1-yl]-2-methyl-N-(2-pyrrolidin-1-ylethyl)aniline | A | B |
| 16 | 4-(4-{5-chloro-2-methyl-3-[(2-morpholin-4-ylethyl)oxy]phenyl}piperazin-1-yl)-3-ethyl-1H-pyrazolo[3,4-d]pyrimidine | A | C |
| 17 | 4-(4-{5-chloro-2-methyl-3-[(2-piperidin-1-ylethyl)oxy]phenyl}piperazin-1-yl)-3-ethyl-1H-pyrazolo[3,4-d]pyrimidine | A | C |
| 18 | 3-bromo-4-{4-[5-chloro-2-methyl-3-(3-morpholin-4-ylpropyl)phenyl]piperazin-1-yl}-1H-pyrazolo[3,4-d]pyrimidine | A | B |
| 19 | 3-bromo-4-(4-{5-chloro-2-methyl-3-[3-(4-methylpiperazin-1-yl)propyl]phenyl}piperazin-1-yl)-1H-pyrazolo[3,4-d]pyrimidine | A | A |
| 20 | 3-bromo-4-(4-{5-chloro-2-methyl-3-[(2-piperidin-1-ylethyl)oxy]phenyl}piperazin-1-yl)-1H-pyrazolo[3,4-d]pyrimidine | A | B |
| 21 | 3-bromo-4-(4-{5-chloro-2-methyl-3-[(2-morpholin-4-ylethyl)oxy]phenyl}piperazin-1-yl)-1H-pyrazolo[3,4-d]pyrimidine | A | C |
| 22 | 4-{4-[5-chloro-2-methyl-3-(3-morpholin-4-ylpropyl)phenyl]piperazin-1-yl}-3-ethyl-1H-pyrazolo[3,4-d]pyrimidine | A | C |
| 23 | N'-{5-chloro-3-[4-(3-ethyl-1H-pyrazolo[3,4-d]pyrimidin-4-yl)piperazin-1-yl]-2-methylphenyl}-N,N-diethylethane-1,2-diamine | A | B |
| 24 | 4-{4-[5-chloro-2-methyl-3-(3-piperidin-1-ylpropyl)phenyl]piperazin-1-yl}-3-ethyl-1H-pyrazolo[3,4-d]pyrimidine | A | B |
| 25 | 4-[4-(5-chloro-3-{[2-(4-ethylpiperazin-1-yl)ethyl]oxy}-2-methylphenyl)piperazin-1-yl]-3-ethyl-1H-pyrazolo[3,4-d]pyrimidine | A | C |
| 26 | 4-(4-{5-chloro-2-methyl-3-[(3-morpholin-4-ylpropyl)oxy]phenyl}piperazin-1-yl)-3-ethyl-1H-pyrazolo[3,4-d]pyrimidine | A | C |
| 27 | 3-bromo-4-{4-[5-chloro-2-methyl-3-(3-piperidin-1-ylpropyl)phenyl]piperazin-1-yl}-1H-pyrazolo[3,4-d]pyrimidine | A | A |
| 28 | N'-{3-[4-(3-bromo-1H-pyrazolo[3,4-d]pyrimidin-4-yl)piperazin-1-yl]-5-chloro-2-methylphenyl}-N,N-diethylethane-1,2-diamine | A | A |
| 29 | 3-[4-(3-bromo-1H-pyrazolo[3,4-d]pyrimidin-4-yl)piperazin-1-yl]-5-chloro-2-methyl-N-(2-pyrrolidin-1-ylethyl)aniline | A | A |

TABLE 1-continued

| Entry | Name | P70S6K IC50 | AKT-1 IC50 |
|---|---|---|---|
| 30 | 4-[4-(5-chloro-2-methyl-3-{[2-(4-methylpiperazin-1-yl)ethyl]oxy}phenyl)piperazin-1-yl]-3-ethyl-1H-pyrazolo[3,4-d]pyrimidine | A | B |
| 31 | 4-[4-(5-chloro-2-methyl-3-{[(1-methylpiperidin-4-yl)methyl]oxy}phenyl)piperazin-1-yl]-3-ethyl-1H-pyrazolo[3,4-d]pyrimidine | A | B |
| 32 | N,N-diethyl-2-({3-[4-(3-ethyl-1H-pyrazolo[3,4-d]pyrimidin-4-yl)piperazin-1-yl]-2-methylphenyl}oxy)ethanamine | B | C |
| 33 | 2-[(5-chloro-3-{4-[1-(1,1-dimethylethyl)-3-(trifluoromethyl)-1H-pyrazolo[3,4-d]pyrimidin-4-yl]piperazin-1-yl}-2-methylphenyl)oxy]-N,N-diethylethanamine | C | C |
| 34 | 2-[(5-chloro-2-methyl-3-{4-[3-(trifluoromethyl)-1H-pyrazolo[3,4-d]pyrimidin-4-yl]piperazin-1-yl}phenyl)oxy]-N,N-diethylethanamine | A | B |
| 35 | 4-(4-{5-chloro-2-methyl-3-[(3-pyrrolidin-1-ylpropyl)oxy]phenyl}piperazin-1-yl)-3-ethyl-1H-pyrazolo[3,4-d]pyrimidine | A | B |
| 36 | 4-[4-(5-chloro-2-methyl-3-{[3-(4-methylpiperazin-1-yl)propyl]oxy}phenyl)piperazin-1-yl]-3-ethyl-1H-pyrazolo[3,4-d]pyrimidine | A | B |
| 37 | 3-bromo-4-(4-{5-chloro-2-methyl-3-[(3-piperidin-1-ylpropyl)oxy]phenyl}piperazin-1-yl)-1H-pyrazolo[3,4-d]pyrimidine | A | B |
| 38 | 3-bromo-4-(4-{5-chloro-2-methyl-3-[(3-morpholin-4-ylpropyl)oxy]phenyl}piperazin-1-yl)-1H-pyrazolo[3,4-d]pyrimidine | A | B |
| 39 | 4-(4-{5-chloro-2-methyl-3-[(2-pyrrolidin-1-ylethyl)oxy]phenyl}piperazin-1-yl)-3-(trifluoromethyl)-1H-pyrazolo[3,4-d]pyrimidine | A | B |
| 40 | 4-(4-{5-chloro-2-methyl-3-[(3-morpholin-4-ylpropyl)oxy]phenyl}piperazin-1-yl)-3-(trifluoromethyl)-1H-pyrazolo[3,4-d]pyrimidine | A | C |
| 41 | 4-(4-{5-chloro-2-methyl-3-[(2-morpholin-4-ylethyl)oxy]phenyl}piperazin-1-yl)-3-(trifluoromethyl)-1H-pyrazolo[3,4-d]pyrimidine | A | C |
| 42 | 4-(4-{5-chloro-2-methyl-3-[(3-piperidin-1-ylpropyl)oxy]phenyl}piperazin-1-yl)-3-ethyl-1H-pyrazolo[3,4-d]pyrimidine | A | B |
| 43 | 4-[4-(5-chloro-3-{[3-(4-ethylpiperazin-1-yl)propyl]oxy}-2-methylphenyl)piperazin-1-yl]-3-ethyl-1H-pyrazolo[3,4-d]pyrimidine | A | B |
| 44 | 5-chloro-2-methyl-3-[4-(1H-pyrazolo[3,4-d]pyrimidin-4-yl)piperazin-1-yl]-N-(2-pyrrolidin-1-ylethyl)aniline | A | C |
| 45 | 5-chloro-2-methyl-3-[4-(3-methyl-1H-pyrazolo[3,4-d]pyrimidin-4-yl)piperazin-1-yl]-N-(2-pyrrolidin-1-ylethyl)aniline | A | B |
| 46 | N'-(5-chloro-2-methyl-3-{4-[3-(trifluoromethyl)-1H-pyrazolo[3,4-d]pyrimidin-4-yl]piperazin-1-yl}phenyl)-N,N-dimethylethane-1,2-diamine | A | A |
| 47 | 3-({5-chloro-3-[4-(3-ethyl-1H-pyrazolo[3,4-d]pyrimidin-4-yl)piperazin-1-yl]-2-methylphenyl}oxy)-N,N-diethylpropan-1-amine | A | B |
| 48 | N'-(5-chloro-2-methyl-3-{4-[3-(trifluoromethyl)-1H-pyrazolo[3,4-d]pyrimidin-4-yl]piperazin-1-yl}phenyl)-N,N-diethylethane-1,2-diamine | A | B |
| 49 | 5-chloro-2-methyl-N-(2-pyrrolidin-1-ylethyl)-3-{4-[3-(trifluoromethyl)-1H-pyrazolo[3,4-d]pyrimidin-4-yl]piperazin-1-yl}aniline | A | B |
| 50 | 3-bromo-4-(4-{4-methyl-3-[(2-pyrrolidin-1-ylethyl)oxy]phenyl}piperazin-1-yl)-1H-pyrazolo[3,4-d]pyrimidine | A | C |
| 51 | 4-(4-{4-methyl-3-[(2-pyrrolidin-1-ylethyl)oxy]phenyl}piperazin-1-yl)-1H-pyrazolo[3,4-d]pyrimidine | C | C |
| 52 | 3-methyl-4-(4-{4-methyl-3-[(2-pyrrolidin-1-ylethyl)oxy]phenyl}piperazin-1-yl)-1H-pyrazolo[3,4-d]pyrimidine | B | C |
| 53 | 4-(4-{5-chloro-2-methyl-3-[(2-pyrrolidin-1-ylethyl)oxy]phenyl}piperazin-1-yl)-1H-pyrazolo[3,4-d]pyrimidine | A | C |
| 54 | 4-(4-{5-chloro-2-methyl-3-[(2-pyrrolidin-1-ylethyl)oxy]phenyl}piperazin-1-yl)-3-methyl-1H-pyrazolo[3,4-d]pyrimidine | A | C |
| 55 | 4-(4-{5-chloro-2-methyl-3-[(2-piperidin-1-ylethyl)oxy]phenyl}piperazin-1-yl)-3-(trifluoromethyl)-1H-pyrazolo[3,4-d]pyrimidine | A | B |
| 56 | 3-[(5-chloro-2-methyl-3-{4-[3-(trifluoromethyl)-1H-pyrazolo[3,4-d]pyrimidin-4-yl]piperazin-1-yl}phenyl)oxy]-N,N-diethylpropan-1-amine | A | B |
| 57 | 5-[4-(3-bromo-1H-pyrazolo[3,4-d]pyrimidin-4-yl)piperazin-1-yl]-2-methyl-N-(2-pyrrolidin-1-ylethyl)aniline | B | C |
| 58 | 3-[4-(3-bromo-1H-pyrazolo[3,4-d]pyrimidin-4-yl)piperazin-1-yl]-5-fluoro-2-methyl-N-(2-pyrrolidin-1-ylethyl)aniline | A | B |
| 59 | 4-{4-[5-chloro-2-methyl-3-(3-pyrrolidin-1-ylpropyl)phenyl]piperazin-1-yl}-1H-pyrazolo[3,4-d]pyrimidine | A | C |
| 60 | 3-bromo-4-{4-[5-fluoro-2-methyl-3-(3-pyrrolidin-1-ylpropyl)phenyl]piperazin-1-yl}-1H-pyrazolo[3,4-d]pyrimidine | A | B |
| 61 | 4-{4-[5-chloro-2-methyl-3-(3-pyrrolidin-1-ylpropyl)phenyl]piperazin-1-yl}-3-(trifluoromethyl)-1H-pyrazolo[3,4-d]pyrimidine | A | A |
| 62 | 4-(4-{5-chloro-2-methyl-3-[3-(4-methylpiperazin-1-yl)propyl]phenyl}piperazin-1-yl)-3-ethyl-1H-pyrazolo[3,4-d]pyrimidine | A | B |
| 63 | 3-bromo-4-(4-pyridin-2-ylpiperazin-1-yl)-1H-pyrazolo[3,4-d]pyrimidine | B | C |
| 64 | 3-bromo-4-[4-(2,4-dimethylphenyl)piperazin-1-yl]-1H-pyrazolo[3,4-d]pyrimidine | B | C |
| 65 | 3-bromo-4-{4-[3-(methyloxy)phenyl]piperazin-1-yl}-1H-pyrazolo[3,4-d]pyrimidine | A | C |
| 66 | 3-bromo-4-{4-[2-(methyloxy)phenyl]piperazin-1-yl}-1H-pyrazolo[3,4-d]pyrimidine | A | D |
| 67 | 3-bromo-4-{4-[4-methyl-3-(3-pyrrolidin-1-ylpropyl)phenyl]piperazin-1-yl}-1H-pyrazolo[3,4-d]pyrimidine | B | C |
| 68 | 4-(4-{5-chloro-2-methyl-3-[(3-pyrrolidin-1-ylpropyl)oxy]phenyl}piperazin-1-yl)-3-(trifluoromethyl)-1H-pyrazolo[3,4-d]pyrimidine | A | B |
| 69 | 4-(4-{5-chloro-2-methyl-3-[(3-piperidin-1-ylpropyl)oxy]phenyl}piperazin-1-yl)-3-(trifluoromethyl)-1H-pyrazolo[3,4-d]pyrimidine | A | B |
| 70 | 4-[4-(5-chloro-2-methyl-3-{[3-(4-methylpiperazin-1-yl)propyl]oxy}phenyl)piperazin-1-yl]-3-(trifluoromethyl)-1H-pyrazolo[3,4-d]pyrimidine | A | B |
| 71 | 4-[4-(5-chloro-3-{[3-(4-ethylpiperazin-1-yl)propyl]oxy}-2-methylphenyl)piperazin-1-yl]-3-(trifluoromethyl)-1H-pyrazolo[3,4-d]pyrimidine | A | B |
| 72 | 3-bromo-4-[4-(5-chloro-2-methyl-3-{[2-(4-methylpiperazin-1-yl)ethyl]oxy}phenyl)piperazin-1-yl]-1H-pyrazolo[3,4-d]pyrimidine | A | B |
| 73 | 4-[4-(5-chloro-2-methyl-3-{[2-(4-methylpiperazin-1-yl)ethyl]oxy}phenyl)piperazin-1-yl]-3-(trifluoromethyl)-1H-pyrazolo[3,4-d]pyrimidine | A | B |
| 74 | 3-bromo-4-[4-(5-chloro-3-{[2-(4-ethylpiperazin-1-yl)ethyl]oxy}-2-methylphenyl)piperazin-1-yl]-1H-pyrazolo[3,4-d]pyrimidine | A | A |
| 75 | 3-bromo-4-[4-(3,4-dichlorophenyl)piperazin-1-yl]-1H-pyrazolo[3,4-d]pyrimidine | B | D |
| 76 | 3-bromo-4-[4-(3,4-difluorophenyl)piperazin-1-yl]-1H-pyrazolo[3,4-d]pyrimidine | B | D |
| 77 | 3-bromo-4-[4-(2,4-dichlorophenyl)piperazin-1-yl]-1H-pyrazolo[3,4-d]pyrimidine | B | D |
| 78 | 3-[4-(3-ethyl-1H-pyrazolo[3,4-d]pyrimidin-4-yl)piperazin-1-yl]-5-fluoro-2-methyl-N-(2-pyrrolidin-1-ylethyl)aniline | A | C |
| 79 | 5-fluoro-2-methyl-N-(2-pyrrolidin-1-ylethyl)-3-{4-[3-(trifluoromethyl)-1H-pyrazolo[3,4-d]pyrimidin-4-yl]piperazin-1-yl}aniline | A | B |
| 80 | 4-{4-[3,5-bis(methyloxy)phenyl]piperazin-1-yl}-3-bromo-1H-pyrazolo[3,4-d]pyrimidine | A | C |
| 81 | 4-[4-(5-chloro-3-{[2-(4-ethylpiperazin-1-yl)ethyl]oxy}-2-methylphenyl)piperazin-1-yl]-3-(trifluoromethyl)-1H-pyrazolo[3,4-d]pyrimidine | A | B |
| 82 | N-{5-chloro-3-[4-(3-ethyl-1H-pyrazolo[3,4-d]pyrimidin-4-yl)piperazin-1-yl]-2-methylphenyl}-N,N',N'-trimethylethane-1,2-diamine | A | C |

TABLE 1-continued

| Entry | Name | P70S6K IC50 | AKT-1 IC50 |
|---|---|---|---|
| 83 | 3-({3-[4-(3-bromo-1H-pyrazolo[3,4-d]pyrimidin-4-yl)piperazin-1-yl]-5-chloro-2-methylphenyl}oxy)-N,N-diethylpropan-1-amine | A | A |
| 84 | 3-bromo-4-(4-{5-chloro-2-methyl-3-[(3-pyrrolidin-1-ylpropyl)oxy]phenyl}piperazin-1-yl)-1H-pyrazolo[3,4-d]pyrimidine | A | A |
| 85 | 3-bromo-4-[4-(5-chloro-2-methyl-3-{[3-(4-methylpiperazin-1-yl)propyl]oxy}phenyl)piperazin-1-yl]-1H-pyrazolo[3,4-d]pyrimidine | A | A |
| 86 | 3-bromo-4-[4-(5-chloro-3-{[3-(4-ethylpiperazin-1-yl)propyl]oxy}-2-methylphenyl)piperazin-1-yl]-1H-pyrazolo[3,4-d]pyrimidine | A | A |
| 87 | 3-(5-chloro-2-methyl-3-{4-[3-(trifluoromethyl)-1H-pyrazolo[3,4-d]pyrimidin-4-yl]piperazin-1-yl}phenyl)-N,N-diethylpropan-1-amine | A | B |
| 88 | 3-bromo-4-[4-(5-chloro-2-methyl-3-{[(1-methyl-piperidin-4-yl)methyl]oxy}phenyl)piperazin-1-yl]-1H-pyrazolo[3,4-d]pyrimidine | A | A |
| 89 | 3-bromo-4-[4-(5-chloro-2-methyl-3-{[2-(1-methyl-piperidin-4-yl)ethyl]oxy}phenyl)piperazin-1-yl]-1H-pyrazolo[3,4-d]pyrimidine | A | A |
| 90 | 4-[4-(5-chloro-2-methyl-3-{[(1-methylpiperidin-4-yl)methyl]oxy}phenyl)piperazin-1-yl]-3-(trifluoro-methyl)-1H-pyrazolo[3,4-d]pyrimidine | A | B |
| 91 | 4-[4-(5-chloro-2-methyl-3-{[2-(1-methylpiperidin-4-yl)ethyl]oxy}phenyl)piperazin-1-yl]-3-(tri-fluoromethyl)-1H-pyrazolo[3,4-d]pyrimidine | A | B |
| 92 | 4-(4-{5-chloro-2-methyl-3-[3-(4-methylpiperazin-1-yl)propyl]phenyl}piperazin-1-yl)-3-(trifluoro-methyl)-1H-pyrazolo[3,4-d]pyrimidine | A | B |
| 93 | 3-bromo-4-[4-(3-chloro-4-fluorophenyl)piperazin-1-yl]-1H-pyrazolo[3,4-d]pyrimidine | A | C |
| 94 | 1-{4-[4-(3-bromo-1H-pyrazolo[3,4-d]pyrimidin-4-yl)piperazin-1-yl]phenyl}ethanone | B | C |
| 95 | 3-bromo-4-[4-(2,5-dichlorophenyl)piperazin-1-yl]-1H-pyrazolo[3,4-d]pyrimidine | A | D |
| 96 | 3-bromo-4-[4-(3,4-dimethylphenyl)piperazin-1-yl]-1H-pyrazolo[3,4-d]pyrimidine | B | D |
| 97 | 3-bromo-4-[4-(4-nitrophenyl)piperazin-1-yl]-1H-pyrazolo[3,4-d]pyrimidine | B | D |
| 98 | 3-ethyl-4-(4-phenylpiperazin-1-yl)-1H-pyrazolo[3,4-d]pyrimidine | B | D |
| 99 | 3-ethyl-4-{4-[3-(methyloxy)phenyl]piperazin-1-yl}-1H-pyrazolo[3,4-d]pyrimidine | B | D |
| 100 | 4-{4-[5-chloro-2-methyl-3-(3-piperidin-1-ylpropyl)phenyl]piperazin-1-yl}-3-(trifluoromethyl)-1H-pyrazolo[3,4-d]pyrimidine | A | B |
| 101 | 4-[4-(3,6-dimethylpyrazin-2-yl)piperazin-1-yl]-3-ethyl-1H-pyrazolo[3,4-d]pyrimidine | B | D |
| 102 | 1-[4-(3-ethyl-1H-pyrazolo[3,4-d]pyrimidin-4-yl)piperazin-1-yl]isoquinoline | A | D |
| 103 | 3-bromo-4-[4-(2,6-dimethylphenyl)piperazin-1-yl]-1H-pyrazolo[3,4-d]pyrimidine | B | D |
| 104 | 3-bromo-4-{4-[4-(ethyloxy)phenyl]piperazin-1-yl}-1H-pyrazolo[3,4-d]pyrimidine | B | D |
| 105 | 3-bromo-4-[4-(2-ethylphenyl)piperazin-1-yl]-1H-pyrazolo[3,4-d]pyrimidine | B | D |
| 106 | 4-{4-[2,4-bis(methyloxy)phenyl]piperazin-1-yl}-3-bromo-1H-pyrazolo[3,4-d]pyrimidine | B | D |
| 107 | 3-bromo-4-(4-pyrazin-2-ylpiperazin-1-yl)-1H-pyrazolo[3,4-d]pyrimidine | B | D |
| 108 | 3-bromo-4-(4-pyrimidin-2-ylpiperazin-1-yl)-1H-pyrazolo[3,4-d]pyrimidine | B | D |
| 109 | 4-[4-(3-bromo-1H-pyrazolo[3,4-d]pyrimidin-4-yl)piperazin-1-yl]-2-(trifluoromethyl)quinoline | A | D |
| 110 | 3-[4-(3-bromo-1H-pyrazolo[3,4-d]pyrimidin-4-yl)piperazin-1-yl]pyrazine-2-carbonitrile | B | D |
| 111 | 4-[4-(4,6-dimethylpyrimidin-2-yl)piperazin-1-yl]-3-ethyl-1H-pyrazolo[3,4-d]pyrimidine | C | D |
| 112 | ethyl 4-[4-(3-ethyl-1H-pyrazolo[3,4-d]pyrimidin-4-yl)piperazin-1-yl]-2-(trifluoromethyl)pyrimidine-5-carboxylate | C | D |
| 113 | 4-{4-[3-chloro-5-(methyloxy)phenyl]piperazin-1-yl}-3-ethyl-1H-pyrazolo[3,4-d]pyrimidine | A | D |
| 114 | 4-[4-(3-bromo-2-chloro-5-fluorophenyl)piperazin-1-yl]-3-ethyl-1H-pyrazolo[3,4-d]pyrimidine | B | D |
| 115 | 2-[4-(3-ethyl-1H-pyrazolo[3,4-d]pyrimidin-4-yl)piperazin-1-yl]pyridine-3-carboxamide | B | D |
| 116 | 3-ethyl-4-{4-[4-(trifluoromethyl)pyridin-2-yl]piperazin-1-yl}-1H-pyrazolo[3,4-d]pyrimidine | B | D |
| 117 | 3-bromo-4-{4-[4-(trifluoromethyl)pyridin-2-yl]piperazin-1-yl}-1H-pyrazolo[3,4-d]pyrimidine | B | D |
| 118 | 3-bromo-4-{4-[4-(trifluoromethyl)pyrimidin-2-yl]piperazin-1-yl}-1H-pyrazolo[3,4-d]pyrimidine | B | D |
| 119 | 2-({3-[4-(3-bromo-1H-pyrazolo[3,4-d]pyrimidin-4-yl)piperazin-1-yl]pyrazin-2-yl}oxy)-N,N-dimethylethanamine | B | C |
| 120 | 4-[4-(3-bromo-1H-pyrazolo[3,4-d]pyrimidin-4-yl)piperazin-1-yl]-2-methylquinoline | A | D |
| 121 | 3-bromo-4-[4-(2-nitrophenyl)piperazin-1-yl]-1H-pyrazolo[3,4-d]pyrimidine | B | D |
| 122 | 2-[4-(3-bromo-1H-pyrazolo[3,4-d]pyrimidin-4-yl)piperazin-1-yl]benzonitrile | B | D |
| 123 | 4-[4-(3-bromo-1H-pyrazolo[3,4-d]pyrimidin-4-yl)piperazin-1-yl]benzonitrile | A | D |
| 124 | 3-bromo-4-{4-[4-(trifluoromethyl)phenyl]piperazin-1-yl}-1H-pyrazolo[3,4-d]pyrimidine | B | D |
| 125 | 3-bromo-4-(4-{4-[(phenylmethyl)oxy]phenyl}piperazin-1-yl)-1H-pyrazolo[3,4-d]pyrimidine | B | D |
| 126 | 4-{4-[5-chloro-2-methyl-3-(methyloxy)phenyl]piperazin-1-yl}-3-ethyl-1H-pyrazolo[3,4-d]pyrimidine | A | D |
| 127 | 2-[4-(3-bromo-1H-pyrazolo[3,4-d]pyrimidin-4-yl)piperazin-1-yl]pyridine-3-carbonitrile | B | D |
| 128 | 3-bromo-4-[4-(3,5-dichlorophenyl)piperazin-1-yl]-1H-pyrazolo[3,4-d]pyrimidine | B | D |
| 129 | 3-[4-(3-bromo-1H-pyrazolo[3,4-d]pyrimidin-4-yl)piperazin-1-yl]-2-chloro-5-fluoro-N-(2-pyrrolidin-1-ylethyl)aniline | A | B |
| 130 | 2-chloro-3-[4-(3-ethyl-1H-pyrazolo[3,4-d]pyrimidin-4-yl)piperazin-1-yl]-5-fluoro-N-(2-pyrrolidin-1-ylethyl)aniline | A | C |
| 131 | 3-bromo-4-[4-(2,5-difluorophenyl)piperazin-1-yl]-1H-pyrazolo[3,4-d]pyrimidine | A | D |
| 132 | 4-[4-(2,5-difluorophenyl)piperazin-1-yl]-3-ethyl-1H-pyrazolo[3,4-d]pyrimidine | B | D |
| 133 | 3-bromo-4-{4-[3-(methyloxy)pyrazin-2-yl]pipera-zin-1-yl}-1H-pyrazolo[3,4-d]pyrimidine | B | D |
| 134 | 3-bromo-4-[4-(3-chlorophenyl)piperazin-1-yl]-1H-pyrazolo[3,4-d]pyrimidine | A | D |
| 135 | 3-bromo-4-{4-[3-(trifluoromethyl)pyridin-2-yl]piperazin-1-yl}-1H-pyrazolo[3,4-d]pyrimidine | B | D |
| 136 | 3-bromo-4-{4-[3-chloro-5-(trifluoromethyl)pyridin-2-yl]piperazin-1-yl}-1H-pyrazolo[3,4-d]pyrimidine | C | D |
| 137 | 4-(4-{5-chloro-2-methyl-3-[(2-pyrrolidin-1-ylethyl)oxy]phenyl}piperazin-1-yl)-3-(1-methylethyl)-1H-pyrazolo[3,4-d]pyrimidine | A | C |
| 138 | 5-chloro-2-methyl-3-{4-[3-(1-methylethyl)-1H-pyrazolo[3,4-d]pyrimidin-4-yl]piperazin-1-yl}-N-(2-pyrrolidin-1-ylethyl)aniline | A | C |
| 139 | 2-({3-[4-(3-bromo-1H-pyrazolo[3,4-d]pyrimidin-4-yl)piperazin-1-yl]phenyl}oxy)-N-ethylacetamide | A | C |
| 140 | 2-[4-(3-bromo-1H-pyrazolo[3,4-d]pyrimidin-4-yl)piperazin-1-yl]-N,N-diethylpyrimidin-4-amine | B | C |
| 141 | 3-bromo-4-(4-{3-[{(3-methylphenyl)methyl]oxy}phenyl]piperazin-1-yl)-1H-pyrazolo[3,4-d]pyrimidine | B | D |
| 142 | 3-bromo-4-(4-{3-[(2-piperidin-1-ylethyl)oxy]phenyl}piperazin-1-yl)-1H-pyrazolo[3,4-d]pyrimidine | B | C |
| 143 | 3-bromo-4-[4-(4-furan-2-ylpyrimidin-2-yl)piperazin-1-yl]-1H-pyrazolo[3,4-d]pyrimidine | B | D |
| 144 | 6-{2-[4-(3-bromo-1H-pyrazolo[3,4-d]pyrimidin-4-yl)piperazin-1-yl]pyrimidin-4-yl}-2H-1,4-benzoxazin-3(4H)-one | C | C |
| 145 | 3-ethyl-4-{4-[2-methyl-3-(methyloxy)phenyl]piper-azin-1-yl}-1H-pyrazolo[3,4-d]pyrimidine | A | D |
| 146 | N'-{5-chloro-3-[4-(3-ethyl-1H-pyrazolo[3,4-d]pyrimidin-4-yl)piperazin-1-yl]-2-methylphenyl}-N-methyl-N-(1-methylethyl)ethane-1,2-diamine | A | B |

TABLE 1-continued

| Entry | Name | P70S6K IC50 | AKT-1 IC50 |
|---|---|---|---|
| 147 | N'-{5-chloro-3-[4-(3-ethyl-1H-pyrazolo[3,4-d]pyrimidin-4-yl)piperazin-1-yl]-2-methylphenyl}-N-ethyl-N-methylethane-1,2-diamine | A | B |
| 148 | N'-{3-[4-(3-bromo-1H-pyrazolo[3,4-d]pyrimidin-4-yl)piperazin-1-yl]-5-chloro-2-methylphenyl}-N,N-dimethylethane-1,2-diamine | A | A |
| 149 | 3-({6-[4-(3-bromo-1H-pyrazolo[3,4-d]pyrimidin-4-yl)piperazin-1-yl]-2-chloro-5-methylpyrimidin-4-yl}oxy)-N,N-diethylpropan-1-amine | B | C |
| 150 | 3-bromo-4-[4-(2,3-dichlorophenyl)piperazin-1-yl]-1H-pyrazolo[3,4-d]pyrimidine | B | D |
| 151 | 3-bromo-4-{4-[2-(trifluoromethyl)phenyl]piperazin-1-yl}-1H-pyrazolo[3,4-d]pyrimidine | B | D |
| 152 | 3-bromo-4-(4-phenylpiperazin-1-yl)-1H-pyrazolo[3,4-d]pyrimidine | A | D |
| 153 | 3-bromo-4-[4-(4-fluorophenyl)piperazin-1-yl]-1H-pyrazolo[3,4-d]pyrimidine | B | D |
| 154 | 3-bromo-4-[4-(4-chlorophenyl)piperazin-1-yl]-1H-pyrazolo[3,4-d]pyrimidine | B | D |
| 155 | 3-bromo-4-{4-[3-(trifluoromethyl)phenyl]piperazin-1-yl}-1H-pyrazolo[3,4-d]pyrimidine | A | D |
| 156 | 4-[4-(5-chloro-2-methylphenyl)piperazin-1-yl]-1H-pyrazolo[3,4-d]pyrimidin-6-amine | C | D |
| 157 | 3-bromo-4-[4-(4-bromophenyl)piperazin-1-yl]-1H-pyrazolo[3,4-d]pyrimidine | B | D |
| 158 | 3-bromo-4-[3-methyl-4-(3-methylphenyl)piperazin-1-yl]-1H-pyrazolo[3,4-d]pyrimidine | A | C |
| 159 | 4-[4-(3-bromo-5-chloro-2-methylphenyl)piperazin-1-yl]-1H-pyrazolo[3,4-d]pyrimidin-6-amine | C | D |
| 160 | 4-(4-{5-chloro-2-methyl-3-[(2-pyrrolidin-1-ylethyl)oxy]phenyl}piperazin-1-yl)-3-cyclopropyl-1H-pyrazolo[3,4-d]pyrimidine | A | C |
| 161 | 5-chloro-3-[4-(3-cyclopropyl-1H-pyrazolo[3,4-d]pyrimidin-4-yl)piperazin-1-yl]-2-methyl-N-(2-pyrrolidin-1-ylethyl)aniline | A | B |
| 162 | 5-chloro-2-methyl-3-{4-[3-(2-methylpropyl)-1H-pyrazolo[3,4-d]pyrimidin-4-yl]piperazin-1-yl}-N-(2-pyrrolidin-1-ylethyl)aniline | A | B |
| 163 | 4-(4-{5-chloro-2-methyl-3-[(2-pyrrolidin-1-ylethyl)oxy]phenyl}piperazin-1-yl)-3-(2-methylpropyl)-1H-pyrazolo[3,4-d]pyrimidine | A | C |
| 164 | 3-bromo-4-[(3S)-4-(5-chloro-2-methylphenyl)-3-methylpiperazin-1-yl]-1H-pyrazolo[3,4-d]pyrimidine | A | B |
| 165 | 5-bromo-3-[4-(3-ethyl-1H-pyrazolo[3,4-d]pyrimidin-4-yl)piperazin-1-yl]-2-methylaniline | A | B |
| 166 | 2-({3-[4-(3-bromo-1H-pyrazolo[3,4-d]pyrimidin-4-yl)piperazin-1-yl]phenyl}oxy)-N-cyclopropylacetamide | A | C |
| 167 | 3-bromo-4-(4-{3-[(2-piperidin-1-ylethyl)oxy]pyrazin-2-yl}piperazin-1-yl)-1H-pyrazolo[3,4-d]pyrimidine | B | C |
| 168 | | | |
| 169 | 4-[4-(3-ethyl-1H-pyrazolo[3,4-d]pyrimidin-4-yl)piperazin-1-yl]-6,7-bis(methyloxy)quinazoline | C | D |
| 170 | 2-({3-chloro-5-[4-(3-ethyl-1H-pyrazolo[3,4-d]pyrimidin-4-yl)piperazin-1-yl]phenyl}oxy)-N,N-diethylethanamine | B | D |
| 171 | 4-{4-[2-chloro-5-(trifluoromethyl)phenyl]piperazin-1-yl}-3-ethyl-1H-pyrazolo[3,4-d]pyrimidine | A | C |
| 172 | 3-[4-(3-ethyl-1H-pyrazolo[3,4-d]pyrimidin-4-yl)piperazin-1-yl]-2-methyl-5-[(2-methylpropyl)oxy]-N-(2-pyrrolidin-1-ylethyl)aniline | A | A |
| 173 | 3-({4-[4-(3-bromo-1H-pyrazolo[3,4-d]pyrimidin-4-yl)piperazin-1-yl]-6-chloro-5-methylpyrimidin-2-yl}oxy)-N,N-diethylpropan-1-amine | B | C |
| 174 | 3-[4-(3-ethyl-1H-pyrazolo[3,4-d]pyrimidin-4-yl)piperazin-1-yl]-2-methyl-5-[(phenylmethyl)oxy]-N-(2-pyrrolidin-1-ylethyl)aniline | A | B |
| 175 | | | |
| 176 | 3-bromo-4-[(3R)-4-(5-chloro-2-methylphenyl)-3-methylpiperazin-1-yl]-1H-pyrazolo[3,4-d]pyrimidine | B | D |
| 177 | 3-[(2S)-4-(3-bromo-1H-pyrazolo[3,4-d]pyrimidin-4-yl)-2-methylpiperazin-1-yl]-4-methyl-N-phenylbenzamide | A | B |
| 178 | 3-[(2S)-4-(3-bromo-1H-pyrazolo[3,4-d]pyrimidin-4-yl)-2-methylpiperazin-1-yl]-4-methyl-N-(phenylmethyl)benzamide | A | C |
| 179 | methyl 3-[4-(3-bromo-1H-pyrazolo[3,4-d]pyrimidin-4-yl)piperazin-1-yl]-4-methylbenzoate | A | A |
| 180 | 3-[4-(3-bromo-1H-pyrazolo[3,4-d]pyrimidin-4-yl)piperazin-1-yl]-4-methylbenzoic acid | A | B |
| 181 | (2E)-3-(4-{4-[5-chloro-2-methyl-3-(3-pyrrolidin-1-ylpropyl)phenyl]piperazin-1-yl}-1H-pyrazolo[3,4-d]pyrimidin-3-yl)prop-2-enoic acid | A | A |
| 182 | 3-(4-{4-[5-chloro-2-methyl-3-(3-pyrrolidin-1-ylpropyl)phenyl]piperazin-1-yl}-1H-pyrazolo[3,4-d]pyrimidin-3-yl)prop-2-yn-1-ol | A | A |
| 183 | 4-(3-bromo-1H-pyrazolo[3,4-d]pyrimidin-4-yl)-1-(5-chloro-2-methylphenyl)piperazin-2-one | A | D |
| 184 | 3-[4-(3-bromo-1H-pyrazolo[3,4-d]pyrimidin-4-yl)piperazin-1-yl]-2-methyl-5-[(2-methylpropyl)oxy]-N-(2-pyrrolidin-1-ylethyl)aniline | A | A |
| 185 | N'-{3-[4-(3-bromo-1H-pyrazolo[3,4-d]pyrimidin-4-yl)piperazin-1-yl]-2-methyl-5-[(2-methylpropyl)oxy]phenyl}-N,N-diethylethane-1,2-diamine | A | A |
| 186 | methyl 3-bromo-5-[4-(3-bromo-1H-pyrazolo[3,4-d]pyrimidin-4-yl)piperazin-1-yl]-4-methylbenzoate | A | B |
| 187 | 3-[4-(3-bromo-1H-pyrazolo[3,4-d]pyrimidin-4-yl)piperazin-1-yl]-4-methyl-N-phenylbenzamide | A | A |
| 188 | 3-[4-(3-bromo-1H-pyrazolo[3,4-d]pyrimidin-4-yl)piperazin-1-yl]-N,4-dimethylbenzamide | A | B |
| 189 | 2-({3-[4-(3-bromo-1H-pyrazolo[3,4-d]pyrimidin-4-yl)piperazin-1-yl]phenyl}oxy)-N,N-diethylethanamine | B | D |
| 190 | methyl 3-[4-(3-bromo-1H-pyrazolo[3,4-d]pyrimidin-4-yl)piperazin-1-yl]-4-methyl-5-[(2-pyrrolidin-1-ylethyl)amino]benzoate | A | A |
| 191 | 3-bromo-5-[4-(3-bromo-1H-pyrazolo[3,4-d]pyrimidin-4-yl)piperazin-1-yl]-4-methyl-N-phenylbenzamide | A | B |
| 192 | 3-bromo-5-[4-(3-ethyl-1H-pyrazolo[3,4-d]pyrimidin-4-yl)piperazin-1-yl]-4-methyl-N-phenylbenzamide | A | B |
| 193 | N'-{3-[4-(3-bromo-1H-pyrazolo[3,4-d]pyrimidin-4-yl)piperazin-1-yl]-5-chloro-2-methylphenyl}-N-methyl-N-(1-methylethyl)ethane-1,2-diamine | A | A |
| 194 | 3-[4-(3-bromo-1H-pyrazolo[3,4-d]pyrimidin-4-yl)piperazin-1-yl]-4-methyl-N-phenyl-5-[(2-pyrrolidin-1-ylethyl)amino]benzamide | A | A |
| 195 | N'-{3-[4-(3-bromo-1H-pyrazolo[3,4-d]pyrimidin-4-yl)piperazin-1-yl]-2-methyl-5-[(2-methylpropyl)oxy]phenyl}-N,N-dimethylethane-1,2-diamine | A | A |
| 196 | 3-[4-(3-bromo-1H-pyrazolo[3,4-d]pyrimidin-4-yl)piperazin-1-yl]-N,N,4-trimethylbenzamide | A | B |
| 197 | 3-[4-(3-chloro-1H-pyrazolo[3,4-d]pyrimidin-4-yl)piperazin-1-yl]-4-methyl-N-(2-methylpropyl)benzamide | A | C |
| 198 | 3-[4-(3-bromo-1H-pyrazolo[3,4-d]pyrimidin-4-yl)piperazin-1-yl]-N,N,4-trimethyl-5-[(2-pyrrolidin-1-ylethyl)amino]benzamide | A | B |
| 199 | 3-[4-(3-bromo-1H-pyrazolo[3,4-d]pyrimidin-4-yl)-2-oxopiperazin-1-yl]-4-methyl-N-phenylbenzamide | A | C |
| 200 | 3-[(2R)-4-(3-bromo-1H-pyrazolo[3,4-d]pyrimidin-4-yl)-2-(hydroxymethyl)piperazin-1-yl]-4-methyl-N-phenylbenzamide | A | A |
| 201 | 3-[4-(3-bromo-1H-pyrazolo[3,4-d]pyrimidin-4-yl)piperazin-1-yl]-2-methyl-5-(pyrrolidin-1-ylcarbonyl)-N-(2-pyrrolidin-1-ylethyl)aniline | A | B |
| 202 | 3-[4-(3-bromo-1H-pyrazolo[3,4-d]pyrimidin-4-yl)piperazin-1-yl]-N,4-dimethyl-5-[(2-pyrrolidin-1-ylethyl)amino]benzamide | A | B |
| 203 | 3-[4-(3-bromo-1H-pyrazolo[3,4-d]pyrimidin-4-yl)piperazin-1-yl]-N-(4-chlorophenyl)-4-methyl-5-[(2-pyrrolidin-1-ylethyl)amino]benzamide | A | A |
| 204 | 3-[4-(3-bromo-1H-pyrazolo[3,4-d]pyrimidin-4-yl)piperazin-1-yl]-N-(2-chlorophenyl)-4-methyl-5-[(2-pyrrolidin-1-ylethyl)amino]benzamide | A | A |
| 205 | 3-[4-(3-bromo-1H-pyrazolo[3,4-d]pyrimidin-4-yl)piperazin-1-yl]-5-[(cyclopropylmethyl)oxy]-2-methyl-N-(2-pyrrolidin-1-ylethyl)aniline | A | A |

TABLE 1-continued

| Entry | Name | P70S6K IC50 | AKT-1 IC50 |
|---|---|---|---|
| 206 | 3-[4-(3-bromo-1H-pyrazolo[3,4-d]pyrimidin-4-yl)piperazin-1-yl]-2-methyl-5-[(3-methylbutyl)oxy]-N-(2-pyrrolidin-1-ylethyl)aniline | A | A |
| 207 | 3-[4-(3-bromo-1H-pyrazolo[3,4-d]pyrimidin-4-yl)piperazin-1-yl]-5-[(2-ethylbutyl)oxy]-2-methyl-N-(2-pyrrolidin-1-ylethyl)aniline | A | A |
| 208 | 3-[4-(3-bromo-1H-pyrazolo[3,4-d]pyrimidin-4-yl)piperazin-1-yl]-5-(butyloxy)-2-methyl-N-(2-pyrrolidin-1-ylethyl)aniline | A | A |
| 209 | 3-[4-(3-bromo-1H-pyrazolo[3,4-d]pyrimidin-4-yl)piperazin-1-yl]-4-methyl-N-(1-methylethyl)-5-[(2-pyrrolidin-1-ylethyl)amino]benzamide | A | A |
| 210 | 3-[4-(3-bromo-1H-pyrazolo[3,4-d]pyrimidin-4-yl)piperazin-1-yl]-N,4-dimethyl-N-(1-methylethyl)-5-[(2-pyrrolidin-1-ylethyl)amino]benzamide | A | B |
| 211 | 3-[4-(3-bromo-1H-pyrazolo[3,4-d]pyrimidin-4-yl)piperazin-1-yl]-5-[(cyclobutylmethyl)oxy]-2-methyl-N-(2-pyrrolidin-1-ylethyl)aniline | A | A |
| 212 | 3-[4-(3-bromo-1H-pyrazolo[3,4-d]pyrimidin-4-yl)piperazin-1-yl]-5-(ethyloxy)-2-methyl-N-(2-pyrrolidin-1-ylethyl)aniline | A | A |
| 213 | 3-[4-(3-bromo-1H-pyrazolo[3,4-d]pyrimidin-4-yl)piperazin-1-yl]-N-[2-(dimethylamino)ethyl]-4-methylbenzamide | A | C |
| 214 | 3-[4-(3-bromo-1H-pyrazolo[3,4-d]pyrimidin-4-yl)piperazin-1-yl]-N-(1,1-dimethylethyl)-4-methyl-5-[(2-pyrrolidin-1-ylethyl)amino]benzamide | A | A |
| 215 | [4-(3-bromo-1H-pyrazolo[3,4-d]pyrimidin-4-yl)piperazin-1-yl]-4-methyl-N-pyridin-3-yl-5-[(2-pyrrolidin-1-ylethyl)amino]benzamide | A | A |
| 216 | 3-[4-(3-bromo-1H-pyrazolo[3,4-d]pyrimidin-4-yl)piperazin-1-yl]-5-[(2-fluoro-2-methylpropyl)oxy]-2-methyl-N-(2-pyrrolidin-1-ylethyl)aniline | A | A |
| 217 | 3-[4-(3-bromo-1H-pyrazolo[3,4-d]pyrimidin-4-yl)piperazin-1-yl]-5-[(cyclohexylmethyl)oxy]-2-methyl-N-(2-pyrrolidin-1-ylethyl)aniline | A | B |
| 218 | 3-[4-(3-bromo-1H-pyrazolo[3,4-d]pyrimidin-4-yl)piperazin-1-yl]-5-[(cyclopentylmethyl)oxy]-2-methyl-N-(2-pyrrolidin-1-ylethyl)aniline | A | A |
| 219 | 3-[4-(3-bromo-1H-pyrazolo[3,4-d]pyrimidin-4-yl)piperazin-1-yl]-N-ethyl-4-methyl-5-[(2-pyrrolidin-1-ylethyl)amino]benzamide | A | A |
| 220 | 3-[4-(3-bromo-1H-pyrazolo[3,4-d]pyrimidin-4-yl)piperazin-1-yl]-2-methyl-5-[(1-methylethyl)oxy]-N-(2-pyrrolidin-1-ylethyl)aniline | A | A |
| 221 | 3-[4-(3-bromo-1H-pyrazolo[3,4-d]pyrimidin-4-yl)piperazin-1-yl]-5-[(2,2-dimethylpropyl)oxy]-2-methyl-N-(2-pyrrolidin-1-ylethyl)aniline | A | A |
| 222 | 3-[4-(3-bromo-1H-pyrazolo[3,4-d]pyrimidin-4-yl)piperazin-1-yl]-2-methyl-N-(2-pyrrolidin-1-ylethyl)-5-[(tetrahydrofuran-2-ylmethyl)oxy]aniline | A | A |
| 223 | 3-[4-(3-bromo-1H-pyrazolo[3,4-d]pyrimidin-4-yl)piperazin-1-yl]-2-methyl-5-{[2-(methyloxy)ethyl]oxy}-N-(2-pyrrolidin-1-ylethyl)aniline | A | B |
| 224 | 3-[4-(3-bromo-1H-pyrazolo[3,4-d]pyrimidin-4-yl)piperazin-1-yl]-2-methyl-5-(propyloxy)-N-(2-pyrrolidin-1-ylethyl)aniline | A | A |
| 225 | 3-[4-(3-bromo-1H-pyrazolo[3,4-d]pyrimidin-4-yl)piperazin-1-yl]-5-{[2-(dimethylamino)ethyl]amino}-4-methyl-N-phenylbenzamide | A | A |
| 226 | N'-{3-[4-(3-bromo-1H-pyrazolo[3,4-d]pyrimidin-4-yl)piperazin-1-yl]-5-[(2-fluoro-2-methylpropyl)oxy]-2-methylphenyl}-N,N-dimethylethane-1,2-diamine | A | A |
| 227 | 3-[4-(3-bromo-1H-pyrazolo[3,4-d]pyrimidin-4-yl)piperazin-1-yl]-5-{[2-(dimethylamino)ethyl]amino}-4-methyl-N-(1-methylethyl)benzamide | A | A |
| 228 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}pentan-1-one | A | A |
| 229 | N'-(3-[4-(3-bromo-1H-pyrazolo[3,4-d]pyrimidin-4-yl)piperazin-1-yl]-5-{[2,3-difluoro-2-(fluoromethyl)propyl]oxy}-2-methylphenyl)-N,N-dimethylethane-1,2-diamine | A | A |
| 230 | 3-[4-(3-bromo-1H-pyrazolo[3,4-d]pyrimidin-4-yl)piperazin-1-yl]-5-{[2,3-difluoro-2-(fluoromethyl)propyl]oxy}-2-methyl-N-(2-pyrrolidin-1-ylethyl)aniline | A | A |
| 231 | 5-[4-(3-bromo-1H-pyrazolo[3,4-d]pyrimidin-4-yl)piperazin-1-yl]-4-methyl-N-(2-pyrrolidin-1-ylethyl)biphenyl-3-amine | A | A |
| 232 | 1-(3-{5-[4-(3-bromo-1H-pyrazolo[3,4-d]pyrimidin-4-yl)piperazin-1-yl]-4-methylbiphenyl-3-yl}propyl)pyridinium | A | A |
| 233 | 3-[4-(3-bromo-1H-pyrazolo[3,4-d]pyrimidin-4-yl)piperazin-1-yl]-2-methyl-N-(2-pyrrolidin-1-ylethyl)-5-(1,3-thiazol-2-yl)aniline | A | A |
| 234 | 3-[4-(3-bromo-1H-pyrazolo[3,4-d]pyrimidin-4-yl)piperazin-1-yl]-4-methyl-5-[(2-pyrrolidin-1-ylethyl)amino]benzoic acid | A | C |
| 235 | 3-[4-(3-bromo-1H-pyrazolo[3,4-d]pyrimidin-4-yl)piperazin-1-yl]-2-methyl-5-(phenylethynyl)-N-(2-pyrrolidin-1-ylethyl)aniline | A | B |
| 236 | {3-[4-(3-bromo-1H-pyrazolo[3,4-d]pyrimidin-4-yl)piperazin-1-yl]-4-methyl-5-[(2-pyrrolidin-1-ylethyl)amino]phenyl}(phenyl)methanone | A | A |
| 237 | 3-[4-(3-bromo-1H-pyrazolo[3,4-d]pyrimidin-4-yl)piperazin-1-yl]-5-ethynyl-2-methyl-N-(2-pyrrolidin-1-ylethyl)aniline | A | A |
| 238 | 3-[4-(3-bromo-1H-pyrazolo[3,4-d]pyrimidin-4-yl)piperazin-1-yl]-5-(3,3-dimethylbut-1-yn-1-yl)-2-methyl-N-(2-pyrrolidin-1-ylethyl)aniline | A | A |
| 239 | 3-bromo-4-{4-[5-{[2,3-difluoro-2-(fluoromethyl)propyl]oxy}-2-methyl-3-(3-pyrrolidin-1-ylpropyl)phenyl]piperazin-1-yl}-1H-pyrazolo[3,4-d]pyrimidine | A | A |
| 240 | 3-bromo-4-{4-[2-methyl-5-[(2-methylpropyl)oxy]-3-(3-pyrrolidin-1-ylpropyl)phenyl]piperazin-1-yl}-1H-pyrazolo[3,4-d]pyrimidine | A | A |
| 241 | 3-[4-(3-bromo-1H-pyrazolo[3,4-d]pyrimidin-4-yl)piperazin-1-yl]-2-methyl-5-(3-phenyl-1,2,4-oxadiazol-5-yl)-N-(2-pyrrolidin-1-ylethyl)aniline | A | C |
| 242 | 3-[4-(3-bromo-1H-pyrazolo[3,4-d]pyrimidin-4-yl)piperazin-1-yl]-2-methyl-5-(3-methyl-1,2,4-oxadiazol-5-yl)-N-(2-pyrrolidin-1-ylethyl)aniline | A | A |
| 243 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}propan-1-one | A | A |
| 244 | 3-[4-(3-bromo-1H-pyrazolo[3,4-d]pyrimidin-4-yl)piperazin-1-yl]-5-(3,3-dimethylbutyl)-2-methyl-N-(2-pyrrolidin-1-ylethyl)aniline | A | A |
| 245 | 3-[4-(3-bromo-1H-pyrazolo[3,4-d]pyrimidin-4-yl)piperazin-1-yl]-5-ethyl-2-methyl-N-(2-pyrrolidin-1-ylethyl)aniline | A | B |
| 246 | 3-[4-(3-bromo-1H-pyrazolo[3,4-d]pyrimidin-4-yl)piperazin-1-yl]-2-methyl-N-(2-pyrrolidin-1-ylethyl)-5-[2-(trimethylsilyl)ethyl]aniline | A | A |
| 247 | 3-[4-(3-bromo-1H-pyrazolo[3,4-d]pyrimidin-4-yl)piperazin-1-yl]-2-methyl-5-(2-phenylethyl)-N-(2-pyrrolidin-1-ylethyl)aniline | A | A |
| 248 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-one | A | A |
| 249 | 3-[4-(3-bromo-1H-pyrazolo[3,4-d]pyrimidin-4-yl)piperazin-1-yl]-N,4-dimethyl-N-(methyloxy)-5-[(2-pyrrolidin-1-ylethyl)amino]benzamide | A | B |
| 250 | 3-bromo-4-[4-(3-bromo-5-{[2,3-difluoro-2-(fluoromethyl)propyl]oxy}-2-methylphenyl)piperazin-1-yl]-1H-pyrazolo[3,4-d]pyrimidine | A | B |
| 251 | 4-[4-(3-bromo-5-{[2,3-difluoro-2-(fluoromethyl)propyl]oxy}-2-methylphenyl)piperazin-1-yl]-3-ethyl-1H-pyrazolo[3,4-d]pyrimidine | A | B |
| 252 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}ethanone | A | A |
| 253 | 3-[4-(3-bromo-1H-pyrazolo[3,4-d]pyrimidin-4-yl)piperazin-1-yl]-5-[(difluoromethyl)oxy]-2-methyl-N-(2-pyrrolidin-1-ylethyl)aniline | A | A |
| 254 | 3-[4-(3-bromo-1H-pyrazolo[3,4-d]pyrimidin-4-yl)piperazin-1-yl]-5-{[(difluoromethyl)oxy]methyl}-2-methyl-N-(2-pyrrolidin-1-ylethyl)aniline | A | A |

TABLE 1-continued

| Entry | Name | P70S6K IC50 | AKT-1 IC50 |
|---|---|---|---|
| 255 | 3-[4-(3-bromo-1H-pyrazolo[3,4-d]pyrimidin-4-yl)piperazin-1-yl]-2-methyl-5-(methyloxy)-N-(2-pyrrolidin-1-ylethyl)aniline | A | B |
| 256 | 5-{[2,3-difluoro-2-(fluoromethyl)propyl]oxy}-3-[4-(3-ethyl-1H-pyrazolo[3,4-d]pyrimidin-4-yl)piperazin-1-yl]-2-methyl-N-(2-pyrrolidin-1-ylethyl)aniline | A | A |
| 257 | 2-[4-(3-bromo-1H-pyrazolo[3,4-d]pyrimidin-4-yl)piperazin-1-yl]-3,5,6-trifluoro-N-(3-methylbutyl)pyridin-4-amine | B | C |
| 258 | 3-[4-(3-bromo-1H-pyrazolo[3,4-d]pyrimidin-4-yl)piperazin-1-yl]-N-[(cyclopropylmethyl)oxy]-4-methyl-5-[(2-pyrrolidin-1-ylethyl)amino]benzamide | A | B |
| 259 | 3-[4-(3-bromo-1H-pyrazolo[3,4-d]pyrimidin-4-yl)piperazin-1-yl]-2-methyl-5-(5-methyl-1,2,4-oxadiazol-3-yl)-N-(2-pyrrolidin-1-ylethyl)aniline | A | A |
| 260 | 3-[4-(3-bromo-1H-pyrazolo[3,4-d]pyrimidin-4-yl)piperazin-1-yl]-5-(ethylsulfonyl)-2-methyl-N-(2-pyrrolidin-1-ylethyl)aniline | A | A |
| 261 | 3-[4-(3-bromo-1H-pyrazolo[3,4-d]pyrimidin-4-yl)piperazin-1-yl]-2-methyl-5-(methylsulfonyl)-N-(2-pyrrolidin-1-ylethyl)aniline | A | B |
| 262 | 1-{3-[4-(3-ethyl-1H-pyrazolo[3,4-d]pyrimidin-4-yl)piperazin-1-yl]-4-methyl-5-[(2-pyrrolidin-1-ylethyl)amino]phenyl}pentan-1-one | A | A |
| 263 | 3-bromo-4-[4-(5-{[2,3-difluoro-2-(fluoromethyl)propyl]oxy}-2-methylphenyl)piperazin-1-yl]-1H-pyrazolo[3,4-d]pyrimidine | A | A |
| 264 | 6-[4-(3-bromo-1H-pyrazolo[3,4-d]pyrimidin-4-yl)piperazin-1-yl]-3,5-difluoro-N~4~-(3-methylbutyl)-N~2~-(2-pyrrolidin-1-ylethyl)pyridine-2,4-diamine | A | B |
| 265 | 3-bromo-5-[4-(3-bromo-1H-pyrazolo[3,4-d]pyrimidin-4-yl)piperazin-1-yl]-N-(2-pyrrolidin-1-ylethyl)aniline | A | A |
| 266 | 3-bromo-4-[4-(3',4',6-trifluoro-4-methylbiphenyl-3-yl)piperazin-1-yl]-1H-pyrazolo[3,4-d]pyrimidine | A | B |
| 267 | 3-[4-(3-bromo-1H-pyrazolo[3,4-d]pyrimidin-4-yl)piperazin-1-yl]-5-chloro-N-(2-pyrrolidin-1-ylethyl)aniline | A | A |
| 268 | {3-[4-(3-bromo-1H-pyrazolo[3,4-d]pyrimidin-4-yl)piperazin-1-yl]-4-methyl-5-[(2-pyrrolidin-1-ylethyl)amino]phenyl}methanol | A | B |
| 269 | 3-bromo-4-(4-{4-methyl-2'-[(2-pyrrolidin-1-ylethyl)oxy]biphenyl-3-yl}piperazin-1-yl)-1H-pyrazolo[3,4-d]pyrimidine | A | A |
| 270 | 3-[4-(3-bromo-1H-pyrazolo[3,4-d]pyrimidin-4-yl)piperazin-1-yl]-5-{[(2,2-difluorocyclopropyl)methyl]oxy}-2-methyl-N-(2-pyrrolidin-1-ylethyl)aniline | A | A |
| 271 | 5-bromo-3-[4-(3-bromo-1H-pyrazolo[3,4-d]pyrimidin-4-yl)piperazin-1-yl]-2-methyl-N-(2-pyrrolidin-1-ylethyl)aniline | A | A |
| 272 | 3-[4-(3-bromo-1H-pyrazolo[3,4-d]pyrimidin-4-yl)piperazin-1-yl]-5-[(ethyloxy)methyl]-2-methyl-N-(2-pyrrolidin-1-ylethyl)aniline | A | A |
| 273 | 3-[4-(3-bromo-1H-pyrazolo[3,4-d]pyrimidin-4-yl)piperazin-1-yl]-1-methyl-6-(trifluoromethyl)-1H-benzimidazol-2-yl]propan-1-ol | A | B |
| 274 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}-4,4,4-trifluorobutan-1-one | A | A |
| 275 | {3-[4-(3-bromo-1H-pyrazolo[3,4-d]pyrimidin-4-yl)piperazin-1-yl]-4-methyl-5-[(2-pyrrolidin-1-ylethyl)amino]phenyl}(cyclopropyl)methanone | A | A |
| 276 | 3-({3'-[4-(3-bromo-1H-pyrazolo[3,4-d]pyrimidin-4-yl)piperazin-1-yl]-4'-methylbiphenyl-2-yl}oxy)-N,N-dimethylpropan-1-amine | A | A |
| 277 | 3-[4-(3-bromo-1H-pyrazolo[3,4-d]pyrimidin-4-yl)piperazin-1-yl]-5-(1,1-difluorobutyl)-2-methyl-N-(2-pyrrolidin-1-ylethyl)aniline | A | A |
| 278 | 3-bromo-4-(4-{4-methyl-2'-[(3-morpholin-4-ylpropyl)oxy]biphenyl-3-yl}piperazin-1-yl)-1H-pyrazolo[3,4-d]pyrimidine | A | A |
| 279 | 3-bromo-4-(4-{4-methyl-2'-[(2-morpholin-4-ylethyl)oxy]biphenyl-3-yl}piperazin-1-yl)-1H-pyrazolo[3,4-d]pyrimidine | A | A |
| 280 | 3-[4-(3-bromo-1H-pyrazolo[3,4-d]pyrimidin-4-yl)piperazin-1-yl]-2-methyl-N-(2-pyrrolidin-1-ylethyl)-5-{[(2,2,2-trifluoroethyl)oxy]methyl}aniline | A | A |
| 281 | 1-[2-({3'-[4-(3-bromo-1H-pyrazolo[3,4-d]pyrimidin-4-yl)piperazin-1-yl]-4'-methylbiphenyl-2-yl}oxy)ethyl]pyrrolidine-2,5-dione | A | A |
| 282 | 3-bromo-4-(4-{3'-fluoro-4-methyl-2'-[(2-pyrrolidin-1-ylethyl)oxy]biphenyl-3-yl}piperazin-1-yl)-1H-pyrazolo[3,4-d]pyrimidine | A | A |
| 283 | 1-{3-[4-(3-bromo-1H-pyrazolo[3,4-d]pyrimidin-4-yl)piperazin-1-yl]-5-[(2-pyrrolidin-1-ylethyl)amino]phenyl}butan-1-one | A | A |
| 284 | 3-[4-(3-bromo-1H-pyrazolo[3,4-d]pyrimidin-4-yl)piperazin-1-yl]-2-methyl-N-(2-pyrrolidin-1-ylethyl)-5-[(3,3,3-trifluoropropyl)oxy]aniline | A | A |
| 285 | 3-[4-(3-bromo-1H-pyrazolo[3,4-d]pyrimidin-4-yl)piperazin-1-yl]-2-methyl-N-(2-pyrrolidin-1-ylethyl)-5-[(2,2,2-trifluoroethyl)oxy]aniline | A | A |
| 286 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-ol | A | A |
| 287 | 3-bromo-4-(4-{4-chloro-2'-[(2-pyrrolidin-1-ylethyl)oxy]biphenyl-3-yl}piperazin-1-yl)-1H-pyrazolo[3,4-d]pyrimidine | A | A |
| 288 | 3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-yn-1-ol | A | A |
| 289 | 3-bromo-4-(4-{4-chloro-4'-fluoro-2'-[(2-pyrrolidin-1-ylethyl)oxy]biphenyl-3-yl}piperazin-1-yl)-1H-pyrazolo[3,4-d]pyrimidine | A | A |
| 290 | 3-bromo-4-(4-{4-methyl-3'-[(2-pyrrolidin-1-ylethyl)oxy]biphenyl-3-yl}piperazin-1-yl)-1H-pyrazolo[3,4-d]pyrimidine | A | A |
| 291 | (2E)-3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-enoic acid | A | A |
| 292 | 3-[4-(3-bromo-1H-pyrazolo[3,4-d]pyrimidin-4-yl)piperazin-1-yl]-2-methyl-N-(2-pyrrolidin-1-ylethyl)-5-[4,4,4-trifluoro-1,1-bis(methyloxy)butyl]aniline | A | A |
| 293 | 6-(4-phenylpiperazin-1-yl)-9H-purine | C | D |
| 294 | 6-[4-(3-chlorophenyl)piperazin-1-yl]-9H-purine | B | D |
| 295 | 4-(4-phenylpiperazin-1-yl)-7H-pyrrolo[2,3-d]pyrimidine | B | D |
| 296 | 4-[4-(3-chlorophenyl)piperazin-1-yl]-7H-pyrrolo[2,3-d]pyrimidine | B | C |
| 297 | 4-(4-phenylpiperazin-1-yl)-1H-pyrazolo[3,4-d]pyrimidine | B | D |
| 298 | 4-[4-(3-chlorophenyl)piperazin-1-yl]-1H-pyrazolo[3,4-d]pyrimidine | B | D |
| 299 | 6-[4-(2-chlorophenyl)piperazin-1-yl]-9H-purine | C | D |
| 300 | 6-[4-(2-fluorophenyl)piperazin-1-yl]-9H-purine | C | D |
| 301 | 4-[4-(2-methylphenyl)piperazin-1-yl]-7H-pyrrolo[2,3-d]pyrimidine | B | D |
| 302 | 4-{4-[2-(methyloxy)phenyl]piperazin-1-yl}-7H-pyrrolo[2,3-d]pyrimidine | B | D |
| 303 | 4-{4-[3-(methyloxy)phenyl]piperazin-1-yl}-7H-pyrrolo[2,3-d]pyrimidine | B | D |
| 304 | 4-{4-[4-(methyloxy)phenyl]piperazin-1-yl}-7H-pyrrolo[2,3-d]pyrimidine | C | D |
| 305 | 4-{4-[3-(trifluoromethyl)phenyl]piperazin-1-yl}-7H-pyrrolo[2,3-d]pyrimidine | B | D |
| 306 | 6-{4-[4-(methyloxy)phenyl]piperazin-1-yl}-9H-purine | C | D |
| 307 | 6-{4-[2-(methyloxy)phenyl]piperazin-1-yl}-9H-purine | B | D |
| 308 | 6-[4-(4-chlorophenyl)piperazin-1-yl]-9H-purine | C | D |
| 309 | 6-[4-(4-fluorophenyl)piperazin-1-yl]-9H-purine | C | D |
| 310 | 4-[4-(3-fluorophenyl)piperazin-1-yl]-7H-pyrrolo[2,3-d]pyrimidine | C | D |
| 311 | 4-[4-(2-chlorophenyl)piperazin-1-yl]-7H-pyrrolo[2,3-d]pyrimidine | B | D |
| 312 | 4-[4-(4-fluorophenyl)piperazin-1-yl]-7H-pyrrolo[2,3-d]pyrimidine | B | D |

TABLE 1-continued

| Entry | Name | P70S6K IC50 | AKT-1 IC50 |
|---|---|---|---|
| 313 | 4-[4-(2-fluorophenyl)piperazin-1-yl]-7H-pyrrolo[2,3-d]pyrimidine | B | D |
| 314 | 6-{4-[3-(trifluoromethyl)phenyl]piperazin-1-yl}-9H-purine | B | D |
| 315 | 6-[4-(2-methylphenyl)piperazin-1-yl]-9H-purine | B | D |
| 316 | 4-{4-[3-(trifluoromethyl)phenyl]piperazin-1-yl}-1H-pyrazolo[3,4-d]pyrimidine | A | D |
| 317 | 4-[4-(2-methylphenyl)piperazin-1-yl]-1H-pyrazolo[3,4-d]pyrimidine | B | D |
| 318 | 4-[4-(3-chlorophenyl)piperazin-1-yl]-3-methyl-1H-pyrazolo[3,4-d]pyrimidine | A | D |
| 319 | 3-methyl-4-[4-(2-methylphenyl)piperazin-1-yl]-1H-pyrazolo[3,4-d]pyrimidine | A | |
| 320 | 4-[4-(5-chloro-2-methylphenyl)piperazin-1-yl]-1H-pyrazolo[3,4-d]pyrimidine | A | C |
| 321 | 4-[4-(5-chloro-2-methylphenyl)piperazin-1-yl]-3-methyl-1H-pyrazolo[3,4-d]pyrimidine | A | C |
| 322 | 4-[4-(5-chloro-2-methylphenyl)piperazin-1-yl]-3-methyl-6-phenyl-1H-pyrazolo[3,4-d]pyrimidine | C | C |
| 323 | 4-[4-(5-chloro-2-methylphenyl)piperazin-1-yl]-3-ethyl-1H-pyrazolo[3,4-d]pyrimidine | A | C |
| 324 | 4-[4-(5-chloro-2-methylphenyl)piperazin-1-yl]-6-methyl-1H-pyrazolo[3,4-d]pyrimidine | C | C |
| 325 | 4-[4-(5-chloro-2-methylphenyl)piperazin-1-yl]-6-ethyl-1H-pyrazolo[3,4-d]pyrimidine | C | C |
| 326 | 4-[4-(5-chloro-2-methylphenyl)piperazin-1-yl]-6-(1-methylethyl)-1H-pyrazolo[3,4-d]pyrimidine | C | C |
| 327 | 4-[4-(5-chloro-2-methylphenyl)piperazin-1-yl]-3-phenyl-1H-pyrazolo[3,4-d]pyrimidine | A | C |
| 328 | 4-[4-(5-chloro-2-methylphenyl)piperazin-1-yl]-3-({[2-(methyloxy)ethyl]oxy}methyl)-1H-pyrazolo[3,4-d]pyrimidine | A | C |
| 329 | 3-bromo-4-[4-(5-chloro-2-methylphenyl)piperazin-1-yl]-1H-pyrazolo[3,4-d]pyrimidine | A | B |
| 330 | 4-[4-(5-chloro-2-methylphenyl)piperazin-1-yl]-3-propyl-1H-pyrazolo[3,4-d]pyrimidine | A | C |
| 331 | 4-{4-[4-(5-chloro-2-methylphenyl)piperazin-1-yl]-1H-pyrazolo[3,4-d]pyrimidin-3-yl}phenol | A | C |
| 332 | 4-[4-(5-chloro-2-methylphenyl)piperazin-1-yl]-N-phenyl-1H-pyrazolo[3,4-d]pyrimidin-3-amine | C | C |
| 333 | 4-[4-(3-chlorophenyl)piperazin-1-yl]-3-ethyl-1H-pyrazolo[3,4-d]pyrimidine | A | C |
| 334 | 4-{4-[5-chloro-2-(methyloxy)phenyl]piperazin-1-yl}-3-ethyl-1H-pyrazolo[3,4-d]pyrimidine | A | C |
| 335 | 3-{4-[4-(5-chloro-2-methylphenyl)piperazin-1-yl]-1H-pyrazolo[3,4-d]pyrimidin-3-yl}phenol | B | C |
| 336 | 4-[4-(5-chloro-2-methylphenyl)piperazin-1-yl]-3-{3-[(phenylmethyl)oxy]phenyl}-1H-pyrazolo[3,4-d]pyrimidine | C | C |
| 337 | 3-(1,3-benzodioxol-5-yl)-4-[4-(5-chloro-2-methylphenyl)piperazin-1-yl]-1H-pyrazolo[3,4-d]pyrimidine | B | C |
| 338 | 4-[4-(5-chloro-2-methylphenyl)piperazin-1-yl]-3-(2-thienyl)-1H-pyrazolo[3,4-d]pyrimidine | A | C |
| 339 | 3-{4-[4-(5-chloro-2-methylphenyl)piperazin-1-yl]-1H-pyrazolo[3,4-d]pyrimidin-3-yl}aniline | B | C |
| 340 | 3-{4-[4-(5-chloro-2-methylphenyl)piperazin-1-yl]-d1H-pyrazolo[3,4-]pyrimidin-3-yl}benzoic acid | C | C |
| 341 | 4-[4-(5-chloro-2-methylphenyl)piperazin-1-yl]-3-(4-methylphenyl)-1H-pyrazolo[3,4-d]pyrimidine | C | C |
| 342 | N-(4-{4-[4-(5-chloro-2-methylphenyl)piperazin-1-yl]-1H-pyrazolo[3,4-d]pyrimidin-3-yl}phenyl)acetamide | B | C |
| 343 | 4-[4-(3-chlorophenyl)-1,4-diazepan-1-yl]-3-ethyl-1H-pyrazolo[3,4-d]pyrimidine | B | D |
| 344 | 4-[5-(3-chlorophenyl)-2,5-diazabicyclo[2.2.1]hept-2-yl]-3-ethyl-1H-pyrazolo[3,4-d]pyrimidine | A | C |
| 345 | 4-(4-{3-chloro-4-[(2-morpholin-4-ylethyl)oxy]phenyl}piperazin-1-yl)-3-ethyl-1H-pyrazolo[3,4-d]pyrimidine | C | D |
| 346 | methyl 1-(3-chlorophenyl)-4-(3-ethyl-1H-pyrazolo[3,4-d]pyrimidin-4-yl)piperazine-2-carboxylate | C | D |
| 347 | 4-[4-(5-chloro-2-methylphenyl)piperazin-1-yl]-3-(3-methylbut-2-en-1-yl)-1H-pyrazolo[3,4-d]pyrimidine | A | |
| 348 | 4-[4-(5-chloro-2-methylphenyl)piperazin-1-yl]-3-(trifluoromethyl)-1H-pyrazolo[3,4-d]pyrimidine | A | C |
| 349 | methyl 4-(3-chlorophenyl)-1-(3-ethyl-1H-pyrazolo[3,4-d]pyrimidin-4-yl)piperazine-2-carboxylate | C | D |
| 350 | 4-(4-{3-chloro-4-[(2-piperidin-1-ylethyl)oxy]phenyl}piperazin-1-yl)-3-ethyl-1H-pyrazolo[3,4-d]pyrimidine | C | D |
| 351 | 4-[4-(5-chloro-2-methylphenyl)piperazin-1-yl]-3-(1-methylethyl)-1H-pyrazolo[3,4-d]pyrimidine | A | C |
| 352 | 1-(3-chlorophenyl)-4-(3-ethyl-1H-pyrazolo[3,4-d]pyrimidin-4-yl)piperazine-2-carboxylic acid | B | D |
| 353 | 1-(3-chlorophenyl)-4-(3-ethyl-1H-pyrazolo[3,4-d]pyrimidin-4-yl)-N-methylpiperazine-2-carboxamide | B | C |
| 354 | 4-[4-(5-chloro-2-methylphenyl)piperazin-1-yl]-3-(phenylmethyl)-1H-pyrazolo[3,4-d]pyrimidine | B | C |
| 355 | 4-[4-(5-chloro-2-methylphenyl)piperazin-1-yl]-3-(2-methylpropyl)-1H-pyrazolo[3,4-d]pyrimidine | A | C |
| 356 | 4-[4-(5-chloro-2-methylphenyl)piperazin-1-yl]-3-[4-(methyloxy)phenyl]-1H-pyrazolo[3,4-d]pyrimidine | B | C |
| 357 | 4-[4-(5-chloro-2-methylphenyl)piperazin-1-yl]-3-(4-fluorophenyl)-1H-pyrazolo[3,4-d]pyrimidine | B | C |
| 358 | 4-[4-(5-chloro-2-methylphenyl)piperazin-1-yl]-3-[4-(phenyloxy)phenyl]-1H-pyrazolo[3,4-d]pyrimidine | B | C |
| 359 | 4-[4-(5-chloro-2-methylphenyl)piperazin-1-yl]-3-{4-[(piperidin-4-ylmethyl)oxy]phenyl}-1H-pyrazolo[3,4-d]pyrimidine | B | |
| 360 | 1-(3-chlorophenyl)-N-[2-(dimethylamino)ethyl]-4-(3-ethyl-1H-pyrazolo[3,4-d]pyrimidin-4-yl)piperazine-2-carboxamide | C | C |
| 361 | 4-[4-(5-chloro-2-methyl-3-morpholin-4-ylphenyl)piperazin-1-yl]-3-ethyl-1H-pyrazolo[3,4-d]pyrimidine | B | C |
| 362 | 4-(3-chlorophenyl)-1-(3-ethyl-1H-pyrazolo[3,4-d]pyrimidin-4-yl)-N-methylpiperazine-2-carboxamide | C | |
| 363 | 4-[4-(5-chloro-2-methylphenyl)piperazin-1-yl]-3-[2-(methyloxy)phenyl]-1H-pyrazolo[3,4-d]pyrimidine | B | C |
| 364 | 4-[4-(5-chloro-2-methylphenyl)piperazin-1-yl]-3-pyridin-4-yl-1H-pyrazolo[3,4-d]pyrimidine | A | C |
| 365 | 4-[4-(5-chloro-2-methylphenyl)piperazin-1-yl]-3-[3-(methyloxy)phenyl]-1H-pyrazolo[3,4-d]pyrimidine | C | C |
| 366 | 4-{4-[4-(5-chloro-2-methylphenyl)piperazin-1-yl]-1H-pyrazolo[3,4-d]pyrimidin-3-yl}benzonitrile | C | C |
| 367 | [5-chloro-3-[4-(3-ethyl-1H-pyrazolo[3,4-d]pyrimidin-4-yl)piperazin-1-yl]-2-(methyloxy)phenyl]methanol | A | C |
| 368 | methyl 5-chloro-3-[4-(3-ethyl-1H-pyrazolo[3,4-d]pyrimidin-4-yl)piperazin-1-yl]-2-(methyloxy)benzoate | B | C |
| 369 | (2E)-3-{4-[4-(5-chloro-2-methylphenyl)piperazin-1-yl]-1H-pyrazolo[3,4-d]pyrimidin-3-yl}prop-2-enoic acid | A | B |
| 370 | 3-{4-[4-(5-chloro-2-methylphenyl)piperazin-1-yl]-1H-pyrazolo[3,4-d]pyrimidin-3-yl}propanoic acid | A | C |
| 371 | 3-{4-[4-(5-chloro-2-methylphenyl)piperazin-1-yl]-1H-pyrazolo[3,4-d]pyrimidin-3-yl}propan-1-ol | A | C |
| 372 | methyl (2E)-3-{4-[4-(5-chloro-2-methylphenyl)piperazin-1-yl]-1H-pyrazolo[3,4-d]pyrimidin-3-yl}prop-2-enoate | A | C |
| 373 | 4-[4-(5-chloro-2-methylphenyl)piperazin-1-yl]-3-{4-[(2-morpholin-4-ylethyl)oxy]phenyl}-1H-pyrazolo[3,4-d]pyrimidine | C | C |
| 374 | 5-chloro-N-[2-(dimethylamino)ethyl]-3-[4-(3-ethyl-1H-pyrazolo[3,4-d]pyrimidin-4-yl)piperazin-1-yl]-2-(methyloxy)benzamide | A | C |

TABLE 1-continued

| Entry | Name | P70S6K IC50 | AKT-1 IC50 |
|---|---|---|---|
| 375 | 4-(4-{5-chloro-2-(methyloxy)-3-[(4-methylpiperazin-1-yl)carbonyl]phenyl}piperazin-1-yl)-3-ethyl-1H-pyrazolo[3,4-d]pyrimidine | B | D |
| 376 | 2-(dimethylamino)ethyl 5-chloro-3-[4-(3-ethyl-1H-pyrazolo[3,4-d]pyrimidin-4-yl)piperazin-1-yl]-2-(methyloxy)benzoate | A | C |
| 377 | 1-[5-chloro-3-[4-(3-ethyl-1H-pyrazolo[3,4-d]pyrimidin-4-yl)piperazin-1-yl]-2-(methyloxy)phenyl]-N,N-dimethylmethanamine | B | D |
| 378 | N'-{[5-chloro-3-[4-(3-ethyl-1H-pyrazolo[3,4-d]pyrimidin-4-yl)piperazin-1-yl]-2-(methyloxy)phenyl]methyl}-N,N-dimethylethane-1,2-diamine | B | C |
| 379 | [1-(3-chlorophenyl)-4-(3-ethyl-1H-pyrazolo[3,4-d]pyrimidin-4-yl)piperazin-2-yl]methanol | A | C |
| 380 | 3-[(4-{4-[4-(5-chloro-2-methylphenyl)piperazin-1-yl]-1H-pyrazolo[3,4-d]pyrimidin-3-yl}phenyl)oxy]-N,N-dimethylpropan-1-amine | C | C |
| 381 | 2-chloro-4-[4-(3-ethyl-1H-pyrazolo[3,4-d]pyrimidin-4-yl)piperazin-1-yl]-5-methylphenol | A | C |
| 382 | 1-(3-chlorophenyl)-4-(3-ethyl-1H-pyrazolo[3,4-d]pyrimidin-4-yl)-N-(1-methylpiperidin-4-yl)piperazine-2-carboxamide | C | D |
| 383 | 1-(3-chlorophenyl)-4-(3-ethyl-1H-pyrazolo[3,4-d]pyrimidin-4-yl)-N-(2-morpholin-4-ylethyl)piperazine-2-carboxamide | C | D |
| 384 | 2-{[5-chloro-3-[4-(3-ethyl-1H-pyrazolo[3,4-d]pyrimidin-4-yl)piperazin-1-yl]-2-(methyloxy)phenyl]oxy}-N,N-dimethylethanamine | A | C |
| 385 | 3-{5-chloro-3-[4-(3-ethyl-1H-pyrazolo[3,4-d]pyrimidin-4-yl)piperazin-1-yl]-2-methylphenyl}-N,N-dimethylprop-2-yn-1-amine | A | C |
| 386 | N'-{5-chloro-3-[4-(3-ethyl-1H-pyrazolo[3,4-d]pyrimidin-4-yl)piperazin-1-yl]-2-methylphenyl}-N,N-dimethylethane-1,2-diamine | A | B |
| 387 | 1,1-dimethylethyl (2E)-3-{4-[4-(5-chloro-2-methylphenyl)piperazin-1-yl]-1H-pyrazolo[3,4-d]pyrimidin-3-yl}prop-2-enoate | B | C |
| 388 | 3-({2-chloro-4-[4-(3-ethyl-1H-pyrazolo[3,4-d]pyrimidin-4-yl)piperazin-1-yl]-5-methylphenyl}oxy)-N,N-dimethylpropan-1-amine | B | C |
| 389 | 2-({2-chloro-4-[4-(3-ethyl-1H-pyrazolo[3,4-d]pyrimidin-4-yl)piperazin-1-yl]-5-methylphenyl}oxy)-N,N-dimethylethanamine | B | C |
| 390 | 4-{4-[5-chloro-2-methyl-4-(methyloxy)phenyl]piperazin-1-yl}-3-ethyl-1H-pyrazolo[3,4-d]pyrimidine | A | C |
| 391 | 4-[4-(5-chloro-2-methylphenyl)piperazin-1-yl]-3-(4-methylpiperazin-1-yl)-1H-pyrazolo[3,4-d]pyrimidine | C | C |
| 392 | 3-{4-[4-(5-chloro-2-methylphenyl)piperazin-1-yl]-1H-pyrazolo[3,4-d]pyrimidin-3-yl}-N,N-diethylprop-2-yn-1-amine | A | C |
| 393 | 3-{4-[4-(5-chloro-2-methylphenyl)piperazin-1-yl]-1H-pyrazolo[3,4-d]pyrimidin-3-yl}prop-2-yn-1-ol | A | B |
| 394 | 4-[4-(5-chloro-2-methylphenyl)piperazin-1-yl]-3-(piperidin-4-ylmethyl)-1H-pyrazolo[3,4-d]pyrimidine | C | C |
| 395 | phenylmethyl (3aR,6aS)-5-({4-[4-(5-chloro-2-methylphenyl)piperazin-1-yl]-1H-pyrazolo[3,4-d]pyrimidin-3-yl}methylidene)hexahydrocyclopenta[c]pyrrole-2(1H)-carboxylate | C | C |
| 396 | 4-[4-(5-chloro-2-methylphenyl)piperazin-1-yl]-3-[(E)-(3aR,6aS)-hexahydrocyclopenta[c]pyrrol-5(1H)-ylidenemethyl]-1H-pyrazolo[3,4-d]pyrimidine | C | C |
| 397 | 4-[4-(5-chloro-2-methylphenyl)piperazin-1-yl]-3-(3-pyrrolidin-1-ylprop-1-yn-1-yl)-1H-pyrazolo[3,4-d]pyrimidine | B | C |
| 398 | 4-[4-(5-chloro-2-methylphenyl)piperazin-1-yl]-3-[3-(4-methylpiperazin-1-yl)prop-1-yn-1-yl]-1H-pyrazolo[3,4-d]pyrimidine | B | C |
| 399 | 3-{4-[4-(5-chloro-2-methylphenyl)piperazin-1-yl]-1H-pyrazolo[3,4-d]pyrimidin-3-yl}-N,N-diethylpropan-1-amine | C | C |
| 400 | 4-[4-(5-chloro-2-methylphenyl)piperazin-1-yl]-3-(3-pyrrolidin-1-ylpropyl)-1H-pyrazolo[3,4-d]pyrimidine | C | C |
| 401 | 4-[4-(5-chloro-2-methylphenyl)piperazin-1-yl]-3-(1,2,3,6-tetrahydropyridin-4-yl)-1H-pyrazolo[3,4-d]pyrimidine | A | C |
| 402 | 3-{5-chloro-3-[4-(3-ethyl-1H-pyrazolo[3,4-d]pyrimidin-4-yl)piperazin-1-yl]-2-methylphenyl}-N,N-diethylpropan-1-amine | A | B |
| 403 | 4-{4-[5-chloro-2-methyl-3-(3-pyrrolidin-1-ylpropyl)phenyl]piperazin-1-yl}-3-ethyl-1H-pyrazolo[3,4-d]pyrimidine | A | B |

As discussed above, the names of the compounds are generated using the nomenclature engine published by ACD/Labs of Toronto Canada. In order to further describe the compounds of the present invention, a representative number of compounds set forth in Table 1 are provided below in Table 2, wherein the structure of the compound is provided as well as the name generated by the nomenclature engine. These examples are provided to further clarify the compounds of the present invention.

TABLE 2

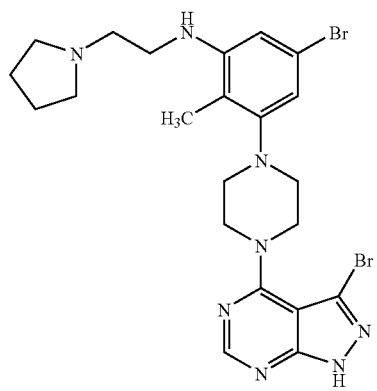

5-bromo-3-[4-(3-bromo-1H-pyrazolo[3,4-d]pyrimidin-4-yl)piperazin-1-yl]-2-methyl-N-(2-pyrrolidin-1-ylethyl)aniline TABLE 2-continued

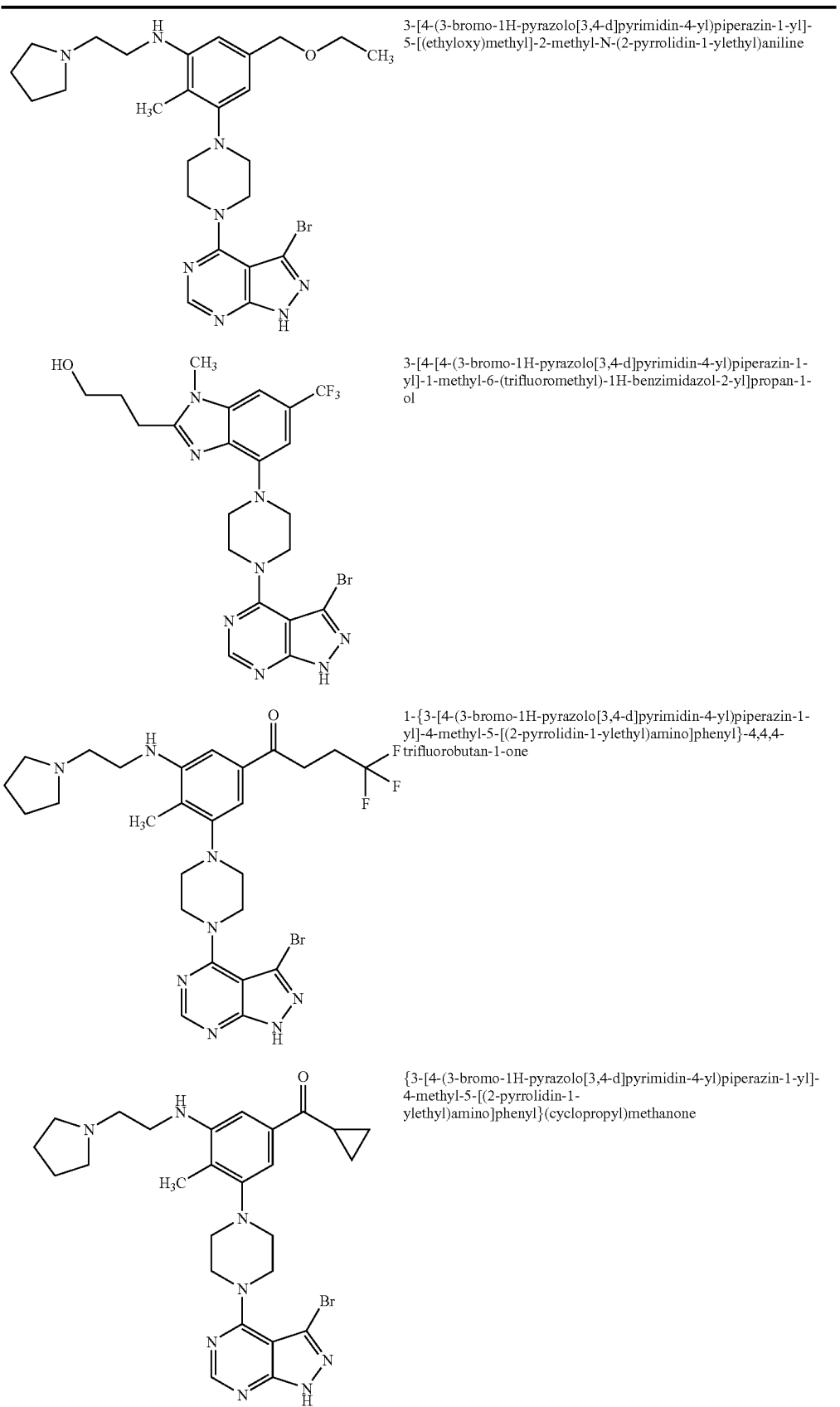

3-[4-(3-bromo-1H-pyrazolo[3,4-d]pyrimidin-4-yl)piperazin-1-yl]-5-[(ethyloxy)methyl]-2-methyl-N-(2-pyrrolidin-1-ylethyl)aniline 3-[4-[4-(3-bromo-1H-pyrazolo[3,4-d]pyrimidin-4-yl)piperazin-1-yl]-1-methyl-6-(trifluoromethyl)-1H-benzimidazol-2-yl]propan-1-ol 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}-4,4,4-trifluorobutan-1-one {3-[4-(3-bromo-1H-pyrazolo[3,4-d]pyrimidin-4-yl)piperazin-1-yl]-4-methyl-5-[(2-pyrrolidin-1-ylethyl)amino]phenyl}(cyclopropyl)methanone TABLE 2-continued
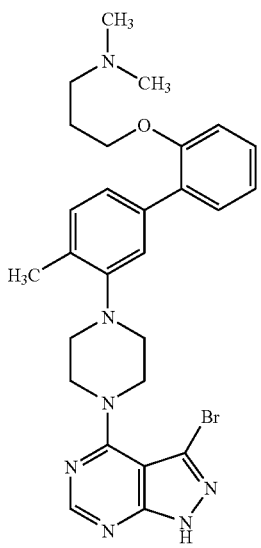
3-({3'-[4-(3-bromo-1H-pyrazolo[3,4-d]pyrimidin-4-yl)piperazin-1-yl]-4'-methylbiphenyl-2-yl}oxy)-N,N-dimethylpropan-1-amine
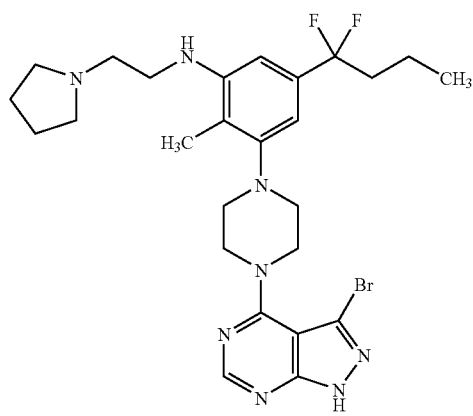
3-[4-(3-bromo-1H-pyrazolo[3,4-d]pyrimidin-4-yl)piperazin-1-yl]-5-(1,1-difluorobutyl)-2-methyl-N-(2-pyrrolidin-1-ylethyl)aniline
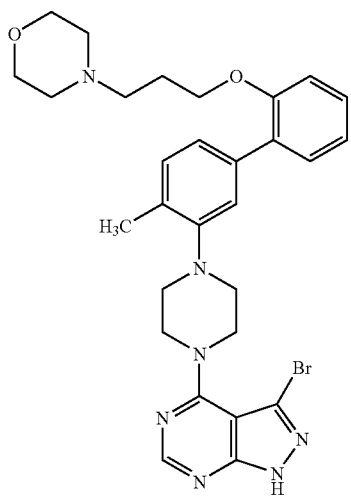
3-bromo-4-(4-{4-methyl-2'-[(3-morpholin-4-ylpropyl)oxy]biphenyl-3-yl}piperazin-1-yl)-1H-pyrazolo[3,4-d]pyrimidine TABLE 2-continued
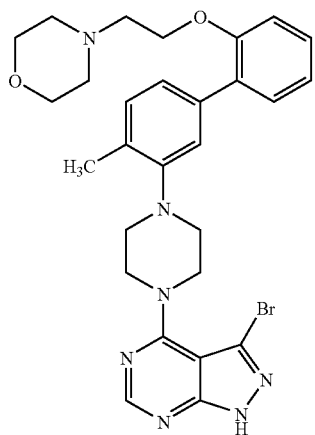
3-bromo-4-(4-{4-methyl-2'-[(2-morpholin-4-ylethyl)oxy]biphenyl-3-yl}piperazin-1-yl)-1H-pyrazolo[3,4-d]pyrimidine
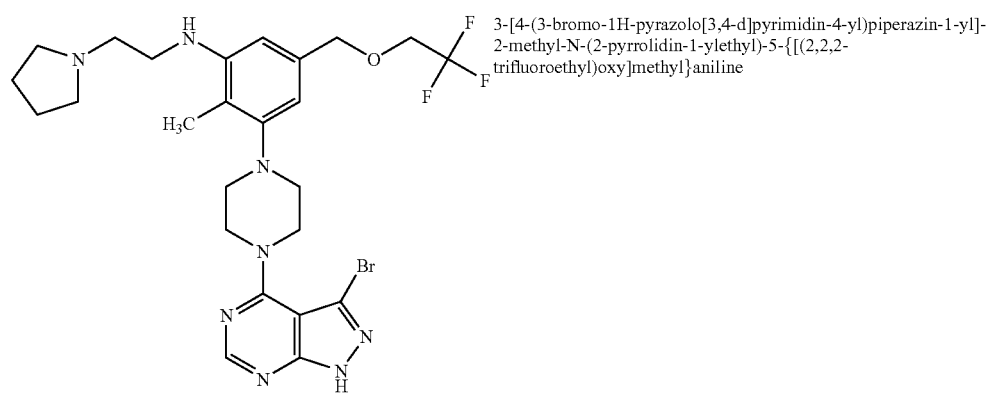
3-[4-(3-bromo-1H-pyrazolo[3,4-d]pyrimidin-4-yl)piperazin-1-yl]-2-methyl-N-(2-pyrrolidin-1-ylethyl)-5-{[(2,2,2-trifluoroethyl)oxy]methyl}aniline
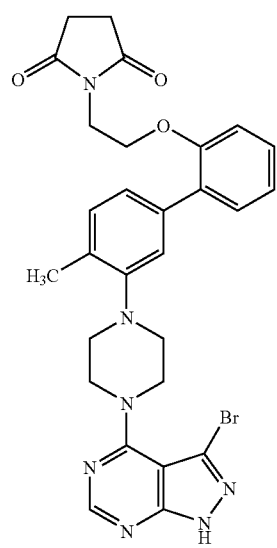
1-[2-({3'-[4-(3-bromo-1H-pyrazolo[3,4-d]pyrimidin-4-yl)piperazin-1-yl]-4'-methylbiphenyl-2-yl}oxy)ethyl]pyrrolidine-2,5-dione TABLE 2-continued
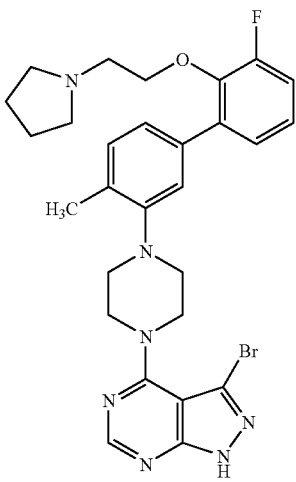
3-bromo-4-(4-{3'-fluoro-4-methyl-2'-[(2-pyrrolidin-1-ylethyl)oxy]biphenyl-3-yl}piperazin-1-yl)-1H-pyrazolo[3,4-d]pyrimidine
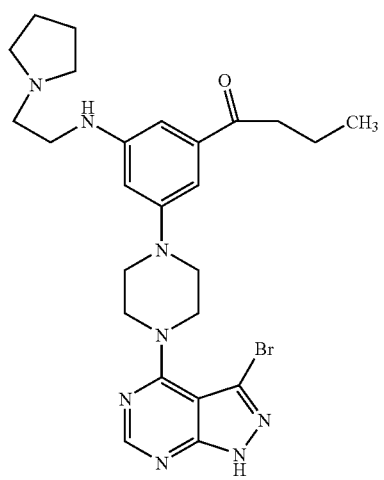
1-{3-[4-(3-bromo-1H-pyrazolo[3,4-d]pyrimidin-4-yl)piperazin-1-yl]-5-[(2-pyrrolidin-1-ylethyl)amino]phenyl}butan-1-one
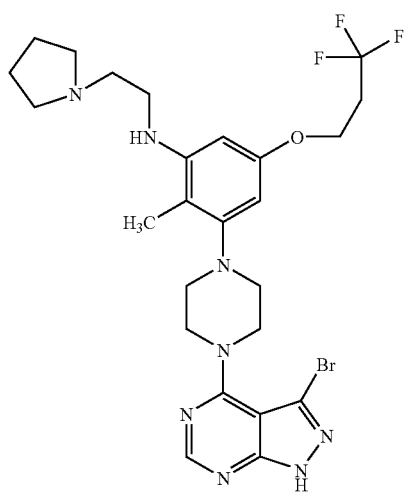
3-[4-(3-bromo-1H-pyrazolo[3,4-d]pyrimidin-4-yl)piperazin-1-yl]-2-methyl-N-(2-pyrrolidin-1-ylethyl)-5-[(3,3,3-trifluoropropyl)oxy]aniline

| | |
|---|---|
| 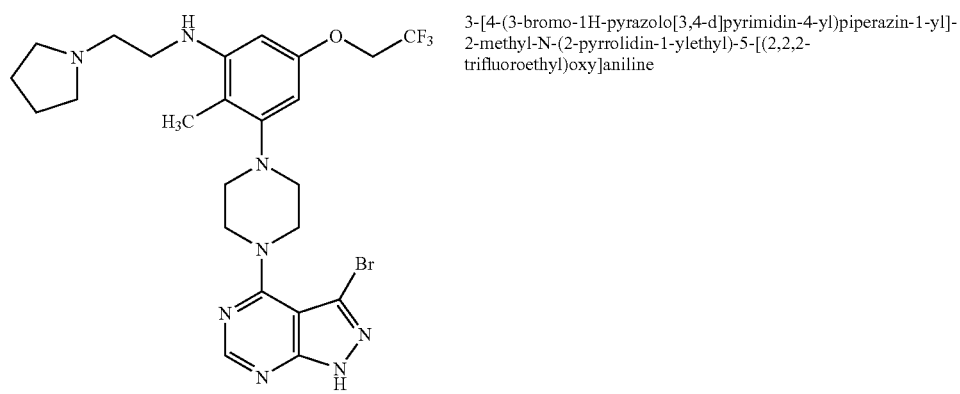 | 3-[4-(3-bromo-1H-pyrazolo[3,4-d]pyrimidin-4-yl)piperazin-1-yl]-2-methyl-N-(2-pyrrolidin-1-ylethyl)-5-[(2,2,2-trifluoroethyl)oxy]aniline |
| 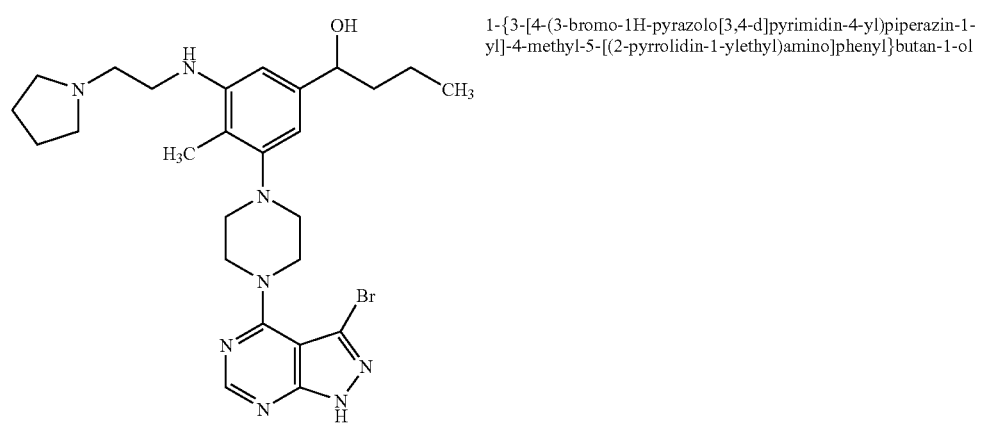 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-ol |
| 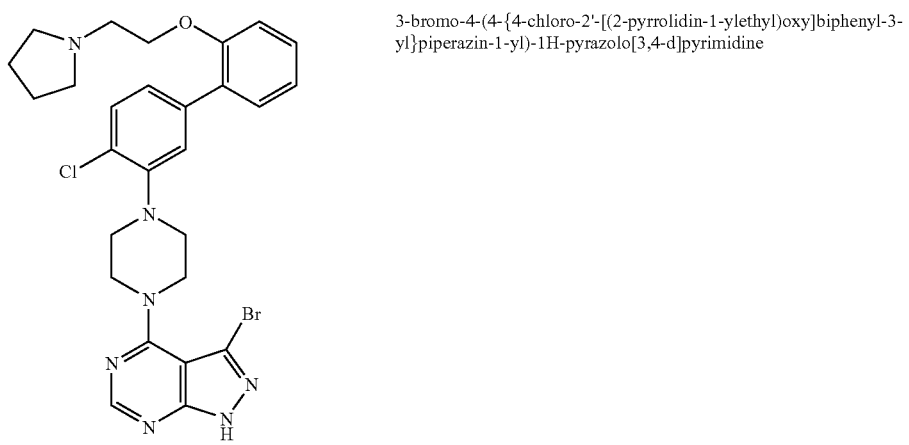 | 3-bromo-4-(4-{4-chloro-2'-[(2-pyrrolidin-1-ylethyl)oxy]biphenyl-3-yl}piperazin-1-yl)-1H-pyrazolo[3,4-d]pyrimidine |

TABLE 2-continued
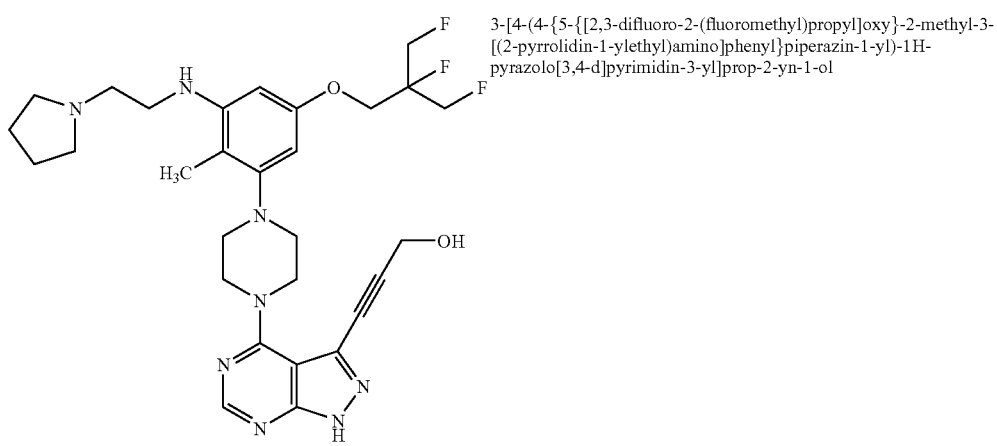
3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-yn-1-ol
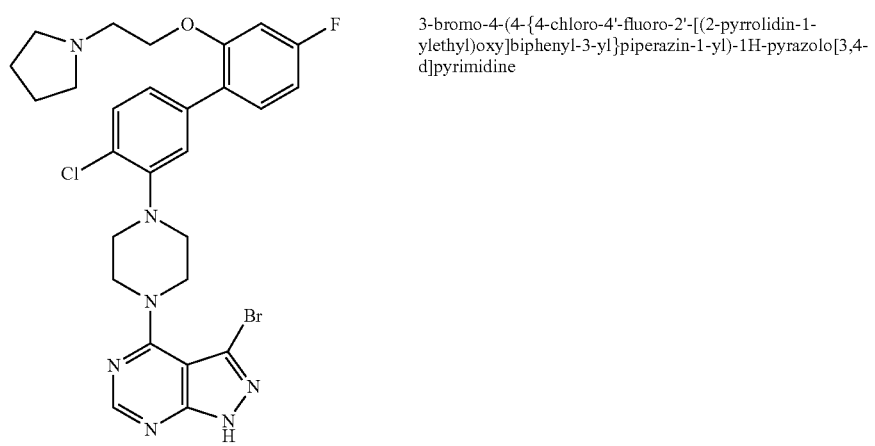
3-bromo-4-(4-{4-chloro-4'-fluoro-2'-[(2-pyrrolidin-1-ylethyl)oxy]biphenyl-3-yl}piperazin-1-yl)-1H-pyrazolo[3,4-d]pyrimidine
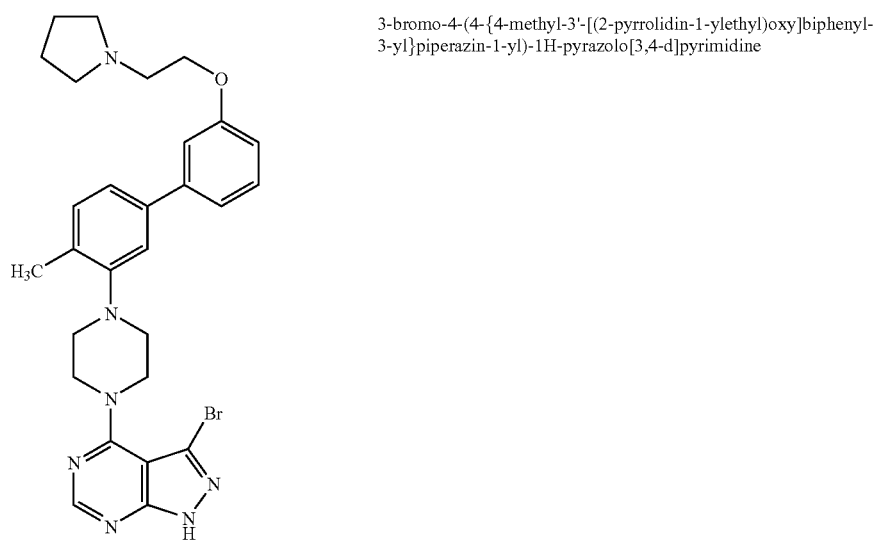
3-bromo-4-(4-{4-methyl-3'-[(2-pyrrolidin-1-ylethyl)oxy]biphenyl-3-yl}piperazin-1-yl)-1H-pyrazolo[3,4-d]pyrimidine

TABLE 2-continued

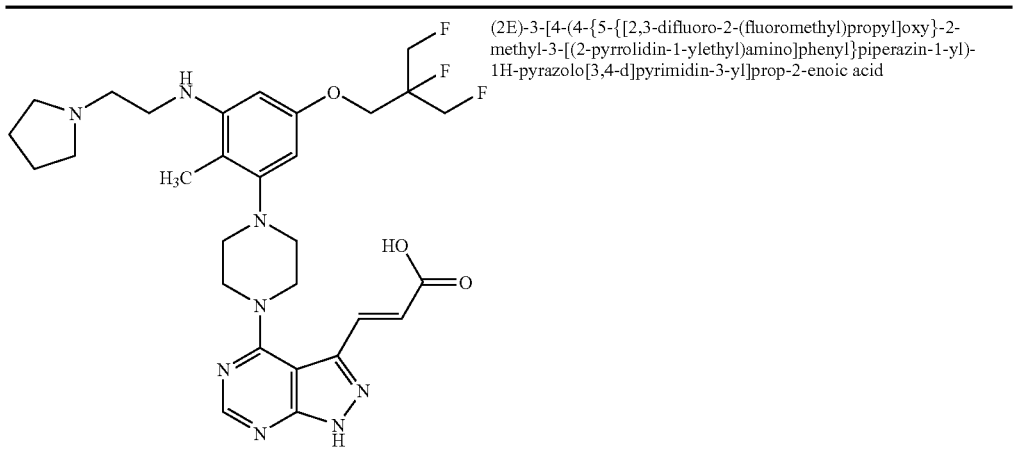

(2E)-3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-enoic acid The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:
1. A compound of Formula I,

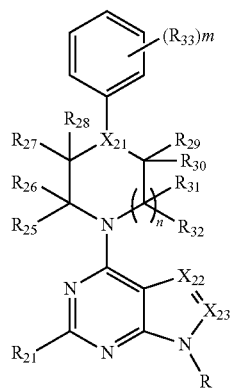

I or a pharmaceutically acceptable salt, hydrate, thereof, wherein,
$X_{21}$ is N;
$X_{22}$ is $CR_{23}$;
$X_{23}$ is N;
each of $R_{21}$, $R_{22}$, $R_{23}$, $R_{24}$, $R_{25}$, $R_{26}$, $R_{27}$, $R_{28}$, $R_{29}$ and $R_{30}$, and each $R_{31}$, $R_{32}$ and $R_{33}$ is independently selected from —H, halogen, trihalomethyl, —CN, —NO$_2$, —NR$_{35}$R$_{35a}$, —S(O)$_{0-2}$R$_{35}$, —SO$_2$NR$_{35}$R$_{35a}$, —CO$_2$R$_{35}$, —C(O)NR$_{35}$R$_{35a}$; —N(R$_{35}$)S$^O_2$R$_{35}$; —N(R$_{35}$)C(O)R$_{35}$, —N(R$_{35}$)CO$_2$R$_{35}$, —OR$_{35}$, —C(O)R$_{35}$, optionally substituted lower alkyl, optionally substituted aryl, optionally substituted heterocyclyl, optionally substituted heterocyclylalkyl, and optionally substituted arylalkyl;

R is selected from —H, halogen, trihalomethyl, —S(O)$_{0-2}$R$_{35}$, —SO$_2$NR$_{35}$R$_{35a}$, —CO$_2$R$_{35}$, —C(O)NR$_{35}$R$_{35a}$, —OR$_{35}$, —C(O)R$_{35}$, optionally substituted lower alkyl, optionally substituted heterocyclylalkyl; or two of $R_{25}$, $R_{26}$, $R_{27}$, $R_{28}$, $R_{29}$, $R_{30}$, $R_{31}$ or $R_{32}$, together with the atom or respective atoms to which they are attached, combine to form an optionally substituted spirocyclic ring system, optionally substituted fused ring system, and optionally substituted saturated bridged ring system;

each of $R_{35}$ and $R_{35a}$ is independently selected from —H, optionally substituted lower alkyl, optionally substituted lower alkoxy, optionally substituted aryl, optionally substituted lower arylalkyl, optionally substituted lower aryl alkoxy, optionally substituted heterocyclyl, and optionally substituted lower heterocyclylalkyl; or $R_{35}$ and $R_{35a}$, together with the atom or respective atoms to which they are attached, combine to form an optionally substituted five- to seven-membered heterocyclyl; and
m is an integer from 0 to 5;
n is 1.
2. A compound according to claim 1, wherein R is —H.
3. A compound according to claim 1, wherein R is optionally substituted alkyl.
4. A compound according to claim 2, wherein $R_{21}$ is —H.
5. A compound according to claim 2, wherein $R_{21}$ is optionally substituted alkyl.
6. A compound according to claim 4, wherein $R_{25}$ and $R_{26}$ are —H.
7. A compound according to claim 6, wherein $R_{27}$ and $R_{28}$ are —H.
8. A compound according to claim 7, wherein $R_{29}$ is —H.
9. A compound according to claim 8, wherein $R_{30}$ is —H.
10. A compound according to claim 8, wherein $R_{30}$ is optionally substituted alkyl.
11. A compound according to claim 8, wherein $R_{30}$ is —C(O)R$_{35}$.
12. A compound according to claim 8, wherein $R_{30}$ is —C(O)NR$_{35}$R$_{35a}$.
13. A compound according to claim 9, wherein $R_{31}$ is —H.
14. A compound according to claim 13, wherein $R_{32}$ is —H.
15. A compound according to claim 13, wherein $R_{32}$ is —C(O)R$_{35}$.

16. A compound according to claim 13, wherein $R_{29}$, $R_{30}$, $R_{31}$, and $R_{32}$ are —H.

17. A compound according to claim 14, wherein $R_{23}$ is optionally substituted alkyl.

18. A compound according to claim 14, wherein $R_{23}$ is halogen.

19. A compound according to claim 18, wherein $R_{23}$ is Br.

20. A compound according to claim 14, wherein $R_{23}$ is —H.

21. A compound according to claim 14, wherein m is 2.

22. A compound according to claim 14, wherein m is 3.

23. A compound according to claim 14, wherein $R_{33}$ is —H.

24. A compound according to claim 14, wherein $R_{33}$ is halogen.

25. A compound according to claim 14, wherein $R_{33}$ is optionally substituted alkyl.

26. A compound according to claim 14, wherein $R_{33}$ is —$NR_{35}R_{35a}$.

27. A compound according to claim 14, wherein $R_{33}$ is —$C(O)R_{35}$.

28. A compound according to claim 14, wherein $R_{33}$ is trihalomethyl.

29. A compound of Formula II,

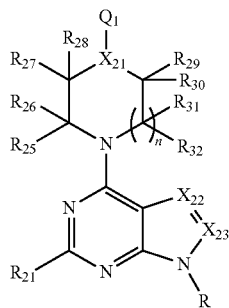

or a pharmaceutically acceptable salt, hydrate, thereof, wherein, $X_{21}$ is N or $CR_{22}$;
$X_{22}$ is N or $CR_{23}$;
$X_{23}$ is N;
each of $R_{21}$, $R_{22}$, $R_{23}$, $R_{24}$, $R_{25}$, $R_{26}$, $R_{27}$, $R_{28}$, $R_{29}$ and $R_{30}$ and each of $R_{31}$, $R_{32}$ and $R_{33}$ is independently selected from —H, halogen, trihalomethyl, —CN, —$NO_2$, —$NR_{35}R_{35a}$, —$S(O)_{0-2}R_{35}$, —$SO_2NR_{35}R_{35a}$, —$CO_2R_{35}$, —$C(O)NR_{35}R_{35a}$, —$N(R_{35})SO_2R_{35}$, —$N(R_{35})C(O)R_{35}$, —$N(R_{35})CO_2R_{35}$, —$OR_{35}$, —$C(O)R_{35}$, optionally substituted lower alkyl, optionally substituted aryl, optionally substituted heterocyclyl, optionally substituted heterocyclylalkyl, and optionally substituted arylalkyl;
R is selected from —H, halogen, trihalomethyl, —$S(O)_{0-2}R_{35}$, —$SO_2NR_{35}R_{35}$, —$CO_2R_{35}$, —$C(O)NR_{35}R_{35a}$, —$OR_{35}$, —$C(O)R_{35}$, optionally substituted lower alkyl, optionally substituted aryl, optionally substituted heterocyclyl, optionally substituted heterocyclylalkyl, and optionally substituted arylalkyl; or
two of $R_{25}$, $R_{26}$, $R_{27}$, $R_{28}$, $R_{29}$, $R_{30}$, $R_{31}$ or $R_{32}$, together with the atom or respective atoms to which they are attached, combine to form an optionally substituted spirocyclic ring system, optionally substituted fused ring system, and optionally substituted saturated bridged ring system;

each $R_{35}$ and $R_{35a}$ is independently selected from —H, optionally substituted lower alkyl, optionally substituted lower alkoxy, optionally substituted aryl, optionally substituted lower arylalkyl, optionally substituted lower aryl alkoxy, optionally substituted heterocyclyl, and optionally substituted lower heterocyclylalkyl; or
$R_{35}$ and $R_{35a}$, together with the atom or respective atoms to which they are attached, combine to form an optionally substituted five- to seven-membered heterocyclyl;
$Q_1$ optionally substituted heterocyclyl;
n is an integer from 1 to 2; and
with the proviso that when $X_{22}$ is $CR_{23}$ and $X_{23}$ is N then R is not optionally substituted aryl, aralkyl or heteroaryl.

30. A compound of claim 29, wherein n is 1.

31. A compound of claim 29, wherein R is —H.

32. A compound of claim 29, wherein R is optionally substituted alkyl.

33. A compound of claim 31, wherein $R_{21}$ is —H.

34. A compound of claim 31, wherein $R_{21}$ is optionally substituted alkyl.

35. A compound of claim 33, wherein $R_{25}$ and $R_{26}$ are —H.

36. A compound of claim 35, wherein $R_{27}$ and $R_{28}$ are —H.

37. A compound of claim 36, wherein $R_{29}$ is —H.

38. A compound of claim 37, wherein $R_{30}$ is —H.

39. A compound of claim 37, wherein $R_{30}$ is optionally substituted alkyl.

40. A compound of claim 37, wherein $R_{30}$ is —$C(O)R_{35}$.

41. A compound of claim 37, wherein $R_{30}$ is —$C(O)NR_{35}R_{35a}$.

42. A compound of claim 38, wherein $R_{31}$ is —H.

43. A compound of claim 42, wherein $R_{32}$ is —H.

44. A compound of claim 43, wherein $R_{32}$ is —$C(O)R_{35}$.

45. A compound of claim 43, wherein $R_{29}$, $R_{30}$, $R_{31}$, and $R_{32}$ are —H.

46. A compound of claim 43, wherein $R_{23}$ is optionally substituted alkyl.

47. A compound of claim 43, wherein $R_{23}$ is halogen.

48. A compound of claim 43, wherein $R_{23}$ is —H.

49. A compound of claim 43, wherein $Q_1$ is a substituted heterocyclyl wherein the heterocyclyl has at least one nitrogen.

50. A compound of claim 48, wherein $Q_1$ is a substituted heterocyclyl wherein the heterocyclyl has at least one oxygen.

51. A composition comprising the compound of claim 29, and at least one pharmaceutically acceptable carrier or excipient.

52. A compound which is
3-(azetidin-3-ylidenemethyl)-4-[4-(5-chloro-2-methylphenyl)piperazin-1-yl]-1H-pyrazolo[3,4-d]pyrimidine;
4-[4-(5-chloro-2-methylphenyl)piperazin-1-yl]-3-(3-fluoropyridin-4-yl)-1H-pyrazolo[3,4-d]pyrimidine;
4-[4-(5-chloro-2-methylphenyl)piperazin-1-yl]-3-(3-chloropyridin-4-yl)-1H-pyrazolo[3,4-d]pyrimidine;
2-({5-chloro-3-[4-(3-ethyl-1H-pyrazolo[3,4-d]pyrimidin-4-yl)piperazin-1-yl]-2-methylphenyl}oxy)-N,N-dimethylethanamine;
2-({5-chloro-3-[4-(3-ethyl-1H-pyrazolo[3,4-d]pyrimidin-4-yl)piperazin-1-yl]-2-methylphenyl}oxy)-N,N-diethylethanamine;
4-(4-{5-chloro-2-methyl-3-[(2-pyrrolidin-1-ylethyl)oxy]phenyl}piperazin-1-yl)-3-ethyl-1H-pyrazolo[3,4-d]pyrimidine;
4-[4-(5-chloro-2-methylphenyl)piperazin-1-yl]-3-piperazin-1-yl-1H-pyrazolo[3,4-d]pyrimidine;

N-(3-{4-[4-(5-chloro-2-methylphenyl)piperazin-1-yl]-1H-pyrazolo[3,4-d]pyrimidin-3-yl}prop-2-yn-1-yl)acetamide;

N,N-diethyl-2-({3-[4-(3-ethyl-1H-pyrazolo[3,4-d]pyrimidin-4-yl)piperazin-1-yl]phenyl}oxy)ethanamine;

3-{3-[4-(3-bromo-1H-pyrazolo[3,4-d]pyrimidin-4-yl)piperazin-1-yl]-5-chloro-2-methylphenyl}-N,N-diethylpropan-1-amine;

3-bromo-4-{4-[5-chloro-2-methyl-3-(3-pyrrolidin-1-ylpropyl)phenyl]piperazin-1-yl}-1H-pyrazolo[3,4-d]pyrimidine;

3-bromo-4-(4-{5-chloro-2-methyl-3-[(2-pyrrolidin-1-ylethyl)oxy]phenyl}piperazin-1-yl)-1H-pyrazolo[3,4-d]pyrimidine;

2-({3-[4-(3-bromo-1H-pyrazolo[3,4-d]pyrimidin-4-yl)piperazin-1-yl]-5-chloro-2-methylphenyl}oxy)-N,N-diethylethanamine;

4-[4-(5-chloro-2-methyl-3-{[2-(1-methylpiperidin-4-yl)ethyl]oxy}phenyl)piperazin-1-yl]-3-ethyl-1H-pyrazolo[3,4-d]pyrimidine;

5-chloro-3-[4-(3-ethyl-1H-pyrazolo[3,4-d]pyrimidin-4-yl)piperazin-1-yl]-2-methyl-N-(2-pyrrolidin-1-ylethyl)aniline;

4-(4-{5-chloro-2-methyl-3-[(2-morpholin-4-ylethyl)oxy]phenyl}piperazin-1-yl)-3-ethyl-1H-pyrazolo[3,4-d]pyrimidine;

4-(4-{5-chloro-2-methyl-3-[(2-piperidin-1-ylethyl)oxy]phenyl}piperazin-1-yl)-3-ethyl-1H-pyrazolo[3,4-d]pyrimidine;

3-bromo-4-{4-[5-chloro-2-methyl-3-(3-morpholin-4-ylpropyl)phenyl]piperazin-1-yl}-1H-pyrazolo[3,4-d]pyrimidine;

3-bromo-4-(4-{5-chloro-2-methyl-3-[3-(4-methylpiperazin-1-yl)propyl]phenyl}piperazin-1-yl)-1H-pyrazolo[3,4-d]pyrimidine;

3-bromo-4-(4-{5-chloro-2-methyl-3-[(2-piperidin-1-ylethyl)oxy]phenyl}piperazin-1-yl)-1H-pyrazolo[3,4-d]pyrimidine;

3-bromo-4-(4-{5-chloro-2-methyl-3-[(2-morpholin-4-ylethyl)oxy]phenyl}piperazin-1-yl)-1H-pyrazolo[3,4-d]pyrimidine;

4-{4-[5-chloro-2-methyl-3-(3-morpholin-4-ylpropyl)phenyl]piperazin-1-yl}-3-ethyl-1H-pyrazolo[3,4-d]pyrimidine;

N'-{5-chloro-3-[4-(3-ethyl-1H-pyrazolo[3,4-d]pyrimidin-4-yl)piperazin-1-yl]-2-methylphenyl}-N,N-diethylethane-1,2-diamine;

4-{4-[5-chloro-2-methyl-3-(3-piperidin-1-ylpropyl)phenyl]piperazin-1-yl}-3-ethyl-1H-pyrazolo[3,4-d]pyrimidine;

4-[4-(5-chloro-3-{[2-(4-ethylpiperazin-1-yl)ethyl]oxy}-2-methylphenyl)piperazin-1-yl]-3-ethyl-1H-pyrazolo[3,4-d]pyrimidine;

4-(4-{5-chloro-2-methyl-3-[(3-morpholin-4-ylpropyl)oxy]phenyl}piperazin-1-yl)-3-ethyl-1H-pyrazolo[3,4-d]pyrimidine;

3-bromo-4-{4-[5-chloro-2-methyl-3-(3-piperidin-1-ylpropyl)phenyl]piperazin-1-yl}-1H-pyrazolo[3,4-d]pyrimidine;

N'-{3-[4-(3-bromo-1H-pyrazolo[3,4-d]pyrimidin-4-yl)piperazin-1-yl]-5-chloro-2-methylphenyl}-N,N-diethylethane-1,2-diamine;

3-[4-(3-bromo-1H-pyrazolo[3,4-d]pyrimidin-4-yl)piperazin-1-yl]-5-chloro-2-methyl-N-(2-pyrrolidin-1-ylethyl)aniline;

4-[4-(5-chloro-2-methyl-3-{[2-(4-methylpiperazin-1-yl)ethyl]oxy}phenyl)piperazin-1-yl]-3-ethyl-1H-pyrazolo[3,4-d]pyrimidine;

4-[4-(5-chloro-2-methyl-3-{[(1-methylpiperidin-4-yl)methyl]oxy}phenyl)piperazin-1-yl]-3-ethyl-1H-pyrazolo[3,4-d]pyrimidine;

N,N-diethyl-2-({3-[4-(3-ethyl-1H-pyrazolo[3,4-d]pyrimidin-4-yl)piperazin-1-yl]-2-methylphenyl}oxy)ethanamine;

2-[(5-chloro-3-{4-[1-(1,1-dimethylethyl)-3-(trifluoromethyl)-1H-pyrazolo[3,4-d]pyrimidin-4-yl]piperazin-1-yl}-2-methylphenyl)oxy]-N,N-diethylethanamine;

2-[(5-chloro-2-methyl-3-{4-[3-(trifluoromethyl)-1H-pyrazolo[3,4-d]pyrimidin-4-yl]piperazin-1-yl}phenyl)oxy]-N,N-diethylethanamine;

4-(4-{5-chloro-2-methyl-3-[(3-pyrrolidin-1-ylpropyl)oxy]phenyl}piperazin-1-yl)-3-ethyl-1H-pyrazolo[3,4-d]pyrimidine;

4-[4-(5-chloro-2-methyl-3-{[3-(4-methylpiperazin-1-yl)propyl]oxy}phenyl)piperazin-1-yl]-3-ethyl-1H-pyrazolo[3,4-d]pyrimidine;

3-bromo-4-(4-{5-chloro-2-methyl-3-[(3-piperidin-1-ylpropyl)oxy]phenyl}piperazin-1-yl)-1H-pyrazolo[3,4-d]pyrimidine;

3-bromo-4-(4-{5-chloro-2-methyl-3-[(3-morpholin-4-ylpropyl)oxy]phenyl}piperazin-1-yl)-1H-pyrazolo[3,4-d]pyrimidine;

4-(4-{5-chloro-2-methyl-3-[(2-pyrrolidin-1-ylethyl)oxy]phenyl}piperazin-1-yl)-3-(trifluoromethyl)-1H-pyrazolo[3,4-d]pyrimidine;

4-(4-{5-chloro-2-methyl-3-[(3-morpholin-4-ylpropyl)oxy]phenyl}piperazin-1-yl)-3-(trifluoromethyl)-1H-pyrazolo[3,4-d]pyrimidine;

4-(4-{5-chloro-2-methyl-3-[(2-morpholin-4-ylethyl)oxy]phenyl}piperazin-1-yl)-3-(trifluoromethyl)-1H-pyrazolo[3,4-d]pyrimidine;

4-(4-{5-chloro-2-methyl-3-[(3-piperidin-1-ylpropyl)oxy]phenyl}piperazin-1-yl)-3-ethyl-1H-pyrazolo[3,4-d]pyrimidine;

4-[4-(5-chloro-3-{[3-(4-ethylpiperazin-1-yl)propyl]oxy}-2-methylphenyl)piperazin-1-yl]-3-ethyl-1H-pyrazolo[3,4-d]pyrimidine;

5-chloro-2-methyl-3-[4-(1H-pyrazolo[3,4-d]pyrimidin-4-yl)piperazin-1-yl]-N-(2-pyrrolidin-1-ylethyl)aniline;

5-chloro-2-methyl-3-[4-(3-methyl-1H-pyrazolo[3,4-d]pyrimidin-4-yl)piperazin-1-yl]-N-(2-pyrrolidin-1-ylethyl)aniline;

N'-(5-chloro-2-methyl-3-{4-[3-(trifluoromethyl)-1H-pyrazolo[3,4-d]pyrimidin-4-yl]piperazin-1-yl}phenyl)-N,N-dimethylethane-1,2-diamine;

3-({5-chloro-3-[4-(3-ethyl-1H-pyrazolo[3,4-d]pyrimidin-4-yl)piperazin-1-yl]-2-methylphenyl}oxy)-N,N-diethylpropan-1-amine;

N'-(5-chloro-2-methyl-3-{4-[3-(trifluoromethyl)-1H-pyrazolo[3,4-d]pyrimidin-4-yl]piperazin-1-yl}phenyl)-N,N-diethylethane-1,2-diamine;

5-chloro-2-methyl-N-(2-pyrrolidin-1-ylethyl)-3-{4-[3-(trifluoromethyl)-1H-pyrazolo[3,4-d]pyrimidin-4-yl]piperazin-1-yl}aniline;

3-bromo-4-(4-{4-methyl-3-[(2-pyrrolidin-1-ylethyl)oxy]phenyl}piperazin-1-yl)-1H-pyrazolo[3,4-d]pyrimidine;

4-(4-{4-methyl-3-[(2-pyrrolidin-1-ylethyl)oxy]phenyl}piperazin-1-yl)-1H-pyrazolo[3,4-d]pyrimidine;

3-methyl-4-(4-{4-methyl-3-[(2-pyrrolidin-1-ylethyl)oxy]phenyl}piperazin-1-yl)-1H-pyrazolo[3,4-d]pyrimidine;

4-(4-{5-chloro-2-methyl-3-[(2-pyrrolidin-1-ylethyl)oxy]phenyl}piperazin-1-yl)-1H-pyrazolo[3,4-d]pyrimidine;

4-(4-{5-chloro-2-methyl-3-[(2-pyrrolidin-1-ylethyl)oxy]
phenyl}piperazin-1-yl)-3-methyl-1H-pyrazolo[3,4-d]
pyrimidine;
4-(4-{5-chloro-2-methyl-3-[(2-piperidin-1-ylethyl)oxy]
phenyl}piperazin-1-yl)-3-(trifluoromethyl)-1H-pyra-
zolo[3,4-d]pyrimidine;
3-[(5-chloro-2-methyl-3-{4-[3-(trifluoromethyl)-1H-
pyrazolo[3,4-d]pyrimidin-4-yl]piperazin-1-yl}phenyl)
oxy]-N,N-diethylpropan-1-amine;
5-[4-(3-bromo-1H-pyrazolo[3,4-d]pyrimidin-4-yl)piper-
azin-1-yl]-2-methyl-N-(2-pyrrolidin-1-ylethyl)aniline;
3-[4-(3-bromo-1H-pyrazolo[3,4-d]pyrimidin-4-yl)piper-
azin-1-yl]-5-fluoro-2-methyl-N-(2-pyrrolidin-1-yl-
ethyl)aniline;
4-{4-[5-chloro-2-methyl-3-(3-pyrrolidin-1-ylpropyl)phe-
nyl]piperazin-1-yl}-1H-pyrazolo[3,4-d]pyrimidine;
3-bromo-4-{4-[5-fluoro-2-methyl-3-(3-pyrrolidin-1-yl-
propyl)phenyl]piperazin-1-yl}-1H-pyrazolo[3,4-d]py-
rimidine;
4-{4-[5-chloro-2-methyl-3-(3-pyrrolidin-1-ylpropyl)phe-
nyl]piperazin-1-yl}-3-(trifluoromethyl)-1H-pyrazolo
[3,4-d]pyrimidine;
4-(4-{5-chloro-2-methyl-3-[3-(4-methylpiperazin-1-yl)
propyl]phenyl}piperazin-1-yl)-3-ethyl-1H-pyrazolo[3,
4-d]pyrimidine;
3-bromo-4-(4-pyridin-2-ylpiperazin-1-yl)-1H-pyrazolo
[3,4-d]pyrimidine;
3-bromo-4-[4-(2,4-dimethylphenyl)piperazin-1-yl]-1H-
pyrazolo[3,4-d]pyrimidine;
3-bromo-4-{4-[3-(methyloxy)phenyl]piperazin-1-yl}-
1H-pyrazolo[3,4-d]pyrimidine;
3-bromo-4-{4-[2-(methyloxy)phenyl]piperazin-1-yl}-
1H-pyrazolo[3,4-d]pyrimidine;
3-bromo-4-{4-[4-methyl-3-(3-pyrrolidin-1-ylpropyl)phe-
nyl]piperazin-1-yl}-1H-pyrazolo[3,4-d]pyrimidine;
4-(4-{5-chloro-2-methyl-3-[(3-pyrrolidin-1-ylpropyl)
oxy]phenyl}piperazin-1-yl)-3-(trifluoromethyl)-1H-
pyrazolo[3,4-d]pyrimidine;
4-(4-{5-chloro-2-methyl-3-[(3-piperidin-1-ylpropyl)oxy]
phenyl}piperazin-1-yl)-3-(trifluoromethyl)-1H-pyra-
zolo[3,4-d]pyrimidine;
4-[4-(5-chloro-2-methyl-3-{[3-(4-methylpiperazin-1-yl)
propyl]oxy}phenyl)piperazin-1-yl]-3-(trifluorom-
ethyl)-1H-pyrazolo[3,4-d]pyrimidine;
4-[4-(5-chloro-3-{[3-(4-ethylpiperazin-1-yl)propyl]oxy}-
2-methylphenyl)piperazin-1-yl]-3-(trifluoromethyl)-
1H-pyrazolo[3,4-d]pyrimidine;
3-bromo-4-[4-(5-chloro-2-methyl-3-{[2-(4-methylpiper-
azin-1-yl)ethyl]oxy}phenyl)piperazin-1-yl]-1H-pyra-
zolo[3,4-d]pyrimidine;
4-[4-(5-chloro-2-methyl-3-{[2-(4-methylpiperazin-1-yl)
ethyl]oxy}phenyl)piperazin-1-yl]-3-(trifluoromethyl)-
1H-pyrazolo[3,4-d]pyrimidine;
3-bromo-4-[4-(5-chloro-3-{[2-(4-ethylpiperazin-1-yl)
ethyl]oxy}-2-methylphenyl)piperazin-1-yl]-1H-pyra-
zolo[3,4-d]pyrimidine;
3-bromo-4-[4-(3,4-dichlorophenyl)piperazin-1-yl]-1H-
pyrazolo[3,4-d]pyrimidine;
3-bromo-4-[4-(3,4-difluorophenyl)piperazin-1-yl]-1H-
pyrazolo[3,4-d]pyrimidine;
3-bromo-4-[4-(2,4-dichlorophenyl)piperazin-1-yl]-1H-
pyrazolo[3,4-d]pyrimidine;
3-[4-(3-ethyl-1H-pyrazolo[3,4-d]pyrimidin-4-yl)piper-
azin-1-yl]-5-fluoro-2-methyl-N-(2-pyrrolidin-1-yl-
ethyl)aniline;
5-fluoro-2-methyl-N-(2-pyrrolidin-1-ylethyl)-3-{4-[3-
(trifluoromethyl)-1H-pyrazolo[3,4-d]pyrimidin-4-yl]
piperazin-1-yl}aniline;
4-{4-[3,5-bis(methyloxy)phenyl]piperazin-1-yl}-3-
bromo-1H-pyrazolo[3,4-d]pyrimidine;
4-[4-(5-chloro-3-{[2-(4-ethylpiperazin-1-yl)ethyl]oxy}-
2-methylphenyl)piperazin-1-yl]-3-(trifluoromethyl)-
1H-pyrazolo[3,4-d]pyrimidine;
N-{5-chloro-3-[4-(3-ethyl-1H-pyrazolo[3,4-d]pyrimidin-
4-yl)piperazin-1-yl]-2-methylphenyl}-N,N',N'-trimeth-
ylethane-1,2-diamine;
3-({3-[4-(3-bromo-1H-pyrazolo[3,4-d]pyrimidin-4-yl)
piperazin-1-yl]-5-chloro-2-methylphenyl}oxy)-N,N-
diethylpropan-1-amine;
3-bromo-4-(4-{5-chloro-2-methyl-3-[(3-pyrrolidin-1-yl-
propyl)oxy]phenyl}piperazin-1-yl)-1H-pyrazolo[3,4-
d]pyrimidine;
3-bromo-4-[4-(5-chloro-2-methyl-3-{[3-(4-methylpiper-
azin-1-yl)propyl]oxy}phenyl)piperazin-1-yl]-1H-pyra-
zolo[3,4-d]pyrimidine;
3-bromo-4-[4-(5-chloro-3-{[3-(4-ethylpiperazin-1-yl)
propyl]oxy}-2-methylphenyl)piperazin-1-yl]-1H-pyra-
zolo[3,4-d]pyrimidine;
3-(5-chloro-2-methyl-3-{4-[3-(trifluoromethyl)-1H-pyra-
zolo[3,4-d]pyrimidin-4-yl]piperazin-1-yl}phenyl)-N,
N-diethylpropan-1-amine;
3-bromo-4-[4-(5-chloro-2-methyl-3-{[(1-methylpiperi-
din-4-yl)methyl]oxy}phenyl)piperazin-1-yl]-1H-pyra-
zolo[3,4-d]pyrimidine;
3-bromo-4-[4-(5-chloro-2-methyl-3-{[2-(1-methylpiperi-
din-4-yl)ethyl]oxy}phenyl)piperazin-1-yl]-1H-pyra-
zolo[3,4-d]pyrimidine;
4-[4-(5-chloro-2-methyl-3-{[(1-methylpiperidin-4-yl)
methyl]oxy}phenyl)piperazin-1-yl]-3-(trifluorom-
ethyl)-1H-pyrazolo[3,4-d]pyrimidine;
4-[4-(5-chloro-2-methyl-3-{[2-(1-methylpiperidin-4-yl)
ethyl]oxy}phenyl)piperazin-1-yl]-3-(trifluoromethyl)-
1H-pyrazolo[3,4-d]pyrimidine;
4-(4-{5-chloro-2-methyl-3-[3-(4-methylpiperazin-1-yl)
propyl]phenyl}piperazin-1-yl)-3-(trifluoromethyl)-1H-
pyrazolo[3,4-d]pyrimidine;
3-bromo-4-[4-(3-chloro-4-fluorophenyl)piperazin-1-yl]-
1H-pyrazolo[3,4-d]pyrimidine;
1-{4-[4-(3-bromo-1H-pyrazolo[3,4-d]pyrimidin-4-yl)
piperazin-1-yl]phenyl}ethanone;
3-bromo-4-[4-(2,5-dichlorophenyl)piperazin-1-yl]-1H-
pyrazolo[3,4-d]pyrimidine;
3-bromo-4-[4-(3,4-dimethylphenyl)piperazin-1-yl]-1H-
pyrazolo[3,4-d]pyrimidine;
3-bromo-4-[4-(4-nitrophenyl)piperazin-1-yl]-1H-pyra-
zolo[3,4-d]pyrimidine;
3-ethyl-4-(4-phenylpiperazin-1-yl)-1H-pyrazolo[3,4-d]
pyrimidine;
3-ethyl-4-{4-[3-(methyloxy)phenyl]piperazin-1-yl}-1H-
pyrazolo[3,4-d]pyrimidine;
4-{4-[5-chloro-2-methyl-3-(3-piperidin-1-ylpropyl)phe-
nyl]piperazin-1-yl}-3-(trifluoromethyl)-1H-pyrazolo
[3,4-d]pyrimidine;
4-[4-(3,6-dimethylpyrazin-2-yl)piperazin-1-yl]-3-ethyl-
1H-pyrazolo[3,4-d]pyrimidine;
1-[4-(3-ethyl-1H-pyrazolo[3,4-d]pyrimidin-4-yl)piper-
azin-1-yl]isoquinoline;
3-bromo-4-[4-(2,6-dimethylphenyl)piperazin-1-yl]-1H-
pyrazolo[3,4-d]pyrimidine;
3-bromo-4-{4-[4-(ethyloxy)phenyl]piperazin-1-yl}-1H-
pyrazolo[3,4-d]pyrimidine;

3-bromo-4-[4-(2-ethylphenyl)piperazin-1-yl]-1H-pyrazolo[3,4-d]pyrimidine;
4-{4-[2,4-bis(methyloxy)phenyl]piperazin-1-yl}-3-bromo-1H-pyrazolo[3,4-d]pyrimidine;
3-bromo-4-(4-pyrazin-2-ylpiperazin-1-yl)-1H-pyrazolo[3,4-d]pyrimidine;
3-bromo-4-(4-pyrimidin-2-ylpiperazin-1-yl)-1H-pyrazolo[3,4-d]pyrimidine;
4-[4-(3-bromo-1H-pyrazolo[3,4-d]pyrimidin-4-yl)piperazin-1-yl]-2-(trifluoromethyl)quinoline;
3-[4-(3-bromo-1H-pyrazolo[3,4-d]pyrimidin-4-yl)piperazin-1-yl]pyrazine-2-carbonitrile;
4-[4-(4,6-dimethylpyrimidin-2-yl)piperazin-1-yl]-3-ethyl-1H-pyrazolo[3,4-d]pyrimidine;
ethyl 4-[4-(3-ethyl-1H-pyrazolo[3,4-d]pyrimidin-4-yl)piperazin-1-yl]-2-(trifluoromethyl)pyrimidine-5-carboxylate;
4-{4-[3-chloro-5-(methyloxy)phenyl]piperazin-1-yl}-3-ethyl-1H-pyrazolo[3,4-d]pyrimidine;
4-[4-(3-bromo-2-chloro-5-fluorophenyl)piperazin-1-yl]-3-ethyl-1H-pyrazolo[3,4-d]pyrimidine;
2-[4-(3-ethyl-1H-pyrazolo[3,4-d]pyrimidin-4-yl)piperazin-1-yl]pyridine-3-carboxamide;
3-ethyl-4-{4-[4-(trifluoromethyl)pyridin-2-yl]piperazin-1-yl}-1H-pyrazolo[3,4-d]pyrimidine;
3-bromo-4-{4-[4-(trifluoromethyl)pyridin-2-yl]piperazin-1-yl}-1H-pyrazolo[3,4-d]pyrimidine;
3-bromo-4-{4-[4-(trifluoromethyl)pyrimidin-2-yl]piperazin-1-yl}-1H-pyrazolo[3,4-d]pyrimidine;
2-({3-[4-(3-bromo-1H-pyrazolo[3,4-d]pyrimidin-4-yl)piperazin-1-yl]pyrazin-2-yl}oxy)-N,N-dimethylethanamine;
4-[4-(3-bromo-1H-pyrazolo[3,4-d]pyrimidin-4-yl)piperazin-1-yl]-2-methylquinoline;
3-bromo-4-[4-(2-nitrophenyl)piperazin-1-yl]-1H-pyrazolo[3,4-d]pyrimidine;
2-[4-(3-bromo-1H-pyrazolo[3,4-d]pyrimidin-4-yl)piperazin-1-yl]benzonitrile;
4-[4-(3-bromo-1H-pyrazolo[3,4-d]pyrimidin-4-yl)piperazin-1-yl]benzonitrile;
3-bromo-4-{4-[4-(trifluoromethyl)phenyl]piperazin-1-yl}-1H-pyrazolo[3,4-d]pyrimidine;
3-bromo-4-(4-{4-[(phenylmethyl)oxy]phenyl}piperazin-1-yl)-1H-pyrazolo[3,4-d]pyrimidine;
4-{4-[5-chloro-2-methyl-3-(methyloxy)phenyl]piperazin-1-yl}-3-ethyl-1H-pyrazolo[3,4-d]pyrimidine;
2-[4-(3-bromo-1H-pyrazolo[3,4-d]pyrimidin-4-yl)piperazin-1-yl]pyridine-3-carbonitrile;
3-bromo-4-[4-(3,5-dichlorophenyl)piperazin-1-yl]-1H-pyrazolo[3,4-d]pyrimidine;
3-[4-(3-bromo-1H-pyrazolo[3,4-d]pyrimidin-4-yl)piperazin-1-yl]-2-chloro-5-fluoro-N-(2-pyrrolidin-1-ylethyl)aniline;
2-chloro-3-[4-(3-ethyl-1H-pyrazolo[3,4-d]pyrimidin-4-yl)piperazin-1-yl]-5-fluoro-N-(2-pyrrolidin-1-ylethyl)aniline;
3-bromo-4-[4-(2,5-difluorophenyl)piperazin-1-yl]-1H-pyrazolo[3,4-d]pyrimidine;
4-[4-(2,5-difluorophenyl)piperazin-1-yl]-3-ethyl-1H-pyrazolo[3,4-d]pyrimidine;
3-bromo-4-{4-[3-(methyloxy)pyrazin-2-yl]piperazin-1-yl}-1H-pyrazolo[3,4-d]pyrimidine;
3-bromo-4-[4-(3-chlorophenyl)piperazin-1-yl]-1H-pyrazolo[3,4-d]pyrimidine;
3-bromo-4-{4-[3-(trifluoromethyl)pyridin-2-yl]piperazin-1-yl}-1H-pyrazolo[3,4-d]pyrimidine;
3-bromo-4-{4-[3-chloro-5-(trifluoromethyl)pyridin-2-yl]piperazin-1-yl}-1H-pyrazolo[3,4-d]pyrimidine;
4-(4-{5-chloro-2-methyl-3-[(2-pyrrolidin-1-ylethyl)oxy]phenyl}piperazin-1-yl)-3-(1-methylethyl)-1H-pyrazolo[3,4-d]pyrimidine;
5-chloro-2-methyl-3-{4-[3-(1-methylethyl)-1H-pyrazolo[3,4-d]pyrimidin-4-yl]piperazin-1-yl}-N-(2-pyrrolidin-1-ylethyl)aniline;
2-({3-[4-(3-bromo-1H-pyrazolo[3,4-d]pyrimidin-4-yl)piperazin-1-yl]phenyl}oxy)-N-ethylacetamide;
2-[4-(3-bromo-1H-pyrazolo[3,4-d]pyrimidin-4-yl)piperazin-1-yl]-N,N-diethylpyrimidin-4-amine;
3-bromo-4-[4-(3-{[(3-methylphenyl)methyl]oxy}phenyl)piperazin-1-yl]-1H-pyrazolo[3,4-d]pyrimidine;
3-bromo-4-(4-{3-[(2-piperidin-1-ylethyl)oxy]phenyl}piperazin-1-yl)-1H-pyrazolo[3,4-d]pyrimidine;
3-bromo-4-[4-(4-furan-2-ylpyrimidin-2-yl)piperazin-1-yl]-1H-pyrazolo[3,4-d]pyrimidine;
6-{2-[4-(3-bromo-1H-pyrazolo[3,4-d]pyrimidin-4-yl)piperazin-1-yl]pyrimidin-4-yl}-2H-1,4-benzoxazin-3(4H)-one;
3-ethyl-4-{4-[2-methyl-3-(methyloxy)phenyl]piperazin-1-yl}-1H-pyrazolo[3,4-d]pyrimidine;
N'-{5-chloro-3-[4-(3-ethyl-1H-pyrazolo[3,4-d]pyrimidin-4-yl)piperazin-1-yl]-2-methylphenyl}-N-methyl-N-(1-methylethyl)ethane-1,2-diamine;
N'-{5-chloro-3-[4-(3-ethyl-1H-pyrazolo[3,4-d]pyrimidin-4-yl)piperazin-1-yl]-2-methylphenyl}-N-ethyl-N-methylethane-1,2-diamine;
N'-{3-[4-(3-bromo-1H-pyrazolo[3,4-d]pyrimidin-4-yl)piperazin-1-yl]-5-chloro-2-methylphenyl}-N,N-dimethylethane-1,2-diamine;
3-({6-[4-(3-bromo-1H-pyrazolo[3,4-d]pyrimidin-4-yl)piperazin-1-yl]-2-chloro-5-methylpyrimidin-4-yl}oxy)-N,N-diethylpropan-1-amine;
3-bromo-4-[4-(2,3-dichlorophenyl)piperazin-1-yl]-1H-pyrazolo[3,4-d]pyrimidine;
3-bromo-4-{4-[2-(trifluoromethyl)phenyl]piperazin-1-yl}-1H-pyrazolo[3,4-d]pyrimidine;
3-bromo-4-(4-phenylpiperazin-1-yl)-1H-pyrazolo[3,4-d]pyrimidine;
3-bromo-4-[4-(4-fluorophenyl)piperazin-1-yl]-1H-pyrazolo[3,4-d]pyrimidine;
3-bromo-4-[4-(4-chlorophenyl)piperazin-1-yl]-1H-pyrazolo[3,4-d]pyrimidine;
3-bromo-4-{4-[3-(trifluoromethyl)phenyl]piperazin-1-yl}-1H-pyrazolo[3,4-d]pyrimidine;
4-[4-(5-chloro-2-methylphenyl)piperazin-1-yl]-1H-pyrazolo[3,4-d]pyrimidin-6-amine;
3-bromo-4-[4-(4-bromophenyl)piperazin-1-yl]-1H-pyrazolo[3,4-d]pyrimidine;
3-bromo-4-[3-methyl-4-(3-methylphenyl)piperazin-1-yl]-1H-pyrazolo[3,4-d]pyrimidine;
4-[4-(3-bromo-5-chloro-2-methylphenyl)piperazin-1-yl]-1H-pyrazolo[3,4-d]pyrimidin-6-amine;
4-(4-{5-chloro-2-methyl-3-[(2-pyrrolidin-1-ylethyl)oxy]phenyl}piperazin-1-yl)-3-cyclopropyl-1H-pyrazolo[3,4-d]pyrimidine;
5-chloro-3-[4-(3-cyclopropyl-1H-pyrazolo[3,4-d]pyrimidin-4-yl)piperazin-1-yl]-2-methyl-N-(2-pyrrolidin-1-ylethyl)aniline;
5-chloro-2-methyl-3-{4-[3-(2-methylpropyl)-1H-pyrazolo[3,4-d]pyrimidin-4-yl]piperazin-1-yl}-N-(2-pyrrolidin-1-ylethyl)aniline;
4-(4-{5-chloro-2-methyl-3-[(2-pyrrolidin-1-ylethyl)oxy]phenyl}piperazin-1-yl)-3-(2-methylpropyl)-1H-pyrazolo[3,4-d]pyrimidine;

3-bromo-4-[(3S)-4-(5-chloro-2-methylphenyl)-3-methylpiperazin-1-yl]-1H-pyrazolo[3,4-d]pyrimidine;
5-bromo-3-[4-(3-ethyl-1H-pyrazolo[3,4-d]pyrimidin-4-yl)piperazin-1-yl]-2-methylaniline;
2-({3-[4-(3-bromo-1H-pyrazolo[3,4-d]pyrimidin-4-yl)piperazin-1-yl]phenyl}oxy)-N-cyclopropylacetamide;
3-bromo-4-(4-{3-[(2-piperidin-1-ylethyl)oxy]pyrazin-2-yl}piperazin-1-yl)-1H-pyrazolo[3,4-d]pyrimidine;
4-[4-(3-ethyl-1H-pyrazolo[3,4-d]pyrimidin-4-yl)piperazin-1-yl]-6,7-bis(methyloxy)quinazoline;
2-({3-chloro-5-[4-(3-ethyl-1H-pyrazolo[3,4-d]pyrimidin-4-yl)piperazin-1-yl]phenyl}oxy)-N,N-diethylethanamine;
4-{4-[2-chloro-5-(trifluoromethyl)phenyl]piperazin-1-yl}-3-ethyl-1H-pyrazolo[3,4-d]pyrimidine;
3-[4-(3-ethyl-1H-pyrazolo[3,4-d]pyrimidin-4-yl)piperazin-1-yl]-2-methyl-5-[(2-methylpropyl)oxy]-N-(2-pyrrolidin-1-ylethyl)aniline;
3-({4-[4-(3-bromo-1H-pyrazolo[3,4-d]pyrimidin-4-yl)piperazin-1-yl]-6-chloro-5-methylpyrimidin-2-yl}oxy)-N,N-diethylpropan-1-amine;
3-[4-(3-ethyl-1H-pyrazolo[3,4-d]pyrimidin-4-yl)piperazin-1-yl]-2-methyl-5-[(phenylmethyl)oxy]-N-(2-pyrrolidin-1-ylethyl)aniline;
3-bromo-4-[(3R)-4-(5-chloro-2-methylphenyl)-3-methylpiperazin-1-yl]-1H-pyrazolo[3,4-d]pyrimidine;
3-[(2S)-4-(3-bromo-1H-pyrazolo[3,4-d]pyrimidin-4-yl)-2-methylpiperazin-1-yl]-4-methyl-N-phenylbenzamide;
3-[(2S)-4-(3-bromo-1H-pyrazolo[3,4-d]pyrimidin-4-yl)-2-methylpiperazin-1-yl]-4-methyl-N-(phenylmethyl)benzamide;
methyl 3-[4-(3-bromo-1H-pyrazolo[3,4-d]pyrimidin-4-yl)piperazin-1-yl]-4-methylbenzoate;
3-[4-(3-bromo-1H-pyrazolo[3,4-d]pyrimidin-4-yl)piperazin-1-yl]-4-methylbenzoic acid;
(2E)-3-(4-{4-[5-chloro-2-methyl-3-(3-pyrrolidin-1-ylpropyl)phenyl]piperazin-1-yl}-1H-pyrazolo[3,4-d]pyrimidin-3-yl)prop-2-enoic acid;
3-(4-{4-[5-chloro-2-methyl-3-(3-pyrrolidin-1-ylpropyl)phenyl]piperazin-1-yl}-1H-pyrazolo[3,4-d]pyrimidin-3-yl)prop-2-yn-1-ol;
4-(3-bromo-1H-pyrazolo[3,4-d]pyrimidin-4-yl)-1-(5-chloro-2-methylphenyl)piperazin-2-one;
3-[4-(3-bromo-1H-pyrazolo[3,4-d]pyrimidin-4-yl)piperazin-1-yl]-2-methyl-5-[(2-methylpropyl)oxy]-N-(2-pyrrolidin-1-ylethyl)aniline;
N'-{3-[4-(3-bromo-1H-pyrazolo[3,4-d]pyrimidin-4-yl)piperazin-1-yl]-2-methyl-5-[(2-methylpropyl)oxy]phenyl}-N,N-diethylethane-1,2-diamine;
methyl 3-bromo-5-[4-(3-bromo-1H-pyrazolo[3,4-d]pyrimidin-4-yl)piperazin-1-yl]-4-methylbenzoate;
3-[4-(3-bromo-1H-pyrazolo[3,4-d]pyrimidin-4-yl)piperazin-1-yl]-4-methyl-N-phenylbenzamide;
3-[4-(3-bromo-1H-pyrazolo[3,4-d]pyrimidin-4-yl)piperazin-1-yl]-N,4-dimethylbenzamide;
2-({3-[4-(3-bromo-1H-pyrazolo[3,4-d]pyrimidin-4-yl)piperazin-1-yl]phenyl}oxy)-N,N-diethylethanamine;
methyl 3-[4-(3-bromo-1H-pyrazolo[3,4-d]pyrimidin-4-yl)piperazin-1-yl]-4-methyl-5-[(2-pyrrolidin-1-ylethyl)amino]benzoate;
3-bromo-5-[4-(3-bromo-1H-pyrazolo[3,4-d]pyrimidin-4-yl)piperazin-1-yl]-4-methyl-N-phenylbenzamide;
3-bromo-5-[4-(3-ethyl-1H-pyrazolo[3,4-d]pyrimidin-4-yl)piperazin-1-yl]-4-methyl-N-phenylbenzamide;
N'-{3-[4-(3-bromo-1H-pyrazolo[3,4-d]pyrimidin-4-yl)piperazin-1-yl]-5-chloro-2-methylphenyl}-N-methyl-N-(1-methylethyl)ethane-1,2-diamine;
3-[4-(3-bromo-1H-pyrazolo[3,4-d]pyrimidin-4-yl)piperazin-1-yl]-4-methyl-N-phenyl-5-[(2-pyrrolidin-1-ylethyl)amino]benzamide;
N'-{3-[4-(3-bromo-1H-pyrazolo[3,4-d]pyrimidin-4-yl)piperazin-1-yl]-2-methyl-5-[(2-methylpropyl)oxy]phenyl}-N,N-dimethylethane-1,2-diamine;
3-[4-(3-bromo-1H-pyrazolo[3,4-d]pyrimidin-4-yl)piperazin-1-yl]-N,N,4-trimethylbenzamide;
3-[4-(3-chloro-1H-pyrazolo[3,4-d]pyrimidin-4-yl)piperazin-1-yl]-4-methyl-N-(2-methylpropyl)benzamide;
3-[4-(3-bromo-1H-pyrazolo[3,4-d]pyrimidin-4-yl)piperazin-1-yl]-N,N,4-trimethyl-5-[(2-pyrrolidin-1-ylethyl)amino]benzamide;
3-[4-(3-bromo-1H-pyrazolo[3,4-d]pyrimidin-4-yl)-2-oxopiperazin-1-yl]-4-methyl-N-phenylbenzamide;
3-[(2R)-4-(3-bromo-1H-pyrazolo[3,4-d]pyrimidin-4-yl)-2-(hydroxymethyl)piperazin-1-yl]-4-methyl-N-phenylbenzamide;
3-[4-(3-bromo-1H-pyrazolo[3,4-d]pyrimidin-4-yl)piperazin-1-yl]-2-methyl-5-(pyrrolidin-1-ylcarbonyl)-N-(2-pyrrolidin-1-ylethyl)aniline;
3-[4-(3-bromo-1H-pyrazolo[3,4-d]pyrimidin-4-yl)piperazin-1-yl]-N,4-dimethyl-5-[(2-pyrrolidin-1-ylethyl)amino]benzamide;
3-[4-(3-bromo-1H-pyrazolo[3,4-d]pyrimidin-4-yl)piperazin-1-yl]-N-(4-chlorophenyl)-4-methyl-5-[(2-pyrrolidin-1-ylethyl)amino]benzamide;
3-[4-(3-bromo-1H-pyrazolo[3,4-d]pyrimidin-4-yl)piperazin-1-yl]-N-(2-chlorophenyl)-4-methyl-5-[(2-pyrrolidin-1-ylethyl)amino]benzamide;
3-[4-(3-bromo-1H-pyrazolo[3,4-d]pyrimidin-4-yl)piperazin-1-yl]-5-[(cyclopropylmethyl)oxy]-2-methyl-N-(2-pyrrolidin-1-ylethyl)aniline;
3-[4-(3-bromo-1H-pyrazolo[3,4-d]pyrimidin-4-yl)piperazin-1-yl]-2-methyl-5-[(3-methylbutyl)oxy]-N-(2-pyrrolidin-1-ylethyl)aniline;
3-[4-(3-bromo-1H-pyrazolo[3,4-d]pyrimidin-4-yl)piperazin-1-yl]-5-[(2-ethylbutyl)oxy]-2-methyl-N-(2-pyrrolidin-1-ylethyl)aniline;
3-[4-(3-bromo-1H-pyrazolo[3,4-d]pyrimidin-4-yl)piperazin-1-yl]-5-(butyloxy)-2-methyl-N-(2-pyrrolidin-1-ylethyl)aniline;
3-[4-(3-bromo-1H-pyrazolo[3,4-d]pyrimidin-4-yl)piperazin-1-yl]-4-methyl-N-(1-methylethyl)-5-[(2-pyrrolidin-1-ylethyl)amino]benzamide;
3-[4-(3-bromo-1H-pyrazolo[3,4-d]pyrimidin-4-yl)piperazin-1-yl]-N,4-dimethyl-N-(1-methylethyl)-5-[(2-pyrrolidin-1-ylethyl)amino]benzamide;
3-[4-(3-bromo-1H-pyrazolo[3,4-d]pyrimidin-4-yl)piperazin-1-yl]-5-[(cyclobutylmethyl)oxy]-2-methyl-N-(2-pyrrolidin-1-ylethyl)aniline;
3-[4-(3-bromo-1H-pyrazolo[3,4-d]pyrimidin-4-yl)piperazin-1-yl]-5-(ethyloxy)-2-methyl-N-(2-pyrrolidin-1-ylethyl)aniline;
3-[4-(3-bromo-1H-pyrazolo[3,4-d]pyrimidin-4-yl)piperazin-1-yl]-N-[2-(dimethylamino)ethyl]-4-methylbenzamide;
3-[4-(3-bromo-1H-pyrazolo[3,4-d]pyrimidin-4-yl)piperazin-1-yl]-N-(1,1-dimethylethyl)-4-methyl-5-[(2-pyrrolidin-1-ylethyl)amino]benzamide;
3-[4-(3-bromo-1H-pyrazolo[3,4-d]pyrimidin-4-yl)piperazin-1-yl]-4-methyl-N-pyridin-3-yl-5-[(2-pyrrolidin-1-ylethyl)amino]benzamide;

3-[4-(3-bromo-1H-pyrazolo[3,4-d]pyrimidin-4-yl)piperazin-1-yl]-5-[(2-fluoro-2-methylpropyl)oxy]-2-methyl-N-(2-pyrrolidin-1-ylethyl)aniline;
3-[4-(3-bromo-1H-pyrazolo[3,4-d]pyrimidin-4-yl)piperazin-1-yl]-5-[(cyclohexylmethyl)oxy]-2-methyl-N-(2-pyrrolidin-1-ylethyl)aniline;
3-[4-(3-bromo-1H-pyrazolo[3,4-d]pyrimidin-4-yl)piperazin-1-yl]-5-[(cyclopentylmethyl)oxy]-2-methyl-N-(2-pyrrolidin-1-ylethyl)aniline;
3-[4-(3-bromo-1H-pyrazolo[3,4-d]pyrimidin-4-yl)piperazin-1-yl]-N-ethyl-4-methyl-5-[(2-pyrrolidin-1-ylethyl)amino]benzamide;
3-[4-(3-bromo-1H-pyrazolo[3,4-d]pyrimidin-4-yl)piperazin-1-yl]-2-methyl-5-[(1-methylethyl)oxy]-N-(2-pyrrolidin-1-ylethyl)aniline;
3-[4-(3-bromo-1H-pyrazolo[3,4-d]pyrimidin-4-yl)piperazin-1-yl]-5-[(2,2-dimethylpropyl)oxy]-2-methyl-N-(2-pyrrolidin-1-ylethyl)aniline;
3-[4-(3-bromo-1H-pyrazolo[3,4-d]pyrimidin-4-yl)piperazin-1-yl]-2-methyl-N-(2-pyrrolidin-1-ylethyl)-5-[(tetrahydrofuran-2-ylmethyl)oxy]aniline;
3-[4-(3-bromo-1H-pyrazolo[3,4-d]pyrimidin-4-yl)piperazin-1-yl]-2-methyl-5-{[2-(methyloxy)ethyl]oxy}-N-(2-pyrrolidin-1-ylethyl)aniline;
3-[4-(3-bromo-1H-pyrazolo[3,4-d]pyrimidin-4-yl)piperazin-1-yl]-2-methyl-5-(propyloxy)-N-(2-pyrrolidin-1-ylethyl)aniline;
3-[4-(3-bromo-1H-pyrazolo[3,4-d]pyrimidin-4-yl)piperazin-1-yl]-5-{[2-(dimethylamino)ethyl]amino}-4-methyl-N-phenylbenzamide;
N'-{3-[4-(3-bromo-1H-pyrazolo[3,4-d]pyrimidin-4-yl)piperazin-1-yl]-5-[(2-fluoro-2-methylpropyl)oxy]-2-methylphenyl}-N,N-dimethylethane-1,2-diamine;
3-[4-(3-bromo-1H-pyrazolo[3,4-d]pyrimidin-4-yl)piperazin-1-yl]-5-{[2-(dimethylamino)ethyl]amino}-4-methyl-N-(1-methylethyl)benzamide;
1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}pentan-1-one;
N'-(3-[4-(3-bromo-1H-pyrazolo[3,4-d]pyrimidin-4-yl)piperazin-1-yl]-5-{[2,3-difluoro-2-(fluoromethyl)propyl]oxy}-2-methylphenyl)-N,N-dimethylethane-1,2-diamine;
3-[4-(3-bromo-1H-pyrazolo[3,4-d]pyrimidin-4-yl)piperazin-1-yl]-5-{[2,3-difluoro-2-(fluoromethyl)propyl]oxy}-2-methyl-N-(2-pyrrolidin-1-ylethyl)aniline;
5-[4-(3-bromo-1H-pyrazolo[3,4-d]pyrimidin-4-yl)piperazin-1-yl]-4-methyl-N-(2-pyrrolidin-1-ylethyl)biphenyl-3-amine;
1-(3-{5-[4-(3-bromo-1H-pyrazolo[3,4-d]pyrimidin-4-yl)piperazin-1-yl]-4-methylbiphenyl-3-yl}propyl)pyridinium;
3-[4-(3-bromo-1H-pyrazolo[3,4-d]pyrimidin-4-yl)piperazin-1-yl]-2-methyl-N-(2-pyrrolidin-1-ylethyl)-5-(1,3-thiazol-2-yl)aniline;
3-[4-(3-bromo-1H-pyrazolo[3,4-d]pyrimidin-4-yl)piperazin-1-yl]-4-methyl-5-[(2-pyrrolidin-1-ylethyl)amino]benzoic acid;
3-[4-(3-bromo-1H-pyrazolo[3,4-d]pyrimidin-4-yl)piperazin-1-yl]-2-methyl-5-(phenylethynyl)-N-(2-pyrrolidin-1-ylethyl)aniline;
{3-[4-(3-bromo-1H-pyrazolo[3,4-d]pyrimidin-4-yl)piperazin-1-yl]-4-methyl-5-[(2-pyrrolidin-1-ylethyl)amino]phenyl}(phenyl)methanone;
3-[4-(3-bromo-1H-pyrazolo[3,4-d]pyrimidin-4-yl)piperazin-1-yl]-5-ethynyl-2-methyl-N-(2-pyrrolidin-1-ylethyl)aniline;
3-[4-(3-bromo-1H-pyrazolo[3,4-d]pyrimidin-4-yl)piperazin-1-yl]-5-(3,3-dimethylbut-1-yn-1-yl)-2-methyl-N-(2-pyrrolidin-1-ylethyl)aniline;
3-bromo-4-{4-[5-{[2,3-difluoro-2-(fluoromethyl)propyl]oxy}-2-methyl-3-(3-pyrrolidin-1-ylpropyl)phenyl]piperazin-1-yl}-1H-pyrazolo[3,4-d]pyrimidine;
3-bromo-4-{4-[2-methyl-5-[(2-methylpropyl)oxy]-3-(3-pyrrolidin-1-ylpropyl)phenyl]piperazin-1-yl}-1H-pyrazolo[3,4-d]pyrimidine;
3-[4-(3-bromo-1H-pyrazolo[3,4-d]pyrimidin-4-yl)piperazin-1-yl]-2-methyl-5-(3-phenyl-1,2,4-oxadiazol-5-yl)-N-(2-pyrrolidin-1-ylethyl)aniline;
3-[4-(3-bromo-1H-pyrazolo[3,4-d]pyrimidin-4-yl)piperazin-1-yl]-2-methyl-5-(3-methyl-1,2,4-oxadiazol-5-yl)-N-(2-pyrrolidin-1-ylethyl)aniline;
1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}propan-1-one;
3-[4-(3-bromo-1H-pyrazolo[3,4-d]pyrimidin-4-yl)piperazin-1-yl]-5-(3,3-dimethylbutyl)-2-methyl-N-(2-pyrrolidin-1-ylethyl)aniline;
3-[4-(3-bromo-1H-pyrazolo[3,4-d]pyrimidin-4-yl)piperazin-1-yl]-5-ethyl-2-methyl-N-(2-pyrrolidin-1-ylethyl)aniline;
3-[4-(3-bromo-1H-pyrazolo[3,4-d]pyrimidin-4-yl)piperazin-1-yl]-2-methyl-N-(2-pyrrolidin-1-ylethyl)-5-[2-(trimethylsilyl)ethyl]aniline;
3-[4-(3-bromo-1H-pyrazolo[3,4-d]pyrimidin-4-yl)piperazin-1-yl]-2-methyl-5-(2-phenylethyl)-N-(2-pyrrolidin-1-ylethyl)aniline;
1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-one;
3-[4-(3-bromo-1H-pyrazolo[3,4-d]pyrimidin-4-yl)piperazin-1-yl]-N,4-dimethyl-N-(methyloxy)-5-[(2-pyrrolidin-1-ylethyl)amino]benzamide;
3-bromo-4-[4-(3-bromo-5-{[2,3-difluoro-2-(fluoromethyl)propyl]oxy}-2-methylphenyl)piperazin-1-yl]-1H-pyrazolo[3,4-d]pyrimidine;
4-[4-(3-bromo-5-{[2,3-difluoro-2-(fluoromethyl)propyl]oxy}-2-methylphenyl)piperazin-1-yl]-3-ethyl-1H-pyrazolo[3,4-d]pyrimidine;
1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}ethanone;
3-[4-(3-bromo-1H-pyrazolo[3,4-d]pyrimidin-4-yl)piperazin-1-yl]-5-[(difluoromethyl)oxy]-2-methyl-N-(2-pyrrolidin-1-ylethyl)aniline;
3-[4-(3-bromo-1H-pyrazolo[3,4-d]pyrimidin-4-yl)piperazin-1-yl]-5-{[(difluoromethyl)oxy]methyl}-2-methyl-N-(2-pyrrolidin-1-ylethyl)aniline;
3-[4-(3-bromo-1H-pyrazolo[3,4-d]pyrimidin-4-yl)piperazin-1-yl]-2-methyl-5-(methyloxy)-N-(2-pyrrolidin-1-ylethyl)aniline;
5-{[2,3-difluoro-2-(fluoromethyl)propyl]oxy}-3-[4-(3-ethyl-1H-pyrazolo[3,4-d]pyrimidin-4-yl)piperazin-1-yl]-2-methyl-N-(2-pyrrolidin-1-ylethyl)aniline;
2-[4-(3-bromo-1H-pyrazolo[3,4-d]pyrimidin-4-yl)piperazin-1-yl]-3,5,6-trifluoro-N-(3-methylbutyl)pyridin-4-amine;
3-[4-(3-bromo-1H-pyrazolo[3,4-d]pyrimidin-4-yl)piperazin-1-yl]-N-[(cyclopropylmethyl)oxy]-4-methyl-5-[(2-pyrrolidin-1-ylethyl)amino]benzamide;
3-[4-(3-bromo-1H-pyrazolo[3,4-d]pyrimidin-4-yl)piperazin-1-yl]-2-methyl-5-(5-methyl-1,2,4-oxadiazol-3-yl)-N-(2-pyrrolidin-1-ylethyl)aniline;

3-[4-(3-bromo-1H-pyrazolo[3,4-d]pyrimidin-4-yl)piperazin-1-yl]-5-[(ethylsulfonyl)-2-methyl-N-(2-pyrrolidin-1-ylethyl)aniline;
3-[4-(3-bromo-1H-pyrazolo[3,4-d]pyrimidin-4-yl)piperazin-1-yl]-2-methyl-5-(methylsulfonyl)-N-(2-pyrrolidin-1-ylethyl)aniline;
1-{3-[4-(3-ethyl-1H-pyrazolo[3,4-d]pyrimidin-4-yl)piperazin-1-yl]-4-methyl-5-[(2-pyrrolidin-1-ylethyl)amino]phenyl}pentan-1-one;
3-bromo-4-[4-(5-{[2,3-difluoro-2-(fluoromethyl)propyl]oxy}-2-methylphenyl)piperazin-1-yl]-1H-pyrazolo[3,4-d]pyrimidine;
6-[4-(3-bromo-1H-pyrazolo[3,4-d]pyrimidin-4-yl)piperazin-1-yl]-3,5-difluoro-N-4-(3-methylbutyl)-N-2-(2-pyrrolidin-1-ylethyl)pyridine-2,4-diamine;
3-bromo-5-[4-(3-bromo-1H-pyrazolo[3,4-d]pyrimidin-4-yl)piperazin-1-yl]-N-(2-pyrrolidin-1-ylethyl)aniline;
3-bromo-4-[4-(3',4',6-trifluoro-4-methylbiphenyl-3-yl)piperazin-1-yl]-1H-pyrazolo[3,4-d]pyrimidine;
3-[4-(3-bromo-1H-pyrazolo[3,4-d]pyrimidin-4-yl)piperazin-1-yl]-5-chloro-N-(2-pyrrolidin-1-ylethyl)aniline;
{3-[4-(3-bromo-1H-pyrazolo[3,4-d]pyrimidin-4-yl)piperazin-1-yl]-4-methyl-5-[(2-pyrrolidin-1-ylethyl)amino]phenyl}methanol;
3-bromo-4-(4-{4-methyl-2'-[(2-pyrrolidin-1-ylethyl)oxy]biphenyl-3-yl}piperazin-1-yl)-1H-pyrazolo[3,4-d]pyrimidine;
3-[4-(3-bromo-1H-pyrazolo[3,4-d]pyrimidin-4-yl)piperazin-1-yl]-5-{[(2,2-difluorocyclopropyl)methyl]oxy}-2-methyl-N-(2-pyrrolidin-1-ylethyl)aniline;
5-bromo-3-[4-(3-bromo-1H-pyrazolo[3,4-d]pyrimidin-4-yl)piperazin-1-yl]-2-methyl-N-(2-pyrrolidin-1-ylethyl)aniline;
3-[4-(3-bromo-1H-pyrazolo[3,4-d]pyrimidin-4-yl)piperazin-1-yl]-5-[(ethyloxy)methyl]-2-methyl-N-(2-pyrrolidin-1-ylethyl)aniline;
3-[4-[4-(3-bromo-1H-pyrazolo[3,4-d]pyrimidin-4-yl)piperazin-1-yl]-1-methyl-6-(trifluoromethyl)-1H-benzimidazol-2-yl]propan-1-ol;
1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}-4,4,4-trifluorobutan-1-one;
{3-[4-(3-bromo-1H-pyrazolo[3,4-d]pyrimidin-4-yl)piperazin-1-yl]-4-methyl-5-[(2-pyrrolidin-1-ylethyl)amino]phenyl}(cyclopropyl)methanone;
3-({3'-[4-(3-bromo-1H-pyrazolo[3,4-d]pyrimidin-4-yl)piperazin-1-yl]-4'-methylbiphenyl-2-yl}oxy)-N,N-dimethylpropan-1-amine;
3-[4-(3-bromo-1H-pyrazolo[3,4-d]pyrimidin-4-yl)piperazin-1-yl]-5-(1,1-difluorobutyl)-2-methyl-N-(2-pyrrolidin-1-ylethyl)aniline;
3-bromo-4-(4-{4-methyl-2'-[(3-morpholin-4-ylpropyl)oxy]biphenyl-3-yl}piperazin-1-yl)-1H-pyrazolo[3,4-d]pyrimidine;
3-bromo-4-(4-{4-methyl-2'-[(2-morpholin-4-ylethyl)oxy]biphenyl-3-yl}piperazin-1-yl)-1H-pyrazolo[3,4-d]pyrimidine;
3-[4-(3-bromo-1H-pyrazolo[3,4-d]pyrimidin-4-yl)piperazin-1-yl]-2-methyl-N-(2-pyrrolidin-1-ylethyl)-5-{[(2,2,2-trifluoroethyl)oxy]methyl}aniline;
1-[2-({3'-[4-(3-bromo-1H-pyrazolo[3,4-d]pyrimidin-4-yl)piperazin-1-yl]-4'-methylbiphenyl-2-yl}oxy)ethyl]pyrrolidine-2,5-dione;
3-bromo-4-(4-{3'-fluoro-4-methyl-2'-[(2-pyrrolidin-1-ylethyl)oxy]biphenyl-3-yl}piperazin-1-yl)-1H-pyrazolo[3,4-d]pyrimidine;
1-{3-[4-(3-bromo-1H-pyrazolo[3,4-d]pyrimidin-4-yl)piperazin-1-yl]-5-[(2-pyrrolidin-1-ylethyl)amino]phenyl}butan-1-one;
3-[4-(3-bromo-1H-pyrazolo[3,4-d]pyrimidin-4-yl)piperazin-1-yl]-2-methyl-N-(2-pyrrolidin-1-ylethyl)-5-[(3,3,3-trifluoropropyl)oxy]aniline;
3-[4-(3-bromo-1H-pyrazolo[3,4-d]pyrimidin-4-yl)piperazin-1-yl]-2-methyl-N-(2-pyrrolidin-1-ylethyl)-5-[(2,2,2-trifluoroethyl)oxy]aniline;
1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-ol;
3-bromo-4-(4-{4-chloro-2'-[(2-pyrrolidin-1-ylethyl)oxy]biphenyl-3-yl}piperazin-1-yl)-1H-pyrazolo[3,4-d]pyrimidine;
3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-yn-1-ol;
3-bromo-4-(4-{4-chloro-4'-fluoro-2'-[(2-pyrrolidin-1-ylethyl)oxy]biphenyl-3-yl}piperazin-1-yl)-1H-pyrazolo[3,4-d]pyrimidine;
3-bromo-4-(4-{4-methyl-3'-[(2-pyrrolidin-1-ylethyl)oxy]biphenyl-3-yl}piperazin-1-yl)-1H-pyrazolo[3,4-d]pyrimidine;
(2E)-3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-enoic acid;
3-[4-(3-bromo-1H-pyrazolo[3,4-d]pyrimidin-4-yl)piperazin-1-yl]-2-methyl-N-(2-pyrrolidin-1-ylethyl)-5-[4,4,4-trifluoro-1,1-bis(methyloxy)butyl]aniline;
4-(4-phenylpiperazin-1-yl)-7H-pyrrolo[2,3-d]pyrimidine;
4-[4-(3-chlorophenyl)piperazin-1-yl]-7H-pyrrolo[2,3-d]pyrimidine;
4-(4-phenylpiperazin-1-yl)-1H-pyrazolo[3,4-d]pyrimidine;
4-[4-(2-methylphenyl)piperazin-1-yl]-7H-pyrrolo[2,3-d]pyrimidine;
4-{4-[2-(methyloxy)phenyl]piperazin-1-yl}-7H-pyrrolo[2,3-d]pyrimidine;
4-{4-[3-(methyloxy)phenyl]piperazin-1-yl}-7H-pyrrolo[2,3-d]pyrimidine;
4-{4-[4-(methyloxy)phenyl]piperazin-1-yl}-7H-pyrrolo[2,3-d]pyrimidine;
4-{4-[3-(trifluoromethyl)phenyl]piperazin-1-yl}-7H-pyrrolo[2,3-d]pyrimidine;
6-[4-(4-chlorophenyl)piperazin-1-yl]-9H-purine;
4-[4-(4-chlorophenyl)piperazin-1-yl]-7H-pyrrolo[2,3-d]pyrimidine;
4-[4-(2-chlorophenyl)piperazin-1-yl]-7H-pyrrolo[2,3-d]pyrimidine;
4-[4-(4-fluorophenyl)piperazin-1-yl]-7H-pyrrolo[2,3-d]pyrimidine;
4-[4-(2-fluorophenyl)piperazin-1-yl]-7H-pyrrolo[2,3-d]pyrimidine;
6-[4-(2-methylphenyl)piperazin-1-yl]-9H-purine;
4-{4-[3-(trifluoromethyl)phenyl]piperazin-1-yl}-1H-pyrazolo[3,4-d]pyrimidine;
4-[4-(2-methylphenyl)piperazin-1-yl]-1H-pyrazolo[3,4-d]pyrimidine;
4-[4-(3-chlorophenyl)piperazin-1-yl]-3-methyl-1H-pyrazolo[3,4-d]pyrimidine;
3-methyl-4-[4-(2-methylphenyl)piperazin-1-yl]-1H-pyrazolo[3,4-d]pyrimidine;
4-[4-(5-chloro-2-methylphenyl)piperazin-1-yl]-1H-pyrazolo[3,4-d]pyrimidine;

4-[4-(5-chloro-2-methylphenyl)piperazin-1-yl]-3-methyl-1H-pyrazolo[3,4-d]pyrimidine;
4-[4-(5-chloro-2-methylphenyl)piperazin-1-yl]-3-methyl-6-phenyl-1H-pyrazolo[3,4-d]pyrimidine;
4-[4-(5-chloro-2-methylphenyl)piperazin-1-yl]-3-ethyl-1H-pyrazolo[3,4-d]pyrimidine;
4-[4-(5-chloro-2-methylphenyl)piperazin-1-yl]-6-methyl-1H-pyrazolo[3,4-d]pyrimidine;
4-[4-(5-chloro-2-methylphenyl)piperazin-1-yl]-6-ethyl-1H-pyrazolo[3,4-d]pyrimidine;
4-[4-(5-chloro-2-methylphenyl)piperazin-1-yl]-6-(1-methylethyl)-1H-pyrazolo[3,4-d]pyrimidine;
4-[4-(5-chloro-2-methylphenyl)piperazin-1-yl]-3-phenyl-1H-pyrazolo[3,4-d]pyrimidine;
4-[4-(5-chloro-2-methylphenyl)piperazin-1-yl]-3-({[2-(methyloxy)ethyl]oxy}methyl)-1H-pyrazolo[3,4-d]pyrimidine;
3-bromo-4-[4-(5-chloro-2-methylphenyl)piperazin-1-yl]-1H-pyrazolo[3,4-d]pyrimidine;
4-[4-(5-chloro-2-methylphenyl)piperazin-1-yl]-3-propyl-1H-pyrazolo[3,4-d]pyrimidine;
4-{4-[4-(5-chloro-2-methylphenyl)piperazin-1-yl]-1H-pyrazolo[3,4-d]pyrimidin-3-yl}phenol;
4-[4-(5-chloro-2-methylphenyl)piperazin-1-yl]-N-phenyl-1H-pyrazolo[3,4-d]pyrimidin-3-amine;
4-[4-(3-chlorophenyl)piperazin-1-yl]-3-ethyl-1H-pyrazolo[3,4-d]pyrimidine;
4-{4-[5-chloro-2-(methyloxy)phenyl]piperazin-1-yl}-3-ethyl-1H-pyrazolo[3,4-d]pyrimidine;
3-{4-[4-(5-chloro-2-methylphenyl)piperazin-1-yl]-1H-pyrazolo[3,4-d]pyrimidin-3-yl}phenol;
4-[4-(5-chloro-2-methylphenyl)piperazin-1-yl]-3-{3-[(phenylmethyl)oxy]phenyl}-1H-pyrazolo[3,4-d]pyrimidine;
3-(1,3-benzodioxol-5-yl)-4-[4-(5-chloro-2-methylphenyl)piperazin-1-yl]-1H-pyrazolo[3,4-d]pyrimidine;
4-[4-(5-chloro-2-methylphenyl)piperazin-1-yl]-3-(2-thienyl)-1H-pyrazolo[3,4-d]pyrimidine;
3-{4-[4-(5-chloro-2-methylphenyl)piperazin-1-yl]-1H-pyrazolo[3,4-d]pyrimidin-3-yl}aniline;
3-{4-[4-(5-chloro-2-methylphenyl)piperazin-1-yl]-1H-pyrazolo[3,4-d]pyrimidin-3-yl}benzoic acid;
4-[4-(5-chloro-2-methylphenyl)piperazin-1-yl]-3-(4-methylphenyl)-1H-pyrazolo[3,4-d]pyrimidine;
N-(4-{4-[4-(5-chloro-2-methylphenyl)piperazin-1-yl]-1H-pyrazolo[3,4-d]pyrimidin-3-yl}phenyl)acetamide;
4-[4-(3-chlorophenyl)-1,4-diazepan-1-yl]-3-ethyl-1H-pyrazolo[3,4-d]pyrimidine;
4-[5-(3-chlorophenyl)-2,5-diazabicyclo [2.2.1]hept-2-yl]-3-ethyl-1H-pyrazolo[3,4-d]pyrimidine;
4-(4-{3-chloro-4-[(2-morpholin-4-ylethyl)oxy]phenyl}piperazin-1-yl)-3-ethyl-1H-pyrazolo[3,4-d]pyrimidine;
methyl 1-(3-chlorophenyl)-4-(3-ethyl-1H-pyrazolo[3,4-d]pyrimidin-4-yl)piperazine-2-carboxylate;
4-[4-(5-chloro-2-methylphenyl)piperazin-1-yl]-3-(3-methylbut-2-en-1-yl)-1H-pyrazolo[3,4-d]pyrimidine;
4-[4-(5-chloro-2-methylphenyl)piperazin-1-yl]-3-(trifluoromethyl)-1H-pyrazolo[3,4-d]pyrimidine;
methyl 4-(3-chlorophenyl)-1-(3-ethyl-1H-pyrazolo[3,4-d]pyrimidin-4-yl)piperazine-2-carboxylate;
4-(4-{3-chloro-4-[(2-piperidin-1-ylethyl)oxy]phenyl}piperazin-1-yl)-3-ethyl-1H-pyrazolo[3,4-d]pyrimidine;
4-[4-(5-chloro-2-methylphenyl)piperazin-1-yl]-3-(1-methylethyl)-1H-pyrazolo[3,4-d]pyrimidine;
1-(3-chlorophenyl)-4-(3-ethyl-1H-pyrazolo[3,4-d]pyrimidin-4-yl)piperazine-2-carboxylic acid;
1-(3-chlorophenyl)-4-(3-ethyl-1H-pyrazolo[3,4-d]pyrimidin-4-yl)-N-methylpiperazine-2-carboxamide;
4-[4-(5-chloro-2-methylphenyl)piperazin-1-yl]-3-(phenylmethyl)-1H-pyrazolo[3,4-d]pyrimidine;
4-[4-(5-chloro-2-methylphenyl)piperazin-1-yl]-3-(2-methylpropyl)-1H-pyrazolo[3,4-d]pyrimidine;
4-[4-(5-chloro-2-methylphenyl)piperazin-1-yl]-3-[4-(methyloxy)phenyl]-1H-pyrazolo[3,4-d]pyrimidine;
4-[4-(5-chloro-2-methylphenyl)piperazin-1-yl]-3-(4-fluorophenyl)-1H-pyrazolo[3,4-d]pyrimidine;
4-[4-(5-chloro-2-methylphenyl)piperazin-1-yl]-3-[4-(phenyloxy)phenyl]-1H-pyrazolo[3,4-d]pyrimidine;
4-[4-(5-chloro-2-methylphenyl)piperazin-1-yl]-3-{4-[(piperidin-4-ylmethyl)oxy]phenyl}-1H-pyrazolo[3,4-d]pyrimidine;
1-(3-chlorophenyl)-N-[2-(dimethylamino)ethyl]-4-(3-ethyl-1H-pyrazolo[3,4-d]pyrimidin-4-yl)piperazine-2-carboxamide;
4-[4-(5-chloro-2-methyl-3-morpholin-4-ylphenyl)piperazin-1-yl]-3-ethyl-1H-pyrazolo[3,4-d]pyrimidine;
4-(3-chlorophenyl)-1-(3-ethyl-1H-pyrazolo[3,4-d]pyrimidin-4-yl)-N-methylpiperazine-2-carboxamide;
4-[4-(5-chloro-2-methylphenyl)piperazin-1-yl]-3-[2-(methyloxy)phenyl]-1H-pyrazolo[3,4-d]pyrimidine;
4-[4-(5-chloro-2-methylphenyl)piperazin-1-yl]-3-pyridin-4-yl-1H-pyrazolo[3,4-d]pyrimidine;
4-[4-(5-chloro-2-methylphenyl)piperazin-1-yl]-3-[3-(methyloxy)phenyl]-1H-pyrazolo[3,4-d]pyrimidine;
4-{4-[4-(5-chloro-2-methylphenyl)piperazin-1-yl]-1H-pyrazolo[3,4-d]pyrimidin-3-yl}benzonitrile;
[5-chloro-3-[4-(3-ethyl-1H-pyrazolo[3,4-d]pyrimidin-4-yl)piperazin-1-yl]-2-(methyloxy)phenyl]methanol;
methyl 5-chloro-3-[4-(3-ethyl-1H-pyrazolo[3,4-d]pyrimidin-4-yl)piperazin-1-yl]-2-(methyloxy)benzoate;
(2E)-3-{4-[4-(5-chloro-2-methylphenyl)piperazin-1-yl]-1H-pyrazolo[3,4-d]pyrimidin-3-yl}prop-2-enoic acid;
3-{4-[4-(5-chloro-2-methylphenyl)piperazin-1-yl]-1H-pyrazolo[3,4-d]pyrimidin-3-yl}propanoic acid;
3-{4-[4-(5-chloro-2-methylphenyl)piperazin-1-yl]-1H-pyrazolo[3,4-d]pyrimidin-3-yl}propan-1-ol;
methyl (2E)-3-{4-[4-(5-chloro-2-methylphenyl)piperazin-1-yl]-1H-pyrazolo[3,4-d]pyrimidin-3-yl}prop-2-enoate;
4-[4-(5-chloro-2-methylphenyl)piperazin-1-yl]-3-{4-[(2-morpholin-4-ylethyl)oxy]phenyl}-1H-pyrazolo[3,4-d]pyrimidine;
5-chloro-N-[2-(dimethylamino)ethyl]-3-[4-(3-ethyl-1H-pyrazolo[3,4-d]pyrimidin-4-yl)piperazin-1-yl]-2-(methyloxy)benzamide;
4-(4-{5-chloro-2-(methyloxy)-3-[(4-methylpiperazin-1-yl)carbonyl]phenyl}piperazin-1-yl)-3-ethyl-1H-pyrazolo[3,4-d]pyrimidine;
2-(dimethylamino)ethyl 5-chloro-3-[4-(3-ethyl-1H-pyrazolo[3,4-d]pyrimidin-4-yl)piperazin-1-yl]-2-(methyloxy)benzoate;
1-[5-chloro-3-[4-(3-ethyl-1H-pyrazolo[3,4-d]pyrimidin-4-yl)piperazin-1-yl]-2-(methyloxy)phenyl]-N,N-dimethylmethanamine;
N'-{[5-chloro-3-[4-(3-ethyl-1H-pyrazolo[3,4-d]pyrimidin-4-yl)piperazin-1-yl]-2-(methyloxy)phenyl]methyl}-N,N-dimethylethane-1,2-diamine;
[1-(3-chlorophenyl)-4-(3-ethyl-1H-pyrazolo[3,4-d]pyrimidin-4-yl)piperazin-2-yl]methanol;

3-[(4-{4-[4-(5-chloro-2-methylphenyl)piperazin-1-yl]-1H-pyrazolo[3,4-d]pyrimidin-3-yl}phenyl)oxy]-N,N-dimethylpropan-1-amine;
2-chloro-4-[4-(3-ethyl-1H-pyrazolo[3,4-d]pyrimidin-4-yl)piperazin-1-yl]-5-methylphenol;
1-(3-chlorophenyl)-4-(3-ethyl-1H-pyrazolo[3,4-d]pyrimidin-4-yl)-N-(1-methylpiperidin-4-yl)piperazine-2-carboxamide;
1-(3-chlorophenyl)-4-(3-ethyl-1H-pyrazolo[3,4-d]pyrimidin-4-yl)-N-(2-morpholin-4-ylethyl)piperazine-2-carboxamide;
2-{[5-chloro-3-[4-(3-ethyl-1H-pyrazolo[3,4-d]pyrimidin-4-yl)piperazin-1-yl]-2-(methyloxy)phenyl]oxy}-N,N-dimethylethanamine;
3-{5-chloro-3-[4-(3-ethyl-1H-pyrazolo[3,4-d]pyrimidin-4-yl)piperazin-1-yl]-2-methylphenyl}-N,N-dimethyl-prop-2-yn-1-amine;
N'-{5-chloro-3-[4-(3-ethyl-1H-pyrazolo[3,4-d]pyrimidin-4-yl)piperazin-1-yl]-2-methylphenyl}-N,N-dimethylethane-1,2-diamine;
1,1-dimethylethyl (2E)-3-{4-[4-(5-chloro-2-methylphenyl)piperazin-1-yl]-1H-pyrazolo[3,4-d]pyrimidin-3-yl}prop-2-enoate;
3-({2-chloro-4-[4-(3-ethyl-1H-pyrazolo[3,4-d]pyrimidin-4-yl)piperazin-1-yl]-5-methylphenyl}oxy)-N,N-dimethylpropan-1-amine;
2-({2-chloro-4-[4-(3-ethyl-1H-pyrazolo[3,4-d]pyrimidin-4-yl)piperazin-1-yl]-5-methylphenyl}oxy)-N,N-dimethylethanamine;
4-{-4-[5-chloro-2-methyl-4-(methyloxy)phenyl]piperazin-1-yl}-3-ethyl-1H-pyrazolo[3,4-d]pyrimidine;
4-[4-(5-chloro-2-methylphenyl)piperazin-1-yl]-3-(4-methylpiperazin-1-yl)-1H-pyrazolo[3,4-d]pyrimidine;
3-{4-[4-(5-chloro-2-methylphenyl)piperazin-1-yl]-1H-pyrazolo[3,4-d]pyrimidin-3-yl}-N,N-diethylprop-2-yn-1-amine;
3-{4-[4-(5-chloro-2-methylphenyl)piperazin-1-yl]-1H-pyrazolo[3,4-d]pyrimidin-3-yl}prop-2-yn-1-ol;
4-[4-(5-chloro-2-methylphenyl)piperazin-1-yl]-3-(piperidin-4-ylmethyl)-1H-pyrazolo[3,4-d]pyrimidine;
phenylmethyl (3aR,6aS)-5-({4-[4-(5-chloro-2-methylphenyl)piperazin-1-yl]-1H-pyrazolo[3,4-d]pyrimidin-3-yl}methylidene)hexahydrocyclopenta[c]pyrrole-2(1H)-carboxylate;
4-[4-(5-chloro-2-methylphenyl)piperazin-1-yl]-3-[(E)-(3aR,6aS)-hexahydrocyclopenta[c]pyrrol-5(1H)-ylidenemethyl]-1H-pyrazolo[3,4-d]pyrimidine;
4-[4-(5-chloro-2-methylphenyl)piperazin-1-yl]-3-(3-pyrrolidin-1-ylprop-1-yn-1-yl)-1H-pyrazolo[3,4-d]pyrimidine;
4-[4-(5-chloro-2-methylphenyl)piperazin-1-yl]-3-[3-(4-methylpiperazin-1-yl)prop-1-yn-1-yl]-1H-pyrazolo[3,4-d]pyrimidine;
3-{4-[4-(5-chloro-2-methylphenyl)piperazin-1-yl]-1H-pyrazolo[3,4-d]pyrimidin-3-yl}-N,N-diethylpropan-1-amine;
4-[4-(5-chloro-2-methylphenyl)piperazin-1-yl]-3-(3-pyrrolidin-1-ylpropyl)-1H-pyrazolo[3,4-d]pyrimidine;
4-[4-(5-chloro-2-methylphenyl)piperazin-1-yl]-3-(1,2,3,6-tetrahydropyridin-4-yl)-1H-pyrazolo[3,4-d]pyrimidine;
3-{5-chloro-3-[4-(3-ethyl-1H-pyrazolo[3,4-d]pyrimidin-4-yl)piperazin-1-yl]-2-methylphenyl}-N,N-diethylpropan-1-amine; or
4-{4-[5-chloro-2-methyl-3-(3-pyrrolidin-1-ylpropyl)phenyl]piperazin-1-yl}-3-ethyl-1H-pyrazolo[3,4-d]pyrimidine.

53. A compound according to claim 1 which is
5-bromo-3-[4-(3-bromo-1H-pyrazolo[3,4-d]pyrimidin-4-yl)piperazin-1-yl]-2-methyl-N-(2-pyrrolidin-1-ylethyl)aniline;
3-[4-(3-bromo-1H-pyrazolo[3,4-d]pyrimidin-4-yl)piperazin-1-yl]-5-[(ethyloxy)methyl]-2-methyl-N-(2-pyrrolidin-1-ylethyl)aniline;
3-[4-[4-(3-bromo-1H-pyrazolo[3,4-d]pyrimidin-4-yl)piperazin-1-yl]-1-methyl-6-(trifluoromethyl)-1H-benzimidazol-2-yl]propan-1-ol;
1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}-4,4,4-trifluorobutan-1-one;
{3-[4-(3-bromo-1H-pyrazolo[3,4-d]pyrimidin-4-yl)piperazin-1-yl]-4-methyl-5-[(2-pyrrolidin-1-ylethyl)amino]phenyl}(cyclopropyl)methanone;
3-({3'-[4-(3-bromo-1H-pyrazolo[3,4-d]pyrimidin-4-yl)piperazin-1-yl]-4'-methylbiphenyl-2-yl}oxy)-N,N-dimethylpropan-1-amine;
3-[4-(3-bromo-1H-pyrazolo[3,4-d]pyrimidin-4-yl)piperazin-1-yl]-5-(1,1-difluorobutyl)-2-methyl-N-(2-pyrrolidin-1-ylethyl)aniline;
3-bromo-4-(4-{4-methyl-2'-[(3-morpholin-4-ylpropyl)oxy]biphenyl-3-yl}piperazin-1-yl)-1H-pyrazolo[3,4-d]pyrimidine;
3-bromo-4-(4-{4-methyl-2'-[(2-morpholin-4-ylethyl)oxy]biphenyl-3-yl}piperazin-1-yl)-1H-pyrazolo[3,4-d]pyrimidine;
3-[4-(3-bromo-1H-pyrazolo[3,4-d]pyrimidin-4-yl)piperazin-1-yl]-2-methyl-N-(2-pyrrolidin-1-ylethyl)-5-{[(2,2,2-trifluoroethyl)oxy]methyl}aniline;
1-[2-({3'-[4-(3-bromo-1H-pyrazolo[3,4-d]pyrimidin-4-yl)piperazin-1-yl]-4'-methylbiphenyl-2-yl}oxy)ethyl]pyrrolidine-2,5-dione;
3-bromo-4-(4-{3'-fluoro-4-methyl-2'-[(2-pyrrolidin-1-ylethyl)oxy]biphenyl-3-yl}piperazin-1-yl)-1H-pyrazolo[3,4-d]pyrimidine;
1-{3-[4-(3-bromo-1H-pyrazolo[3,4-d]pyrimidin-4-yl)piperazin-1-yl]-5-[(2-pyrrolidin-1-ylethyl)amino]phenyl}butan-1-one;
3-[4-(3-bromo-1H-pyrazolo[3,4-d]pyrimidin-4-yl)piperazin-1-yl]-2-methyl-N-(2-pyrrolidin-1-ylethyl)-5-[(3,3,3-trifluoropropyl)oxy]aniline;
3-[4-(3-bromo-1H-pyrazolo[3,4-d]pyrimidin-4-yl)piperazin-1-yl]-2-methyl-N-(2-pyrrolidin-1-ylethyl)-5-[(2,2,2-trifluoroethyl)oxy]aniline;
1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-ol;
3-bromo-4-(4-{4-chloro-2'-[(2-pyrrolidin-1-ylethyl)oxy]biphenyl-3-yl}piperazin-1-yl)-1H-pyrazolo[3,4-d]pyrimidine;
3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-yn-1-ol;
3-bromo-4-(4-{4-chloro-4'-fluoro-2'-[(2-pyrrolidin-1-ylethyl)oxy]biphenyl-3-yl}piperazin-1-yl)-1H-pyrazolo[3,4-d]pyrimidine;
3-bromo-4-(4-{4-methyl-3'-[(2-pyrrolidin-1-ylethyl)oxy]biphenyl-3-yl}piperazin-1-yl)-1H-pyrazolo[3,4-d]pyrimidine; or
(2E)-3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-enoic acid.

* * * * *